United States Patent
Ahn et al.

(10) Patent No.: US 9,296,745 B2
(45) Date of Patent: Mar. 29, 2016

(54) DIACYLGLYCEROL ACYLTRANSFERASE 2 INHIBITORS

(71) Applicant: Pfizer Inc., New York, NY (US)

(72) Inventors: Kay Ahn, Lexington, MA (US); Markus Boehm, Mansfield, MA (US); Shawn Cabral, Groton, CT (US); Philip A. Carpino, Newton, MA (US); Kentaro Futatsugi, Quincy, MA (US); David Hepworth, Concord, MA (US); Daniel W. Kung, Salem, CT (US); Suvi Orr, San Diego, CA (US); Jian Wang, Belmont, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/384,508

(22) PCT Filed: Mar. 26, 2013

(86) PCT No.: PCT/IB2013/052404
§ 371 (c)(1),
(2) Date: Sep. 11, 2014

(87) PCT Pub. No.: WO2013/150416
PCT Pub. Date: Oct. 10, 2013

(65) Prior Publication Data
US 2015/0087585 A1    Mar. 26, 2015

Related U.S. Application Data

(60) Provisional application No. 61/621,144, filed on Apr. 6, 2012.

(51) Int. Cl.
| | | |
|---|---|---|
| *C07D 471/04* | (2006.01) |
| *A61K 45/06* | (2006.01) |
| *C07D 487/04* | (2006.01) |
| *C07D 519/00* | (2006.01) |
| *A61K 31/437* | (2006.01) |
| *A61K 31/506* | (2006.01) |
| *A61K 31/52* | (2006.01) |
| *A61K 31/5377* | (2006.01) |
| *A61K 31/538* | (2006.01) |

(52) U.S. Cl.
CPC ............ *C07D 471/04* (2013.01); *A61K 31/437* (2013.01); *A61K 31/506* (2013.01); *A61K 31/52* (2013.01); *A61K 31/538* (2013.01); *A61K 31/5377* (2013.01); *A61K 45/06* (2013.01); *C07D 487/04* (2013.01); *C07D 519/00* (2013.01)

(58) Field of Classification Search
CPC .. C07D 471/04; C07D 487/14; A61K 31/437; A61K 31/52
See application file for complete search history.

(56) References Cited

U.S. PATENT DOCUMENTS

2003/0207883 A1    11/2003    Renhowe et al.

FOREIGN PATENT DOCUMENTS

WO    2010/125402    11/2010

OTHER PUBLICATIONS

MedlinePlus. Familial combined hyperlipidemia. (2015) 1-5. <www.nlm.nih.gov/medlineplus/ency/article/000396.htm>.*
Xian Yu, Xing. Hepatology (2005) 42:2 362-371.*
Zhou, et al., "Antibacterial activity in serum of the 3,5-diamino-piperidine translation inhibitors", Bioorganic & Medicinal Chemistry Letters, vol. 18(11), pp. 3369-3375 (2008).

* cited by examiner

*Primary Examiner* — Golam M Shameem
*Assistant Examiner* — Laura Daniel
(74) *Attorney, Agent, or Firm* — Lisa A. Samuels

(57) ABSTRACT

Derivatives of purine, 3H-imidazo[4,5-b]pyrimidine and 1H-imidazo[4,5-d]pyrazine of Formula I that inhibit the activity of the diacylglycerol acyltransferase 2 (DGAT2) and their uses in the treatment of diseases linked thereto in animals are described herein.

17 Claims, 5 Drawing Sheets

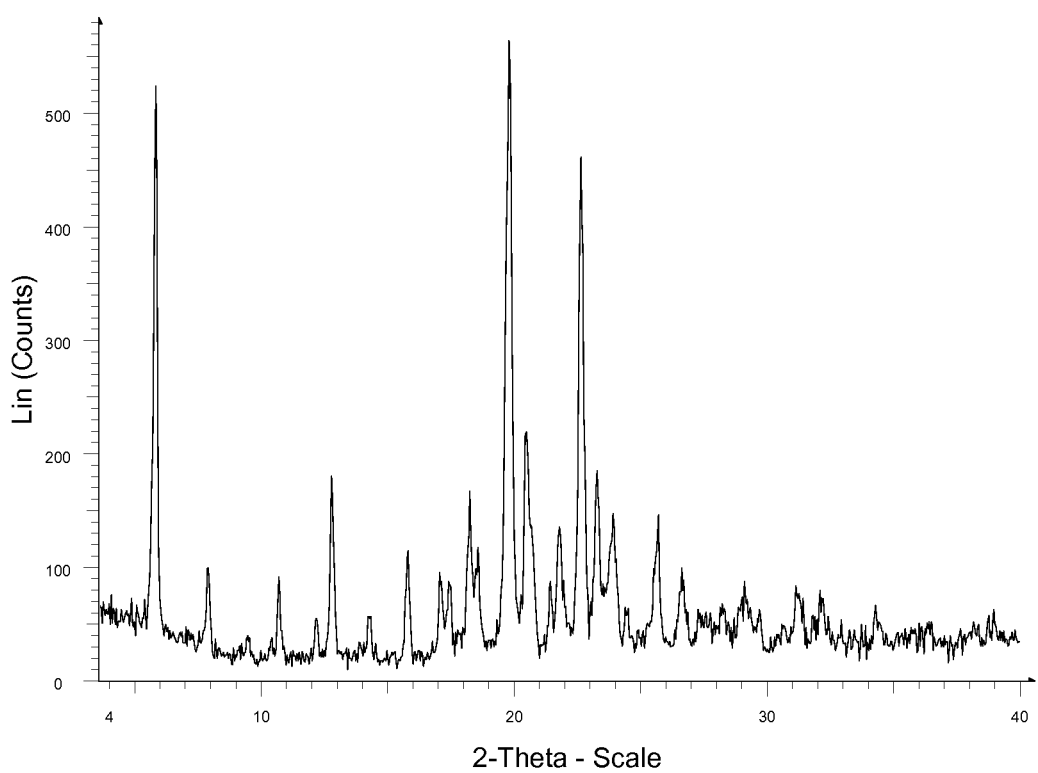
FIG. 1. X-ray powder diffraction pattern of Example 109-B.

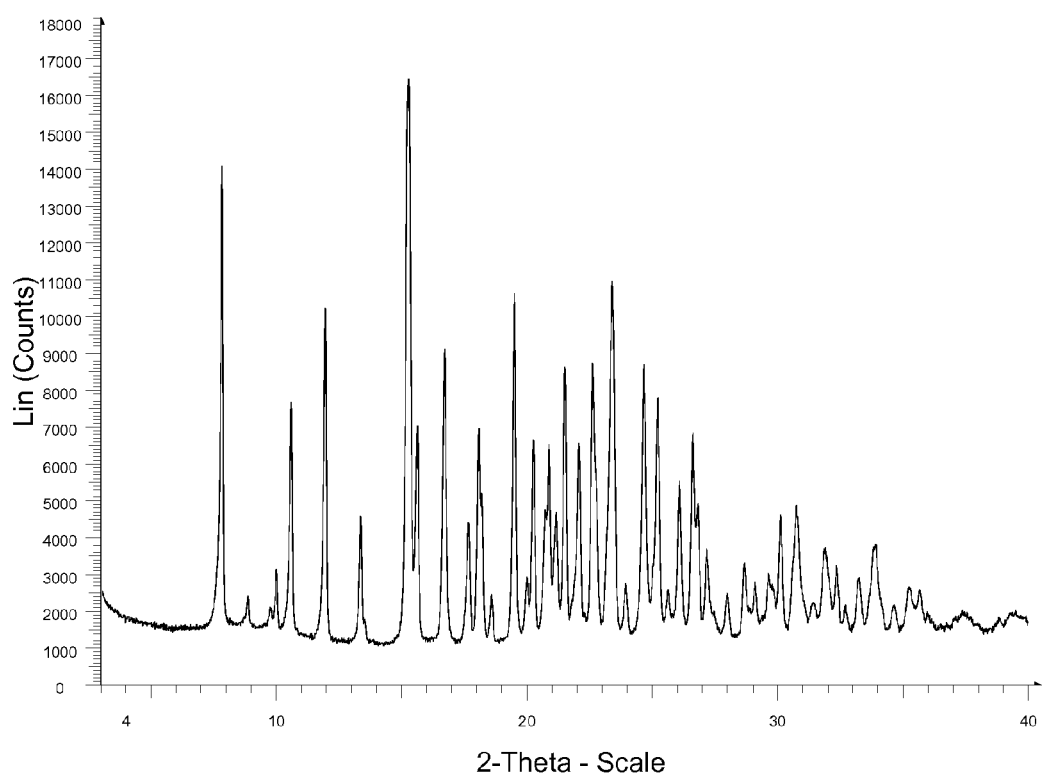
FIG. 2. X-ray powder diffraction pattern of Example 109-C.

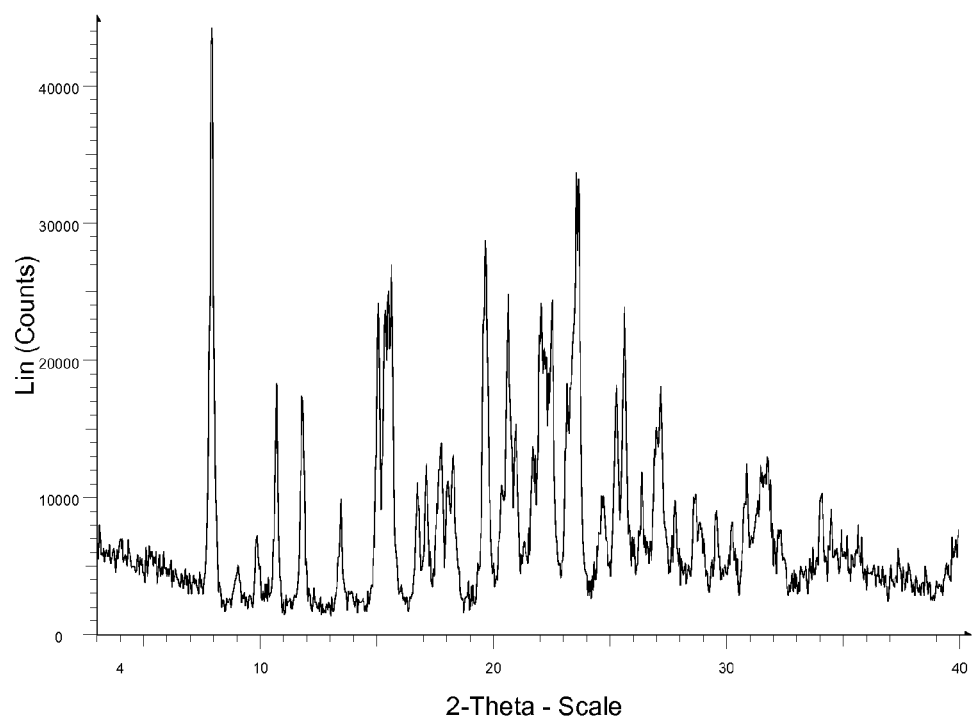
FIG. 3. X-ray powder diffraction pattern of Example 196-B.

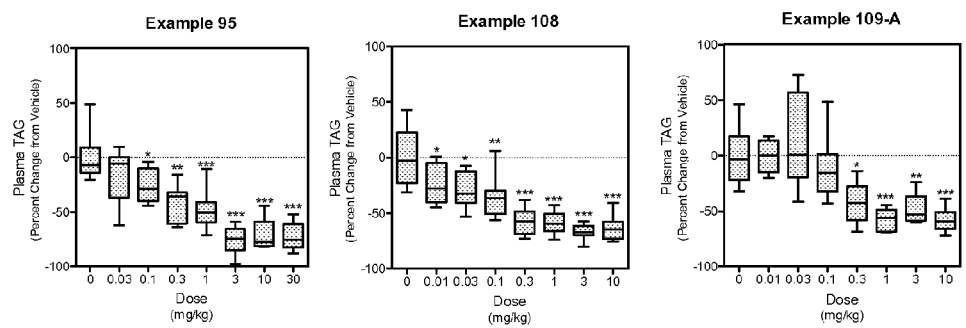
FIG. 4. Acute effects of DGAT2 inhibitors on plamsa TAG levels in Sprague Dawley rats

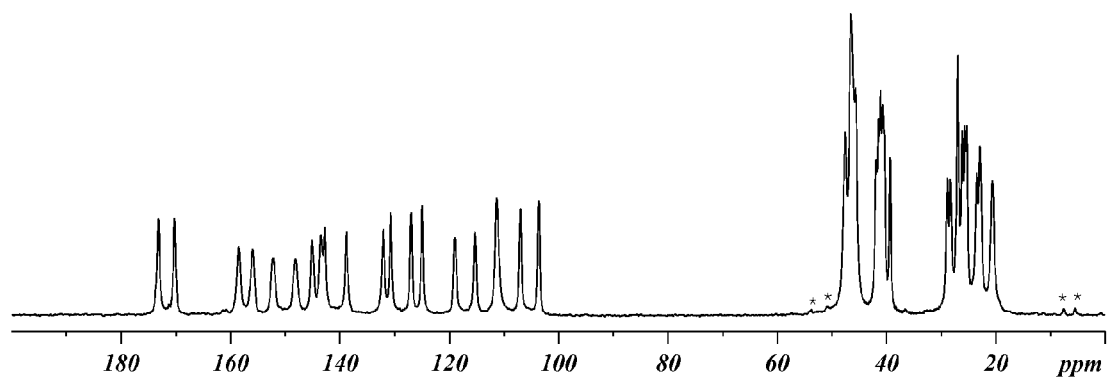
FIG. 5. ssNMR spectrum of Example 109-B.

DIACYLGLYCEROL ACYLTRANSFERASE 2 INHIBITORS

CROSS REFERENCE TO RELATED APPLICATIONS

This application claims the benefit of priority under 35 U.S.C. 371 of international application number PCT/IB2013/052404 filed on Mar. 26, 2013, which claims priority from U.S. Provisional Application Ser. No. 61/521,144, filed Apr. 6, 2012, all of which are incorporated in their entireties for all purposes.

FIELD OF THE INVENTION

The present invention relates to new pharmaceutical compounds, pharmaceutical compositions containing these compounds, and their use to inhibit the activity of the diacylglycerol acyltransferase 2 (DGAT2).

BACKGROUND OF THE INVENTION

Triglycerides or triacylglycerols (TAG) represent a major form of energy storage in mammals. TAG's are formed by the sequential esterification of glycerol with three fatty acids of varying chain lengths and degrees of saturation. TAG synthesized in the intestine or liver are packaged into chylomicrons or very low-density lipoprotein (VLDL), respectively, and exported to peripheral tissues where they are hydrolysed to their constituent fatty acids and glycerol by lipoprotein lipase (LPL). The resultant non-esterified fatty acids (NEFA) can either be metabolised further to produce energy or reesterified and stored.

Under normal physiological conditions, the energy-dense TAG remains sequestered in various adipose depots until there is a demand for its release, whereupon, it is hydrolyzed to glycerol and free fatty acids which are then released into the blood stream. This process is tightly regulated by the opposing actions of insulin and hormones such as catecholamines which promote the deposition and mobilization of TAG stores under various physiological conditions. In the postprandial setting, insulin acts to inhibit lipolysis, thereby, restraining the release of energy in the form of NEFA and ensuring the appropriate storage of dietary lipids in adipose depots. However, in patients with type 2 diabetes, the ability of insulin to suppress lipolysis is ameliorated and NEFA flux from adipocytes is inappropriately elevated. This, in turn, results in increased delivery of lipid to tissues such as muscle and liver. In the absence of energetic demand the TAG and other lipid metabolites, such as diacylglycerol (DAG) can accumulate and cause a loss of insulin sensitivity. Insulin resistance in muscle is characterized by reduced glucose uptake and glycogen storage, whilst in the liver, loss of insulin signaling gives rise to dysregulated glucose output and overproduction of TAG-rich VLDL, a hallmark of type 2 diabetes. Elevated secretion of TAG-enriched VLDL, so called VLDL1 particles, is thought to stimulate the production of small, dense low-density lipoprotein (sdLDL), a proatherogenic subfraction of LDL that is associated with elevated risk of coronary heart disease.

Diacylglycerol acyltransferases (DGAT) catalyze the terminal step in TAG synthesis, specifically, the esterification of a fatty acid with diacylglycerol resulting in the formation of TAG. In mammals, two DGAT enzymes (DGAT1 and DGAT2) have been characterized. Although these enzymes catalyze the same enzymatic reaction their respective amino acid sequences are unrelated and they occupy distinct gene families. Mice harboring a disruption in the gene encoding DGAT1 are resistant to diet-induced obesity and have elevated energy expenditure and activity. Dgat1−/− mice exhibit dysregulated postaborpative release of chylomicrons and accumulate lipid in the enterocytes. The metabolically favorable phenotype observed in these mice is suggested to be driven by loss of DGAT1 expression in the intestine. Importantly, despite a defect in lactation in female Dgat1−/− mice, these animals retain the capacity to synthesize TAG suggesting the existence of additional DGAT enzymes. This observation and the isolation of a second DGAT from the fungus *Mortierella rammaniana* led to the identification and characterization of DGAT2.

DGAT2 is highly expressed in liver and adipose, and unlike DGAT1, exhibits exquisite substrate specificity for DAG. Deletion of the DGAT2 gene in rodents results in defective intrauterine growth, severe lipemia, impaired skin barrier function, and early post-natal death. Due to the lethality caused by loss of DGAT2, much of our understanding of the physiological role of DGAT2 derives from studies performed with antisense oligonucleotides (ASO) in rodent models of metabolic disease. In this setting, inhibition of hepatic DGAT2 resulted in improvements in plasma lipoprotein profile (decrease in total cholesterol and TAG) and a reduction of hepatic lipid burden which was accompanied by improved insulin sensitivity and whole-body glucose control. Although the molecular mechanisms underlying these observations are not fully elucidated, it is clear that suppression of DGAT2 results in a down-regulation of the expression of multiple genes encoding proteins involved in lipogenesis, including sterol regulatory element-binding proteins 1c (SREBP1c) and stearoyl CoA-desaturase 1 (SCD1). In parallel, oxidative pathways are induced as evidenced by increased expression of genes such as carnitine palmitoyl transferase 1 (CPT1). The net result of these changes is to decrease the levels of hepatic DAG and TAG lipid which, in turn, leads to improved insulin responsiveness in the liver. Furthermore, DGAT2 inhibition suppresses hepatic VLDL TAG secretion and reduction in circulating cholesterol levels. Finally, plasma apolipoprotein B (APOB) levels were suppressed, possibly due to decreased supply of TAG for lipidation of the newly synthesized APOB protein. The beneficial effects of DGAT2 inhibition on both glycemic control and plasma cholesterol profile support that this target might be valuable in the treatment of metabolic disease.

SUMMARY OF THE INVENTION

The present application is directed at compounds of Formula (I)

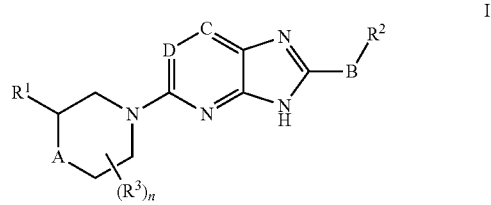

wherein:

A is $CR^6R^7$, O or S;

B is a bond, oxetanyl,

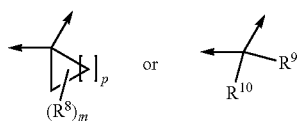

wherein
m is 0, 1 or 2;
p is 1, 2, 3 or 4;
C and D are each individually selected from N, CH, CF and C(CH$_3$), wherein only one of C and D is N;
$R^1$ is —C(O)-heterocyclyl, —C(O)—NR$^4$R$^5$, or a heteroaryl, wherein said heterocyclyl or heteroaryl is optionally substituted with 1 or 2 substituents selected independently from (C$_1$-C$_4$)alkyl, (C$_3$-C$_6$)cycloalkyl, (C$_1$-C$_4$)alkoxy, (C$_3$-C$_6$)cycloalkoxy, halo, hydroxy(C$_1$-C$_4$)alkyl, mono-N— or di-N,N—(C$_1$-C$_4$)alkylamino, mono-N— or di-N,N—(C$_3$-C$_6$)cycloalkylamino, heterocyclyl, hydroxyl and cyano;
$R^2$ is (C$_1$-C$_4$)alkyl, (C$_1$-C$_4$)alkoxy, (C$_3$-C$_6$)cycloalkyl, (C$_3$-C$_6$)cycloalkoxy, aryl, aryloxy, heteroaryloxy, heteroaryl, heterocyclyl, aralkyl, heteroaralkyl, —C(O)-heterocyclyl, —C(O)—NR$^4$R$^5$, or —NR$^4$—C(O)—R$^5$, wherein alkyl, alkoxy, cycloalkyl, cycloalkoxy, aralkyl, heteroaralkyl, aryl, aryloxy, heteroaryloxy, heteroaryl, heterocyclyl are each optionally substituted with one, two or three substituents selected independently from (C$_1$-C$_4$)alkyl, (C$_1$-C$_4$)alkoxy, (C$_3$-C$_6$)cycloalkyl, (C$_3$-C$_6$)cycloalkoxy, —C(O)—(C$_1$-C$_4$)alkyl, —C(O)—(C$_3$-C$_6$)cycloalkyl, halo, —C(O)—(C$_1$-C$_4$)alkoxy, —C(O)—(C$_3$-C$_6$)cycloalkoxy, mono-N— or di-N,N—(C$_1$-C$_4$)alkylamino, mono-N— or di-N,N—(C$_3$-C$_6$)cycloalkylamino, (C$_1$-C$_4$)alkylcarbonylamino, (C$_3$-C$_6$)cycloalkylcarbonylamino, (C$_1$-C$_4$)alkylcarbonyl-N—(C$_1$-C$_4$)alkylamino, (C$_1$-C$_4$)alkylcarbonyl-N—(C$_3$-C$_6$)cycloalkylamino, (C$_3$-C$_6$)cycloalkylcarbonyl-N—(C$_1$-C$_4$)alkylamino, (C$_3$-C$_6$)cycloalkylcarbonyl-N—(C$_3$-C$_6$)cycloalkylamino, aminocarbonyl, mono-N— or di-N,N—(C$_1$-C$_4$)alkylaminocarbonyl, mono-N— or di-N,N—(C$_3$-C$_6$)cycloaminocarbonyl, mono-N— or di-N,N—(C$_1$-C$_4$)alkylcarbonyl, mono-N— or di-N,N—(C$_3$-C$_6$)cycloalkylcarbonyl, mono-N— or di-N,N—(C$_1$-C$_4$)alkoxycarbonyl, mono-N— or di-N,N—(C$_3$-C$_6$)cycloalkoxycarbonyl, (C$_1$-C$_4$)alkylthio, (C$_3$-C$_6$)cycloalkylthio, aminosulfonyl, (C$_1$-C$_4$)alkylsulfinyl, (C$_1$-C$_4$)alkylsulfonyl, (C$_3$-C$_6$)cycloalkylsulfinyl, (C$_3$-C$_6$)cycloalkylsulfonyl, mono-N— or di-N,N—(C$_1$-C$_4$)alkylaminosulfonyl, mono-N— or di-N,N—(C$_3$-C$_6$)cycloalkylaminosulfonyl, (C$_1$-C$_4$)alkylsulfonylamino, (C$_3$-C$_6$)cycloalkylsulfonylamino, (C$_1$-C$_4$)alkylsulfonyl-N—(C$_1$-C$_4$)alkylamino, (C$_1$-C$_4$)alkylsulfonyl-N—(C$_3$-C$_6$)cycloalkylamino, (C$_3$-C$_6$)cycloalkylsulfonyl-N—(C$_1$-C$_4$)alkylamino, (C$_3$-C$_6$)cycloalkylsulfonyl-N—(C$_3$-C$_6$)cycloalkylamino, aryl, heteroaryl, heterocyclyl, oxo, carboxyl, amino, hydroxyl and cyano, wherein said alkyl, cycloalkyl, aryl, heteroaryl, heterocyclyl, alkoxy and cycloalkoxy are optionally substituted independently with one to nine fluoro, or 1, 2 or 3 substituents selected from halo, —C(O)—OH, —C(O)—(C$_1$-C$_4$)alkoxy, aminocarbonyl, mono-N— or di-N,N—(C$_1$-C$_4$)alkylcarbonyl, mono-N— or di-N,N—(C$_3$-C$_6$)cycloalkylcarbonyl, cyano, amino and hydroxyl;
$R^3$ is (C$_1$-C$_4$)alkyl, (C$_3$-C$_6$)cycloalkyl, hydroxyl or fluoro, wherein said alkyl is optionally substituted with one to nine fluoros and said (C$_3$-C$_6$)cycloalkyl is optionally substituted with one to six fluoros;
$R^4$ and $R^5$ are each independently selected from hydrogen, (C$_1$-C$_4$)alkyl, (C$_3$-C$_6$)cycloalkyl, aryl, heteroaryl, aryloxy, heteroaryloxy, aralkyl, heteroaralkyl, heterocyclyl, (C$_1$-C$_4$)alkoxy, and (C$_3$-C$_6$)cycloalkoxy, wherein R$^4$ and R$^5$ are each optionally substituted with (C$_1$-C$_4$)alkyl, (C$_1$-C$_4$)alkoxy, (C$_3$-C$_6$)cycloalkyl, (C$_3$-C$_6$)cycloalkoxy, halo or cyano, wherein each of said alkyl, cycloalkyl, alkoxy or cycloalkoxy is optionally substituted with one to nine fluoros;
$R^6$ and $R^7$ are each independently hydrogen, (C$_1$-C$_4$)alkyl, fluoro, (C$_1$-C$_4$)alkoxy, hydroxyl or cyano, wherein said alkyl is optionally substituted with one to nine fluoros;
$R^8$ is selected from fluoro, methyl or trifluoromethyl;
$R^9$ and $R^{10}$ are each independently selected from hydrogen, fluoro, (C$_1$-C$_4$)alkyl, (C$_3$-C$_6$)cycloalkyl, aryl or heteroaryl, wherein said alkyl is optionally substituted with one to nine fluoros, and said cycloalkyl is optionally substituted with one to six fluoros, and said aryl and heteroaryl are optionally substituted with 1, 2 or 3 substituents independently selected from fluoro, chloro, methyl, ethyl, isopropyl, cyclopropyl, methylthio, methoxy, cyano, trifluoromethyl, difluoromethyl, trifluoromethoxy, difluoromethoxy, oxo and trifluoromethylthio; and
n is 0, 1 or 2;
or a tautomer thereof or a pharmaceutically acceptable salt of said compound or tautomer.

The present invention is also directed at pharmaceutical compositions that include a compound of Formula I or a tautomer thereof or a pharmaceutically acceptable salt of said compound or tautomer, present in a therapeutically effective amount, in admixture with at least one pharmaceutically acceptable excipient.

Furthermore, the present invention is directed at pharmaceutical compositions that include a compound of Formula I or a tautomer thereof or a pharmaceutically acceptable salt of said compound or tautomer, present in a therapeutically effective amount, in admixture with at least one pharmaceutically acceptable excipient and further including at least one additional pharmaceutical agent selected from the group consisting of an anti-obesity agent, an anti-diabetic agent, and a cholesterol/lipid modulating agent.

The present invention is also directed at a method for the treatment of diabetes comprising the administration of an effective amount of compound of Formula I or a tautomer thereof or a pharmaceutically acceptable salt of said compound or tautomer to a patient in need thereof.

The present invention is also directed at a method for treating a metabolic or metabolic-related disease, condition or disorder comprising the step of administering to a patient a therapeutically effective amount of a compound of Formula I or a tautomer thereof or a pharmaceutically acceptable salt of said compound or tautomer.

The present invention is also directed at a method for treating a metabolic or metabolic-related disease, condition or disorder comprising the step of administering to a patient in need of such treatment two separate pharmaceutical compositions comprising
(i) a first pharmaceutical composition that includes a compound of Formula I or a tautomer thereof or a pharmaceutically acceptable salt of said compound or tautomer, present in a therapeutically effective amount, in admixture with at least one pharmaceutically acceptable excipient; and
(ii) a second composition comprising at least one additional pharmaceutical agent selected from the group consisting of an anti-obesity agent and an anti-diabetic agent, and at least one pharmaceutically acceptable excipient.

The present invention is also directed at a method for treating a disease, condition or disorder modulated by the inhibition of DGAT2 in animals comprising the step of administer to an animal in need of such treatment a DGAT2 inhibiting compound or pharmaceutically acceptable salt thereof, wherein the DGAT2 inhibiting compound is a substituted 5-(piperidin-1-yl)-3H-imidazo[4,5-b]pyridine, a substituted 5-morpholino-3H-imidazo[4,5-b]pyridine, a substituted 6-(piperidin-1-yl)-1H-imidazo[4,5-b]pyrazine, a substituted 6-morpholino-1H-imidazo[4,5-b]pyrazine, a substituted 2-(piperidin-1-yl)-9H-purine, or a substituted 2-morpholino-9H-purine compound.

It is to be understood that both the foregoing general description and the following detailed description are exemplary and explanatory only and are not restrictive of the invention, as claimed.

BRIEF DESCRIPTION OF THE DRAWINGS

FIG. 1 is a characteristic x-ray powder diffraction pattern showing a crystalline form of Example 109-B (Vertical Axis: Intensity (CPS); Horizontal Axis: Two theta (degrees)).

FIG. 2 is a characteristic x-ray powder diffraction pattern showing a crystalline form of Example 109-C (Vertical Axis: Intensity (CPS); Horizontal Axis: Two theta (degrees)).

FIG. 3 is a characteristic x-ray powder diffraction pattern showing a crystalline form of Example 196-B (Vertical Axis: Intensity (CPS); Horizontal Axis: Two theta (degrees)).

FIG. 4 is acute effects of DGAT2 inhibitors on plasma TAG levels in Sprague Dawley rats for the Examples 95, 108 and 109-A FIG. 5 represents an observed $^{13}$C solid state nuclear magnetic resonance spectrum for Example 109B. The peaks marked by asterisks are spinning sidebands. (Vertical Axis Intensity (CPS); Horizontal Axis $^{13}$C Chemical shift (ppm)).

DETAILED DESCRIPTION OF THE INVENTION

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated require a tighter range.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. By "tautomers" is meant chemical compounds that may exist in two or more forms of different structure (isomers) in equilibrium, the forms differing, usually, in the position of a hydrogen atom. Various types of tautomerism can occur, including keto-enol, ring-chain and ring-ring tautomerism. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the present invention include but are not limited to those having a carboxyl moiety wherein the free hydrogen is replaced by ($C_1$-$C_4$)alkyl, ($C_2$-$C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as 6-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

As used herein, an arrowhead, "∕" or wavy line, "⌇" denotes a point of attachment of a substituent to another group.

By "halo" or "halogen" is meant chloro, bromo, iodo, or fluoro.

By "alkyl" is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, isobutyl, pentyl, isopentyl, neopentyl, tertiary pentyl, 1-methylbutyl, 2-methylbutyl, 3-methylbutyl, hexyl, isohexyl, heptyl and octyl.

By "alkoxy" is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (i.e., attached or formed) by having two adjacent atoms in common (i.e., shared) with the first ring. The term "fused" is equivalent to the term "condensed". The term "aryl" embraces aromatic radicals such as phenyl, naphthyl, tetrahydronaphthyl, indanyl, biphenyl, benzo[b][1,4]oxazin-3(4H)-onyl, 2,3-dihydro-1H indenyl, and 1,2,3,4-tetrahydronaphthalenyl.

The term "aralkyl" means an alkyl group with an aryl group (defined above) substituting for a hydrogen atom of the alkyl group. Exemplary of such aralkyl groups are benzyl and phenethyl.

"Aryloxy" means an O-aryl group wherein aryl is defined above. Exemplary of such aryloxy groups are phenyloxy and naphthyloxy.

"Cycloalkyl" refers to a nonaromatic ring that is fully hydrogenated and exists as a single ring. Examples of such carbocyclic rings include cyclopropyl, cyclobutyl, cyclopentyl, and cyclohexyl.

By "cycloalkoxy" is meant cycloalkyl bonded through an oxy. Exemplary of such cycloalkoxy groups are cyclopropoxy, cyclobutoxy, cyclopentoxy and cyclohexoxy.

The term "heteroaryl" means an aromatic carbocyclic system containing one, two, three or four heteroatoms selected independently from oxygen, nitrogen and sulfur and having one, two or three rings wherein such rings may be fused, wherein fused is defined above. The term "heteroaryl" includes but is not limited to furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

The term "heteroaralkyl" means an alkyl group with an heteroaryl group substituting for a hydrogen atom of the alkyl group. Exemplary of such heteroaralkyl groups are pyridinyl-$(CH_2)$— and pyrazolyl-$(CH_2)$—.

By "heteroaryloxy" is meant an O-heteroaryl wherein heteroaryl is defined above. Exemplary of such heteroaryloxy groups are pyrazolyloxy, pyridinyloxy and pyrimidinyloxy.

The term "heterocyclyl" means a nonaromatic carbocyclic system containing one, two, three or four heteroatoms selected independently from oxygen, nitrogen and sulfur and having one, two or three rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O or S atoms. The term "heterocyclyl" includes but is not limited to lactones, lactams, cyclic ethers and cyclic amines, including the following exemplary ring systems: pyrrolidinonyl, 2,5-dihydro-1H-pyrrolyl, piperidinonyl, morpholinonyl, piperazinonyl, oxazolidinonyl, imidazolidinonyl, 1,3-oxazinan-2-onyl, tetrahydropyrimidin-2(1H)-onyl, epoxidyl, tetrahydrofuranyl, tetrahydropyranyl, dioxanyl, aziridinyl, azetidinyl, oxetanyl, pyrrolidinyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl and 2-oxa-6-azaspiro[3.3]heptanyl.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

"Patient" refers to warm blooded animals such as, for example, guinea pigs, mice, rats, gerbils, cats, rabbits, dogs, cattle, goats, sheep, horses, monkeys, chimpanzees, and humans.

By "pharmaceutically acceptable" is meant that the substance or composition must be compatible chemically and/or toxicologically, with the other ingredients comprising a formulation, and/or the mammal being treated therewith.

As used herein, the expressions "reaction-inert solvent" and "inert solvent" refer to a solvent or a mixture thereof which does not interact with starting materials, reagents, intermediates or products in a manner which adversely affects the yield of the desired product.

As used herein, the term "selectivity" or "selective" refers to a greater effect of a compound in a first assay, compared to the effect of the same compound in a second assay. For example, in "gut selective" compounds, the first assay is for the half life of the compound in the intestine and the second assay is for the half life of the compound in the liver.

"Therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", "treat" or "treatment" as used herein embraces both preventative, i.e., prophylactic, and palliative treatment, i.e., relieve, alleviate, or slow the progression of the patient's disease (or condition) or any tissue damage associated with the disease.

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA). Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form. The compounds and intermediates described below were named using the naming convention provided with ChemBioDraw Ultra, Version 12.0 (CambridgeSoft Corp., Cambridge, Mass.).

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. For example, the following is illustrative of tautomers of the compounds of Formula I.

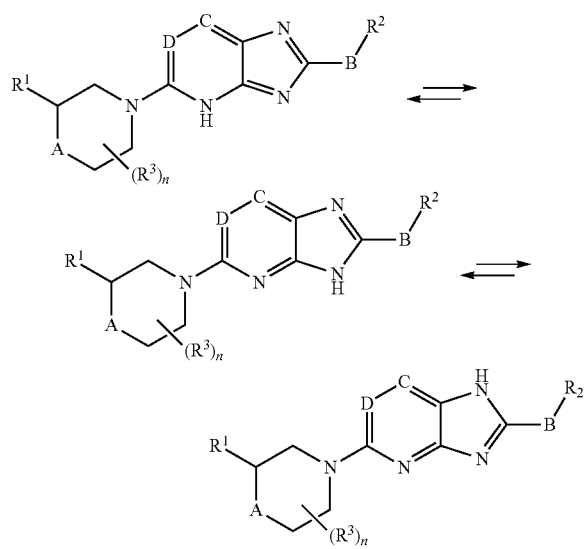

Valence tautomers include interconversions by reorganization of some of the bonding electrons.

Included within the scope of the claimed compounds present invention are all stereoisomers, geometric isomers and tautomeric forms of the compounds of Formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labelled compounds of Formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy.

Isotopically-labelled compounds of Formula (I) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately treating the compound with a suitable organic or inorganic acid or base and isolating the salt thus formed. The acids which are used to prepare the pharmaceutically acceptable acid addition salts of the aforementioned base compounds of this invention are those which form non-toxic acid addition salts, (i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, naphthylate, mesylate, glucoheptonate, lactobionate, laurylsulphonate, hexafluorophosphate, benzene sulfonate, tosylate, formate, trifluoroacetate, oxalate, besylate, palmitiate, pamoate, malonate, stearate, laurate, malate, borate, p-toluenesulfonate and pamoate (i.e., 1,1'-methylene-bis-(2-hydroxy-3-naphthoate)) salts.

The invention also relates to base addition salts of the compounds of the present invention. The chemical bases that may be used as reagents to prepare pharmaceutically acceptable base salts of those compounds of the present invention that are acidic in nature are those that form non-toxic base salts with such compounds. Such non-toxic base salts include, but are not limited to those derived from such pharmacologically acceptable cations such as alkali metal cations (e.g., lithium, potassium and sodium) and alkaline earth metal cations (e.g., calcium and magnesium), ammonium or water-soluble amine addition salts such as N-methylglucamine-(meglumine), tetramethylammonium, tetraethylammonium, methylamine, dimethylamine, trimethylamine, triethylamine, ethylamine, and the lower alkanolammonium and other base salts of pharmaceutically acceptable organic amines. See e.g. Berge, et al. J. Pharm. Sci. 66, 1-19 (1977).

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

In one embodiment of compounds of Formula 1, $R^1$ is —C(O)-heterocyclyl, —C(O)—$NR^4R^5$, pyridyl, 6,7-dihydro-5H-pyrrolo[2,1-c][1,2,4]triazolyl, 6,7-dihydro-5H-pyrrolo[1,2-c]imidazolyl, wherein $R^1$ is optionally substituted with 1 or 2 substituents independently selected from fluoro, methyl, hydroxyl or —$CH_2OH$;

D is CH, N, or CF;

B is a bond, oxetanyl or

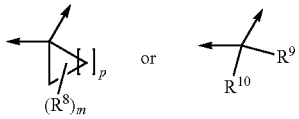

wherein p is 1 or 2;

$R^3$ is fluoro or methyl;

$R^6$ and $R^7$ are each independently hydrogen, fluoro or methyl;

$R^8$ is selected from fluoro or methyl; and $R^9$ and $R^{10}$ are each individually selected from hydrogen, fluoro, or methyl;

or a tautomer thereof or a pharmaceutically acceptable salt of said compound or tautomer.

In another embodiment of compounds of Formula 1, $R^1$ is —C(O)-heterocyclyl or —C(O)—$NR^4R^5$ wherein said heterocyclyl is optionally substituted with 1 or 2 substituents independently selected from fluoro and methyl;

B is a bond,

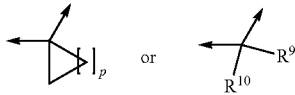

wherein p is 1 or 2;

$R^2$ is selected from phenyl, furyl, thienyl, oxazolyl, thiazolyl, imidazolyl, pyrazolyl, 1,2,3-triazolyl, 1,2,4-triazolyl, tetrazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 2H-benzo[b][1,4]oxazin-3(4H)onyl, 2,3-dihydro-1H-indenyl, 1,2,3,4-tetrahydronaphthalenyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl, 4,5,6,7-tetrahydro-2H-indazolyl, phenyloxy, pyridinyloxy, benzyl, pyridinyl-($CH_2$)—, pyrazolyl-($CH_2$)—, cyclopropyl, and cyclobutyl; wherein said $R^2$ is optionally substituted with 1, 2 or 3 substituents independently selected from ($C_1$-$C_4$)alkyl, ($C_1$-$C_4$)alkoxy, ($C_3$-$C_6$)cycloalkoxy, cyclopropyl, halo, hydroxyl, amino, dimethylamino, methylamino, cyclopropylamino, aminocarbonyl, methylaminocarbonyl, ($C_1$-$C_4$)alkylthio, ($C_3$-$C_6$)cycloalkylthio, aminosulfonyl, methylaminosulfonyl, phenyl, and heteroaryl wherein heteroaryl is selected from furyl, thienyl, oxazolyl, thiazolyl, imidazolyl, pyrazolyl, triazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-only, pyrazin-2(1H)-onyl, oxetanyl, azetidinyl, and pyrrolidinyl, wherein said alkyl, cyclopropyl, azetidinyl, pyrrolidinyl, alkoxy and cycloalkoxy are optionally substituted with oxo, cyano, or up to three fluoro or hydroxyl, and said phenyl or heteroaryl is optionally substituted independently with up to three groups selected from halo, methyl, trifluoromethyl, difluoromethyl, methoxy, trifluoromethoxy, difluoromethoxy, cyano, cyclopropryl, methylthio, oxo and trifluoromethylthio; and $R^9$ and $R^{10}$ are each individually selected from hydrogen and methyl;

or a tautomer thereof or a pharmaceutically acceptable salt of said compound or tautomer.

In a further embodiment of compounds of Formula 1, $R^1$ is —C(O)-heterocyclyl or —C(O)—$NR^4R^5$ wherein said heterocyclyl is selected from pyrrolidinyl, 2,5-dihydro-1H-pyrrolyl, azetidinyl, piperidinyl and morpholinyl and said heterocyclyl is optionally substituted with 1 or 2 substituents independently selected from fluoro and methyl;

C is CH, N or CF;

A is $CH_2$ or O;

$R^2$ is phenyl, furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-onyl, pyrazin-2(1H)-onyl, phenyloxy, pyridinyloxy, benzyl, pyridinyl-($CH_2$)— or pyrazolyl-($CH_2$)—, wherein $R^2$ is optionally substituted with 1, 2 or 3 substituents independently selected from fluoro, chloro, methyl, ethyl, isopropyl, cyclopropyl, hydroxyl, amino, methylthio, methoxy, cyano, trifluoromethyl, difluoromethyl, trifluoromethoxy, difluoromethoxy, oxo and trifluoromethylthio;

$R^4$ is hydrogen or methyl;

$R^5$ is hydrogen or methyl;

or a tautomer thereof or a pharmaceutically acceptable salt of said compound or tautomer.

In another embodiment of compounds of Formula I, $R^1$ is —C(O)-heterocyclyl, wherein said heterocyclyl is selected from pyrrolidinyl, 2,5-dihydro-1H-pyrrolyl, 3,3-difluoroazetidinyl, 3,3-difluoropyrrolidinyl and morpholinyl;

B is

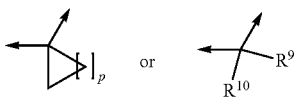

wherein
p is 1 or 2; and
R² is phenyl, furyl, thienyl, oxazolyl, thiazolyl, imidazolyl, pyrazolyl, triazolyl, isoxazolyl, isothiazolyl, oxadiazolyl, thiadiazolyl, pyridinyl, pyridiazinyl, pyrimidinyl, pyrazinyl, phenyloxy, pyridinyloxy, benzyl, pyridinyl-(CH₂)—, or pyrazolyl-(CH₂)—; wherein R² is optionally substituted with 1, 2 or 3 substituents selected from independently fluoro, chloro, methyl, ethyl, isopropyl, cyclopropyl, methylthio, methoxy, cyano, trifluoromethyl, difluoromethyl, trifluoromethoxy, difluoromethoxy, oxo and trifluoromethylthio;

or a tautomer thereof or a pharmaceutically acceptable salt of said compound or tautomer.

In another embodiment of compounds of Formula I, R² is N-linked pyrazolyl optionally substituted with 1, 2 or 3 substituents independently selected from fluoro, chloro, methyl, ethyl, isopropyl, cyclopropyl, hydroxyl, amino, methylthio, methoxy, cyano, trifluoromethyl, difluoromethyl, trifluoromethoxy, difluoromethoxy and trifluoromethylthio or a tautomer thereof or a pharmaceutically acceptable salt of said compound or tautomer.

In another embodiment of compounds of Formula I, R¹ is

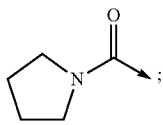

C is CH or CF;
A is CH₂;
n is 0; and
R² is N-linked pyrazolyl substituted at the 4 position with fluoro or chloro;

or a tautomer thereof or a pharmaceutically acceptable salt of said compound or tautomer.

Another embodiment includes the compounds:
(1-(2-(1-(4-fluoro-1H-pyrazol-1-yl)cyclopropyl)-3H-imidazo[4,5-b]pyridin-5-yl)piperidin-3-yl)(pyrrolidin-1-yl)methanone;
(1-(8-(1-(4-chloro-1H-pyrazol-1-yl)cyclopropyl)-9H-purin-2-yl)piperidin-3-yl)(pyrrolidin-1-yl)methanone;
(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone;
(1-(2-(2-(4-chloro-1H-pyrazol-1-yl)propan-2-yl)-3H-imidazo[4,5-b]pyridin-5-yl)piperidin-3-yl)(pyrrolidin-1-yl)methanone;
(1-{2-[1-(4-chloro-1H-pyrazol-1-yl)cyclopropyl]-3H-imidazo[4,5-b]pyridin-5-yl}(2,2,6,6-²H₄)piperidin-3-yl](pyrrolidin-1-yl)methanone;
(1-(2-((R)-1-(4-fluoro-1H-pyrazol-1-yl)ethyl)-3H-imidazo[4,5-b]pyridin-5-yl)piperidin-3-yl)(pyrrolidin-1-yl)methanone;
(1-(2-((S)-1-(4-fluoro-1H-pyrazol-1-yl)ethyl)-3H-imidazo[4,5-b]pyridin-5-yl)piperidin-3-yl)(pyrrolidin-1-yl)methanone;
(1-(2-((S)-1-(4-chloro-1H-pyrazol-1-yl)ethyl)-3H-imidazo[4,5-b]pyridin-5-yl)piperidin-3-yl)(pyrrolidin-1-yl)methanone;
(1-(2-((R)-1-(4-chloro-1H-pyrazol-1-yl)ethyl)-3H-imidazo[4,5-b]pyridin-5-yl)piperidin-3-yl)(pyrrolidin-1-yl)methanone;
(1-(8-((S)-1-(4-chloro-1H-pyrazol-1-yl)ethyl)-9H-purin-2-yl)piperidin-3-yl)(pyrrolidin-1-yl)methanone;
(1-(8-((R)-1-(4-chloro-1H-pyrazol-1-yl)ethyl)-9H-purin-2-yl)piperidin-3-yl)(pyrrolidin-1-yl)methanone; and
(1-(8-(1-(4-fluoro-1H-pyrazol-1-yl)cyclopropyl)-9H-purin-2-yl)piperidin-3-yl)(pyrrolidin-1-yl)methanone;

or a tautomer thereof or a pharmaceutically acceptable salt of said compound or tautomer.

Another embodiment includes the compounds:
((R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone,
((R)-1-(2-((R)-1-(4-Chloro-1H-pyrazol-1-yl)ethyl)-3H-imidazo[4,5-b]pyridin-5-yl)piperidin-3-yl)(pyrrolidin-1-yl)methanone,
((S)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone, or
((S)-1-(2-((R)-1-(4-Chloro-1H-pyrazol-1-yl)ethyl)-3H-imidazo[4,5-b]pyridin-5-yl)piperidin-3-yl)(pyrrolidin-1-yl)methanone,
or a mixture of thereof;
or a tautomer thereof or a pharmaceutically acceptable salt of said compound or tautomer.

Another embodiment includes the compounds:
(R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone, and
(S)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone,
or a mixture of thereof;
or tautomer thereof or a pharmaceutically acceptable salt of said compound or tautomer.

Another embodiment includes a compound having the structure:

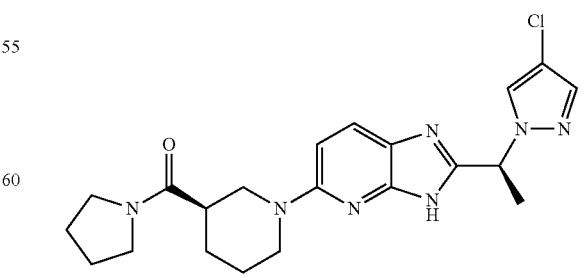

or a tautomer thereof or a pharmaceutically acceptable salt of said compound or tautomer.

Another embodiment includes a compound having the structure:

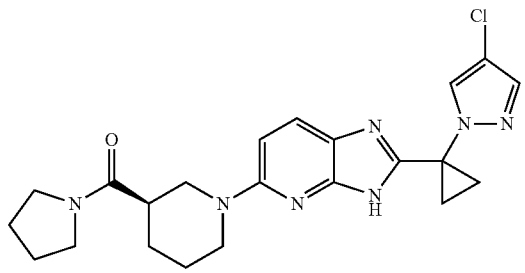

or a tautomer thereof or a pharmaceutically acceptable salt of said compound or tautomer.

In one embodiment of the pharmaceutical compositions of the present invention, the anti-obesity agent is selected from the group consisting of gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), PYY$_{3-36}$ (as used herein "PYY$_{3-36}$" includes analogs, such as peglated PYY$_{3-36}$ e.g., those described in US Publication 2006/0178501), opioid antagonists (e.g., naltrexone), the combination of naltrexone with buprorpion, oleoylestrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine.

In another embodiment of the pharmaceutical compositions of the present invention, the anti-diabetic agent is selected from the group consisting of an acetyl-CoA carboxylase-(ACC) inhibitor such as those described in WO2009144554, WO2003072197, WO2009144555 and WO2008065508, a diacylglycerol 0-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARy agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, N,N-9924, TTP-054, a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 activator (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235, listing of anti-diabetic agents found at page 28, line 35 through page 30, line 19 of WO2011005611, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha, suitable antidiabetic agents include mechanisms listed by Carpino, P. A., Goodwin, B. Expert Opin. Ther. Pat, 2010, 20(12), 1627-51.

In another embodiment of the pharmaceutical compositions of the present invention, the cholesterol/lipid modulating agent is selected from the group consisting of HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors;

fibrates; bile acid sequestrants (such as questran); ACAT inhibitors; MTP inhibitors; lipooxygenase inhibitors; choesterol absorption inhibitors; and cholesteryl ester transfer protein inhibitors. Other atherosclerotic agents include PCSK9 modulators.

In another embodiment, the condition treated is selected from the group consisting of hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), non-alcoholic fatty liver disease (NAFLD).

In one embodiment, when two compositions are administered, the first composition and the second composition are administered simultaneously. In another embodiment, the first composition and the second composition are administered sequentially and in any order.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the *Beilstein* online database)). Many of the compounds used herein, are related to, or are derived from compounds in which there is a large scientific interest and commercial need, and accordingly many such compounds are commercially available or are reported in the literature or are easily prepared from other commonly available substances by methods which are reported in the literature. For example, general methods to synthesize substituted pyrazole derivatives can be found in *Comprehensive Heterocyclic Chemistry II*, Elsevier, Oxford, UK, 1996, 3, 1-75, 817-932; *Chem. Rev.* 2011, 111, 6984-7034; *Modern Heterocyclic Chemistry*, Wiley-VCH, Weinheim, Germany, 2011, 2, 635-725.

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and can typically be removed without chemically altering other functionality in the Formula I compound.

The Reaction Schemes described below are intended to provide a general description of the methodology employed in the preparation of the compounds of the present invention. Some of the compounds of the present invention contain a single chiral center with stereochemical designation R. In the following Schemes, the general methods for the preparation of the compounds are shown either in racemic or enantioenriched form. It will be apparent to one skilled in the art that all of the synthetic transformations can be conducted in a precisely similar manner whether the materials are enantioenriched or racemic. Moreover the resolution to the desired optically active material may take place at any desired point in the sequence using well known methods such as described herein and in the chemistry literature.

In the Reaction Schemes that follow, the variables A, B, C, D, $R^1$, $R^2$, $R^3$, $R^4$, $R^5$, $R^8$, $R^9$, $R^{10}$, m, n and p are as described in the summary except where otherwise noted.

Reaction Scheme I outlines the general procedures that can be used to provide compounds of the present invention having Formula I.

Reaction Scheme I

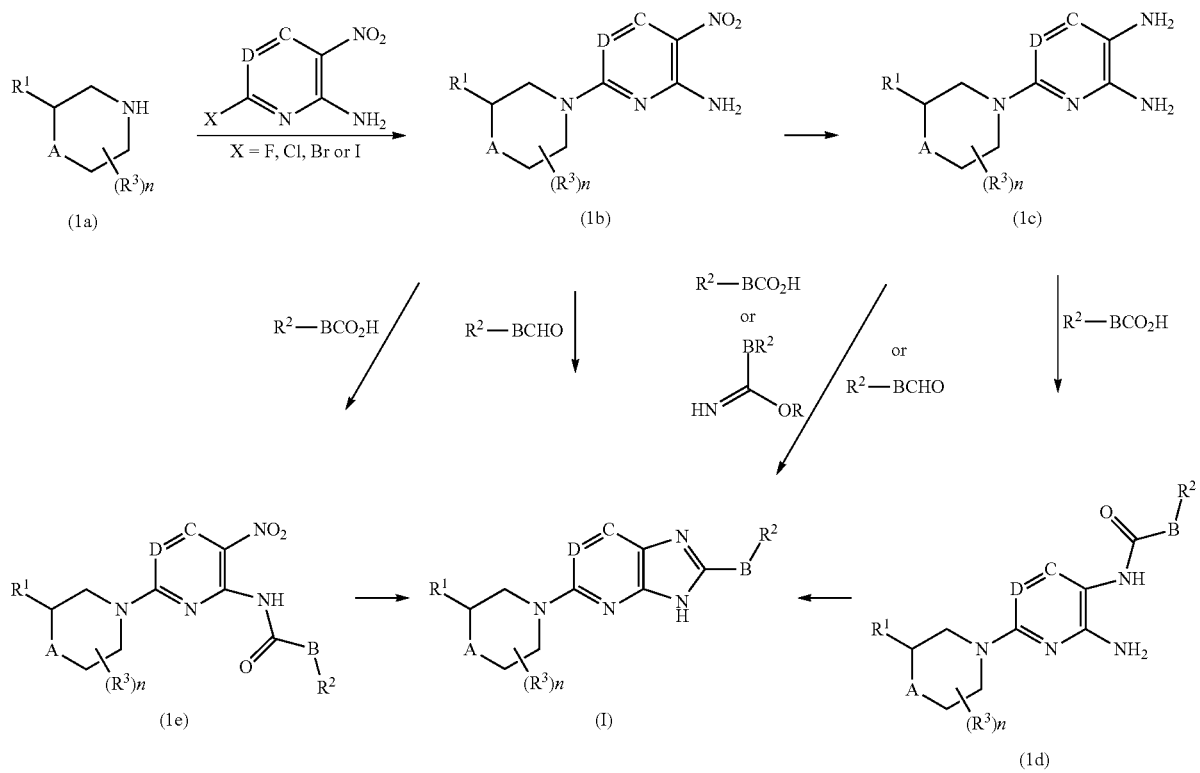

Compounds of the Formula (I) may be synthesized starting from appropriate intermediates through methods described in the literature such as *Synlett* 2010, 2759; *Tetrahedron Lett.* 2009, 50, 1780; *Tetrahedron Lett.* 2006, 47, 2883; Synthesis, 2005, 47; *J. Org. Chem.* 2003, 68, 6814; *Tetrahedron Lett.* 2002, 43, 1893; *Tetrahedron Lett.* 2001, 42, 751; *Synthesis*, 2000, 1380; *Heterocycles* 1995, 41, 1045; *J. Org. Chem.* 1989, 54, 1144; Grimmet, M. R. in *Comprehensive Heterocyclic Chemistry*, 1984, Vol. 5, pp 457; *Chem. Rev.* 1974, 74, 279; *J. Heterocycl. Chem.* 1970, 7, 947; *Chem. Rev.* 1951, 48, 397. Starting materials (1a) are commercially available or may prepared via methods known to those skilled in the art. The syntheses of some derivatives (1a) have been reviewed (*Bioorg. Med. Chem.* 2008, 16, 601-635; *Tetrahedron* 2004, 60, 1701-1729; *Tetrahedron* 2003, 59, 2953-2989; *Synthesis* 2004, 641-662). The syntheses of starting materials, which may be converted to (1a) via protecting group or functional group manipulations that are well known to those skilled in the art, are described in the literature. For derivatives (1a) where $R^3$ is alkyl, methods of synthesis may be utilized such as those described in: *J. Med. Chem.* 2011, 54, 1871-1895; *Eur. J. Org. Chem.* 2007, 476-486; *Org. Lett.* 2005, 7, 55-58; *Org. Biomol. Chem.* 2010, 8, 3635-3637. For derivatives (1a) where $R^3$ is fluoro, methods of synthesis may be utilized such as those described in: *J. Med. Chem.* 2010, 53, 7778-7795; *J. Fluorine Chem.* 2011, 132, 838-845; *Bioorg. Med. Chem. Lett.* 2010, 20, 755-758.

Intermediate (1b) may be prepared from amines (1a) via nucleophilic aromatic substitution of an heteroaryl halide compound in a reaction inert solvent such as dimethylsulfoxide (DMSO), N,N'-dimethylformamide (DMF) or acetonitrile, in the presence of a suitable base, such as triethylamine or diisopropylethylamine at a temperature between 10° C. and 120° C., preferably between 30° C. and 110° C. Intermediate (1c) may be prepared from (1b) by a reduction of the nitro group via methods known to those skilled in the art. For example, intermediate (1c) may be prepared from (1b) via hydrogenation in the presence of a suitable hydrogenation catalyst such as palladium on carbon in a reaction inert solvent such as methanol, ethanol or ethyl acetate in the presence or absence of hydrochloric acid at a temperature between 0° C. and 60° C., preferably at ambient temperature. Alternatively, the nitro group can be reduced via dissolving metal reduction with iron or zinc in the presence of calcium chloride, ammonium chloride or ammonium formate in a suitable solvent such as water, methanol, ethanol or acetic acid at a temperature between 20° C. and 120° C., preferably between 45° C. and 100° C.

Compounds of Formula (I) may be prepared from intermediate (1b) and an aldehyde of the formula $R^2$—BCHO in the presence of sulfur or sodium hydrosulfite and a base such as triethylamine in a suitable solvent such as DMF, ethanol or water at a temperature between 20° C. and 120° C., preferably between 80° C. and 110° C. Alternatively, compounds of formula (I) may be prepared in one step from intermediate (1c) and a carboxylic acid of the formula $R^2$—BCO$_2$H in the presence of a dehydrating reagent such as triphenylphosphite in organic base such as pyridine or triethylamine at a temperature between 20° C. and 200° C., preferably 200° C. Compounds of Formula (I) may also be prepared in one step from intermediate (1c) and an imidate of the formula $R^2$-BCNH(OR) (wherein R is a small alkyl or fluoroalkyl group such as methyl, ethyl or trifluoroethyl) in the presence of acetic acid, optionally with a base such as triethylamine or diisopropylethylamine, in a suitable solvent such as methanol or ethanol at a temperature between 20° C. and 130° C., preferably between 60° C. and 130° C. In addition, compounds of Formula (I) may be prepared in one step from intermediate (1c) and an aldehyde of the formula R²—BCHO in the presence of sulfur and a base such as triethylamine in a suitable solvent such as DMF, ethanol or water at a temperature between 20° C. and 120° C., preferably at 110° C.

Compounds of Formula (I) may also be prepared in two steps from intermediate (1b). Intermediate (1e) may be prepared from intermediate (1b) and a carboxylic acid of the formula R²—BCO₂H in the presence of an amide coupling reagent, such as propane phosphonic acid anhydride (T₃P) or 1,1'-carbonyldiimidazole (CDI) in a reaction solvent such as DMF, ethyl acetate, dioxane or toluene in the presence of a base such as triethylamine or diisopropylethylamine in the presence of another organic base such as N,N-dimethyl-4-aminopyridine (DMAP) at a temperature between 20° C. and 150° C., preferably between 40° C. and 110° C. Intermediate (1e) may then be converted to compounds of Formula (I) by a reduction of the nitro group and subsequent cyclization reaction via hydrogenation or via dissolving metal reduction as described above for intermediate (1b).

Alternatively, compounds of Formula (I) may be prepared from intermediate (1d). Intermediate (1d) may be prepared from intermediate (1c) and a carboxylic acid of the formula R²—BCO₂H in the presence of an amide coupling reagent, such as T₃P, CDI, benzotriazo-1-yloxytris(dimethylamino) phosphonium hexafluorophosphate (BOP), 2-(1H-7-azabenzotriazol-1-yl)-1,1,3,3-tetramethyl uronium hexafluorophosphate methanaminium (HATU), O-benzotriazol-1-yl-N,N,N',N'-tetramethyluronium hexafluoro phosphate (HBTU), N-(3-dimethylaminopropyl)-N'-ethylcarbodiimide (EDCl) or 1-hydroxybenzotriazole (HOBT) in a reaction inert solvent such as dichloromethane, DMF or ethyl acetate in the presence of a base such as triethylamine or diisopropylethylamine at a temperature between 20° C. and 140° C., preferably between 40° C. and 60° C. Intermediate (1d) may then be converted to compounds of Formula (I) (1) in the presence of sodium methoxide or sodium ethoxide in a suitable solvent such as methanol, ethanol, s-butanol or isobutanol at a temperature between 20° C. and 120° C., preferably 110° C. or (2) in the presence of acetic acid, HCl, polyphospholic acid or para-toluene sulfonic acid in a solvent such as xylene, water, ethylene glycol, 1,4-dioxane or acetic acid at a temperature between 20° C. and 200° C.

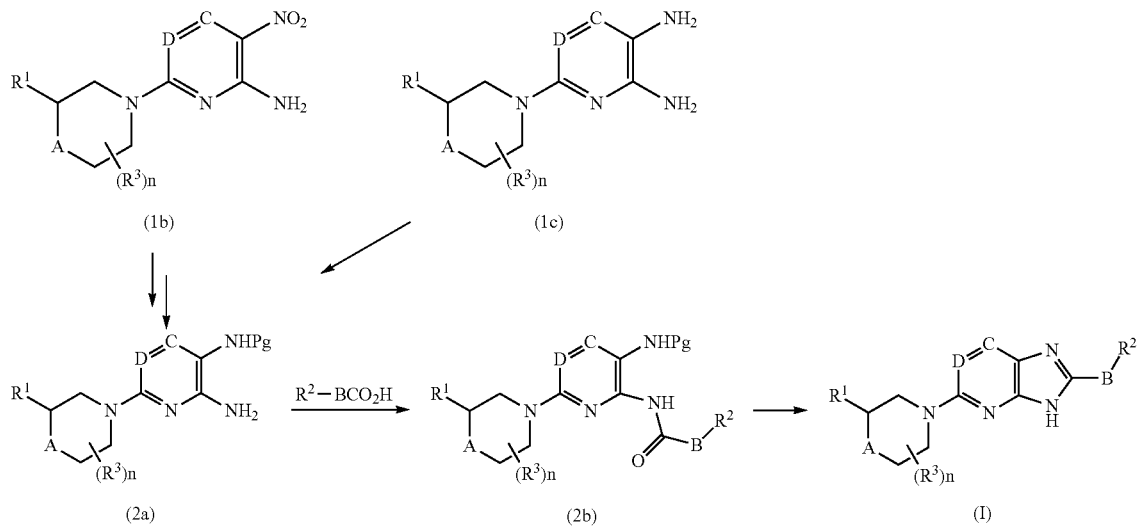

Reaction Scheme II

Alternatively, compounds of Formula (I) may be prepared from intermediate (2b) that can be accessed from intermediate (2a) by incorporating the desired amino protecting group (Pg) as shown in Reaction Scheme II. A preferred amino-protecting group is a carbamate group such as t-butoxycarbonyl (Boc). Intermediate (2a) may be prepared from intermediate (1b) by a reduction of the nitro group via methods known to those skilled in the art or methods described in reaction scheme I, followed by protection of the desired amino group. For example, intermediate (2a) wherein Pg is Boc may be prepared from (1b) via hydrogenation in the presence of a suitable hydrogenation catalyst such as palladium on carbon in the presence of di-tert-butyl dicarbonate ((Boc)₂O) in a reaction inert solvent such as methanol, ethanol or ethyl acetate in the presence or absence of a base such as triethylamine at a temperature between 0° C. and 60° C., preferably between ambient temperature and 50° C. Alternatively, intermediate (2a) may be prepared from intermediate (1c) by incorporating a suitable amino protecting group by methods known to those skilled in the art. Intermediate (2b) may be prepared from intermediate (2a) and a carboxylic acid of the formula R²—BCO₂H in the presence of an amide coupling reagent, such as T₃P in a reaction solvent such as DMF, ethyl acetate, dioxane or toluene in the presence of a base such as pyridine, triethylamine or diisopropylethylamine at a temperature between 0° C. and 100° C., preferably between 20° C. and 60° C. Intermediate (2b) may then be converted to compounds of Formula (I) by removal of the protecting group and subsequent cyclization reaction under acidic conditions with an acid such as hydrochloric acid, trifluoroacetic acid, acetic acid, methane sulfonic acid or combinations thereof, optionally with a base such as sodium acetate in a solvent such as acetonitrile, ethylacetate, water or combinations thereof at a temperature between 0° C. and 100° C.

Reaction Scheme III

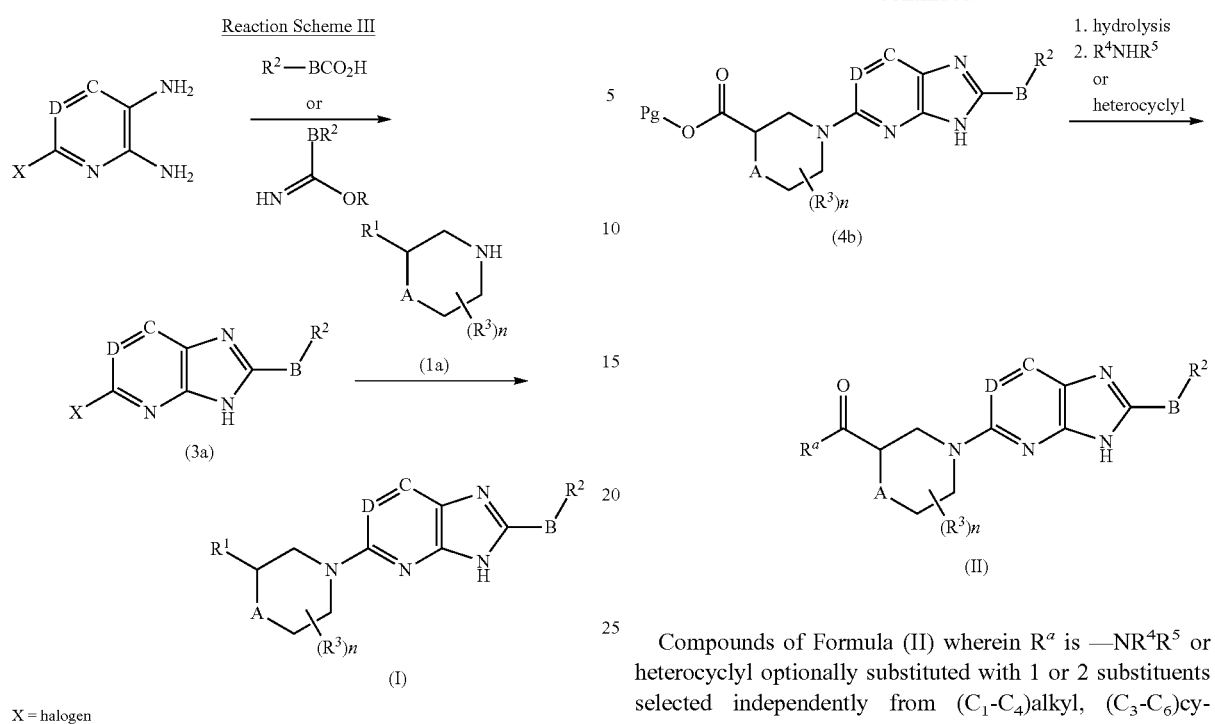

X = halogen

Alternatively, compounds of Formula (I) may be prepared from intermediate (3a) as shown in Reaction Scheme III. Intermediate (3a) can be prepared from 6-halopyridine-2,3-diamine, 6-halopyrimidine-2,3-diamine or 6-halopyrazine-2,3-diamine and a carboxylic acid of the formula $R^2$—$BCO_2H$ using the conditions described for intermediate (1c) in Scheme I or with an imidate of the formula $R^2$—B—CNH(OR) (wherein R is a small alkyl or fluoroalkyl group such as methyl, ethyl or trifluoroethyl) using the conditions described for intermediate (1c) in Reaction Scheme I. Intermediate (3a) may then be converted to compounds of Formula (I) by nucleophilic aromatic substitution with amines (1a) in the presence of base such as potassium carbonate and cesium fluoride in a suitable solvent such as diglyme at a temperature between 100° C. and 150° C., preferably 150° C.

Reaction Scheme IV

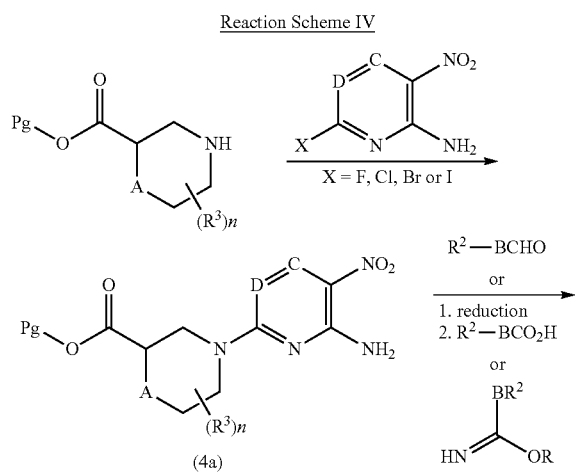

Compounds of Formula (II) wherein $R^a$ is —$NR^4R^5$ or heterocyclyl optionally substituted with 1 or 2 substituents selected independently from $(C_1$-$C_4)$alkyl, $(C_3$-$C_6)$cycloalkyl, $(C_1$-$C_4)$alkoxy, $(C_3$-$C_6)$cycloalkoxy, halo, hydroxy $(C_1$-$C_4)$alkyl, mono-N— or di-N,N—$(C_1$-$C_4)$alkylamino, mono-N— or di-N,N—$(C_3$-$C_6)$cycloalkylamino, heterocyclyl, hydroxyl and cyano as described in the summary above, may be prepared according to Reaction Scheme IV. Intermediate (4a) may be prepared from amino acid esters via nucleophilic aromatic substitution of heteroaryl halide compound as described for intermediate (1a) in Reaction Scheme I. Intermediate (4a) may be converted to intermediate (4b) with an aldehyde of the formula $R^2$—BCHO by the methods as described in Reaction Scheme I. Alternatively, intermediate (4b) may be prepared from intermediate (4a) in two steps via a reduction of the nitro group and reaction of the intermediate diamine with a carboxylic acid of the formula $R^2$—$BCO_2H$ or imidate $R^2$—BCNH(OR) (wherein R is a small alkyl or fluoroalkyl group such as methyl, ethyl or trifluoroethyl) as described in Reaction Scheme I. Compounds of Formula (II) (wherein $R^a$ is $NR^4R^5$ or heterocyclyl) may be prepared in two steps from intermediate (4b) via hydrolysis of the ester in the presence of an aqueous inorganic base such as sodium hydroxide, lithium hydroxide, potassium hydroxide or potassium carbonate in a suitable solvent such as methanol, ethanol, tetrahydrofuran or water, or a combination thereof at a temperature between 0° C. and 50° C., preferably between 0° C. and 20° C., followed by a coupling reaction with amines of formula $R^4NHR^5$ or heterocyclyl in the presence of a coupling reagent, such as HATU, HBTU, CDI, HOBT, or EDCl in the presence of a base such as triethylamine or diisopropylamine and 4-dimethylaminopyridine (DMAP) in a reaction solvent such as dichloromethane, DMF or tetrahydrofuran at a temperature between 0° C. and 50° C., preferably at ambient temperature. In addition, compounds of Formula (II) may be prepared according to procedures shown in Reaction Scheme I.

Reaction Scheme V

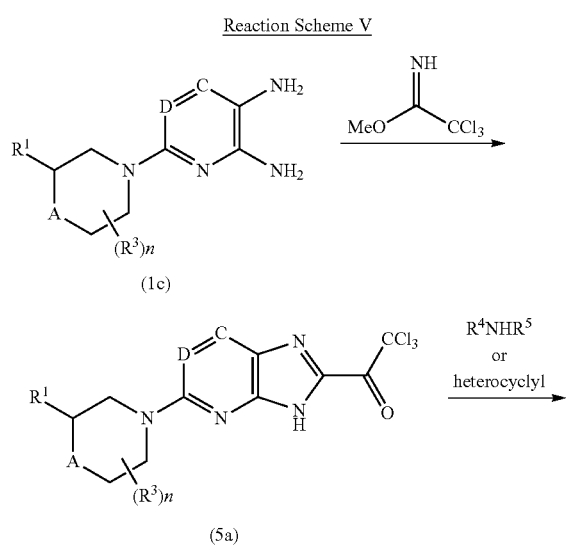

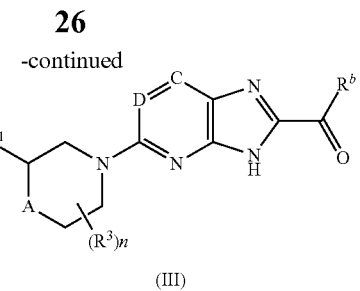

Compounds of Formula (III) wherein $R^b$ is —$NR^4R^5$ or heterocyclyl, may be prepared using intermediate (5a) as shown in Reaction Scheme V. Intermediate (5a) may be prepared from intermediate (1c) and methyl 2,2,2-trichloroacetimidate in the presence of formic acid in a suitable solvent such as 2,2,2-trifluoroethanol at a temperature between 20° C. and 100° C., preferably between 20° C. and 60° C. Intermediate (5a) may be converted to compounds of Formula (III) (wherein $R^b$ is $NR^4R^5$ or heterocyclyl) with an amine of formula $R^4NHR^5$ or a heterocyclyl in a suitable solvent, such as 2,2,2-trifluoroethanol at a temperature between 20° C. and 100° C., preferably at 60° C.

Reaction Scheme VI

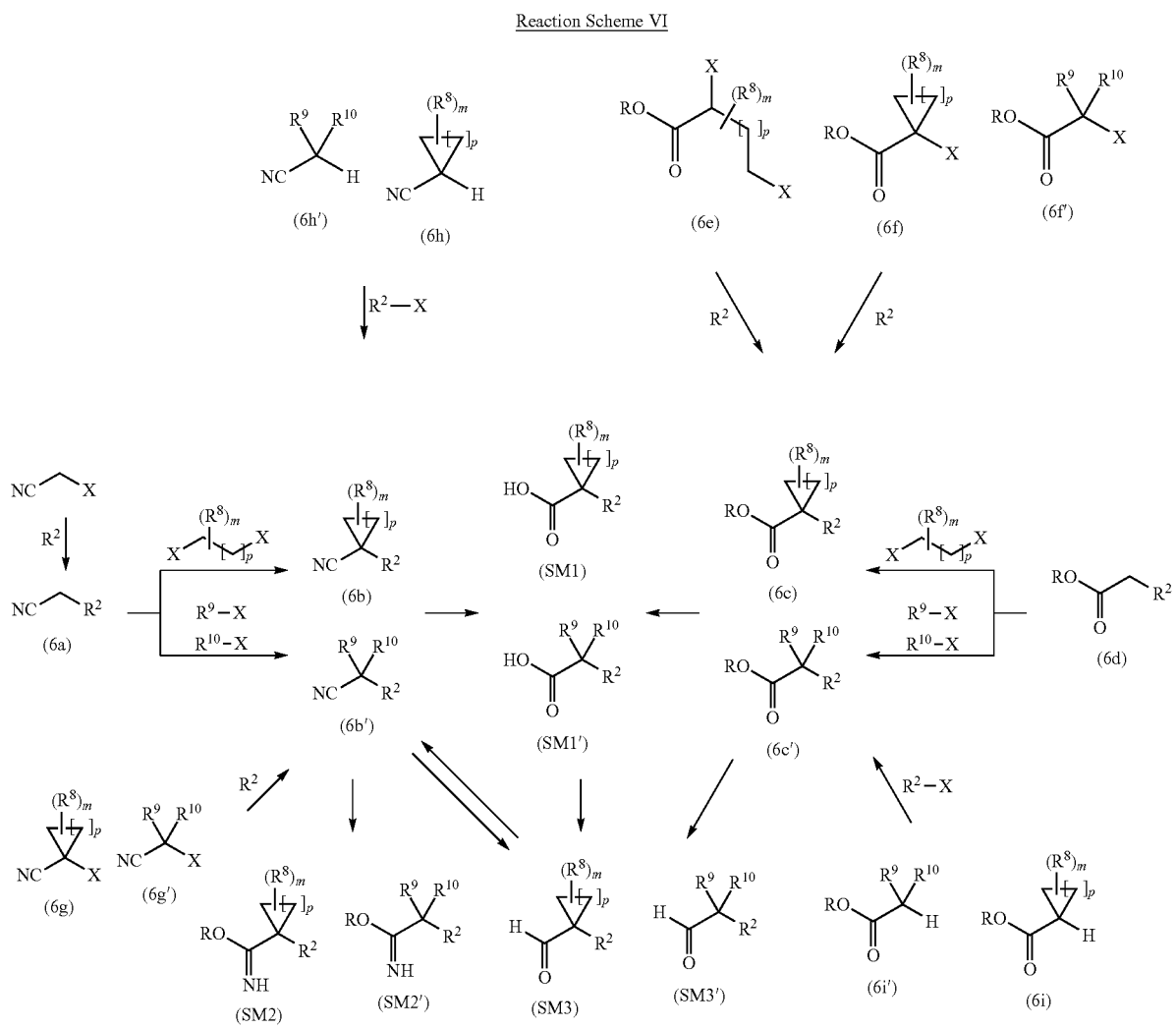

X = Leaving Group

Starting materials of formula SM1, SM1', SM2, SM2', SM3 and SM3' may be prepared according to Reaction Scheme VI. Those skilled in the art will recognize that there exists a variety of methods for preparing intermediate (6a). For example, intermediate (6a) may be prepared from the formula X—CH$_2$—CN (X is leaving group) such as bromoacetonitrile and a nucleophile to introduce the R$^2$ moiety. The nucleophilic reactant may be defined as R$^2$H, where R$^2$ is defined as for the compound of formula I, and the H-atom is located on a heteroatom (N, O or S). Examples of R$^2$H reactants would include but are not limited to heteroaryl or heterocycle containing NH groups (such as pyrazoles, pyridones, morpholinones etc), or phenolic compounds, in the presence of a base such as sodium hydride, potassium carbonate, sodium carbonate or cesium carbonate in a solvent such as acetonitrile, ethyl acetate, tetrahydrofuran, DMF or a combination of thereof at a temperature between 0° C. and 100° C. Intermediate (6b) may be prepared from acetonitriles (6a) and an alkane containing two leaving groups, such as dibromoethane (when m is 0 and p is 1) in the presence of a base such as sodium hydroxide and tert-butylammonium bromide in a water or sodium hydride in a solvent such as toluene, DMF or DMSO at a temperature between 0° C. and 25° C. Intermediate (6b', R$^{10}$ is H) may be prepared analogously from acetonitriles (6a) and an alkylating agent of the formula R$^9$—X such as iodomethane using the methods described for intermediate (6b). Under the analogous reaction conditions, subsequent reaction with the second alkylating agent of the formula R$^{10}$—X may be performed for the synthesis of intermediate (6b', R$^{10}$ is not H). In addition, intermediates (6b) and (6b') may be prepared from intermediate (6h) and (6h') respectively, and R$^2$—X by (1) nucleophilic displacement reaction using the methods described in the literature such as *J. Org. Chem.* 2005, 70, 10186-10189 and *J. Am. Chem. Soc.* 2000, 122, 712-713 or (2) a transition metal mediated arylation reaction (when R$^2$ is aryl or heteroaryl) using the methods described in the literature such as *J. Am. Chem. Soc.* 2002, 124, 9330-9371, *J. Org. Chem.* 2003, 68, 8003-8007 or *Angew. Chem. Int. Ed.* 2003, 42, 5031-5053. Intermediates (6c) and (6c') may be prepared from intermediates (6i) and (6i') and R$^2$—X in a similar manner to that described for intermediates (6b) and (6b') via a nucleophilic displacement reaction, or a transition metal mediated arylation reaction (when R$^2$ is aryl or heteroaryl) using the methods reported in the literature such as *Org. Lett.* 2008, 10, 1545-1548, *Org. Lett.* 2008, 10, 1549-1552 or *J. Am. Chem. Soc.* 2002, 124, 12557-12565. Intermediates (6b) and (6b') may be converted to SM1 and SM1' respectively in the presence of an aqueous inorganic base such as sodium hydroxide, lithium hydroxide, or potassium hydroxide in a suitable solvent such as methanol, ethanol, tetrahydrofuran or water at a temperature between 0° C. and 50° C., preferably between 0° C. and 20° C. Intermediates (6b) and (6b') may be converted to SM2 and SM2' respectively in the presence of hydrochloric acid or acetyl chloride in a solvent such as ethanol or methanol at a temperature between 0° C. and 70° C. Alternatively, intermediates (6b) and (6b') may be converted to SM2 and SM2' respectively in the presence of sodium ethoxide or sodium methoxide in a solvent such as ethanol or methanol at a temperature between 0° C. and 80° C. Intermediate (6c) may be prepared from acetate derivatives (6d) and an alkane containing two leaving groups, such as dibromoethane (when m is 0 and p is 1) in the presence of a base, such as cesium carbonate, potassium carbonate, sodium carbonate or sodium hydride in a reaction solvent such DMF or DMSO at a temperature between 0° C. and 25° C. Intermediate (6b', R$^{10}$ is H) may be prepared analogously from acetate derivatives (6d) and an alkylating agent of formula R$^9$—X such as iodomethane using the methods described for intermediate (6c). Subsequent reaction with a second alkylating agent of formula R$^{10}$—X may be performed for the synthesis of intermediate (6c', R$^{10}$ is not H). If R is an alkyl group, intermediates (6c) and (6c') may be converted to SM1 and SM1' respectively (1) in the presence of an aqueous inorganic base such as sodium hydroxide, lithium hydroxide, potassium hydroxide or potassium carbonate in a suitable solvent such as methanol, ethanol, tetrahydrofuran or water at a temperature between 0° C. and 50° C., preferably between 0° C. and 20° C., or (2) in the presence of an aqueous acid such as hydrochloric acid in a suitable solvent such as water at a temperature between 0° C. and 120° C. If R$^1$ is a benzyl group, intermediates (6c) and (6c') may be converted to SM1 and SM1' respectively via hydrogenation in the presence of palladium on carbon in a reaction solvent such as methanol, ethanol or ethyl acetate at ambient temperature. If R is a tert-butyl group, intermediates (6c) and (6c') may be converted to SM1 and SM1' respectively in the presence of an acid, such as trifluoroacetic acid, hydrochloric acid, methanesulfonic acid in a solvent such as dichloromethane, dioxane, toluene, methanol or ethyl ether at a temperature between 0° C. and 45° C. Alternatively, intermediate (6c) may be prepared from (6e) and a nucleophilic reactant R$^2$H, where R$^2$ is defined as for the compound of formula I, and the H-atom is located on a heteroatom (N, O or S). Examples of R$^2$H reactants would include but not limited to heteroaryl or heterocycle containing NH groups (such as pyrazoles, pyridones, morpholinones etc), or phenolic compounds, in the presence of a base such as sodium hydride or potassium trimethylsilanolate in a reaction solvent such as tetrahydrofuran, 2-methyl tetrahydrofuran, DMF, DMSO or combinations thereof at a temperature between 0° C. and 40° C. In addition, intermediates (6c) and (6c') may be prepared from the suitable alkylating agent (6f) for intermediate (6c), (6f') for intermediate (6c')) and a nucleophilic reactant R$^2$H, where R$^2$ is defined as for the compound of formula I, and the H-atom is located on a heteroatom (N, O or S). Examples of R$^2$H reactants would include but not limited to heteroaryl or heterocycle containing NH groups (such as pyrazoles, pyridones, morpholinones etc), or phenolic compounds, n the presence of a base such as sodium hydride, potassium carbonate, sodium carbonate or cesium carbonate in a solvent such as acetonitrile, ethyl acetate, tetrahydrofuran or DMF or a combination of thereof at a temperature between 0° C. and 100° C. Intermediates (6b) and (6b') may be prepared from (6g) and (6g') respectively, and a nucleophilic reactant R$^2$H, where R$^2$ is defined as for the compound of formula I, and the H-atom is located on a heteroatom (N, O or S). Examples of R$^2$H reactants would include but not limited to heteroaryl or heterocycle containing NH groups (such as pyrazoles, pyridones, morpholinones etc), or phenolic compounds, in the manner described for intermediates (6c) and (6c'). Starting materials of formula SM3 and SM3' may be prepared through the reduction of SM1, SM1', SM2, SM2', (6c) or (6c') using the methods well-known to those skilled in the art. In addition, starting materials of formula SM1 and SM1' may be prepared from SM3 and SM3' respectively by methods known to those skilled in the art.

Reaction Scheme VII

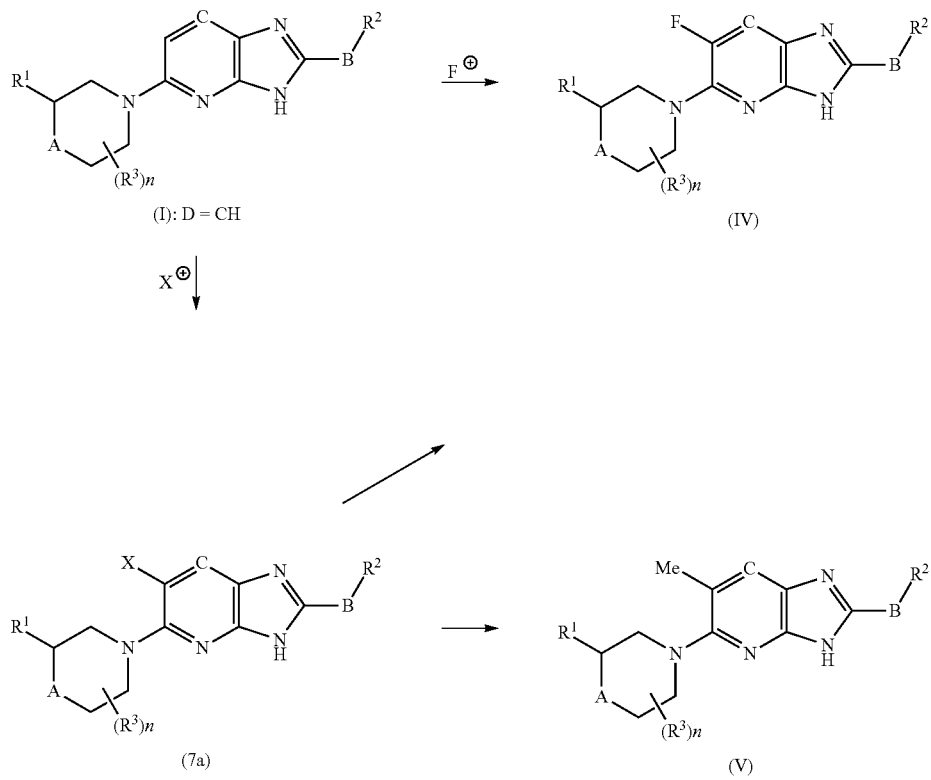

Compounds of Formula (IV) and (V) may be prepared according to Reaction Scheme VII. Compounds of Formula (IV) may be prepared from compounds of formula (I) wherein D is CH, by reaction with an electrophilic fluorinating agent such as Selectfluor® in a solvent such as acetonitrile or DMF at a temperature between 0° C. and 100° C. Alternatively, compounds of Formula (IV) may be prepared from the intermediate (7a) via (1) fluorination of the corresponding organometallic species prepared by halogen-metal exchange reaction of NH-protected intermediate (7a), analogous to the methods described in WO2008080015, or (2) nucleophilic fluorination with a fluorinating agent such as potassium fluoride in the presence or absence of a crown ether such as 18-crown-6 in a polar solvent such as DMSO or NMP at a temperature between 20° C. and 180° C. Intermediate (7a) may be prepared from compounds of Formula (I) wherein D is CH, by reaction with an electrophilic halogenating agent such as N-Bromosuccinimide (NBS) or N-iodosuccinimide (NIS) in a solvent such as dichloromethane, DMF or acetonitrile at a temperature between 0° C. and 100° C. Compounds of the formula (V) may be prepared from the intermediate (7a) via a transition metal mediated coupling reaction with the appropriate metal species such as methyl boronic acid by the methods described by Hikawa et al in *Tetrahedron*, 2010, 66, 9552-9559 or other methods known to those skilled in the art.

Reaction Scheme VIII

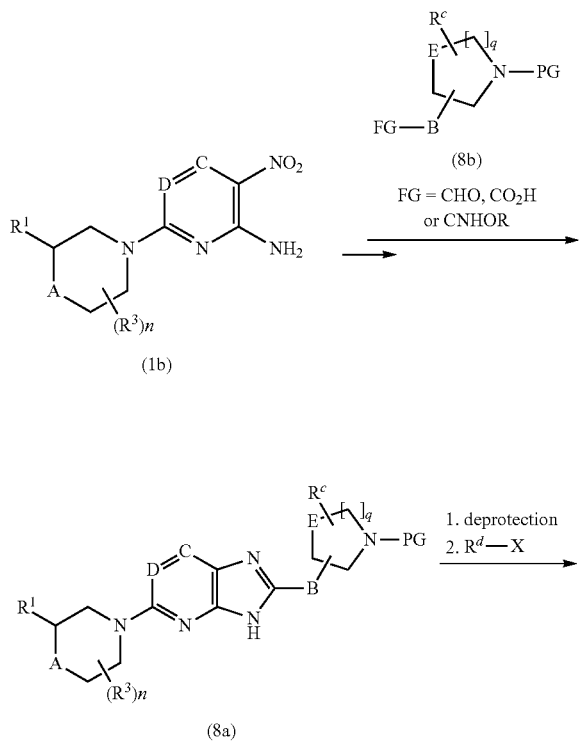

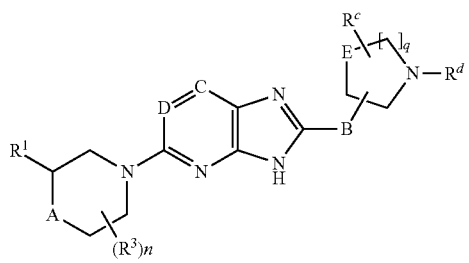

(VI)
PG = Protecting group
E = CH$_2$, O, NR$^e$, S
q = 0, 1, 2
X = Leaving group Compounds of Formula (VI) may be prepared through the intermediate (8a), that can be accessed from intermediate (1b) and intermediate (8b) (wherein E is CH$_2$, O, NR$^e$ or S, q is 0, 1 or 2, and R$^c$ and R$^e$ are groups described as optional substituents for R$^2$ in the summary above) by the methods described in Reaction Scheme I-IV, or VII, as shown in Reaction Scheme VIII. Compounds of Formula (VI) may be prepared by removal of the amino-protecting group such as Boc using the methods described in T. W. Greene, *Protective Groups in Organic Synthesis*, John Wiley & Sons, New York, 1991, followed by reaction with the appropriate electrophilic agent R$^d$—X (wherein R$^d$ is a group described as an optional substituent for R$^2$ in the summary above, X is leaving group) such as heteroaryl halide, acid chloride, chloroformate or sulfonyl chloride under conditions well known to those skilled in the art.

Reaction Scheme IX

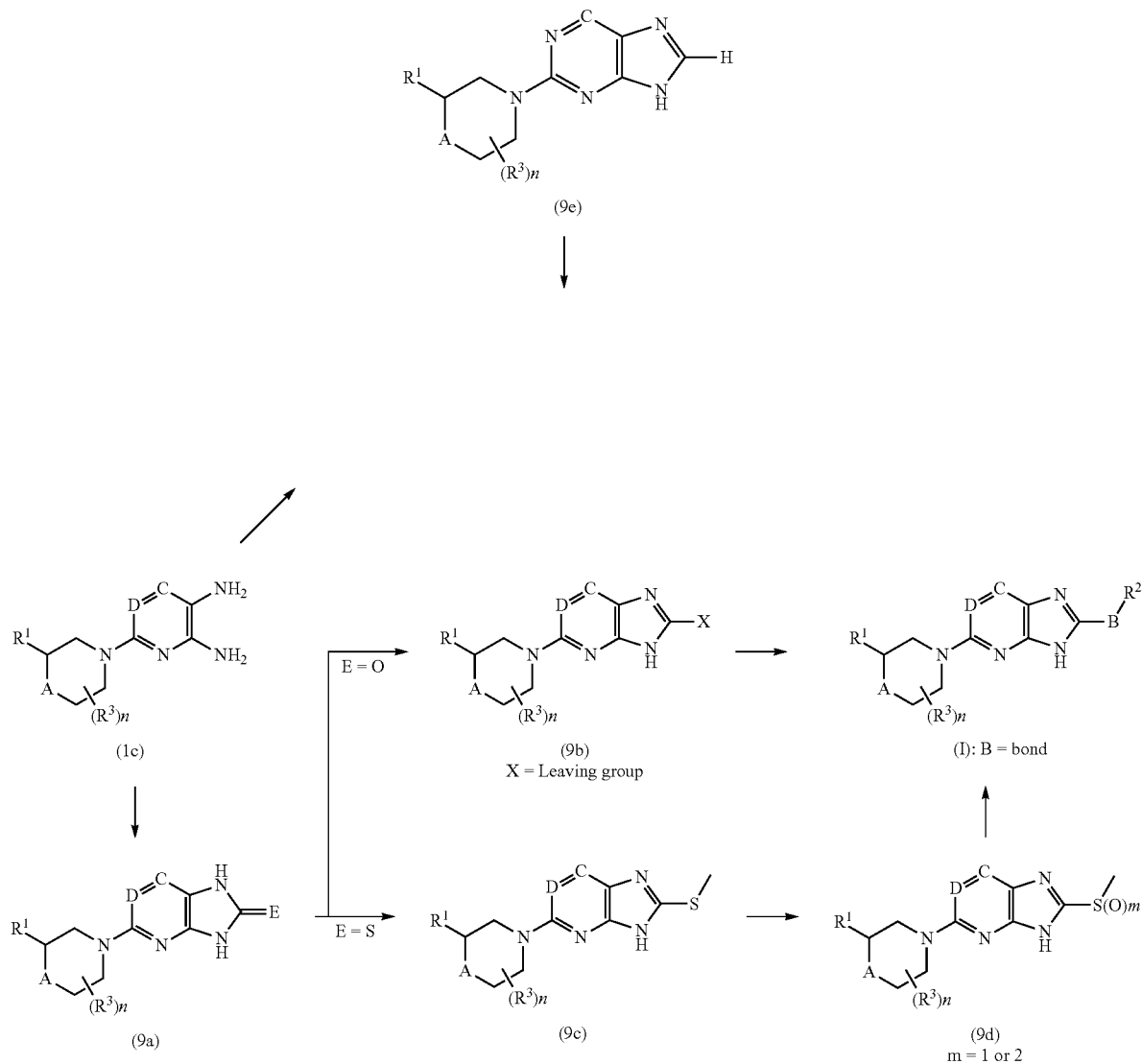

Compounds of Formula (I) wherein B is a bond may be prepared according to Reaction Scheme IX. An appropriate nitrogen-protecting group such as [2-(Trimethylsilyl)ethoxy]methyl (SEM) group may be introduced for intermediate (1c) or (9a-e) depending on the nature of remote functionality and the conditions of the preparation methods. The methods for protection/deprotection of such nitrogen-protecting groups can be found in T. W. Greene, *Protective Groups in Organic Synthesis*, John Wiley & Sons, New York, 1991. Compounds of Formula (I) wherein B is a bond and $R^2$ is aryloxy, N-linked heterocyclyl or N-linked heteroaryl, may be prepared from the intermediate (9b) or (9d) and $R^2$—H with a base such as sodium hydride, cesium carbonate, potassium carbonate or sodium carbonate in a solvent such as acetonitrile, DMF or DMSO at a temperature between 0° C. and 100° C., or by the methods described in WO2007039297 or *J. Med. Chem.* 2006, 49, 3719-3742, or other methods known to those skilled in the art. Compounds of Formula (I) wherein B is a bond and $R^2$ is C-linked, may be prepared via a transition metal mediated coupling reaction starting from the intermediate (9b) and $R^2$-metal species such as boronic acid derivatives by the methods described by Grivas et al in *J. Heterocyclic. Chem.*, 1995, 32, 467-471 or other methods known to those skilled in the art. Intermediate (9b) and (9d) may be prepared from intermediate (1c) using the methods described in WO2007039297 or *J. Med. Chem.* 2006, 49, 3719-3742, or other methods known to those skilled in the art. In addition, intermediate (9b) wherein D is N may be prepared from the intermediate (9e) (accessible from the intermediate (1c) as described in reaction scheme I, II or IV) using the methods described in *J. Med. Chem.* 2011, 54, 655-668.

COMBINATION AGENTS

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/condition e.g., obesity, diabetes, and cardiovascular conditions such as anti-hypertensive agents and coronary heart disease.

Examples of suitable anti-diabetic agents include (e.g. insulins, metfomin, DPPIV inhibitors, GLP-1 agonists, analogues and mimetics, SGLT1 and SGLT2 inhibitors). Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, N,N-9924, TTP-054, a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 activator (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, β₃ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buproprion and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818, 658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), the combination of naltrexone with buproprion, oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesteryl ester transfer protein inhibitors. Other atherosclerotic agents include PCSK9 modulators.

In another embodiment, a compound of Formula I may be co-administered with agents for the treatment of non-alcoholic steatohepatitis (NASH) and/or non-alcoholic fatty liver disease (NAFLD), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 Inhibitors, Phentermine, Topiramate, Incretin (GLP and GIP) analogs and Angiotensin-receptor blockers.

Additional therapeutic agents include anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diuretics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, dpinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another preferred embodiment the second agent is at least one agent selected from warfarin, dabigatran, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred second agent is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, dabigatran, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); K+ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/All antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mibefradil.

Examples of suitable cardiac glycosides include digitalis and ouabain.

In one embodiment, a Formulae I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™) hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETICT™).

In another embodiment, a compound of Formulae I may be co-administered with a loop diuretic. In still another embodiment, the loop diuretic is selected from furosemide and torsemide. In still another embodiment, one or more compounds of Formulae I or II may be co-administered with furosemide. In still another embodiment, one or more compounds of Formulae I or II may be co-administered with torsemide which may optionally be a controlled or modified release form of torsemide.

In another embodiment, a compound of Formulae I may be co-administered with a thiazide-type diuretic. In still another embodiment, the thiazide-type diuretic is selected from the group consisting of chlorothiazide and hydrochlorothiazide. In still another embodiment, one or more compounds of Formulae I or II may be co-administered with chlorothiazide. In still another embodiment, one or more compounds of Formulae I or II may be co-administered with hydrochlorothiazide.

In another embodiment, one or more compounds of Formulae I or II may be co-administered with a phthalimidine-type diuretic. In still another embodiment, the phthalimidine-type diuretic is chlorthalidone.

Examples of suitable mineralocorticoid receptor antagonists include spironolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of treatment of the invention, a compound of the present invention or a combination of a compound of the present invention and at least one additional pharmaceutical agent (referred to herein as a "combination") is administered to a subject in need of such treatment, preferably in the form of a pharmaceutical composition. In the combination aspect of the invention, the compound of the present invention and at least one other pharmaceutical agent (e.g., another anti-obesity agent) may be administered either separately or in a pharmaceutical composition comprising both. It is generally preferred that such administration be oral.

When a combination of a compound of the present invention and at least one other pharmaceutical agent are administered together, such administration may be sequential in time or simultaneous. Simultaneous administration of drug combinations is generally preferred. For sequential administration, a compound of the present invention and the additional pharmaceutical agent may be administered in any order. It is generally preferred that such administration be oral. It is especially preferred that such administration be oral and simultaneous. When a compound of the present invention and the additional pharmaceutical agent are administered sequentially, the administration of each may be by the same or by different methods.

According to the methods of the invention, a compound of the present invention or a combination is preferably administered in the form of a pharmaceutical composition. Accordingly, a compound of the present invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-Sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-Sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyole® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, from Abitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Many of the present compounds are poorly soluble in water, e.g., less than about 1 μg/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup. (R0-102) (15.8%), sodium starch (7%), sodium lauryl sulfate (2%) and magnesium stearate (1%).

The HPMCAS polymers are available in low, medium and high grades as Aqoa.sup.®-LF, Aqoat.sup.®-MF and Aqoat-.sup.®-HF respectively from Shin-Etsu Chemical Co., LTD, Tokyo, Japan. The higher MF and HF grades are generally preferred.

The following paragraphs describe exemplary formulations, dosages, etc. useful for non-human animals. The administration of the compounds of the present invention and combinations of the compounds of the present invention with anti-obesity agents can be effected orally or non-orally.

An amount of a compound of the present invention or combination of a compound of the present invention with another anti-obesity agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about 10.sub.-3 to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing an effective amount of a compound of the present invention, pharmaceutical composition, or combination may be prepared by admixing a compound of the present invention or combination with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England) and Tyger Scientific (Princeton, N.J.). Certain common abbreviations and acronyms have been employed which may include: AcOH (acetic acid), BOP (benzotriazo-1-yloxytris(dimethylamino)phosphonium hexafluorophosphate), DBU (1,8-diazabicyclo[5.4.0]undec-7-ene), CDI (1,1'-carbonyldiimidazole), DCM (dichloromethane), DEA (diethylamine), DMAP (4-dimethylaminopyridine), DMF (N,N'-dimethylformamide), DMSO (dimethylsulfoxide), EDCl (N-(3-dimethylaminopropyl)-N'-ethylcarbodiimide), $Et_2O$ (diethyl ether), EtOAc (ethyl acetate), EtOH (ethanol), HATU (2-(1H-7-azabenzotriazol-1-yl)-1,1,3,3-tetramethyl uronium hexafluorophosphate methanaminium), HBTU (O-benzotriazol-1-yl-N,N,N',N'-tetramethyluronium hexafluoro phosphate), HOBT (1-hydroxybenzotriazole), IPA (isopropyl alcohol), KHMDS (potassium hexamethyldisilazane), MeOH (methanol), MTBE (tert-butyl methyl ether), $NaBH(OAc)_3$ (sodium triacetoxyborohydride), NaHMDS (sodium hexamethyldisilazane), NMP (N-methylpyrrolidone), SEM ([2-(Trimethylsilyl)ethoxy]methyl), TFA (trifluoroacetic acid), THF (tetrahydrofuran), and $T_3P$ (propane phosphonic acid anhydride).

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wis. or DriSolv™ products from EMD Chemicals, Gibbstown, N.J.) were employed. Commercial solvents and reagents were used without further purification. When indicated, reactions were heated by microwave irradiation using Biotage Initiator or Personal Chemistry Emuys Optimizer microwaves. Reaction progress was monitored using thin layer chromatography (TLC), liquid chromatography-mass spectrometry (LCMS), high performance liquid chromatography (HPLC), and/or gas chromatography-mass spectrometry (GCMS) analyses. TLC was performed on pre-coated silica gel plates with a fluorescence indicator (254 nm exitation wavelength) and visualized under UV light and/or with $I_2$, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, MeCN/water gradients, and either TFA, formic acid, or ammonium hydroxide modifiers. The column eluent was analyzed using Waters ZQ mass spectrometer scanning in both positive and negative ion modes from 100 to 1200 Da. Other similar instruments were also used. HPLC data were acquired on an Agilent 1100 Series instrument using Gemini or XBridge C18 columns, MeCN/water gradients, and either TFA or ammonium hydroxide modifiers. GCMS data were acquired using a Hewlett Packard 6890 oven with an HP 6890 injector, HP-1 column (12 m×0.2 mm×0.33 μm), and helium carrier gas. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC) using Berger or Thar instruments; ChiralPAK-AD, -AS, -IC, Chiralcel-OD, or -OJ columns; and $CO_2$ mixtures with MeOH, EtOH, iPrOH, or MeCN, alone or modified using TFA or $iPrNH_2$. UV detection was used to trigger fraction collection.

Mass spectrometry data are reported from LCMS analyses. Nuclear magnetic resonance (NMR) spectra were recorded on 400 and 500 MHz Varian spectrometers. Chemical shifts are expressed in parts per million (ppm, δ) referenced to the deuterated solvent residual peaks. Analytical SFC data were acquired on a Berger analytical instrument as described above. Optical rotation data were acquired on a Perkin Elmer model 343 polarimeter using a 1 dm cell.

Concentration in vacuo refers to evaporation of solvent under reduced pressure using a rotary evaporator.

Unless otherwise noted, chemical reactions were performed at room temperature (about 23 degrees Celsius).

The compounds and intermediates described below were named using the naming convention provided with ChemBioDraw Ultra, Version 12.0 (CambridgeSoft Corp., Cambridge, Mass.). The naming convention provided with ChemBioDraw Ultra, Version 12.0 are well known by those skilled in the art and it is believed that the naming convention provided with ChemBioDraw Ultra, Version 12.0 generally comports with the IUPAC (International Union for Pure and Applied Chemistry) recommendations on Nomenclature of Organic Chemistry and the CAS Index rules. Unless noted otherwise, all reactants were obtained commercially without further purifications or were prepared using methods known in the literature.

Proton nuclear magnetic spectroscopy ($^1$H NMR) chemical shifts are given in parts per million downfield from tetramethylsilane and were recorded on a Varian Unity 300, 400 or 500 MHz (megaHertz) spectrometer (Varian Inc.; Palo Alto, Calif.). Chemical shifts are expressed in parts per million downfield from tetramethylsilane. The peak shapes are denoted as follows: s, singlet; d, doublet; t, triplet; q, quartet; quin, quintet; m, multiplet; br s, broad singlet. Mass spectrometry (MS) was performed via atmospheric pressure chemical ionization (APCI), electrospray Ionization (ESI), electron impact ionization (EI) or electron scatter (ES) ionization sources. Silica gel chromatography was performed primarily using a medium pressure Biotage or ISCO systems using columns pre-packaged by various commercial vendors including Biotage and ISCO. Microanalyses were performed by Quantitative Technologies Inc. and were within 0.4% of the calculated values.

The terms "concentrated" and "evaporated" refer to the removal of solvent at reduced pressure on a rotary evaporator with a bath temperature less than 60° C. The abbreviation "min" and "h" stand for "minutes" and "hours" respectively.

The term "TLC" refers to thin layer chromatography, "room temperature or ambient temperature" means a temperature between 18 to 25° C., "GCMS" refers to gas chromatography-mass spectrometry, "LCMS" refers to liquid chromatography-mass spectrometry, "UPLC" refers to ultra performance liquid chromatography and "HPLC" refers to high pressure liquid chromatography.

Hydrogenation may be performed in a Parr Shaker under pressurized hydrogen gas, or in Thales-nano H-Cube flow hydrogenation apparatus at full hydrogen and a flow rate between 1-2 mL/min at specified temperature.

Microwave heating of reactions was conducted using a Biotage® Initiator microwave synthesizer.

HPLC, UPLC, LCMS and GCMS retention times were measured using the following methods:

Method A: Column: Waters Atlantis dC18 4.6×50 mm, 5 μm; Mobile Phase A: 0.05% trifluoroacetic acid in water (v/v); Mobile phase B: 0.05% trifluoroacetic acid in acetonitrile (v/v); Gradient: 95% A/5% B linear to 5% A/95% B in 4.0 minutes, hold at 5% A/95% B for 5.0 minutes; Flow rate: 2.0 mL/minute.

Method B: Column: Waters XBridge C18 4.6×50 mm, 5 μm; Mobile Phase A: 0.03% ammonium hydroxide in water (v/v); Mobile Phase B: 0.03% ammonium hydroxide in acetonitrile (v/v); Gradient: 95% A/5% B linear to 5% A/95% B in 4.0 minutes, hold at 5% A/95% B to 5.0 minutes; Flow rate: 2.0 mL/minute.

Method C: Column: XBridge C18 2.1×50 mm 5 μm; Mobile Phase A: 0.0375% trifluoroacetic acid in water; Mobile Phase B: 0.01875% trifluoroacetic acid in acetonitrile; Gradient: Initial—1% B, Time (min)/% B: 0.00/1, 0.60/5, 4.00/100, 4.30/1, 4.70/1; Flow Rate: 0.8 mL/min; Column Temperature: 50° C.

Method D: Column: XBridge C18 2.1×50 mm 5 μm; Mobile Phase A: 0.0375% trifluoroacetic acid in water; Mobile Phase B: 0.01875% trifluoroacetic acid in acetonitrile; Gradient: Initial—10% B, Time (min)/% B: 0.00/10, 0.50/10, 4.00/100, 4.30/10, 4.70/10; Flow Rate: 0.8 mL/min; Column Temperature: 50° C.

Method E: Column: Zorbax SB-C18 (2.1×30) mm, 3.5 μm; Mobile Phase A: 0.1% formic acid in water; Mobile Phase B: 0.1% formic acid in acetonitrile; Gradient: Initial 2%, Time (min)/% B: 0.00/2, 0.40/2, 1.60/90, 2.9/90, 3.0/2; Flow Rate: 0.8 mL/min; Column Temperature: 40° C.

Method F: Column: AQUITY BEH C-18, 2.1×50 mm, 1.7 μm; Mobile Phase A: 0.1% formic acid in acetonitrile, Mobile Phase B: 0.1% formic acid in water; Gradient: Time (min)/% B: 0/90, 0.7/90, 2/15, 4/15, 4.01/90; Flow: 0.5 mL/min.

Method G: Column: AQUITY BEH C-18, 2.1×50 mm, 1.7 μm; Mobile Phase A: 0.1% formic acid in acetonitrile; Mobile Phase B: 0.1% formic acid in water; Gradient: Time (min)/% B: 0/90, 0.7/90, 2/55, 3/55, 3.8/5, 5.8/5, 6/90; Flow: 0.5 mL/min.

Method H: Column: XBridge C-18 4.6×150 mm, 3.5 μm; Mobile Phase A: acetonitrile; Mobile Phase B: 5 mM ammonium acetate in water; Time (min)/% B: 0/95, 1/95, 3/5, 10/5, 10.5/95; Flow: 0.8 mL/min Method I: Column: XBridge-C18 4.6 75 mm 3.5 μm; Mobile Phase A: 0.1% formic acid in acetonitrile; Mobile Phase B: 0.1% formic acid in water; Time (min)/% B: 0/90, 0.8/90, 1.8/55, 3/5, 6.5/5, 7/90; Flow: 0.8 ml/min, Column Temperature: 40° C.

Method J: Column: Symmetry C-18 2.1×50 mm 3.5 μm; Mobile Phase A: 0.1% formic acid in acetonitrile; Mobile Phase B: 0.1% formic acid in water; Time (min)/% B: 0/90, 0.5/90, 2/55, 3/55, 3.5/10, 6/10, 7/90; Flow: 0.5 mL/min, Column Temperature: 45° C.

Method K: Column: Discovery C8, 250×4.6 mm; Mobile Phase A: methanol; Mobile Phase B: 0.1% formic acid in water; Time (min)/% B: 0/80, 2/80, 8/20, 18/20, 19/20, 20/80; Flow rate: 1.0 mL/min; Column Temperature: 40° C.

Method L: Column: Phenomenex Gemini-NX, 4.6 mm×50 mm, C18, 3 µm, 110 Å; Mobile phase A: 0.1% formic acid in water (v/v); Mobile phase B: 0.1% formic acid in acetonitrile (v/v); Gradient: Initial conditions: A-95%:B-5%, Linear Ramp to A-0%:B-100% over 0.0-4.10 min, hold at A-0%:B-100% from 4.10-4.50 min, return to initial conditions: 4.60-5.0 min; Flow rate: 1.5 mL/minute. Temperature: 60° C.

Method M: Column: Phenomenex Gemini-NX, 4.6 mm×50 mm, C18, 3 µm, 110 Å; Mobile phase A: 0.1% formic acid in water (v/v); Mobile phase B: 0.1% formic acid in acetonitrile (v/v); Gradient: Initial conditions: A-95%:B-5%, Linear ramp from 0.0-1.90 min; hold from 1.90-2.25 min; return to initial conditions 2.25-2.50 min.; Flow rate: 1.50 mL/minute. Temperature: 60° C.

Method N: Column: Waters Acquity UPLC BEH, 2.1 mm×50 mm, C18, 1.7 µm; Column Temperature 60° C.; Mobile Phase A: 0.1% formic acid in water (v/v); Mobile phase B: 0.1% formic acid in acetonitrile (v/v); Flow-1.25 ml/min; Gradient: Initial conditions: A-95%:B-5%; hold at initial from 0.0-0.1 min; Linear Ramp to A-5%:B-95% over 0.1-0.8 min; hold at A-5%:B-95% from 0.8-0.9 min; return to initial conditions 0.9-1.2 min Method O: Column: 12 m×0.2 mm; HP-1 Methyl Siloxane, 0.33 µm film, 1.0 mL/min column flow; 7.6 min: Initial Oven Temperature 105° C., 0.1 min hold, 30° C./min ramp to 300° C. endpoint at 7.6 min; Inlet parameters: front inlet, split 30:1, He, 8 PSI pressure, 250° C. injector, 33.9 mL/min total flow; Instrument Agilent 5890 GC Oven with Agilent 5973 Mass Selective Detector Method P: Column: Waters Acquity UPLC BEH, 2.1 mm×50 mm, C18, 1.7 µm; Column Temperature: 60° C.; Mobile Phase A: 0.1% formic acid in water (v/v); Mobile Phase B: 0.1% formic acid in acetonitrile (v/v); Flow-1.25 ml/min; Gradient: Initial conditions: A-95%:B-5%; hold at initial from 0.0-0.1 min; Linear Ramp to A-5%:B-95% over 0.1-2.6 min; hold at A-5%:B-95% from 2.6-2.95 min; return to initial conditions 2.95-3.0 min Method Q: Column: Phenomenex Kinetex C18 50×3.0 mm 2.6 µm; Mobile Phase A: 0.1% Formic acid in water; Mobile Phase B: 0.1% Formic acid in methanol; Gradient: Time (min)/% B: 0.00/0, 0.30/0, 3.00/100, 3.70/100, 3.71/0, 4.00/0; Flow: 1.0 mL/min;

Method R: Column: AQUITY BEH C-18, 2.1×50 mm, 1.7 µm; Mobile Phase A: 0.1% formic acid in acetonitrile; Mobile Phase B: 0.1% formic acid in water; Time (min)/% B: 0/90, 0.7/90, 2/15, 4/15, 4.01/90; Flow: 0.5 mL/min Method S: Column: AQUITY BEH C18 1.7 µm, 2.1×50 mm; Mobile Phase A: 0.1% formic acid in acetonitrile; Mobile Phase B: 0.1% formic acid in water; Time (min)/% B: 0/100, 1.5/100, 4.0/10, 6.0/10, 6.01/100; Flow: 0.4 mL/min; Column Temperature: 40° C.

Method T: Column: Acquity BEH C18(2.1×50) 1.7 µm; Mobile Phase A: 0.1% formic acid in water; Mobile Phase B: 0.1% formic acid in acetonitrile; Time (min)/% B: 0.00/2, 1.30/90, 1.55/90, 1.56/2; Flow rate: 1.0 mL/min; Column Temperature: 50° C.

Method U: Column: Resteck C18 (2.1×30) 3.0 µm; Mobile Phase A: 0.1% formic acid in water; Mobile Phase B: 0.1% formic acid in acetonitrile; Time (min)/% B: 0.00/2, 1.33/90, 1.55/90, 1.56/2; Flow rate: 1.0 mL/min; Column Temperature: 25° C.

Method V: Column: AQUITY CSH C18 1.7 µm 2.1×50; Mobile Phase A: 0.1% formic acid in water; Mobile Phase B: 0.1% formic acid in acetonitrile; Time (min)/% B: 0.00/2, 1.3/90, 1.55/90, 1.56/2; Flow Rate: 1.0 mL/min; Column Temperature: 50° C.

Method W: Column: AQUITY BEH C18, (2.1×50) mm, 1.7 µm; Mobile Phase A: 0.1% formic acid in acetonitrile; Mobile Phase B: 0.1% formic acid in water; Time (min)/% B: 0/90, 0.7/90, 2/10, 4/10, 4.01/90; Flow: 0.5 ml/min, Column Temperature: 40° C.

Method X: Column: XBridge C-18 4.6×150 mm, 3.5 µm; Mobile Phase A: acetonitrile; Mobile Phase B: 5 mM ammonium acetate in water; Time (min)/% B: 0/95, 1/95, 3/5, 8/5, 9/95, 10/80; Flow: 0.8 mL/min Method Y: Column: X-Bridge C-18, 4.6×150 mm, 3.5 µm. Mobile Phase A: 0.1% formic acid in acetonitrile; Mobile Phase B: 0.1% formic acid in water; Time (min)/% B: 0/95, 2/95, 4/5, 6.5/5, 7/100, 8/100; Flow: 0.8 mL/min Method Z: Column: X-Bridge C18 4.6×75 mm 3.5 µm; Mobile phase A: 0.1% formic acid in acetonitrile, Mobile Phase B: 0.1% formic acid in water; Time (min)/% B: 0/90, 0.8/90, 2.0/55, 3.0/55, 3.5/10, 6.0/10, 7/90; Flow: 0.8 mL/min, Column Temp: 35° C.;

Method A1: Column: X-Bridge C18 4.6×150 mm 3.5 µm; Mobile phase A: acetonitrile:water (90:10) 0.1% formic acid, Mobile Phase B: water:acetonitrile (90:10) 0.1% formic acid; Time (min)/% B: 0/100, 1/100, 2.0/50, 4/5, 6.5/5, 8/100; Flow: 0.8 mL/min, Column Temp: 40° C.

Method B1: Column: XBRIDGE-C18 4.6×75 mm 3.5 µm; Mobile phase A: acetonitrile; Mobile Phase B: 5 mM ammonium acetate; Time (min)/% B: 0/95, 2/95, 3.5/5, 5/5, 6.5/95, 7/95; Flow: 0.8 mL/min, Column Temp: 40° C.;

Method C1: Column: Symmetry-C18 2.1×50 mm 3.5 µm; Mobile phase A: 0.1% formic acid; Mobile Phase B: 0.1% formic acid in water; Time (min)/% B: 0/90, 0.5/90, 2/55, 3/55, 3.5/10, 6.5/10, 7/90; Flow: 0.5 mL/min, Column Temp: 40° C.

Method D1: Column: Nucleodurbiowidepore C8, 4.6×50 mm, 5 µm; Mobile Phase: A: acetonitrile, Mobile Phase B: 0.1% formic acid in water; Time (min)/% B: 0/80, 0.5/80, 1.2/10, 5.5/10, 5.8/80, 6/80 Flow: 0.7 mL/min; Column Temp: 45° C.

Method E1: Nucleodurbiowidepore C8, 4.6×50 mm, 5 µm; Mobile phase A: acetonitrile; Mobile Phase B: 0.1% formic acid in water; Time (min)/% B: 0/80, 0.5/80, 1.2/10, 5.5/10, 5.8/80, 6/80; Flow: 0.7 mL/min; Column Temperature: 50° C.

Method F1: HP-5 (30 m×0.32 mm×0.25 µm) N2=1.2 psi, Inj=230° C., Det=250° C., Split=20:1, I.V=3.0 µL Programme: 80° C./min/20° C./min/250° C./15 min Method G1: Column: Zorbax SB-C18 2.1×30 mm, 3.5 µm; Mobile Phase A: 0.1% formic acid in acetonitrile; Mobile Phase B: 0.1% formic acid in water; Gradient: Time (min)/% B: 0/90, 1/90, 2.5/15, 4.5./15, 4.8/90, 5/90; Flow: 0.6 ml/min; Temperature: 40° C.

Method H1: Column: Symmetry C18 2.1×50 mm 3.5 µm; Mobile Phase A: 0.1% formic acid in acetonitrile; Mobile Phase B: 0.1% formic acid in water; Time (min)/% B: 0/90, 0.5/90, 2/55, 3/55, 3.5/10, 6.5/10, 7/90; Flow: 0.5 mL/min; Column Temperature: 45° C.

Method I1: Column: Symmetry RP-18 4.6×75 mm, 3.5 um; Mobile Phase A: acetonitrile; Mobile Phase B: 5 mM Ammonium acetate in water; Time (min)/% B: 0/80, 1/80, 2.0/45, 6.3/45, 7.2/10, 10/10, 10.2/80; Flow: 0.8 mL/min; Column Temp: 30° C.

Method J1: Column: Symmetry RP-18 4.6×75 mm, 3.5 um; Mobile Phase A: acetonitrile; Mobile Phase B: 5 mM Ammonium acetate in Water; Time (min)/% B: 0/80, 1/80, 1.5/5, 8.5/5, 9/80, 10/80; Flow: 0.7 mL/min.

Method K1: Column: ZORBAX C-18 4.6×50 mm, 1.8 um; Mobile Phase A: acetonitrile; Mobile Phase B: 5 mM Ammonium acetate In Water; Time (min)/% B: 0/80, 1.0/80, 1.5/5, 5.5/5, 6.0/80, 7.0/80; Flow: 0.7 mL/min.
Method L1: Column: Symmetry-C18 2.1×50 mm 3.5 µm; Mobile phase A: acetonitrile; Mobile Phase B: 0.1% formic acid in water; Time (min)/% B: 0/90, 0.7/90, 1.5/10, 4/10, 4.5/90, 5/90; Flow: 0.5 mL/min, Column Temperature: 40° C.
Method M1: Column: AQUITY BEH C18 1.7 µm, 2.1×50 mm; Mobile Phase A: 0.1% formic acid in acetonitrile, Mobile Phase B: 0.1% formic acid in water; Time (min)/% B: 0/100, 1.5/100, 4.0/20, 4.5/20, 5.5/100, 6/100; Flow: 0.4 mL/min; Column Temperature: 40° C.
Method N1: Column: AQUITY BEH C-18, 2.1×50 mm, 1.7 µm; Mobile Phase A: 0.1% formic acid in 90:10 acetonitrile: water; Mobile Phase B: 0.1% formic acid in 90:10 water: acetonitrile; Time (min)/% B: 0/100, 0.7/100, 2/55, 3/55, 3.8/5, 5.8/5, 6.0/100; Flow: 0.5 mL/min; Column Temperature: 40° C.
Method O1: Column: Zorbax Eclipse C18 4.6×50 mm, 1.8 µm; Mobile Phase A: acetonitrile; Mobile Phase B: 0.1% formic acid in water; Time (min)/% B: 0/80, 0.5/80, 1.5/5, 5.5/5, 6/80, 7/80; Flow: 0.7 mL/min
Method P1: Column: Symmetry C-18, 2.1×50 mm 5 µm; Mobile Phase A: 0.1% formic acid in acetonitrile; Mobile Phase B: 0.1% formic acid in water; Time (min)/% B: 0/90, 1.5/90, 2/15, 5.5/5, 6/90, 7/90; Flow: 0.5 mL/min, Column Temperature: 40° C.
Method Q1: Column: X-Bridge C18 4.6×75 mm 3.5 µm; Mobile Phase A: 0.1% formic acid in acetonitrile:water (90: 10); Mobile Phase B: 0.1% formic acid in water:acetonitrile (90:10); Time (min)/% B: 0/90, 1/90, 2/50, 4/5, 7.5/5, 8.0/90; Flow: 0.8 mL/min; Column Temperature: 40° C.
Method R1: Column: XBRIDGE-C18 4.6×75 mm 3.5 µm; Mobile Phase A: acetonitrile; Mobile Phase B: 5 mM ammonium acetate; Time (min)/% B: 0/100, 2/100, 2.8/55, 3.2/5, 6.8/5, 7.5/100; Flow: 0.8 mL/min; Column Temperature: 40° C.
Method S1: Column: X-Bridge C18 4.6×75 mm 3.5 µm; Mobile Phase A: acetonitrile:water (90:10) 0.1% formic acid; Mobile Phase B: water:acetonitrile (90:10) 0.1% formic acid; Time (min)/% B: 0/90, 1/90, 2.0/50, 4/5, 6.5/5, 8/90; Flow: 0.8 mL/min; Column Temperature: 40° C.
Method T1: Column: XBRIDGE-C18 4.6×75 mM 3.5 µM; Mobile Phase A: acetonitrile; Mobile Phase B: 5 mM ammonium acetate; Time (min)/% B: 0/100, 2/100, 2.8/5, 6.8/5, 7.5/100; Flow: 0.8 mL/min; Column Temperature: 40° C.
Method U1: Column: Symmetry-C18 2.1×50 mm 3.5 µm; Mobile Phase A: acetonitrile; Mobile Phase B: 0.1% formic acid in water; Time (min)/% B: 0/90, 1.5/90, 2/15, 5.5/15, 6/90, 7/90; Flow: 0.5 mL/min; Column Temperature: 45° C.
Method V1: Column: X-Bridge C18 4.6×75 mm 3.5 µm; Mobile Phase A: acetonitrile:water (90:10) 0.1% formic acid; Mobile Phase B: water:acetonitrile (90:10) 0.1% formic acid in water; Time (min)/% B: 0/100, 1/100, 1.8/50, 3.1/5, 7/5, 7.01/100; Flow: 0.8 mL/min; Column Temperature: 40° C.
Method W1: Column: X-Bridge C18 4.6×75 mm 3.5 µm; Mobile Phase A: acetonitrile:water (90:10) 0.1% formic acid; Mobile Phase B: water:acetonitrile (90:10) 0.1% formic acid in water; Time (min)/% B: 0/100, 1/100, 2.0/50, 4/5, 7.5/5, 8/100; Flow: 0.8 mL/min; Column Temperature: 40° C.
Method X1: Column: XBridge-C18 4.6×75 mm 3.5 µm; Mobile Phase A: acetonitrile, Mobile Phase B: 5 Mm ammonium acetate; Time (min)/% B: 0/100, 2/55, 2.8/5, 6.8/5, 7.5/100; Flow: 0.8 ml/min; Column Temperature: 40° C.
Method Y1: Column: X-Bridge C18 4.6×75 mm 3.5 µm; Mobile Phase A: acetonitrile:water (90:10) 0.1% formic acid; Mobile Phase B: water:acetonitrile (90:10) 0.1% formic acid in water; Time (min)/% B: 0/100, 1/100, 1.8/50, 3.1/5, 7/5, 7.01/100; Flow: 0.8 mL/min; Column Temperature: 40° C.
Method Z1: Column: Symmetry-C18 2.1×50 mm 3.5 µm; Mobile Phase a: 0.1% formic acid in acetonitrile; Mobile Phase B: 0.1% formic acid in water; Time (min)/% B: 0/90, 0.5/90, 2.0/55, 3.0/55, 3.5/10, 6.0/10, 7.0/90; Flow: 0.5 mL/min; Column Temperature: 45° C.
Method A2: Column: Symmetry-C18 2.1×50 mm 3.5 µm; Mobile Phase A: acetonitrile; Mobile Phase B: 0.1% formic acid in water; Time (min)/% B: 0/90, 1.5/90, 2/15, 4.5/15, 6.5/90, 7.0/90; Flow: 0.5 mL/min; Column Temperature: 45° C.
Method B2: Column: Symmetry-C18 2.1×50 mm 3.5 µm; Mobile Phase A: acetonitrile; Mobile Phase B: 0.1% formic acid in water; Time (min)/% B: 0/90, 1.5/90, 2/15, 5.5/15, 6.5/90, 7/90; Flow: 0.5 mL/min; Column Temperature: 45° C.

Preparation of Intermediates and Examples

Intermediate 1: (R)-(1-(5,6-Diaminopyridin-2-yl) piperidin-3-yl)(pyrrolidin-1-yl)methanone dihydrochloride Step 1: (R)-tert-Butyl 3-(pyrrolidine-1-carbonyl) piperidine-1-carboxylate To a solution of (R)-1-(tert-butoxycarbonyl)piperidine-3-carboxylic acid (50.64 g, 220.9 mmol) in anhydrous tetrahydrofuran (552 mL) at 2° C. was added 1,1'-carbonyldiimidazole (77.59 g, 460 mmol). The mixture was stirred at room temperature for 2 h, cooled to 10° C. and then pyrrolidine (74 mL, 890 mmol) was added slowly. The reaction mixture was stirred at room temperature for 18 h. The solvent was removed under reduced pressure and water (200 mL) was added to the residue. The mixture was extracted with ethyl acetate (2×). The combined organics were washed with aqueous hydrochloric acid (200 mL×4, 1N) and with a saturated aqueous solution of sodium bicarbonate (200 mL×2). The organics were dried over magnesium sulfate, filtered and concentrated under reduced pressure to afford (R)-tert-butyl 3-(pyrrolidine-1-carbonyl)piperidine-1-carboxylate as a white solid (58.82 g). The compound was used for the next step without further purification. $^1$H NMR (400 MHz, CD$_3$OD) δ 1.39-1.54 (m, 10H) 1.59-1.65 (m, 1H) 1.67 (d, 1H) 1.69-1.77 (m, 1H) 1.80-2.05 (m, 5H) 2.58 (tt, 1H) 2.77 (br s, 1H) 3.33-3.46 (m, 2H) 3.51-3.66 (m, 2H) 3.98-4.12 (m, 2H); MS (AP+) (M+H) 283.3.

Step 2: (R)-Piperidin-3-yl(pyrrolidin-1-yl)methanone hydrochloride

To a solution of (R)-tert-butyl 3-(pyrrolidine-1-carbonyl) piperidine-1-carboxylate (58.82 g, 208.3 mmol) in anhydrous dichloromethane (100 mL) was added hydrogen chloride in 1,4-dioxane (260 mL, 1040 mmol, 4M). The reaction mixture was stirred vigorously at room temperature for 1 h. The solvent was removed under reduced pressure and the residue was left standing overnight at room temperature. The residue was triturated with ether (250 mL). The ether was decanted and dichloromethane was added followed by sonication in a warm bath. The solvent was removed under reduced pressure and the resulting solid was placed under high vacuum at 40° C. for 1 h to afford (R)-piperidin-3-yl(pyrrolidin-1-yl)methanone hydrochloride (48.41 g). The material was used for the next step without further purification. $^1$H NMR (400 MHz, CD$_3$OD) δ 1.75-2.05 (m, 8H) 3.04-3.17 (m, 2H) 3.19-3.28 (m, 3H) 3.35-3.66 (m, 4H); MS (ES+) (M+H) 183.3.

Step 3: (R)-(1-(6-Amino-5-nitropyridin-2-yl)piperidin-3-yl)(pyrrolidin-1-yl)methanone To a suspension of (R)-piperidin-3-yl(pyrrolidin-1-yl)methanone hydrochloride (45.56 g, 208.3 mmol) in anhydrous acetonitrile (200 mL) at 10° C. was added triethylamine (50 mL). The suspension was poured into a 2 L 3-neck flask equipped with a thermometer and a magnetic stirrer. To the original flask was added anhydrous acetonitrile followed by sonication and addition of triethylamine (80 mL). The suspensions were combined and cooled to 10° C. and 6-chloro-3-nitropyridin-2-amine (32.97 g, 190 mmol) was added. The bright yellow solution was stirred under nitrogen while the temperature was increased gradually to 80° C. over 1 h. The reaction mixture was cooled to room temperature. The resulting suspension was filtered and the solids were rinsed with ethyl acetate. The filtrate was concentrated under reduced pressure. A saturated aqueous solution of ammonium chloride (500 mL) was added to the residue and the mixture was extracted into ethyl acetate (2×). The combined organics were washed with brine, dried over magnesium sulfate, filtered, concentrated under reduced pressure and dried for 18 h under high vacuum to afford (R)-(1-(6-amino-5-nitropyridin-2-yl)piperidin-3-yl)(pyrrolidin-1-yl)methanone as a yellow foam (63.51 g). $^1$H NMR (400 MHz, CD$_3$OD) δ 1.47-1.64 (m, 1H) 1.71-2.07 (m, 7H) 2.68 (tt, 1H) 3.01 (q, 2H) 3.33-3.46 (m, 2H) 3.52 (dt, 1H) 3.60-3.70 (m, 1H) 4.41 (br s, 1H) 4.71 (d, 1H) 6.23 (d, 1H) 8.05 (d, 1H); MS (ES+) (M+H) 320.4.

Step 4: (R)-(1-(5,6-Diaminopyridin-2-yl)piperidin-3-yl)(pyrrolidin-1-yl)methanone dihydrochloride Into a Parr bottle was added 10% palladium-on-carbon (50% wet, 1487.2 mg) followed by ethanol (10 mL) which was previously bubbled with nitrogen and cooled to 0° C. with an ice-water bath. (R)-(1-(6-Amino-5-nitropyridin-2-yl)piperidin-3-yl)(pyrrolidin-1-yl)methanone (10.612 g, 33.228 mmol) in ethanol (84 mL) was added into the Parr bottle followed by concentrated hydrochloric acid (8.59 mL, 99.6 mmol) dissolved in ethanol (10 mL) under a nitrogen atmosphere. The reaction mixture was purged with nitrogen and evacuated 3 times. The mixture was submitted to a hydrogen atmosphere (45 PSI). A drop in pressure was observed and it was increased to 46 PSI. This process was repeated several times over a period of 30 minutes. The reaction mixture was shaken for a total of 1 h. Then it was filtered through Celite and the residue was rinsed with ethanol (1 L). The solvent was removed under reduced pressure and the residue was redissolved in methanol. The solvent was removed under reduced pressure and the solid was dried under high vacuum to afford the title compound (12.0 g). The material was used without further purification. $^1$H NMR (400 MHz, CD$_3$OD) δ 1.67-1.81 (m, 2H) 1.83-2.10 (m, 6H) 2.85-2.95 (m, 1H) 3.32-3.55 (m, 5H) 3.66 (dt, 1H) 3.89 (d, 1H) 3.97 (dd, 1H) 6.38 (d, 1H) 7.64 (d, 1H); MS (ES+) (M+H) 290.2.

Alternative preparation of (R)-(1-(5,6-diaminopyridin-2-yl)piperidin-3-yl)(pyrrolidin-1-yl)methanone To a solution of (R)-(1-(6-amino-5-nitropyridin-2-yl)piperidin-3-yl)(pyrrolidin-1-yl)methanone (150 mg, 0.47 mmol) in ethanol (20 mL) was added 10% palladium-on-carbon (100 mg). The reaction mixture was stirred under a hydrogen atmosphere using a balloon filled with hydrogen gas for 2 h at room temperature. The reaction mixture was filtered through Celite and the residue was rinsed with ethanol under a nitrogen atmosphere. The filtrate was used without further purification.

Alternative preparation for (R)-(1-(6-Amino-5-nitropyridin-2-yl)piperidin-3-yl)(pyrrolidin-1-yl)methanone (Intermediate 1, Steps 1-3)

Step 1: (R)-tert-Butyl 3-(pyrrolidine-1-carbonyl)piperidine-1-carboxylate (R)-1-(tert-Butoxycarbonyl)piperidine-3-carboxylic acid (6.0 kg, 26 mol) was added in portions to a mixture of 1,1'-carbonyldiimidazole (5.1 kg, 31 mol) in tetrahydrofuran (48 L) at a temperature of 18-22° C. The mixture was held at this temperature for 3 h, then pyrrolidine (2.28 kg, 32 mol) was added while maintaining a temperature of 18-25° C., and the resulting reaction mixture was held at this temperature for 2 h. Cyclohexane (48 L) and aqueous potassium carbonate solution (prepared from 4.8 kg potassium carbonate and 48 L water) were then added sequentially, and the mixture was stirred for 30 min before separation of the layers. The organic layer was then washed with another portion of aqueous potassium carbonate solution (prepared from 4.8 kg potassium carbonate and 48 L water). The combined aqueous layers were extracted with cyclohexane (30 L). The combined organic layers were then washed with aqueous sodium chloride solution (prepared from 3.0 kg sodium chloride and 30 L water). The organic layer was dried over sodium sulfate (2.0 kg), then the cyclohexane was removed by distillation under reduced pressure at 45° C. Isopropanol (43 L) was added and the mixture was stirred for 30 min. The presence of (R)-tert-butyl 3-(pyrrolidine-1-carbonyl)piperidine-1-carboxylate was confirmed by HPLC analysis: HPLC retention time: 5.98 min (Column: Halo C18, 4.6×150 mm, 2.7 μm; Mobile Phase A: 0.1% orthophosphoric acid and 2% acetonitrile in water, Mobile Phase B: acetonitrile; Gradient: 20% B to 90% B over 7 min, then held for 3 min; Flow: 0.8 mL/min; Temperature: 25° C.; UV detection at 210 and 226 nM). This material was used in the next step without further purification.

Step 2: (R)-Piperidin-3-yl(pyrrolidin-1-yl)methanone hydrochloride

Over a period of 1 h, hydrochloric acid (9.8 kg) was added to the solution of (R)-tert-butyl 3-(pyrrolidine-1-carbonyl)piperidine-1-carboxylate in isopropanol from the previous step, maintaining a temperature of 20-25° C. The reaction mixture was heated to 50-55° C. and was held at that temperature for 6 h. Solvent was removed by distillation under reduced pressure at 50° C. Four cycles of solvation and then distillation under reduced pressure at 50° C. were conducted sequentially: isopropanol (2×14.5 L), toluene (18.5 L), and tetrahydrofuran (12.0 L). Another portion of tetrahydrofuran (12.0 L) was added and the mixture was stirred at 25-30° C. for 1 h. The mixture was centrifuged and the mother liquor was removed; the resulting cake was washed with tetrahydrofuran (3.7 L), then was dried at 40-50° C. to afford (R)-piperidin-3-yl(pyrrolidin-1-yl)methanone hydrochloride (4.8 kg, 84% over two steps). HPLC retention time: 1.67 min (Column: Halo C18, 4.6×150 mm, 2.7 μm; Mobile Phase A: 0.1% orthophosphoric acid and 2% acetonitrile in water, Mobile Phase B: acetonitrile; Gradient: 20% B to 90% B over 7 min, then held for 3 min; Flow: 0.8 mL/min; Temperature: 25° C.; UV detection at 210 and 226 nM).

Step 3: (R)-(1-(6-Amino-5-nitropyridin-2-yl)piperidin-3-yl)(pyrrolidin-1-yl)methanone Triethylamine (4.65 kg, 46 mol) was added over a period of 1 h to a mixture of (R)-piperidin-3-yl(pyrrolidin-1-yl)methanone hydrochloride (4.8 kg, 22 mol) and acetonitrile (48 L), maintaining a temperature of 15-20° C. The mixture was held at that temperature for 30 min, then was warmed to 38-42° C. 6-Chloro-3-nitropyridin-2-amine (3.8 kg, 22 mol) was added portion-wise, and the mixture was held at 38-42° C. for 3 h. The mixture was then cooled to 15-20° C. and an aqueous solution of ammonium chloride (prepared from 6.24 kg ammonium chloride and 48 L water) and ethyl acetate (48 L) were added sequentially, and the layers were stirred and then separated. The aqueous layer was further extracted with ethyl acetate (2×24 L). The combined organic layers were washed with an aqueous solution of sodium chloride (prepared from 4.8 kg sodium chloride and 24 L water) and then were dried with sodium sulfate (1.92 kg). The organic layer was removed and solvent was evaporated under reduced pressure at 40° C. Ethyl acetate (14.4 L) was added to the crude product, and the mixture was heated to 35-40° C. and was held at that temperature for 15 min. The mixture was cooled to 20-25° C. and held at that temperature for 6 h, then cooled to 10-15° C. and held at that temperature for 1 h. The suspension was centrifuged and the mother liquor was removed. The resulting cake was washed with chilled ethyl acetate (4.8 L) and then was dried at 40-50° C. to afford (R)-(1-(6-amino-5-nitropyridin-2-yl)piperidin-3-yl)(pyrrolidin-1-yl)methanone (4.6 kg, 66%). HPLC retention time: 5.30 min (Column: Halo C18, 4.6×150 mm, 2.7 μm; Mobile Phase A: 0.1% orthophosphoric acid and 2% acetonitrile in water, Mobile Phase B: acetonitrile; Gradient: 20% B to 90% B over 7 min, then held for 3 min; Flow: 0.8 mL/min; Temperature: 25° C.; UV detection at 210 and 226 nM). Melting point: 118.5-123.5° C. Water content by Karl Fischer titration: 0.36% by weight.

Intermediate 2: (R)-(1(4,5-Diaminopyrimidin-2-yl)piperidin-3-yl)(pyrrolidin-1-yl)methanone dihydrochloride

Step 1: (R)-(1-(4-Amino-5-nitropyrimidin-2-yl)piperidin-3-yl)(pyrrolidin-1-yl)methanone A mixture of 2-chloro-5-nitropyrimidin-4-amine (670 mg, 3.84 mmol, 80% pure), (R)-piperidin-3-yl(pyrrolidin-1-yl)methanone hydrochloride (prepared by the method described in Steps 1 and 2 of Intermediate 1, 560 mg, 2.56 mmol) and triethylamine (0.761 mL, 5.46 mmol) in dimethylsulfoxide (5 mL) was heated to 100° C. for 5 h. The mixture was diluted with ethyl acetate (80 mL), washed with water and brine, dried over sodium sulfate and concentrated. The crude material was purified via flash chromatography (ethyl acetate/heptane: 40-70-100%) to afford (R)-(1-(4-amino-5-nitropyrimidin-2-yl)piperidin-3-yl)(pyrrolidin-1-yl)methanone as a yellow solid (420 mg). $^1$H NMR (500 MHz, DMSO-d$_6$) δ 1.45 (t, 1H), 1.62 (d, 1H), 1.72-1.82 (m, 4H), 1.88 (d, 4H), 2.56 (br s, 1H), 2.90-3.04 (m, 2H), 3.28 (t, 2H), 3.37-3.62 (m, 2H), 4.59-4.87 (m, 2H), 8.00 (br s, 1H), 8.16 (br s, 1H), 8.90 (s, 1H); MS (ES+) (M+H) 321.2.

Step 2: (R)-(1-(4,5-Diaminopyrimidin-2-yl)piperidin-3-yl)(pyrrolidin-1-yl)methanone dihydrochloride Concentrated hydrochloric acid (470 μL, 37 wt % aq) was added to a solution of (R)-(1-(4-amino-5-nitropyrimidin-2-yl)piperidin-3-yl)(pyrrolidin-1-yl)methanone (380 mg, 1.13 mmol) in methanol (30 mL). The solution was hydrogenated using the H-Cube (10% Pd/C, full H$_2$, 18° C., 1 mL/min). A second cycle was run using the same conditions. The solvent was removed under reduced pressure and the residue was co-evaporated with toluene several times to afford the title compound as a yellow solid (405 mg). The material was used without further purification. $^1$H NMR (CD$_3$OD) δ 1.68 (d, 1H), 1.81 (d, 1H), 1.91 (quin, 3H), 1.96-2.09 (m, 3H), 2.84 (t, 1H), 3.34-3.47 (m, 4H), 3.52-3.59 (m, 1H), 3.61-3.70 (m, 1H), 4.32 (d, 1H), 4.17 (d, 1H), 7.70 (s, 1H); MS (ES+) (M+H) 291.2.

Alternative preparation for (R)-(1-(4,5-diaminopyrimidin-2-yl)piperidin-3-yl)(pyrrolidin-1-yl)methanone To a stirred solution of (R)-(1-(4-amino-5-nitropyrimidin-2-yl)piperidin-3-yl)(pyrrolidin-1-yl)methanone (300 mg, 0.937 mmol) in ethanol (15 mL) was added under a nitrogen atmosphere a suspension of 10% palladium-on-carbon (300 mg) in ethanol. The reaction mixture was hydrogenated using a balloon filled with hydrogen gas for 2 h at room temperature. The suspension was filtered through Celite and the filtrate was used without further purification.

Intermediate 3: 1-(4-Methyl-1H-pyrazol-1-yl)cyclopropanecarboxylic acid

Step 1: tert-Butyl 1-(4-methyl-1H-pyrazol-1-yl)cyclopropanecarboxylate

Into a 25 mL round bottom flask were added sodium hydride (60% dispersion in mineral oil, 164.3 mg, 4.1 mmol) and anhydrous tetrahydrofuran (8 mL). The mixture was cooled with an ice-water bath before a solution of 4-methylpyrazole (204.2 mg, 2.487 mmol) in anhydrous tetrahydrofuran (2 mL) was added. The mixture was stirred in the ice-water bath for 30 minutes before tert-butyl 2,4-dibromobutanoate (0.48 mL, 2.2 mmol) was added dropwise at 0° C. The reaction mixture was stirred at 0° C. for 30 minutes and then at room temperature for 18 h. The solvent was removed under reduced pressure and water and ethyl acetate were added to the residue. The layers were separated and the aqueous layer was extracted with ethyl acetate (3×). The combined organics were dried over magnesium sulfate, filtered and concentrated under reduced pressure. The crude material was purified via flash chromatography (0-50% ethyl acetate in heptanes) to afford tert-butyl 1-(4-methyl-1H-pyrazol-1-yl)cyclopropanecarboxylate (218 mg, 44%). $^1$H NMR (400 MHz, CDCl$_3$) δ 1.33 (s, 9H), 1.45-1.51 (m, 2H), 1.61-1.67 (m, 2H)H), 1.98-2.01 (m, 3H)H), 7.21 (s, 1H), 7.23-7.26 (m, 1H).

Step 2: 1-(4-Methyl-1H-pyrazol-1-yl)cyclopropanecarboxylic acid

Into a 100 mL pear shaped flask containing tert-butyl 1-(4-methyl-1H-pyrazol-1-yl)cyclopropanecarboxylate (218 mg, 0.981 mmol) were added dichloromethane (5 mL) and trifluoroacetic acid (0.2 mL, 3 mmol). The clear solution was stirred at room temperature for 30 minutes after which another 0.3 mL of trifluoroacetic acid were added. The mixture was stirred at room temperature for 45 minutes and another 0.3 mL of trifluoroacetic acid were added. The mixture was stirred at room temperature for 18 h. The solvent and excess of trifluoroacetic acid were removed under reduced pressure to afford the title compound (360 mg). The material was used without further purification. $^1$H NMR (400 MHz, CDCl$_3$) δ 1.78 (m, 2H), 2.02 (m, 2H), 2.17 (s, 3H), 7.54 (s, 1H), 7.74 (s, 1H).

Intermediate 4:
1-(4-Fluoro-1H-pyrazol-1-yl)cyclopropanecarboxylic acid

Step 1: Benzyl 1-(4-fluoro-1H-pyrazol-1-yl)cyclopropanecarboxylate

To a solution of 4-fluoropyrazole (125 mg, 1.45 mmol) in tetrahydrofuran (4 mL) at 0° C. was added sodium hydride (60% suspension in mineral oil, 116 mg, 2.90 mmol). The mixture was stirred at 0° C. for 40 min before benzyl 2,4-dibromobutyrate (0.30 mL, 1.50 mmol) was added dropwise. The reaction mixture was stirred at room temperature for 18 h. The reaction mixture was diluted with ethyl acetate and washed with water and brine. The organics were dried over sodium sulfate, filtered and concentrated under reduced pressure. The residue was purified via flash chromatography to afford benzyl 1-(4-fluoro-1H-pyrazol-1-yl)cyclopropanecarboxylate as a clear oil (115 mg, 30.4%). $^1$H NMR (400 MHz, CDCl$_3$) δ 1.64-1.70 (m, 2H), 1.81-1.86 (m, 2H), 5.14 (s, 2H), 7.22-7.26 (m, 2H), 7.31-7.36 (m, 3H), 7.40 (td, 2H).

Step 2: 1-(4-Fluoro-1H-pyrazol-1-yl)cyclopropanecarboxylic acid

A solution of benzyl 1-(4-fluoro-1H-pyrazol-1-yl)cyclopropanecarboxylate (115 mg, 0.442 mmol) in methanol (20 mL) was hydrogenated using the H-Cube (full H2, room temperature). The solvent was removed under reduced pressure to afford the title compound as a solid (70 mg). MS (AP+) (M+H) 171.4; LCMS retention time 1.06 minutes (Method M).

Intermediate 5:
1-(4-Cyano-1H-pyrazol-1-yl)cyclopropanecarboxylic acid

The title compound was prepared by a method analogous to Intermediate 4 but using 1H-pyrazole-4-carbonitrile in Step 1. $^1$H NMR (400 MHz, CDCl$_3$) δ 1.65 (m, 2H), 1.89 (m, 2H), 7.80 (s, 1H), 8.02 (s, 1H); MS (ES−) (M−H) 176.4, LCMS retention time: 1.04 minutes (Method M).

Intermediate 6: 1-(4-Cyclopropyl-1H-pyrazol-1-yl)cyclopropanecarboxylic acid

Step 1: Benzyl 1-(4-bromo-1H-pyrazol-1-yl)cyclopropanecarboxylate

Benzyl 1-(4-bromo-1H-pyrazol-1-yl)cyclopropanecarboxylate was prepared by a method analogous to Intermediate 4 using 4-bromo-1H-pyrazole in Step 1. $^1$H NMR (400 MHz, CDCl$_3$) δ 1.64-1.69 (m, 2H), 1.83-1.88 (m, 2H), 5.14 (s, 2H), 7.21-7.25 (m, 2H), 7.31-7.38 (m, 3H), 7.50 (d, 1H), 7.56 (d, 1H).

Step 2: Benzyl 1-(4-cyclopropyl-1H-pyrazol-1-yl)cyclopropanecarboxylate

Into a 20 mL microwave vial were added benzyl 1-(4-bromo-1H-pyrazol-1-yl)cyclopropanecarboxylate (421 mg, 1.31 mmol), cyclopropyltrifluoroborate potassium salt (582 mg, 3.93 mmol), 1,1'-Bis(diphenylphosphino)ferrocene] dichloropalladium(II) complex with dichloromethane (42.5 mg, 0.052 mmol) and cesium carbonate (1710 mg, 5.24 mmol). The vial was sealed, evacuated and backflushed with nitrogen two times followed by the addition of tetrahydrofuran (7 mL). The reaction mixture was stirred at 80° C. for 18 h. The solvent was removed under reduced pressure and to the residue was added water (100 mL) and ethyl acetate. The layers were separated and the aqueous layer was extracted with ethyl acetate (2×). After the second extraction an emulsion formed that was cleared with the addition of brine, ethyl acetate and aqueous hydrochloric acid (1N). The aqueous layers were extracted again with ethyl acetate (2×), the solvent was removed under reduced pressure and the residue was purified via flash chromatography (0-100% ethyl acetate in heptanes) to afford benzyl 1-(4-cyclopropyl-1H-pyrazol-1-yl)cyclopropanecarboxylate (91 mg, 25%). MS (ES+) (M+H) 283.3; LCMS retention time: 3.38 minutes (Method L).

Step 3: 1-(4-Cyclopropyl-1H-pyrazol-1-yl)cyclopropanecarboxylic acid

The title compound was prepared by a method analogous to Intermediate 4, Step 2. The material was used without further purification. MS (EI+) (M+) 192; GCMS retention time: 3.096 minutes (Method O).

Intermediate 7: 1-(4-(Trifluoromethyl)-1H-pyrazol-1-yl)cyclopropanecarboxylic acid The title compound was prepared by a method analogous to Intermediate 4 but using 4-(trifluoromethyl)-1H-pyrazole in Step 1. $^1$H NMR (400 MHz, CDCl$_3$) δ 1.60-1.79 (m, 2H), 1.83-1.95 (m, 2H), 7.75 (s, 1H), 7.78-7.89 (m, 1H), 11.82 (br s, 1H).

Intermediate 8:
1-(3-methylisoxazol-5-yl)cyclopropanecarboxylic acid

Step 1: Methyl 1-(3-methylisoxazol-5-yl)cyclopropanecarboxylate

Into a 15 mL round bottom flask was added methyl 2-(3-methylisoxazol-5-yl)acetate (250 mg, 1.61 mmol) dissolved in N,N-dimethylformamide (7 mL) followed by addition of sodium hydride (60% suspension in mineral oil, 322 mg, 8.06 mmol). The mixture was stirred at room temperature for 15 minutes. 1,2-Dibromoethane (417 µL, 4.83 mmol) was added dropwise. The reaction mixture was stirred at room temperature for 18 h. A saturated aqueous solution of sodium bicarbonate was added to the mixture and it was extracted with dichloromethane (3×). The combined organics were washed with brine, dried over sodium sulfate, filtered and concentrated under reduced pressure. The residue was dissolved in dichloromethane (1.5 mL) and washed (3×) with an aqueous (10%) lithium chloride solution to remove residues of N,N-dimethylformamide. The organics were dried over sodium sulfate, decanted and concentrated under reduced pressure to afford methyl 1-(3-methylisoxazol-5-yl)cyclopropanecarboxylate MS (ES+) (M+H) 182.0; LCMS retention time: 2.53 minutes (Method L). The material was used for the next step without further purification.

Step 2: 1-(3-Methylisoxazol-5-yl)cyclopropanecarboxylic acid

To methyl 1-(3-methylisoxazol-5-yl)cyclopropanecarboxylate (100 mg, 0.552 mmol) was added a solution of lithium hydroxide monohydrate (32 mg, 0.76 mmol) in methanol (2 mL) and water (1 mL). The reaction mixture was stirred at room temperature for 18 h. The solvent was reduced to about 1 mL in volume. A saturated aqueous solution of ammonium chloride (2 mL) was added followed by aqueous hydrochloric acid (1N) until pH was approximately 4. The mixture was extracted with ether (15 mL×2). The combined organics were dried over sodium sulfate, filtered and concentrated under reduced pressure to afford 1-(3-methylisoxazol-5-yl)cyclopropanecarboxylic acid as a white solid (43 mg, 47%). The material was used without further purification. MS (ES+) (M+H) 168.0; LCMS retention time: 2.0 minutes (Method L). $^1$H NMR (500 MHz, CD$_3$OD) δ 1.44-1.48 (m, 2H), 1.66-1.69 (m, 2H), 2.25 (s, 3H), 6.38 (s, 1H).

Intermediate 9: 1-(5-Methylisoxazol-3-yl)cyclopropanecarboxylic acid

The title compound was prepared by a method analogous to the one used for Intermediate 8, but using ethyl 5-methylisoxazole-3-carboxylate as the starting material. MS (ES+) (M+H) 168.0; LCMS retention time: 2.06 minutes. (Method L). $^1$H NMR (500 MHz, CD$_3$OD) δ 1.38-1.42 (m, 2H), 1.58-1.62 (m, 2H), 2.39 (s, 3H), 6.32 (s, 1H).

Intermediates 10 and 11: 1-(3-Methyl-1H-pyrazol-1-yl)cyclopropanecarboxylic acid and 1-(5-methyl-1H-pyrazol-1-yl)cyclopropanecarboxylic acid

Step 1: tert-Butyl 1-(3-methyl-1H-pyrazol-1-yl)cyclopropanecarboxylate and tert-butyl 1-(5-methyl-1H-pyrazol-1-yl)cyclopropanecarboxylate To a solution of 3-methylpyrazole (306 mg, 3.73 mmol) in tetrahydrofuran (10.0 mL) cooled to 0° C. was added sodium hydride (60% suspension in mineral oil, 242 mg, 6.05 mmol). The mixture was stirred at 0° C. for 40 minutes. tert-Butyl 2,4-dibromobutanoate (0.65 mL, 3.4 mmol) was added dropwise. The reaction mixture was stirred at room temperature for 2 h. The mixture was diluted with ethyl acetate, washed with water, dried over sodium sulfate, filtered and concentrated under reduced pressure. The residue was purified via flash chromatography (0-25% ethyl acetate in heptanes) to afford a mixture of two regioisomers, tert-butyl 1-(3-methyl-1H-pyrazol-1-yl)cyclopropanecarboxylate and tert-butyl 1-(5-methyl-1H-pyrazol-1-yl)cyclopropanecarboxylate (Total weight of mixture: 264 mg).

Step 2: 1-(3-Methyl-1H-pyrazol-1-yl)cyclopropanecarboxylic acid and 1-(5-methyl-1H-pyrazol-1-yl)cyclopropanecarboxylic acid To a solution of the regioisomers, prepared in the previous step, (320 mg, 1.44 mmol) in dichloromethane (2 mL) was added trifluoroacetic acid (1.0 mL, 13.0 mmol). The reaction mixture was stirred at room temperature for 18 h. The solvent was removed under reduced pressure. The residue was purified via HPLC to afford two regioisomers. Regioisomer 1 (Intermediate 10, 69 mg): $^1$H NMR (400 MHz, CDCl$_3$) δ 1.33-1.42 (m, 2H), 1.71 (d, 2H), 2.28 (s, 3H), 5.97 (dd, 1H), 7.31 (d, 1H). Regioisomer 2 (Intermediate 11, 82 mg): $^1$H NMR (400 MHz, CDCl$_3$) δ 1.30-1.37 (m, 2H), 1.59-1.66 (m, 2H), 2.22 (s, 3H), 5.96 (d, 1H), 7.36 (d, 1H).

Intermediate 12: 1-(1H-pyrazol-1-yl)cyclobutanecarboxylic acid

Step 1: Ethyl 1-(1H-pyrazol-1-yl)cyclobutanecarboxylate

Into a 50 mL round bottom flask was added sodium hydride (60% dispersion in mineral oil, 452 mg, 11 mmol) and anhydrous tetrahydrofuran (18 mL). To the mixture was added pyrazole (511.6 mg, 7.515 mmol) and anhydrous tetrahydrofuran (1 mL). The mixture was stirred at room temperature for 2 h and then cooled to 0° C. Ethyl 1-bromocyclobutanecarboxylate (1.3 mL, 7.5 mmol) was added dropwise. The reaction mixture was stirred at 0° C. for 45 minutes and at room temperature over three days. HMPA (1.35 mL, 7.5 mmol) was added and the mixture was stirred at room temperature for 2 h. The reaction mixture was warmed to 70° C. for 2 h followed by the addition of N,N-dimethylformamide (4 mL). The reaction mixture was stirred at 70° C. for another 2 h before more N,N-dimethylformamide (2 mL) was added and then stirred at 70° C. for 18 h. The solvent was removed under reduced pressure. To the residue was added water and extracted with a mixture of heptanes and ethyl acetate (3×). The combined organics were dried over magnesium sulfate, filtered and concentrated under reduced pressure. Flash chromatography (0-40% ethyl acetate in heptanes) provided impure ethyl 1-(1H-pyrazol-1-yl)cyclobutanecarboxylate (688 mg), which was used without further purification.

Step 2: 1-(1H-Pyrazol-1-yl)cyclobutanecarboxylic acid

To ethyl 1-(1H-pyrazol-1-yl)cyclobutanecarboxylate (688 mg, 3.54 mmol) were added tetrahydrofuran (8 mL) and water (0.9 mL). Aqueous sodium hydroxide (1N, 4 mL, 4 mmol) was added to the mixture. The reaction mixture was stirred at room temperature for 18 h. The solvent was removed under reduced pressure and to the residue was added aqueous hydrochloric acid (1N, 1 mL). The mixture was extracted with dichloromethane (3×). The combined organics were dried over magnesium sulfate, filtered and concentrated under reduced pressure to afford the title compound (108.9 mg). The material was used without further purification.

Intermediate 13: Ethyl 1-(pyrimidin-5-yl)cyclopropanecarbimidate hydrochloride

Step 1: 1-(Pyrimidin-5-yl)cyclopropanecarbonitrile

To a mixture of 2-(pyrimidin-5-yl)acetonitrile (104 mg, 0.873 mmol), dibromoethane (113 μL, 1.31 mmol) and tetrabutylammonium bromide (65 mg, 0.23 mmol) dissolved in toluene was added an aqueous solution of sodium hydroxide (50%, 500 mg in 0.5 mL of water, 12.5 mmol). The reaction mixture was stirred at room temperature for 16 h. The reaction mixture was diluted with ethyl acetate (2 mL), washed with water (0.5 mL×2) and brine (0.5 mL). The organics were dried over magnesium sulfate, filtered and concentrated under reduced pressure. The residue was purified via flash chromatography (0-80% ethyl acetate in heptanes) to afford 1-(pyrimidin-5-yl)cyclopropanecarbonitrile as a solid (28 mg, 22%). ¹H NMR (500 MHz, CDCl₃) δ 1.50-1.56 (m, 2H), 1.85-1.95 (m, 2H), 8.72 (s, 2H), 9.19 (s, 1H).

Step 2: Ethyl 1-(pyrimidin-5-yl)cyclopropanecarbimidate hydrochloride 1-(Pyrimidin-5-yl)cyclopropanecarbonitrile (28 mg, 0.19 mmol) was suspended into ethanol (2 mL) previously saturated with gaseous hydrogen chloride. Hydrogen chloride was bubbled for an additional 30 seconds through the mixture and the resulting mixture was stirred for 18 h at room temperature. The solvent was removed under a flow of nitrogen to afford the title compound as a white solid (43 mg) which was used without further purification. ¹H NMR (500 MHz, CD₃OD) δ 1.45 (t, 3H), 1.70-1.76 (m, 2H), 1.98-2.07 (m, 15H), 4.43 (q, 2H), 8.96 (s, 2H), 9.24 (s, 1H).

Intermediate 14: Ethyl 1-(isoxazol-3-yl)cyclopropanecarbimidate

Step 1: 1-(Isoxazol-3-yl)cyclopropanecarbonitrile

To a suspension of sodium hydride (136 mg, 5.39 mmol) in N,N-dimethylformamide (5 mL) was added a solution of 2-(isoxazol-3-yl)acetonitrile (233 mg, 2.16 mmol) in N,N-dimethylformamide (2.5 mL) at 0° C. After the addition, the mixture was warmed to room temperature and stirred for 1 h. The mixture was cooled to 0° C. and 1,2-dibromoethane (0.3 mL, 3.48 mmol) was added. The reaction mixture was stirred at 0° C. for 4 h. Water was added to the mixture. The mixture was extracted with ethyl acetate (3×). The combined organics were washed with water, washed with aqueous hydrochloric acid (1N), washed with aqueous sodium bicarbonate and brine. The organics were dried over sodium sulfate, filtered and concentrated under reduced pressure. The residue was dissolved with dichloromethane and washed with aqueous lithium chloride solution (10%). The organics were dried over sodium sulfate, filtered and concentrated under reduced pressure and dried under a stream of nitrogen to afford 1-(isoxazol-3-yl)cyclopropanecarbonitrile (243 mg). ¹H NMR (500 MHz, CDCl₃) δ 1.71-1.76 (m, 2H), 1.79-1.83 (m, 2H), 6.51 (s, 1H), 8.40 (s, 1H). The material was used without further purification.

Step 2: Ethyl 1-(isoxazol-3-yl)cyclopropanecarbimidate hydrochloride

Into an 8 mL vial containing 1-(isoxazol-3-yl)cyclopropanecarbonitrile (243 mg, 1.4 mmol) and ethanol (1.98 mL, 34 mmol) was added acetyl chloride (1.45 mL, 20.4 mmol) at 0° C. The reaction mixture was stirred for 18 h at room temperature. An aliquot was removed and the solvent evaporated; ¹H NMR showed the presence of product. ¹H NMR (500 MHz, CDCl₃) δ 1.44 (t, 3H), 1.74-1.79 (m, 2H), 2.16-2.20 (m, 2H), 4.77 (q, 2H), 6.35 (d, 1H), 8.46 (d, 1H). The reaction mixture was concentrated under reduced pressure to afford the title compound (203 mg). The material was used without further purification.

Intermediate 15: Methyl 1-(3-methoxyphenyl)cyclopropanecarbimidate hydrochloride Step 1: 1-(3-Methoxyphenyl)cyclopropanecarbonitrile To a mixture of 2-(3-methoxyphenyl)acetonitrile (100 mg, 0.679 mmol), 1,2-dibromoethane (88 μL, 1.02 mmol) and tetrabutylammonium bromide (50 mg, 0.16 mmol) in toluene (1.0 mL) was added an aqueous solution of sodium hydroxide (50%, 500 mg in 0.5 mL of water, 12.5 mmol) at room temperature. The reaction mixture was stirred at room temperature for 16 h. The reaction mixture was diluted with ethyl acetate (2 mL) and washed with water (0.5 mL×2) and brine (0.5 mL). The organics were dried over magnesium sulfate, filtered, concentrated under reduced pressure and dried under high vacuum. The residue was purified via flash chromatography (0-60% ethyl acetate in heptanes) to afford 1-(3-methoxyphenyl)cyclopropanecarbonitrile as an oil (56 mg, 48%). ¹H NMR (500 MHz, CDCl₃) δ 1.38-1.44 (m, 2H), 1.69-1.76 (m, 2H), 3.83 (s, 3H), 6.74-6.96 (m, 3H), 7.22-7.31 (m, 1H).

Step 2: Methyl 1-(3-methoxyphenyl)cyclopropanecarbimidate hydrochloride 1-(3-Methoxyphenyl)cyclopropanecarbonitrile (56 mg, 0.32 mmol) was dissolved into a saturated solution of hydrogen chloride in ethanol (1 mL). The reaction mixture was stored in the refrigerator (4° C.) for three days. The reaction mixture was concentrated under reduced pressure and dried under high vacuum. The residue was dissolved in ethanol (0.5 mL) and silica sulfuric acid (125 mg), prepared by following the literature (*Tetrahedron*, 2001, 57, 9509-9511), was added. The reaction mixture was stirred at room temperature for 2 h. The silica was filtered off and the filtrate was cooled to 0° C. and gaseous hydrogen chloride was bubbled through the solution for 30 seconds. The reaction mixture was stirred at room temperature for 18 h. The mixture was concentrated under reduced pressure to give an oil. The oil was dissolved into a solution of hydrogen chloride in methanol (1.25 M, 1 mL). Gaseous hydrochloric acid was bubbled into the solution and the mixture was stirred at room temperature for 18 h. The reaction mixture was concentrated under reduced pressure to afford the title compound as an oil (40 mg, 51%). The material was used without further purification.

Intermediate 16: Ethyl 1-(p-tolyl)cyclopropanecarbimidate hydrochloride

A saturated solution of hydrogen chloride in ethanol (2 mL) was prepared and was added to 1-(p-tolyl)cyclopropanecarbonitrile (100 mg, 0.64 mmol). The reaction mixture was stirred at room temperature for 16 h. The temperature of the reaction mixture was increased to 70° C. and the mixture was stirred at that temperature for 2 h and then allowed to cool to room temperature. The reaction mixture was left stirring at room temperature for another 16 h. The solvent was removed under reduced pressure and the residue was dried under high vacuum. The material was used without further purification.

Intermediate 17: Ethyl 2-(ethoxy(imino)methyl)-6-methoxyisonicotinate

Step 1: Ethyl 2-chloro-6-methoxyisonicotinate

To a previously sonicated suspension of 2-chloro-6-methoxyisonicotinic acid (4.0 g, 21 mmol) in ethanol (50 mL) was added thionyl chloride (4.64 mL, 64.0 mmol) at 0° C. The reaction mixture was stirred at 0° C. for 2 h and then at room temperature for 18 h. Thionyl chloride (4.64 mL, 64.0 mmol) was slowly added and the mixture was stirred at room temperature for 4 h. The reaction mixture was quenched by slowly pouring into a saturated aqueous solution of sodium bicarbonate (200 mL). Ice was added to the mixture to lower the temperature. The mixture was extracted with diethyl ether (150 mL×2). The combined organics were washed with brine, dried over sodium sulfate, filtered and concentrated under reduced pressure to afford a clear syrup as crude product. The crude product was dried for 2 h under high vacuum while heating to 80° C. The resulting residue was concentrated from toluene (500 mL) to afford ethyl 2-chloro-6-methoxyisonicotinate as an off white solid (3.205 g). $^1$H NMR (400 MHz, CDCl$_3$) δ 1.40 (s, 3H), 3.98 (s, 3H), 4.39 (s, 2H), 7.22 (s, 1H), 7.44 (s, 1H).

Step 2: 2-Cyano-6-methoxyisonicotinic acid

Into an oven-dried microwave vial was added ethyl 2-chloro-6-methoxyisonicotinate (0.6 g, 2.78 mmol), zinc cyanide (392 mg, 3.34 mmol), zinc dust (36.4 mg, 0.2 mmol) and N,N-dimethylacetamide (10 mL). The vial was capped, evacuated, and filled with nitrogen. This process was repeated 3 times. Then the cap of the vial was removed and bis(tri-t-butylphosphine)palladium(0) (142 mg, 0.278 mmol) was added. The vial was capped again, evacuated, and filled with nitrogen (3×). The reaction mixture was heated to 95° C. and left stirring for 18 h. The reaction mixture was diluted with ethyl acetate (100 mL) and filtered through Celite. The filtrate was poured into a saturated aqueous solution of sodium bicarbonate (100 mL). Then the mixture was extracted with ethyl acetate (50 mL×3). The combined organics were washed with a saturated aqueous solution of ammonium chloride, washed with brine and dried over sodium sulfate. The solvent was removed under reduced pressure and the residue was purified via flash chromatography to afford 2-cyano-6-methoxyisonicotinic acid (260 mg, 45.3%) as a white solid. $^1$H NMR (400 MHz, CDCl$_3$) δ 1.42 (s, 3H), 4.01 (s, 3H), 4.43 (s, 2H), 7.53 (s, 1H), 7.82 (s, 1H).

Step 3: Ethyl 2-(ethoxy(imino)methyl)-6-methoxyisonicotinate

Sodium metal (previously rinsed with heptanes, 10 mg, 0.44 mmol) was added into a flask containing anhydrous ethanol (2.0 mL) cooled with an ice-water bath. Evolution of gas was observed immediately after addition. The sodium ethoxide formed was added to a stirring suspension of 2-cyano-6-methoxyisonicotinic acid (150 mg, 0.727 mmol) in anhydrous ethanol (5.0 mL) at room temperature under nitrogen. The reaction mixture was sonicated for 5 minutes, stirred at 0° C. for 30 minutes and then warmed to room temperature over a period of 30 minutes. GCMS analysis (MS (EI+) (M+) 252; GCMS retention time 3.601 minutes, Method O) of the mixture showed conversion of the starting material to the title compound. The reaction mixture was used without further purification.

Intermediate 18: Ethyl 2-(ethoxy(imino)methyl)-6-ethylisonicotinate

The title compound was prepared by a method analogous to Intermediate 17 but using ethyl 2-chloro-6-ethylisonicotinate as the starting material. GCMS analysis of the reaction mixture showed the presence of the desired product. MS (EI+) (M+) 250; GCMS retention time 3.611 minutes (Method O).

Intermediate 19: Ethyl 2-cyclopropylpyrimidine-4-carbimidate

Step 1: 2-Cyclopropylpyrimidine-4-carbonitrile

To a solution of 2-cyclopropylpyrimidine-4-carbaldehyde (29.13 g, 196.6 mmol) in N,N-dimethylformamide (200 mL) was added hydroxylamine hydrochloride (13.9 g, 197 mmol) followed by triethylamine (35 mL, 250 mmol) dissolved in N,N-dimethylformamide (40 mL) at room temperature. A 50% solution of propylphosphonic anhydride in N,N-dimethylformamide (140 mL, 230 mmol) was added and the reaction mixture was stirred at 110° C. for 18 h. The reaction mixture was cooled to room temperature and a saturated aqueous solution of sodium bicarbonate was added with ethyl acetate. The mixture was stirred vigorously and solid sodium bicarbonate was added. The mixture was filtered to remove undissolved solids and the layers were separated. The aqueous layer was extracted with ethyl acetate (3×) The combined organics were washed with water and brine, dried over sodium sulfate, filtered, and concentrated under reduced pressure, and the resulting residue was dried under high vacuum to afford 2-cyclopropylpyrimidine-4-carbonitrile (20.97 g). The material was used without further purification. $^1$H NMR (400 MHz, CDCl$_3$) δ 1.15-1.22 (m, 4H), 7.36 (s, 1H), 8.76 (s, 1H).

Step 2: Ethyl 2-cyclopropylpyrimidine-4-carbimidate

To a solution of 2-cyclopropylpyrimidine-4-carbonitrile (20.97 g, 144.5 mmol) in ethanol (100 mL) was added sodium ethoxide (1.8 g, 78.9 mmol of sodium metal in 30 mL of ethanol). The reaction mixture was stirred at room temperature for 30 minutes. Diethyl ether (300 mL) was added to the reaction mixture followed by a saturated aqueous solution of ammonium chloride (50 mL). The mixture was extracted with diethyl ether (100 mL×3). The combined organics were washed with brine (50 mL×2), dried over magnesium sulfate, filtered, concentrated under reduced pressure and dried under high vacuum to afford the title compound. The material was used without further purification. $^1$H NMR (500 MHz, CDCl$_3$) δ 1.10-1.15 (m, 2H), 1.16-1.22 (m, 2H), 1.43 (t, 3H), 2.32 (tt, 1H), 4.44 (q, 2H), 7.50 (d, 1H), 8.72 (d, 1H).

Intermediate 20: Ethyl 1-(4-(trifluoromethyl)phenyl) cyclopropanecarbimidate hydrochloride Into a 4 mL vial was added 1-(4-(trifluoromethyl)phenyl) cyclopropanecarbonitrile (21 mg, 0.1 mmol), ethanol (70 µL) and acetyl chloride (56 µL, 0.792 mmol). The reaction mixture was stirred at room temperature for 18 h. The solvent was removed under reduced pressure to afford the title compound as a white solid (30 mg). The material was used without further purification. $^1$H NMR (500 MHz, CD$_3$OD) δ 1.45 (t, 3H), 1.61-1.66 (m, 2H), 1.95-2.00 (m, 2H), 4.44 (d, 2H), 7.70 (d, 2H), 7.75 (d, 2H).

Intermediate 21: 6-(3-Hydroxyoxetan-3-yl)picolinaldehyde

Step 1: 2-Bromo-6-(1,3-dioxolan-2-yl)pyridine

To a solution of 6-bromopyridine-2-carbaldehyde (3 g, 16.22 mmol) in toluene (60 mL) was added ethylene glycol (4.97 g, 80.2 mmol) and p-toluenesulphonic acid (0.152 g, 0.8 mmol). The reaction mixture was refluxed for 3 h. The solvent was removed under reduced pressure to afford the crude which was dissolved in ethyl acetate and washed with water. The organic layers were washed with a brine solution, and dried over sodium sulfate. The solvent was removed under reduced pressure to afford 2-bromo-6-(1,3-dioxolan-2-yl)pyridine (3.7 g). The material was used for the next step without further purification.

Step 2: 3-(6-(1,3-Dioxolan-2-yl)pyridin-2-yl)oxetan-3-ol

To a solution of 2-bromo-6-(1,3-dioxolan-2-yl)pyridine (2.49 g, 10.8 mmol) in anhydrous tetrahydrofuran (40 mL) was added a solution of n-butyllithium (2.5 M, 4.3 mL, 10.8 mmol) at −78° C. After stirring for 30 min., a solution of oxetan-3-one (0.6 g, 8.32 mmol) in anhydrous tetrahydrofuran (12 mL) was added slowly and the mixture was stirred at that temperature for 1 h. The reaction mixture was quenched with water and extracted with ethyl acetate. The organic layer was washed with brine, dried over sodium sulfate, filtered and concentrated under reduced pressure to afford the crude compound. The crude material was purified via preparative TLC eluting with 35% ethyl acetate in petroleum ether to afford 3-(6-(1,3-dioxolan-2-yl)pyridin-2-yl)oxetan-3-ol (500 mg, 27%). MS (ES+) (M+H) 224.20; LCMS retention time: 2.76 minutes (Method S).

Step 3: 6-(3-Hydroxyoxetan-3-yl)picolinaldehyde

A solution of 3-(6-(1,3-dioxolan-2-yl)pyridin-2-yl)oxetan-3-ol (67 mf, 0.30 mmol) and p-toluenesulphonic acid (14.8 mg, 0.26 mmol) in acetone (3.00 mL) was heated to 50° C. and stirred for 18 h. The reaction mixture was cooled to room temperature. The solvent was removed under reduced pressure to afford the title compound. The material was used without further purification. MS (ES+) (M+H) 180.0; LCMS retention time: 1.57 minutes (Method L).

Intermediate 22: Ethyl 1-(3-formylphenyl)cyclopropanecarboxylate

Step 1: Ethyl 1-(3-bromophenyl)cyclopropanecarboxylate 1-(3-Bromophenyl)cyclopropanecarboxylic acid (976 mg, 4.05 mmol) was dissolved in ethanol (20 mL) and p-toluenesulfonic acid (139 mg, 0.810 mmol) was added. The reaction mixture was heated at reflux for 15 h. The temperature of the oil bath was increased from 80° C. to 110° C. and the reaction mixture was stirred for 2 h at that temperature, after which the mixture was cooled and the solvent was removed under reduced pressure. The crude material was purified via flash chromatography (pentane:ethyl acetate 9:1) to afford ethyl 1-(3-bromophenyl)cyclopropanecarboxylate as a colorless oil (950 mg, 87.2%). $^1$H NMR (400 MHz, CDCl$_3$) δ 1.13-1.20 (m, 5H), 1.57-1.62 (m, 2H), 4.10 (q, 2H), 7.17 (s, 1H), 7.27 (s, 1H), 7.38 (s, 1H), 7.47-7.50 (m, 1H).

Step 2: (E)-Ethyl 1-(3-(3-ethoxy-3-oxoprop-1-en-1-yl)phenyl)cyclopropanecarboxylate Ethyl 1-(3-bromophenyl)cyclopropanecarboxylate (740 mg, 2.75 mmol) was dissolved in acetonitrile (20 mL) and the solution was treated with ethyl acrylate (3.90 mL, 35.7 mmol) and tri-o-tolyl phosphine (83.7 mg, 0.275 mmol). The reaction mixture was stirred at room temperature until all of the tri-o-tolyl phosphine had dissolved. Palladium acetate (30.9 mg, 0.137 mmol) was added in a single portion and the reaction mixture was stirred at reflux for 16 hr. Palladium acetate was added (10 mg) and the reaction mixture was stirred for another 4 h. The solvent was removed under reduced pressure and the crude material was purified via flash chromatography (pentane/ethyl acetate 95/5 to 92/8) to afford (E)-ethyl 1-(3-(3-ethoxy-3-oxoprop-1-en-1-yl)phenyl)cyclopropanecarboxylate (438 mg, 55%). $^1$H NMR (400 MHz, CDCl$_3$) δ 1.09-1.19 (m, 5H), 1.31 (t, 3H), 1.56-1.63 (m, 2H), 4.03-4.11 (m, 2H), 4.23 (q, 2H), 6.40 (d, 1H), 7.20-7.36 (m, 2H), 7.36-7.42 (m, 1H), 7.44-7.51 (m, 1H), 7.66 (d, 1H).

Step 3: Ethyl 1-(3-formylphenyl)cyclopropanecarboxylate

Ethyl 1-(3-bromophenyl)cyclopropanecarboxylate (538 mg, 1.9 mmol) was dissolved in acetone (20 mL). Osmium tetroxide (17.1 µL, 0.07 mmol) and NaIO$_4$ (1.1 g, 5.6 mmol) were added followed by water (10 mL). The reaction mixture was stirred at room temperature for 18 h. Water was added (10 mL) followed by pentane (35 mL). The layers were separated and the aqueous layer was extracted with pentane (20 mL×2) and ethyl acetate (20 mL×2). The combined organics were washed with water, dried over magnesium sulfate, filtered and concentrated under reduced pressure. The residue was purified via flash chromatography (pentane/ethyl acetate 95:5) to afford the title compound as an oil (327 mg, 80%). MS (ES+) (M+H) 219.

Intermediate 23: 3-Benzyloxetane-3-carboxylic acid

Step 1: 2-Benzyl-2-(hydroxymethyl)propane-1,3-diol

A solution of 3-phenylpropanal (100 g, 0.7 mol), formaldehyde (540 mL, 7.5 mol) and calcium oxide (56 g, 1 mol) in ethanol (1 L) was stirred at 40° C. under nitrogen for 18 h. The reaction mixture was filtered and the filtrate was concentrated. Water (1 L) was added to the residue. The mixture was extracted with ethyl acetate (1 L×3), the combined organic layers were concentrated and purified via silica gel chromatography (petroleum ether/ethyl acetate 3:1) to afford 2-benzyl-2-(hydroxymethyl)propane-1,3-diol as a white solid (90 mg).

Step 2: (3-Benzyloxetan-3-yl)methanol

A solution of potassium t-butoxide in tetrahydrofuran (1M, 24 mL) was added into a solution of 2-benzyl-2-(hydroxymethyl)propane-1,3-diol (90 g, 0.5 mol) and diethyl carbonate (55 g, 0.5 mol) in tetrahydrofuran (500 mL) under nitrogen. The reaction mixture was refluxed for 6 h and then heated to 110° C. to distill the solvent. Then the mixture was stirred at 155° C. for 24 h. The mixture was purified via silica gel chromatography (petroleum ether/ethyl acetate 10:1 to 2:1) to afford (3-benzyloxetan-3-yl)methanol (40 g, 0.226 mol, 49%) was a white solid.

Step 3: 3-Benzyloxetane-3-carboxylic acid

Jones reagent, (130 mL of a 2.3 M solution) previously prepared by adding hydrochloric acid (46 mL) to water (150 mL) followed by chromium (VI) oxide (55.5 g), was added dropwise to a solution of (3-benzyloxetan-3-yl)methanol (40 g, 0.2 mol) in acetone (600 mL). The reaction mixture was stirred at room temperature for 5 h. Isopropanol (18 g) was added and the mixture was extracted with ether (4 L), washed with NaH$_2$PO$_4$ (1M in water, 200 mL) and sodium chloride (1 M in water, 200 mL). The organics were dried over sodium sulfate, filtered and concentrated. The residue was triturated with ether (100 mL) to afford the title compound (37 g, 0.2 mol, 85%) as a white solid. $^1$H NMR (300 MHz, DMSO-d$_6$) δ 3.22 (s, 2H), 4.49-4.51 (d, 2H), 4.65-4.67 (d, 2H), 7.12-7.27 (m, 5H), 12.85 (s, 1H).

Intermediate 24: (R)-(1-(5,6-Diaminopyridin-2-yl) piperidin-3-yl)(3,3-difluoropyrrolidin-1-yl)methanone dihydrochloride The title compound was prepared by a method analogous to the one used for Intermediate 1, but using 3,3-difluoropyrrolidine instead of pyrrolidine for Step 1 and a solution of hydrogen chloride in methanol (1.25 M) for Step 2. MS (ES+) (M+H) 326.1; LCMS retention time: 0.26 minutes (Method M). $^1$H NMR (DMSO, 400 MHz): δ 1.45-1.62 (m, 2H), 1.65-1.72 (m, 1H), 1.82-1.90 (m, 1H), 2.30-2.45 (m, 2H), 2.76-2.91 (m, 2H), 3.46-3.54 (m, 1H), 3.64-3.78 (m, 2H), 3.84-3.92 (m, 1H), 3.95-4.04 (m, 2H), 4.06-4.13 (m, 1H), 4.13-4.62 (m, 6H), 6.14 (d, 1H), 7.24 (d, 1H).

Intermediate 25: ((R)-1-(5,6-Diaminopyridin-2-yl) piperidin-3-yl)((S)-3-hydroxypyrrolidin-1-yl)methanone dihydrochloride The title compound was prepared by a method analogous to the one used for Intermediate 1, but using (S)-pyrrolidin-3-ol instead of pyrrolidine for Step 1 and a hydrogen chloride solution in methanol (1.25 M) for Step 2. MS (ES+) (M+H) 306.1; LCMS retention time: 0.26 minutes (Method M).

Intermediate 26: 6-(3-(6,7-Dihydro-5H-pyrrolo[1,2-c]imidazol-3-yl)piperidin-1-yl)pyridine-2,3-diamine hydrochloride salt

Step 1: tert-Butyl 3-(5,6,7,7a-tetrahydro-1H-pyrrolo[1,2-c]imidazol-3-yl)piperidine-1-carboxylate To a solution of pyrrolidin-2-ylmethanamine (250 mg, 2.5 mmol) in toluene (8.5 mL) was added 1-tert-butyl 3-ethyl piperidine-1,3-dicarboxylate (635 mg, 2.5 mmol) under nitrogen. The solution was cooled with an ice-water bath and trimethylaluminum (2M in toluene, 2.2 mL, 4.4 mmol) was added. The resulting solution was transferred to a pressure tube and heated to 110° C. for 18 h. The reaction mixture was cooled to room temperature and water was added (10 mL). The mixture was extracted with dichloromethane (40 mL×2). The combined organics were dried over sodium sulfate, filtered, and concentrated under reduced pressure. The residue was purified via flash chromatography (0-12% methanol in dichloromethane) to afford tert-butyl 3-(5,6,7,7a-tetrahydro-1H-pyrrolo[1,2-c]imidazol-3-yl)piperidine-1-carboxylate as a colorless oil (317 mg, 43.8%). MS (ES+) (M+H) 294.2; LCMS retention time: 1.03 minutes (Method M).

Step 2: tert-Butyl 3-(6,7-dihydro-5H-pyrrolo[1,2-c]imidazol-3-yl)piperidine-1-carboxylate To a solution of tert-butyl 3-(5,6,7,7a-tetrahydro-1H-pyrrolo[1,2-c]imidazol-3-yl)piperidine-1-carboxylate (175 mg, 0.6 mmol) in toluene (5 mL) was added BaMnO$_4$ (2.1 g, 18 mmol) and the reaction was heated at 115° C. for 42 h. The reaction was cooled to room temperature and BaMnO$_4$ (2 g) was added followed by toluene (2 mL). The reaction mixture was heated to 115° C. for 3 days. The mixture was cooled to room temperature and filtered through Celite followed by rinsing with dichloromethane. The filtrate was concentrated under reduced pressure and the residue was purified via HPLC to afford tert-butyl 3-(6,7-dihydro-5H-pyrrolo[1,2-c]imidazol-3-yl)piperidine-1-carboxylate as an oil (25 mg, 14%). MS (ES+) (M+H) 292.2; LCMS retention time: 1.69 minutes (Method M).

Step 3: 3-(Piperidin-3-yl)-6,7-dihydro-5H-pyrrolo[1,2-c]imidazole trifluoroacetate t-Butyl 3-(6,7-dihydro-5H-pyrrolo[1,2-c]imidazol-3-yl) piperidine-1-carboxylate (65 mg, 0.1 mmol) was dissolved into a 20% trifluoroacetic acid in dichloromethane solution (2.4 mL). The reaction mixture was stirred at room temperature for 2.5 h. The solvent was removed under reduced pressure to afford 3-(piperidin-3-yl)-6,7-dihydro-5H-pyrrolo[1,2-c]imidazole trifluoroacetate salt as an oil (94 mg, 100%). The material was used without further purification.

Step 4: 6-(3-(6,7-Dihydro-5H-pyrrolo[1,2-c]imidazol-3-yl)piperidin-1-yl)-3-nitropyridin-2-amine To a solution of 3-(piperidin-3-yl)-6,7-dihydro-5H-pyrrolo[1,2-c]imidazole trifluoroacetate salt (94 mg) in anhydrous acetonitrile (1.1 mL) at 10° C. was added triethylamine (130 µL, 0.93 mmol). Then 6-chloro-3-nitropyridin-2-amine (39 mg, 0.2 mmol) was added. The reaction mixture was shaken at 80° C. for 2 h and then for 18 h at room temperature. The solvent was removed under reduced pressure and the residue was dissolved in dichloromethane (3 mL). The mixture was washed with a saturated aqueous solution of sodium bicarbonate (1 mL), washed with water (1 mL), washed with brine (1 mL), dried over sodium sulfate, filtered and concentrated under reduced pressure. The residue was purified via flash chromatography (0-10% methanol in dichloromethane) to afford 6-(3-(6,7-dihydro-5H-pyrrolo[1,2-c]imidazol-3-yl) piperidin-1-yl)-3-nitropyridin-2-amine as a yellow oil (60 mg, 82%). MS (ES+) (M+H) 329.2; LCMS retention time: 1.61 minutes (Method L).

Step 5: 6-(3-(6,7-Dihydro-5H-pyrrolo[1,2-c]imidazol-3-yl)piperidin-1-yl)pyridine-2,3-diamine hydrochloride salt 6-(3-(6,7-Dihydro-5H-pyrrolo[1,2-c]imidazol-3-yl)piperidin-1-yl)-3-nitropyridin-2-amine (20 mg, 0.1 mmol) was dissolved in ethanol (0.5 mL) and water (0.1 mL) under nitrogen. Then iron 200 mesh (27 mg, 0.5 mmol) and calcium chloride (3.3 mg, 0.03 mmol) were added and the mixture was heated to 70° C. for 18 h. The reaction mixture was cooled to room temperature followed by filtration through a 0.2 µm nylon syringe filter and rinsing with ethanol (0.5 mL) to afford the title compound. The filtrate was carried on to the next step without further purification. MS (AP+) (M+H) 299.1; LCMS retention time: 0.44 minutes (Method L)

Intermediate 27: 1-(3-Oxomorpholino)cyclopropanecarboxylic acid

The title compound was prepared by a method analogous to the one used for Intermediate 4, but using morpholin-3-one in Step 1. MS (ES+) (M+H) 186.3; LCMS retention time: 0.59 minutes (Method M).

Intermediate 28: 6-(1-((tert-Butyldimethylsilyl)oxy) cyclopropyl)picolinonitrile

Step 1: 2-Bromo-6-(1-((tert-butyldimethylsilyl)oxy) vinyl)pyridine

To a solution of 1-(6-bromopyridin-2-yl)ethanone (1000 mg, 5.0 mmol) and triethylamine (2.1 mL, 15.0 mmol) at 0° C. in dichloromethane (14 mL) was added trifluoromethyl tert-butyldimethylsilanesulfonate (1.4 mL, 6.2 mmol). The reaction mixture was stirred at room temperature for 2 h. The reaction mixture was diluted with ethyl acetate, washed with water and brine, dried over sodium sulfate, and concentrated. The residue was purified via flash chromatography (0-30% ethyl acetate in heptanes) to afford 2-bromo-6-(1-((tert-butyldimethylsilyl)oxy)vinyl)pyridine as a colorless oil (1450 mg, 92%). $^1$H NMR (400 MHz, DMSO-d$_6$) δ 0.22 (s, 6H), 0.98 (s, 9H), 4.62-4.63 (m, 1H), 5.52 (s, 1H), 7.56-7.62 (m, 2H), 7.82 (s, 1H).

Step 2: 2-Bromo-6-(1-((tert-butyldimethylsilyl)oxy)cyclopropyl)pyridine

To a solution of diethylzinc (1M in hexane, 2.0 mL, 2.0 mmol) in dichloromethane (3.7 mL) at −4° C. was added chloroiodomethane (714 mg, 4.0 mmol) dissolved in dichloromethane (1 mL) dropwise. The reaction mixture was stirred at 0° C. for 15 minutes. A solution 2-bromo-6-(1-((tert-butyldimethylsilyl)oxy)vinyl)pyridine (200 mg, 0.6 mmol) in dichloromethane (3.0 mL) was added. The reaction mixture was stirred at 0° C. for 2 h. A cold saturated aqueous solution of ammonium chloride was added and the mixture was extracted with dichloromethane. The organics were dried over sodium sulfate and concentrated under reduced pressure. The crude material was purified via flash chromatography (100% heptanes) to afford 2-bromo-6-(1-((tert-butyldimethylsilyl)oxy)cyclopropyl)pyridine (120 mg, 58%). $^1$H NMR (400 MHz, CDCl$_3$) δ 0.11 (s, 6H), 0.95 (s, 9H), 1.22-1.28 (m, 2H), 1.39-1.45 (m, 2H), 7.23 (dd, 1H), 7.47 (t, 1H), 7.60 (dd, 1H).

Step 3: 6-(1-((tert-Butyldimethylsilyl)oxy)cyclopropyl)picolinonitrile

Into a vial was added 2-bromo-6-(1-((tert-butyldimethylsilyl)oxy)cyclopropyl)pyridine (60.0 mg, 0.2 mmol), zinc acetate (2.8 mg, 0.01 mmol), zinc dust (3.6 mg, 0.1 mmol), (1,1'-bis(diphenylphosphino)ferrocene)-dichloropalladium (II) (2.9 mg, 0.004 mmol) and zinc cyanide (14.0, 0.1 mmol). The solids were purged with nitrogen and then N,N-dimethylformamide (0.7 mL) and water (0.1 mL) were added. The suspension was heated to 100° C. for 2 h. The reaction mixture was directly loaded onto a silica gel column and purified via flash chromatography (0-5% ethyl acetate in heptanes) to afford the title compound (45 mg, 90%). $^1$H NMR (400 MHz, CDCl$_3$) δ 0.10 (s, 6H), 0.96 (s, 9H), 1.27-1.33 (m, 2H), 1.43-1.48 (m, 2H), 7.46 (s, 1H), 7.73-7.80 (m, 1H), 7.89 (s, 1H).

Intermediate 29: (R)-(4-(5,6-Diaminopyridin-2-yl)morpholin-2-yl)(pyrrolidin-1-yl)methanone dihydrochloride The title compound was prepared by a method analogous to the one used for Intermediate 1, but using (R)-4-(tert-butoxycarbonyl)morpholine-2-carboxylic acid for Step 1. $^1$H NMR (400 MHz, CD$_3$OD) δ 1.81-2.03 (m, 4H) 3.37-3.51 (m, 3H) 3.60-3.73 (m, 3H) 3.75-3.85 (m, 2H) 3.90-3.97 (m, 2H) 4.49 (dd, 1H) 6.40 (d, 1H) 7.73 (d, 1H).

Intermediate 30: Ethyl 6-cyclopropylpyrazine-2-carbimidate

Step 1: 6-Cyclopropylpyrazine-2-carbonitrile

A suspension of 6-cyano-2-chloropyrazine (0.3 g, 2.1 mmol), (1,1'-bis(diphenylphosphino)ferrocene)-dichloropalladium (II) (153.6 mg, 0.21 mmol), potassium phosphate (1.3 g, 6.30 mmol) and cyclopropylboronic acid (0.184 mg, 2.1 mmol) in tetrahydrofuran (25 mL, nitrogen bubbled) was degassed for 15 min. using nitrogen. The reaction mixture was refluxed for 16 h. The reaction mixture was filtered through Celite and the filtrate was concentrated under reduced pressure. The crude material was purified via column chromatography (100-200 mesh silica gel, 5-20% ethyl acetate in petroleum ether) to afford 6-cyclopropylpyrazine-2-carbonitrile (250 mg, 50%).

Step 2: Ethyl 6-cyclopropylpyrazine-2-carbimidate

Sodium ethoxide (140 mg, 2.06 mmol) was added to a solution of 6-cyclopropylpyrazine-2-carbonitrile (150 mg, 1.03 mmol) in ethanol (6 mL) at room temperature. The reaction mixture was stirred at room temperature for 1 h. The solvent was removed under reduced pressure. The residue was partitioned between water and ethyl acetate. The organics were dried over sodium sulfate and concentrated under reduced pressure to afford the title compound (250 mg). MS (ES+) (M+H) 192.1012

Intermediate 31: (R)-(4-(6-amino-5-nitropyridin-2-yl)morpholin-2-yl)(pyrrolidin-1-yl)methanone The title compound was prepared by a method analogous to Intermediate 1, Steps 1, 2 and 3, but using (R)-4-(tert-butoxycarbonyl)morpholine-2-carboxylic acid as the starting material. $^1$H NMR (400 MHz, CD$_3$OD) δ 1.82-2.05 (m, 5H), 3.45 (s, 2H), 3.55-3.77 (m, 4H), 3.94-4.05 (m, 1H), 4.26 (s, 2H), 4.58 (s, 1H), 6.28 (s, 1H), 8.16 (s, 1H).

Intermediate 32: 3-Nitro-6-(2-(pyridin-2-yl)morpholino)pyridin-2-amine

To a solution of 2-(pyridin-2-yl)morpholine hydrochloride (1000 mg, 4.22 mmol) and triethylamine (1.3 mL, 9.3 mmol) in dimethylsulfoxide (10 mL) was added 6-chloro-3-nitropyridin-2-amine (734 mg, 4.23 mmol). The reaction mixture was stirred at 100° C. for 18 h. The reaction mixture was cooled to room temperature. Ethyl acetate was added and the mixture was washed with water (20 mL). The aqueous layer was extracted with ethyl acetate (20 mL×2). The combined organics were washed with brine (20 mL), dried over magnesium sulfate, filtered and concentrated under reduced pressure. The crude material was purified via flash chromatography (40-100% ethyl acetate in heptanes) to afford the title compound (0.897 g, 70%). $^1$H NMR (400 MHz, CDCl$_3$) δ 3.08 (s, 1H), 3.18-3.29 (m, 1H), 3.83 (s, 1H), 4.20 (s, 1H), 4.41 (d, 1H), 4.63 (dd, 1H), 4.67-4.80 (m, 1H), 6.18 (s, 1H), 7.23-7.26 (m, 1H), 7.54 (s, 1H), 7.75 (s, 1H), 8.22 (s, 1H), 8.60 (s, 1H).

Intermediate 33: 2-Cyclobutylpyrimidine-4-carbaldehyde

Step 1: 4-(Dimethylamino)-1,1-dimethoxybut-3-en-2-one

A mixture of 1,1-dimethoxy-N,N-dimethylmethanamine (5.0 g, 41.96 mmol) and 1,1-dimethoxypropan-2-one (5.0 g, 41.96 mmol) was heated to 80° C. for 16 h. The solvent was removed under reduced pressure to afford 4-(dimethylamino)-1,1-dimethoxybut-3-en-2-one as a black colored liquid. The material was used without further purification.

Step 2: Cyclobutanecarboximidamide hydrochloride

Hydrogen chloride gas was bubbled through a solution of cyclobutanecarbonitrile (2.0 g, 24.65 mmol) in methanol (10 mL) and diethyl ether (12 mL) for 2 h at 0° C. The reaction mixture was concentrated under reduced pressure and the residue was dissolved in methanol and cooled to 0° C. Methanolic ammonia was added and the reaction mixture was stirred for 1 h at room temperature. The solvent was removed under reduced pressure to afford cyclobutanecarboximidamide hydrochloride (3.0 g, 92%). The material was used for the next step without further purification.

Step 3:
2-Cyclobutyl-4-(dimethoxymethyl)pyrimidine

To a solution of 4-(dimethylamino)-1,1-dimethoxybut-3-en-2-one (2.0 g, 11.5 mmol) in ethanol was added cyclobutanecarboximidamide hydrochloride (3.0 g, 22.3 mmol) and triethylamine (2.33 g, 23.0 mmol) under nitrogen at room temperature. The reaction mixture was refluxed for 16 h. The solvent was removed under reduced pressure. To the residue was added water and the mixture was extracted with ethyl acetate. The combined organics were dried over sodium sulfate and concentrated under reduced pressure. The crude material was purified via column chromatography to afford 2-cyclobutyl-4-(dimethoxymethyl)pyrimidine as a colorless liquid (300 mg, 12%). MS (ES+APCI) (M+H) 209.2; LCMS retention time: 3.257 minutes (Method J).

Step 4: 2-Cyclobutylpyrimidine-4-carbaldehyde

A solution of 2-cyclobutyl-4-(dimethoxymethyl)pyrimidine (300 mg, 1.4 mmol) in aqueous hydrochloric acid (3N, 5 mL) was heated to 50° C. for 16 h. The reaction mixture was cooled to room temperature, then was diluted with water, neutralized with a saturated aqueous solution of sodium bicarbonate and extracted with ethyl acetate. The combined organics were dried over sodium sulfate and concentrated under reduced pressure to afford the title compound as a brown colored liquid (200 mg). MS (ES+) (M+H) 163.16.

Intermediate 34:
2-Cyclopropyloxazole-4-carbaldehyde

Step 1: 2-Cyclopropyl-N-methoxy-N-methyloxazole-4-carboxamide

To a solution of 2-cyclopropyloxazole-4-carboxylic acid (0.1 g, 0.653 mmol) in dry dichloromethane (15 mL) were added 1-ethyl-3-(3-dimethylaminopropyl) carbodiimide (0.25 g, 1.3 mmol) and hydroxybenzotriazole (0.175 g, 1.3 mmol) at 0° C. portion wise. N,O-dimethylhydroxylamine (64 mg, 0.653 mmol) was then added followed by triethylamine (0.26 mL, 1.95 mmol). The reaction mixture was stirred at room temperature for 18 h then diluted with ethyl acetate and washed with water and brine solution. The organic layer was dried over sodium sulfate and concentrated under reduced pressure. The crude compound was purified by preparative TLC (25% ethyl acetate in petroleum ether) to afford 2-cyclopropyl-N-methoxy-N-methyloxazole-4-carboxamide (100 mg, 83%). MS (ES+) (M+H) 197.25; LCMS retention time: 2.82 min (Method S).

Step 2: 2-Cyclopropyloxazole-4-carbaldehyde

To a solution of 2-cyclopropyl-N-methoxy-N-methyloxazole-4-carboxamide (0.102 g, 0.52 mmol) in dry dichloromethane (15 mL) was added diisobutylaluminum hydride (1M in toluene) (1.04 ml, 1.04 mmol) at −78° C. The reaction mixture was stirred at −78° C. for 45 minutes. The reaction mixture was quenched with aqueous sodium hydroxide (2M) and extracted with ethyl acetate. The organic layer was dried over sodium sulfate and concentrated under reduced pressure to afford 2-cyclopropyloxazole-4-carbaldehyde which was used without further purification. (65 mg) MS (API-ES+) (M+H) 138.2.

Intermediate 35: 6-(Azetidin-1-yl)picolinaldehyde

Step 1: 2-(Azetidin-1-yl)-6-bromopyridine

To a solution of 2,6-dibromopyridine (100 mg, 0.424 mmol) in dimethylsulfoxide (5 mL) was added potassium carbonate (175.4 mg, 1.27 mmol) and azetidine hydrogen chloride (24.2 mg, 0.424 mmol) at room temperature. The reaction mixture was heated to 80° C. for 16 h, then was poured into ice cold water and extracted with ethyl acetate. The combined organic layers were dried over sodium sulfate, and concentrated under reduced pressure to afford 2-(azetidin-1-yl)-6-bromopyridine (30 mg)

Step 2: 6-(Azetidin-1-yl)picolinaldehyde

A solution of n-butyllithium in hexanes (0.3 g, 4.69 mmol) was added dropwise to a solution of 2-(azetidin-1-yl)-6-bromopyridine (0.5 g, 2.34 mmol) in dry tetrahydrofuran (20 mL) at −78° C. After stirring for 30 min at −78° C., N,N-dimethylformamide (0.34 g, 4.69 mmol) was added. The reaction mixture was stirred for 3 h at −78° C., then the reaction mixture was quenched with an aqueous ammonium chloride solution and extracted with ethyl acetate. The organic layers were dried over sodium sulfate, filtered and concentrated under reduced pressure. The crude material was purified via flash chromatography (60-120 mesh silica; 4-5% ethyl acetate in petroleum ether, twice) to afford 6-(azetidin-1-yl)picolinaldehyde (0.2 g, 43%). MS (ES+) (M+H) 163.1380; LCMS retention time: 5.59 minutes (Method X).

Intermediate 36:
6-(Difluoromethoxy)picolinaldehyde

To a solution of 6-hydroxypicolinaldehyde (2 g, 16.24 mmol) in acetonitrile (20 mL) was added sodium 2-chloro-2,2-difluoroacetate (4.46 g, 29.24 mmol) at room temperature. The reaction mixture was heated at 70° C. for 18 h. The reaction mixture was cooled to room temperature and the solid was filtered off. Then the crude material was purified via flash chromatography (100-200 mesh silica gel, 10% ethyl acetate in hexane) to afford the title compound (1.2 g, 42.85%). MS (ES+) (M+H) 174.10

Intermediate 37: 6-(Difluoromethyl)picolinaldehyde

Step 1: 6-(1,3-Dioxolan-2-yl)picolinaldehyde

To a solution of pyridine-2,6-dicarbaldehyde (5 g, 37.4 mmol) in benzene (100 mL) was added ethylene glycol (1.1 g, 18.5 mmol) and p-toluenesulfonic acid (0.3 g, 1.8 mmol). The reaction mixture was equipped with a dean stark condenser and refluxed for 15 min. The reaction mixture was concentrated under reduced pressure and the resulting crude was purified via column chromatography to afford 6-(1,3-dioxolan-2-yl)picolinaldehyde (2 g, 30%). MS (ES+) (M+H) 180.0495

Step 2:
2-(Difluoromethyl)-6-(1,3-dioxolan-2-yl)pyridine

To a solution of 6-(1,3-dioxolan-2-yl)picolinaldehyde (2 g, 11.1 mmol) in chloroform (50 mL) was added diethylaminosulfur trifluoride (DAST) (2 mL) at 0° C. The reaction mixture was stirred at room temperature for 12 h. The mixture was then concentrated under reduced pressure, diluted with ice cold water and extracted with ethyl acetate. The combined organic layers were dried over sodium sulfate, filtered, concentrated and purified via flash chromatography to afford 2-(difluoromethyl)-6-(1,3-dioxolan-2-yl)pyridine (1.62 g, 71%). MS (ES+APCI) (M+H) 202.1; LCMS retention time: 2.876 min (Method H1).

Step 3: 6-(Difluoromethyl)picolinaldehyde

To a solution of 2-(difluoromethyl)-6-(1,3-dioxolan-2-yl)pyridine (0.5 g, 2.4 mmol) was added 85% formic acid (5 mL). The reaction mixture was warmed to 60° C. for 1.5 h. The mixture was then concentrated under reduced pressure, diluted with ice cold water, neutralized with aqueous sodium hydroxide (4N) and extracted with ethyl acetate. The combined organic layers were dried over sodium sulfate, filtered, concentrated and purified via flash chromatography to afford 6-(difluoromethyl)picolinaldehyde (0.2 g, 51%). MS (ES+) (M+H) 158.16; LCMS retention time: 5.28 min (Method H).

Intermediate 38: 3-Nitro-6-(2-(pyridin-2-yl)morpholino)pyridin-2-amine

To a solution of 2-(pyridin-2-yl)morpholine (0.1 g, 0.609 mmol) in dimethylsulfoxide (5 mL) was added triethylamine (0.17 mL, 1.2 mmol). The resulting solution was stirred for 10 min at room temperature, and then 6-chloro-3-nitropyridin-2-amine (105 mg, 0.609 mmol) was added. The reaction mixture was heated at 110° C. for 4 h, and then was cooled to room temperature. Ice water was added and the mixture was extracted with ethyl acetate. The combined organic layer was dried over sodium sulfate, filtered and concentrated under reduced pressure. The crude material was purified via flash chromatography (80% ethyl acetate in petroleum ether) to afford the title compound (0.1 g, 55%). MS (ES+) (M+H) 302.25.

Intermediate 39: (R)-1-(6-Amino-5-nitropyridin-2-yl)-N,N-dimethylpiperidine-3-carboxamide Step 1: (R)-tert-Butyl 3-(dimethylcarbamoyl)piperidine-1-carboxylate To a solution of (R)-1-(tert-butoxycarbonyl)piperidine-3-carboxylic acid (10 g, 43.6 mmol) in N,N-dimethylformamide (150 mL) was added 1,1'-carbonyldiimidazole (14.13 g, 87.23 mmol). The reaction mixture was stirred at room temperature for 10 min. Triethylamine (18.3 mL, 130.2 mmol) and dimethylamine hydrochloride (7.1 g, 87.2 mmol) were then added sequentially. The reaction mixture was stirred at room temperature for 16 h. The solvent was evaporated and the residue was treated with cold water and was extracted with ethyl acetate. The organic layer was dried over anhydrous sodium sulfate, filtered and concentrated. The residue was purified via flash chromatography to afford (R)-tert-butyl 3-(dimethylcarbamoyl)piperidine-1-carboxylate (0.9 g, 80%). MS (ES+APCI) (M+H) 257.1; LCMS retention time: 2.829 min (Method D1)

Step 2: (R)—N,N-Dimethylpiperidine-3-carboxamide hydrochloride

To a solution of (R)-tert-butyl 3-(dimethylcarbamoyl)piperidine-1-carboxylate (9 g, 35.15 mmol) in methanol (20 mL) at 0° C. was added hydrogen chloride in methanol (50 mL). The reaction mixture was stirred at room temperature for 2 h. The solvent was evaporated in vacuo to afford (R)—N,N-dimethylpiperidine-3-carboxamide hydrochloride (7 g, 90%). MS (ES+APCI) [(M-2HCl)+H] 157.1; LCMS retention time: 6.36 min (Method F1).

Step 3: (R)-1-(6-Amino-5-nitropyridin-2-yl)-N,N-dimethylpiperidine-3-carboxamide To a solution of (R)—N,N-dimethylpiperidine-3-carboxamide (10 g, 64.04 mmol) in dimethylsulfoxide (100 mL) were added triethylamine (17.8 mL, 128.08 mmol) and 6-chloro-3-nitropyridin-2-amine (7.76 g, 44.82 mmol) at room temperature under a nitrogen atmosphere. The reaction mixture was heated at 110° C. for 16 h. The reaction mixture was added to cold water and extracted with ethyl acetate. The organic layer was washed with cold water 3 times, dried over sodium sulfate and evaporated under reduced pressure. The crude compound was purified via flash chromatography and then treated with 1:1 petroleum ether and diethyl ether to afford (R)-1-(6-amino-5-nitropyridin-2-yl)-N,N-dimethylpiperidine-3-carboxamide (11 g, 72%). MS (ES+APCI) (M+H) 294.1; LCMS retention time: 2.777 min (Method E1)

Intermediate 40: (R)-(1-(6-Amino-5-nitropyridin-2-yl)piperidin-3-yl)(morpholino)methanone The title compound was prepared using procedures analogous to the ones used for Intermediate 39, but using morpholine for Step 1, a saturated solution of hydrogen chloride in ether, and diethyl ether as a solvent for Step 2 and acetonitrile for Step 3. MS (ES+APCI) (M+H) 336.1; LCMS retention time: 4.033 min (Method I).

Intermediate 41: Ethyl 4-cyclopropylpicolinimidate

Step 1: 4-Cyclopropylpicolinonitrile

To a solution of 4-bromopicolinonitrile (0.2 g, 1.1 mmol) in tetrahydrofuran were added cyclopropyl boronic acid (0.093 g, 1.1 mmol), and potassium phosphate tribasic (0.694 g, 3.2 mmol). The resulting reaction mixture was degassed with nitrogen for 10 minutes and then added Pd(OAc)$_2$ and S-phos were added. The reaction mixture was heated at reflux for 16 h, then was diluted with water and extracted with ethyl acetate. The organic layer was concentrated under reduced pressure and the residue was purified via flash chromatography (10% ethyl acetate in petroleum ether) to afford 4-cyclopropylpicolinonitrile (0.1 g, 70%). MS (ES+APCI) (M+H) 145.2; LCMS retention time 3.02 min (Method J).

Step 2: Ethyl 4-cyclopropylpicolinimidate

To a solution of 4-cyclopropylpicolinonitrile (0.04 g, 0.27 mmol) in ethanol was added sodium ethoxide (0.022 g, 0.33 mmol) and the reaction mixture was stirred at room temperature for 3 h. The reaction mixture was concentrated under vacuum, quenched with water, extracted with ethyl acetate, dried over sodium sulfate, filtered and concentrated under reduced pressure to afford ethyl 4-cyclopropylpicolinimidate (0.045 g). The material was used without further purification. MS (ES+APCI) (M+H) 190.9; LCMS retention time 1.700 min (Method G).

Intermediate 42: Ethyl 4-cyclopropylpyrimidine-2-carbimidate

Step 1: 4-Cyclopropylpyrimidine-2-carbonitrile

To a solution of diazabicyclooctane (0.013 g, 0.12 mmol) in dimethylsulfoxide and water was added a solution of 2-chloro-4-cyclopropylpyrimidine (0.2 g, 1.2 mmol) in dimethylsulfoxide followed by sodium cyanide (0.066 g, 1.3 mmol). The reaction mixture was stirred at room temperature for 48 h. The mixture was then poured into water and extracted with ethyl acetate, dried over sodium sulfate and concentrated under reduced pressure. The crude compound was purified via flash chromatography (10% ethyl acetate in petroleum ether) to afford 4-cyclopropylpyrimidine-2-carbonitrile (0.14 g, 77%). MS (ES+APCI) (M+H) 146.1; LCMS retention time 3.054 min (Method J).

Step 2: Ethyl 4-cyclopropylpyrimidine-2-carbimidate

Ethyl 4-cyclopropylpyrimidine-2-carbimidate was prepared using a method analogous to the one used for Intermediate 41 step 2 but running the reaction for 16 h instead of 3 h. MS (ES+APCI) (M+H) 192.0.

Intermediate 43: Ethyl 5-(N-methylsulfamoyl)nicotinimidate

Step 1: 5-Cyano-N-methylpyridine-3-sulfonamide

To a solution of 5-bromo-N-methylpyridine-3-sulfonamide (0.1 g, 0.39 mmol) in N,N-dimethylformamide was added zinc cyanide (0.056 g, 0.47 mmol). The solution was degassed with nitrogen for 10 min, then tetrakis(triphenylphosphine)palladium(0) (30 mg) was added. The reaction mixture was heated to 100° C. for 2 h. The mixture was then diluted with water and extracted with ethyl acetate. The organic layer was dried, filtered, and concentrated under reduced pressure. The crude compound was purified by rinsing with diethyl ether to afford 5-cyano-N-methylpyridine-3-sulfonamide (60 mg) which was used without further purification.

Step 2: Ethyl 5-(N-methylsulfamoyl)nicotinimidate

To a solution of 5-cyano-N-methylpyridine-3-sulfonamide (0.1 g, 0.5 mmol) in ethanol was added sodium ethoxide (0.03 g, 0.55 mmol). After 2 h, the mixture was concentrated under reduced pressure. The residue was partitioned between ethyl acetate and water. The organic layer was concentrated under reduced pressure to afford ethyl 5-(N-methylsulfamoyl)nicotinimidate (120 mg) as an off-white solid. The material was used without further purification. MS (ES+APCI) 244.0; LCMS retention time: 3.047 min (Method I).

Intermediate 44: 3-(1-Carboxycyclopropyl)pyridine 1-oxide

70% meta-Chloroperoxybenzoic acid (1.2 g, 4.9 mmol) was added to a solution of ethyl 1-(pyridin-3-yl)cyclopropanecarboxylate (400 mg, 2.4 mmol) in dichloromethane (5 mL) at room temperature and stirred for 16 h. The resulting precipitate was filtered and triturated with dichloromethane to afford the title compound (250 mg).

Intermediate 45: 6-(3-(6,7-Dihydro-5H-pyrrolo[2,1-c][1,2,4]-triazol-3-yl)piperidin-1-yl)-3-nitropyridin-2-amine To a solution of 3-(piperidin-3-yl)-6,7-dihydro-5H-pyrrolo[2,1-c][1,2,4]triazole (900 mg, 4.68 mmol) in acetonitrile (50 mL) was added 6-chloro-3-nitropyridin-2-amine (730 mg, 4.2 mmol) and triethylamine (1.42 g, 14.04 mmol) at room temperature under a nitrogen atmosphere. The reaction mixture was stirred for 30 min at reflux, then allowed to cool down to room temperature and stirred for 16 h. The solvent was removed under reduced pressure and the resulting residue was partitioned between water and ethyl acetate. The organics were dried over sodium sulfate, concentrated under reduced pressure and purified via column chromatography to afford the title compound (1.0 g, 64.9%). MS (ES+) (M+H) 330.33; LCMS retention time: 2.85 min (Method S).

Intermediate 46: 1-(1-Methyl-1H-pyrazol-5-yl)cyclopropanecarbonitrile

Step 1: tert-Butyl 2-cyano-2-(1-methyl-1H-pyrazol-5-yl)acetate

To a solution of tert-butyl cyanoacetate (340 µL, 2.40 mmol) in 1,4-dioxane (5 mL) was added potassium t-butoxide (1M in tetrahydrofuran, 5 mL, 5.0 mmol) at room temperature. After 10 min, a solution of 5-iodo-1-methyl-1H-pyrazole (500 mg, 2.40 mmol) in 1,4-dioxane (5 mL) and tetrakis(triphenylphosphine)palladium(0) (75 mg, 0.065 mmol) were added. The reaction mixture was stirred for 16 h at 70° C. The mixture was cooled and then was diluted with diethyl ether (50 mL) and a 10% aqueous solution of citric acid. The organic layer was separated and the aqueous layer was extracted with diethyl ether (2×10 mL). The combined organics were washed with brine (15 mL), dried over magnesium sulfate, filtered, and concentrated under reduced pressure. The residue was purified by silica gel chromatography (Gradient: 30% to 40% ethyl acetate in heptane) to afford tert-butyl 2-cyano-2-(1-methyl-1H-pyrazol-5-yl)acetate (132.8 mg) as a pale brown oil. MS (ES+) (M+H) 222.0, LCMS retention time: 2.74 min (Method L); $^1$H NMR (500 MHz, CDCl$_3$) δ 1.50 (s, 9H), 3.93 (s, 3H), 4.80 (s, 1H), 6.39 (d, 1H), 7.48 (d 1H).

Step 2: 2-(1-Methyl-1H-pyrazol-5-yl)acetonitrile

A mixture of tert-butyl 2-cyano-2-(1-methyl-1H-pyrazol-5-yl)acetate (130 mg, 0.588 mmol) in hexafluoroisopropanol (1 mL) was submitted to microwave radiation at 130° C. for 15 minutes. The reaction mixture was diluted with diethyl ether (30 mL), washed with water (5 mL) and brine (5 mL), dried over magnesium sulfate, filtered, concentrated under reduced pressure and dried under high vacuum to afford 2-(1-methyl-1H-pyrazol-5-yl)acetonitrile (68.3 mg) as a pale yellow oil. $^1$H NMR (500 MHz, CDCl$_3$) δ 3.77 (s, 2H), 3.89 (s, 3H), 6.30 (s, 1H), 7.45 (s, 1H).

Step 3: 1-(1-Methyl-1H-pyrazol-5-yl)cyclopropanecarbonitrile

To a solution of 2-(1-methyl-1H-pyrazol-5-yl)acetonitrile (65 mg, 0.54 mmol) in N,N-dimethylformamide (3 mL) were added potassium t-butoxide (1M in tetrahydrofuran, 1.2 mL, 1.2 mmol) and 1,2-dibromoethane (130 µL, 1.5 mmol). The reaction mixture was stirred for 16 h at room temperature then at 70° C. for 7 h. The mixture was cooled to room temperature, quenched with water (2 mL) and extracted with diethyl ether (3×10 mL). The combined organic layers were washed with brine (3 mL), dried over magnesium sulfate, filtered, and concentrated in vacuo. The residue was dried under high vacuum. A solution of the residue and 1,2-dibromoethane (65 µL, 0.75 mmol) in N,N-dimethylformamide (0.5 mL) was added dropwise to a suspension of sodium hydride (washed, 23 mg, 1.0 mmol) in N,N-dimethylformamide (1.0 mL) at room temperature. After 16 h, additional portions of 1,2-dibromoethane (25 µL, 0.29 mmol) and sodium hydride (8 mg, 0.35 mmol) were added to the reaction mixture at room temperature. After 2 h, the mixture was quenched with water (3 mL) and extracted with diethyl ether (2×10 mL). The combined organic layers were washed with brine (3 mL), dried over magnesium sulfate, filtered, and concentrated under reduced pressure. The residue was dried under high vacuum to yield the volatile 1-(1-methyl-1H-pyrazol-5-yl)cyclopropanecarbonitrile (20.1 mg, 25%) as a brown oil. $^1$H NMR (500 MHz, CDCl$_3$) δ 1.34-1.41 (m, 2H), 1.70-1.76 (m, 2H), 4.03 (s, 3H), 6.10 (d, 1H), 7.39 (d, 1H).

Intermediate 47: Ethyl 1-(m-tolyl)cyclopropanecarbimidate hydrochloride

To 1-(m-tolyl)cyclopropanecarbonitrile (100 mg, 0.64 mmol) was added a saturated solution of hydrogen chloride in ethanol (2 mL). After 16 h at room temperature and 2 h at 70° C. and another 16 h at room temperature, the mixture was concentrated in vacuo and the residue was dried under high vacuum to afford the title compound (147.1 mg, 96.5%) as a colorless solid. MS (ES+) (M+H) 204.1, LCMS retention time: 3.10 minutes (Method L).

Intermediate 48: Ethyl 1-(4-methoxyphenyl)cyclopropanecarbimidate hydrochloride

To a cooled solution of 1-(4-methoxyphenyl)cyclopropanecarbonitrile (35 mg, 0.2 mmol) in ethanol (100 µL, 2 mmol) was added acetyl chloride (170 µl, 2.39 mmol). The mixture was shaken at room temperature for 16 h, then was concentrated in vacuo and dried. To the residue was added a freshly prepared saturated solution of hydrogen chloride in ethanol (1 mL). After 16 h, the reaction mixture was concentrated under reduced pressure to afford the title compound (56 mg) as an oil which was used without further purification.

Intermediate 49: Ethyl 1-(2-methoxyphenyl)cyclopropanecarbimidate hydrochloride

The title compound (50 mg, oil) was prepared by a method analogous to the one used for Intermediate 48 but using 1-(2-methoxyphenyl)cyclopropanecarbonitrile.

Intermediate 50: Ethyl 5-cyclopropylnicotinimidate

Step 1: 5-Cyclopropylnicotinonitrile

To a solution of 3-bromo-5-cyanopyridine (1 g, 5.3 mmol) in tetrahydrofuran was added cyclopropyl boronic acid (0.5 g, 5.6 mmol) and potassium phosphate (1.08 g, 15.9 mmol). The resulting solution was degassed with nitrogen for 10 minutes and then palladium (II) acetate and S-phos were added. The reaction mixture was refluxed for 16 h. The reaction mixture was diluted with water, extracted with ethyl acetate and concentrated under reduced pressure. The crude material was purified via column chromatography to afford 5-cyclopropylnicotinonitrile (0.45 g, 58%). MS (ES+) (M+H) 145.1774.

Step 2: Ethyl 5-cyclopropylnicotinimidate

To a solution of 5-cyclopropylnicotinonitrile (0.45 g, 3.1 mmol) in ethanol was added sodium ethoxide (0.212 g, 3.1 mmol). The reaction mixture was stirred at room temperature for 12 h. The solvent was removed under reduced pressure, and the residue was partitioned between water and ethyl acetate. The organic layer was concentrated under reduced pressure to afford the title compound (0.45 g) which was used without further purification. MS (ES+APCI) (M+H) 191.2; LCMS retention time 1.149 min (Method L1).

Intermediate 51: (R)-1-(5,6-Diaminopyridin-2-yl)-N-ethyl-N-methylpiperidine-3-carboxamide Step 1: (R)-tert-Butyl 3-(ethyl(methyl)carbamoyl)piperidine-1-carboxylate (R)-tert-Butyl 3-(ethyl(methyl)carbamoyl)piperidine-1-carboxylate was prepared by a method analogous to the one used for Intermediate 1, Step 1, but using N-methylethanamine and N,N-dimethylformamide. MS (ES+) (M+H) 271.2; LCMS retention time 2.191 min (Method W).

Step 2: (R)—N-Ethyl-N-methylpiperidine-3-carboxamide

To a solution of (R)-tert-butyl 3-(ethyl(methyl)carbamoyl)piperidine-1-carboxylate (1 g, 3.7 mmol) in diethyl ether (10 mL) at 0° C. was added ethereal hydrogen chloride (15 mL). The reaction mixture was warmed to room temperature and was stirred at that temperature for 30 min. The solvent was distilled and the resulting residue was washed with diethyl ether to afford (R)—N-ethyl-N-methylpiperidine-3-carboxamide (1 g). MS (ES+) (M+H) 171.23; LCMS retention time 2.38 min (Method M1).

Step 3: (R)-1-(6-Amino-5-nitropyridin-2-yl)-N-ethyl-N-methylpiperidine-3-carboxamide To a solution of (R)—N-ethyl-N-methylpiperidine-3-carboxamide (600 mg, 4.1 mmol) in dimethylsulfoxide (6 mL) were added 6-chloro-3-nitropyridin-2-amine (0.58 g, 3.3 mmol) and triethylamine (1.2 mL, 8.3 mmol) at room temperature. The reaction mixture was heated to 80° C. for 18 h. The reaction mixture was poured into ice water, extracted with ethyl acetate and concentrated under reduced pressure. The crude material was purified via column chromatography (10% ethyl acetate in petroleum ether) to afford (R)-1-(6-amino-5-nitropyridin-2-yl)-N-ethyl-N-methylpiperidine-3-carboxamide (500 mg, 28.4%). MS (ES+) (M+H) 308.31.

Step 4: (R)-1-(5,6-Diaminopyridin-2-yl)-N-ethyl-N-methylpiperidine-3-carboxamide To a solution of (R)-1-(6-amino-5-nitropyridin-2-yl)-N-ethyl-N-methylpiperidine-3-carboxamide (200 mg, 0.65 mmol) in ethanol (10 mL) was added palladium-on-carbon (0.2 g) in ethanol (10 mL) at room temperature. The mixture was subjected to a hydrogen atmosphere using a balloon filled with hydrogen gas. The mixture was filtered through Celite to afford the title compound. The filtrate was used without further purification.

Intermediate 52: (R)-(4-(6-Amino-5-nitropyridin-2-yl)morpholin-2-yl)(morpholino)methanone The title compound was prepared by a method analogous to Intermediate 51, but refluxing the reaction mixture for 30 min and then stirring at room temperature for 18 h during Step 3 and omitting the final step. MS (ES+APCI) (M+H) 338.2; LCMS retention time: 2.734 min (Method J).

Intermediate 53: Ethyl 6-(trifluoromethyl)picolinimidate

Sodium ethoxide (197 mg, 2.9 mmol) was added to a solution of 6-(trifluoromethyl)picolinonitrile (250 mg, 1.45 mmol) in ethanol (10 mL) at room temperature. The reaction mixture was stirred for 2 h. The solvent was removed under reduced pressure and the resulting residue was dissolved in dichloromethane, washed with water, dried over sodium sulfate, and concentrated under reduced pressure to afford the title compound (291 mg) which was used without further purification. MS (ES+) (M+H) 219.16

Intermediate 54: Ethyl 2-(4-chloro-1H-pyrazol-1-yl)-2-methylpropanimidate

Step 1: 2-(4-Chloro-1H-pyrazol-1-yl)-2-methylpropanenitrile

To a suspension of sodium hydride (630 mg, 16 mmol, 60% dispersion in mineral oil) in dimethylsulfoxide (10 mL) cooled to 18° C. was added a solution of 2-(4-chloro-1H-pyrazol-1-yl)acetonitrile (500 mg, 3.53 mmol) and methyliodide (650 µL, 10.0 mmol) in dimethylsulfoxide (5 mL) under nitrogen. The suspension was stirred at room temperature for 1.5 h. The reaction mixture was added to a cooled solution of saturated aqueous ammonium chloride (25 mL) over a period of 5 min. The mixture was extracted with diethyl ether (20 mL×3). The combined organics were washed with water (5 mL×4) and brine (5 mL), dried over magnesium sulfate, filtered and concentrated under reduced pressure to afford 2-(4-chloro-1H-pyrazol-1-yl)-2-methylpropanenitrile (654.6 mg, >99%) which was used without further purification. MS (ES+) M+H 170.0; LCMS retention time 2.70 (Method L).

Step 2: Ethyl 2-(4-chloro-1H-pyrazol-1-yl)-2-methylpropanimidate

To a sodium ethoxide solution, prepared from sodium (20 mg, 1 mmol) and ethanol (4 mL), was added a solution of 2-(4-chloro-1H-pyrazol-1-yl)-2-methylpropanenitrile (225 mg, 1.33 mmol) in ethanol (1 mL). The reaction mixture was stirred at 70° C. for 30 min. The solvent was removed under a stream of nitrogen and the residue was dried under high vacuum to afford the crude title compound as a colorless solid, which was used without further purification.

Intermediate 55: Ethyl 1-(4-(methylthio)-1H-pyrazol-1-yl)cyclopropanecarbimidate hydrochloride

Step 1: 4-(Methylthio)-1H-pyrazole

A suspension of 4-bromopyrazole (4 g, 27 mmol) in tetrahydrofuran (68 mL) was cooled to 0° C. and n-butyllithium (2.5 M in hexanes, 35.9 mL, 90 mmol) was added dropwise over a period of 20 min. The reaction mixture was stirred at room temperature for 1 h and then was cooled to 0° C. 1,2-Dimethyldisulfide (2.66 mL, 30.0 mmol) was added dropwise. The reaction mixture was stirred at 0° C. for 1.5 h. The reaction mixture was poured into water (150 mL) and then it was acidified to pH~8 with a saturated aqueous solution of ammonium chloride and a solution of aqueous hydrochloric acid (1N). The mixture was extracted with ethyl acetate (150 mL×3) and the combined organic layers were dried over sodium sulfate, filtered and concentrated under reduced pressure to afford 4-(methylthio)-1H-pyrazole (3300 mg). $^1$H NMR (500 MHz, CDCl$_3$) δ 2.36 (s, 3H), 7.63 (s, 2H).

Step 2: 2-(4-(Methylthio)-1H-pyrazol-1-yl)acetonitrile

Sodium hydride (631 mg, 16 mmol) was added to a solution of 4-(methylthio)-1H-pyrazole (1500 mg, 13.14 mmol) in anhydrous tetrahydrofuran (30 mL) under nitrogen at 0° C. The reaction mixture was stirred at 0° C. until gas evolution was no longer observed. Bromoacetonitrile (1.005 mL, 14.43 mmol) was added dropwise and the reaction mixture was stirred at room temperature for 18 h. The mixture was poured into a solution of aqueous ammonium chloride (30 mL) and was extracted with ethyl acetate (60 mL×3). The combined organics were dried over sodium sulfate. The residue was filtered through a plug of silica gel which was eluted with ethyl acetate and the filtrate was concentrated under reduced pressure. The crude material was purified via flash chromatography (0-50% ethyl acetate in heptanes) to afford 2-(4-(methylthio)-1H-pyrazol-1-yl)acetonitrile (1460 mg, 72.54%). MS (ES+) (M+H) 154.1; LCMS retention time 0.40 min (Method N).

Step 3: 1-(4-(Methylthio)-1H-pyrazol-1-yl)cyclopropanecarbonitrile

To sodium hydride (2.29 g, 57 mmol, 60% dispersion in mineral oil) was added petroleum ether (40 mL). The suspension was stirred for 10 min and the supernatant was removed. Petroleum ether (40 mL) was added again and the suspension was stirred for another 10 min. The supernatant was removed again after the suspension settled in order to remove the mineral oil. Dimethylsulfoxide (25 mL) was slowly added at 20° C. under nitrogen. A solution of 2-(4-(methylthio)-1H-pyrazol-1-yl)acetonitrile (1.46 g, 9.53 mmol) and 1,2-dibromoethane (2.46 mL, 28.5 mmol) in dimethylsulfoxide (23 mL) was added dropwise over a period of 15 minutes. Additional 1,2-dibromoethane (0.5 mL) was added and the reaction mixture was stirred at room temperature for 18 h. The reaction mixture was poured into a cold saturated aqueous solution of ammonium chloride (150 mL). The mixture was stirred for 10 min and then it was extracted with diethyl ether (100 mL×3). The combined organics were washed with brine, dried over sodium sulfate, filtered and concentrated under reduced pressure. The crude material was purified via flash chromatography (95:5 to 60:40 heptane:ethyl acetate) to afford 1-(4-(methylthio)-1H-pyrazol-1-yl)cyclopropanecarbonitrile (390 mg, 22.8%). $^1$H NMR (500 MHz, CDCl$_3$) δ 1.79-1.83 (m, 4H), 2.36 (s, 3H), 7.52 (s, 1H), 7.58-7.60 (m, 1H).

Step 4: Ethyl 1-(4-(methylthio)-1H-pyrazol-1-yl)cyclopropanecarbimidate hydrochloride To a saturated solution of hydrogen chloride in ethanol (3.5 mL) at 0° C. was added a solution of 1-(4-(methylthio)-1H-pyrazol-1-yl)cyclopropanecarbonitrile (125 mg, 0.697 mmol) in ethanol (0.5 mL). The reaction mixture was stirred at room temperature for 1.5 h. The solvent was removed under a stream of nitrogen to afford the title compound (210 mg). The material was used without further purification.

Intermediate 56: Ethyl 1-(4-chloro-1H-pyrazol-1-yl)cyclopropanecarbimidate

Step 1: 1-(4-Chloro-1H-pyrazol-1-yl)cyclopropanecarbonitrile

Into a 4-neck 2 L round bottom flask, previously dried with a heat gun under high vacuum, was added dimethylsulfoxide (175 mL). The flask was placed in a 10° C. bath and sodium hydride (60% oil dispersion, 17.0 g, 300 mmol) was added portionwise with stirring under nitrogen. The resulting suspension was stirred for 10 min before a solution of 2-(4-chloro-1H-pyrazol-1-yl)acetonitrile (10.0 g, 70.6 mmol) and 1,2-dibromoethane (18.3 mL, 213 mmol) in dimethylsulfoxide (175 mL) was added dropwise over a period of 30 min. The internal temperature was kept between 13 and 20° C. during the addition process. The reaction mixture was stirred for 5.5 h while keeping the internal temperature at or below 20° C., followed by stirring for an additional 1 h at room temperature. The mixture was cooled to 10° C., and then a saturated aqueous solution of ammonium chloride (600 mL) was slowly added. The mixture was stirred at 10° C. for 15 min, then extracted with ethyl acetate (1000 mL×3). The combined organics were washed with brine, dried over sodium sulfate, filtered and concentrated under reduced pressure. The crude material was purified via flash chromatography (10-100% dichloromethane in hexanes), and the residue was crystallized from a mixture of hexanes/diethyl ether to afford 1-(4-chloro-1H-pyrazol-1-yl)cyclopropanecarbonitrile (7.654 g). $^1$H NMR (400 MHz, CDCl$_3$) δ 1.80-1.82 (m, 4H) 7.47 (d, 1H) 7.62 (d, 1H); MS (EI+) (M+) 167; GCMS retention time 1.64 minutes (Method O).

Step 2: Ethyl 1-(4-chloro-1H-pyrazol-1-yl)cyclopropanecarbimidate

To a solution of 1-(4-chloro-1H-pyrazol-1-yl)cyclopropanecarbonitrile (17.3 g, 103 mmol) in ethanol (50 mL) was added sodium ethoxide (prepared from 3.2 g, 139 mmol of sodium metal dissolved in 150 mL of ethanol). The reaction mixture was stirred at 70° C. for 2 h to afford ethyl 1-(4-chloro-1H-pyrazol-1-yl)cyclopropanecarbimidate which was used for the next step without further purification. An aliquot of the solution was concentrated for analysis: $^1$H NMR (400 MHz, CDCl$_3$): δ 1.25 (t, 3H), 1.46 (q, 2H), 1.73 (q, 2H), 4.15 (q, 2H), 7.51 (s, 1H), 7.52 (s, 1H).

Intermediate 57: Ethyl 1-(4-methoxy-1H-pyrazol-1-yl)cyclopropanecarbimidate

The title compound was prepared by a method analogous to the one used for Intermediate 56, but using 2-(4-methoxy-1H-pyrazol-1-yl)acetonitrile as the starting material. $^1$H NMR (500 MHz, CDCl$_3$) δ 1.37 (t, 3H), 1.63-1.72 (m, 4H), 3.76 (s, 3H), 4.16 (q, 2H), 7.17 (s, 1H), 7.35 (s, 1H).

Intermediate 58: 1-(2-Cyclopropyloxazol-4-yl)cyclopropanecarboxylic acid

Step 1: Ethyl 2-(2-cyclopropyloxazol-4-yl)acetate

To a solution of cyclopropanecarboxamide (3.5 g, 41.46 mmol) in toluene and 1,4-dioxane (50 mL, 1:1) was added ethyl 4-chloro-3-oxobutanoate (20.0 g, 121.95 mmol). The mixture was heated to 100° C. for 18 h, then was diluted with water and extracted with ethyl acetate. The organic layer was dried and concentrated under reduced pressure. The crude material was purified via column chromatography on 100-200 mesh silica (20% ethyl acetate in petroleum ether) to afford ethyl 2-(2-cyclopropyloxazol-4-yl)acetate (3.5 g). MS (ES+APCI) 196.1; LCMS retention time: 4.029 min (Method Q1).

Step 2: Ethyl 1-(2-cyclopropyloxazol-4-yl)cyclopropanecarboxylate

Cesium carbonate (8.39 g, 25.78 mmol) 1,2-dibromoethane were added to a solution of ethyl 2-(2-cyclopropyloxazol-4-yl)acetate (2.0 g, 10.03 mmol) in N,N-dimethylformamide (10 mL) at room temperature. The reaction mixture was stirred at room temperature for 18 h. The mixture was diluted with water, then was extracted with ethyl acetate, dried and concentrated under reduced pressure. The crude material was purified via column chromatography on 100-200 mesh silica (10% ethyl acetate in petroleum ether) to afford ethyl 1-(2-cyclopropyloxazol-4-yl)cyclopropanecarboxylate (200 mg). MS (ES+) (M+H) 222.2; LCMS retention time: 2.514 min (Method N1).

Step 3: 1-(2-Cyclopropyloxazol-4-yl)cyclopropanecarboxylic acid

An aqueous solution of sodium hydroxide (4N, 5 mL) was added to a solution of ethyl 1-(2-cyclopropyloxazol-4-yl)cyclopropanecarboxylate (200 mg, 0.9 mmol) in tetrahydrofuran and water (4 mL, 1:1). The reaction mixture was stirred at room temperature for 12 h. The mixture was acidified with an aqueous solution of hydrochloric acid (4N), extracted with ethyl acetate, dried and concentrated under reduced pressure to afford the title compound (150 mg). MS (ES+APCI) (M+H) 194.1; LCMS retention time: 3.515 min (Method Q1).

Intermediate 59: Ethyl 2-(4-fluoro-1H-pyrazol-1-yl)propanimidate

Step 1: 2-(4-Fluoro-1H-pyrazol-1-yl)propanenitrile

4-Fluoro-1H-pyrazole (300 mg, 3.49 mmol), 2-chloropropanenitrile (374 mg, 4.18 mmol), cesium carbonate (1.84 g, 5.23 mmol) and anhydrous acetonitrile (5.0 mL) were added into a round bottom flask. The reaction mixture was heated to 100° C. for 2 h. Water was added and the mixture was extracted with ether (100 mL×3). The combined organic layers were dried over sodium sulfate, filtered and concentrated under reduced pressure. The crude material was purified via flash chromatography (0-50% ethyl acetate in heptanes) to afford 2-(4-Fluoro-1H-pyrazol-1-yl)propanenitrile (398 mg, 82%). MS (EI+) (M+) 139, GCMS retention time: 0.78 min (Method O).

Step 2: Ethyl 2-(4-fluoro-1H-pyrazol-1-yl)propanimidate

To a solution of sodium ethoxide, prepared by adding solid sodium metal (64.4 mg, 2.80 mmol) to ethanol (10 mL), was added a solution of 2-(4-fluoro-1H-pyrazol-1-yl)propanenitrile (390 mg, 2.80 mmol) in ethanol (2 mL). The reaction mixture was stirred at 70° C. for 18 h. The mixture was cooled to room temperature and used without further purification. MS (EI+) (M+) 186; GCMS retention time: 1.27 min (Method O).

Intermediate 60: Ethyl 2-(4-chloro-1H-pyrazol-1-yl)propanimidate

Step 1: 2-(4-Chloro-1H-pyrazol-1-yl)propanenitrile

4-Chloro-1H-pyrazole (4.05 g, 39.5 mmol), 2-chloropropanenitrile (3.71 g, 41.5 mmol), cesium carbonate (15.6 g, 44.3 mmol) and anhydrous tetrahydrofuran (20 mL) were added into a sealed tube and the reaction mixture was heated to 100° C. for 2 h. The mixture was diluted with ether (100 mL) and filtered. The solids were rinsed with ether (30 mL×3) and the filtrate was diluted with dichloromethane (10 mL). The solution was concentrated under reduced pressure to afford the title compound as oil (7.15 g). The material was taken to the next step without further purification. $^1$H NMR (500 MHz, CDCl$_3$) δ 1.90 (d, 3H), 5.21-5.30 (m, 1H), 7.51 (s, 1H), 7.58 (s, 1H); MS (EI+) (M+) 155; GCMS retention time: 1.23 minutes (Method O).

Step 2: Ethyl 2-(4-chloro-1H-pyrazol-1-yl)propanimidate

A solution of sodium ethoxide, prepared by adding solid sodium (420 mg, 18.2 mmol) into ethanol (20 mL), was added to a solution of 2-(4-chloro-1H-pyrazol-1-yl)propanenitrile (2530 mg, 13.0 mmol) in ethanol (4 mL). The reaction mixture was stirred at 70° C. for 3 h. $^1$H NMR analysis of the reaction mixture showed desired product. The mixture was used without further purification. $^1$H NMR (500 MHz, CDCl$_3$) δ 1.30 (t, 3H), 1.75 (m, 3H), 4.19 (m, 2H), 4.86 (m, 1H), 7.47 (s, 1H), 7.52 (s, 1H).

Intermediate 61: 1-(Pyrazin-2-yl)cyclopropanecarboxylic acid

Step 1: 1-(Pyrazin-2-yl)cyclopropanecarbonitrile

To a suspension of sodium hydride (0.386 g, 16.1 mmol) in anhydrous N,N-dimethylformamide (5 mL) was added dropwise a solution of 2-(pyrazin-2-yl)acetonitrile (0.55 g, 4.6 mmol) and 1,2-dibromoethane (2.25 g, 11.9 mmol) in anhydrous N,N-dimethylformamide (8 mL) over a period of 10 min at room temperature. The mixture was stirred for 18 h, then was quenched with water and extracted with ethyl acetate. The organic layer was washed with brine, dried over sodium sulfate, filtered, and concentrated under reduced pressure. The crude material was purified via column chromatography (100-200 mesh silica gel, 100% dichloromethane) to afford 1-(pyrazin-2-yl)cyclopropanecarbonitrile (210 mg, 31%).

Step 2: 1-(Pyrazin-2-yl)cyclopropanecarboxylic acid

A 20% aqueous sodium hydroxide solution (1 mL) was added to a solution of 1-(pyrazin-2-yl)cyclopropanecarbonitrile (0.2 g, 1.37 mmol) in methanol (10 mL) at room temperature. The reaction mixture was heated at reflux for 36 h. The mixture was cooled, and then the solvent was removed under reduced pressure. The resulting residue was partitioned between water and ethyl acetate. The aqueous layer was neutralized with aqueous hydrochloric acid (3N) and the water was removed under reduced pressure. To the residue was added methanol and dichloromethane. The mixture was filtered to remove the insoluble solids and the filtrate was dried over sodium sulfate, filtered and concentrated under reduced pressure to afford the title compound (100 mg). MS (ES−) (M−1) 162.9.

Intermediate 62: 1-(Pyrimidin-2-yl)cyclopropanecarbaldehyde

Step 1: 1-(Pyrimidin-2-yl)cyclopropanecarbonitrile 1-(Pyrimidin-2-yl)cyclopropanecarbonitrile was prepared by a method analogous to the one used for Intermediate 61, Step 1. MS (ES+) (M+H) 146.1.

Step 2: 1-(Pyrimidin-2-yl)cyclopropanecarbaldehyde

Diisobutylaluminum hydride (1M in tetrahydrofuran, 10.9 mL, 11 mmol) was added dropwise to a solution of 1-(pyrimidin-2-yl)cyclopropanecarbonitrile (0.2 g, 1.37 mmol) in anhydrous toluene (10 mL) at −78° C. over a period of 15 min. The reaction mixture was warmed to room temperature and was stirred at room temperature for 30 min. The mixture was then cooled back to −78° C. and another portion of diisobutylaluminum hydride (1M in tetrahydrofuran, 10.9 mL, 11 mmol) was added. The reaction mixture was warmed to room temperature and stirred for another 30 min. The mixture was quenched with aqueous sodium hydroxide (2N) at −20° C. and then stirred at room temperature for 30 min. The mixture was filtered through a pad of Celite and the filtrate was extracted with ethyl acetate. The organics were dried over sodium sulfate, filtered and concentrated under reduced pressure to afford the title compound (0.125 g). The material was used without further purification. MS (ES+APCI) (M+H) 149.0.

Intermediate 63: Ethyl 1-(1H-pyrazol-1-yl)cyclopropanecarbimidate

Step 1: 1-(1H-Pyrazol-1-yl)cyclopropanecarbonitrile

Sodium hydride (4.65 g, 121 mmol, 60% oil dispersion) was washed with petroleum ether under a nitrogen atmosphere. The supernatant was removed after the suspension settled in order to remove the mineral oil. Then a solution of 2-(1H-pyrazol-1-yl)acetonitrile (3 g, 27 mmol) and 1,2-dibromoethane (6.98 mL, 81 mmol) in dimethylsulfoxide (90 mL) was added at 20° C. over a period of 40 min. The reaction mixture was stirred at room temperature for 5 d. A saturated aqueous solution of ammonium chloride was added and the mixture was stirred at 0° C. for 15 min, extracted with diethyl ether, washed with brine, dried over sodium sulfate and concentrated under reduced pressure. The resulting crude was purified via column chromatography (100-200 mesh silica gel, 5-12% ethyl acetate in petroleum ether) to afford 1-(1H-pyrazol-1-yl)cyclopropanecarbonitrile (1 g, 28%).

Step 2: Ethyl 1-(1H-pyrazol-1-yl)cyclopropanecarbimidate

Sodium metal (12 mg, 0.52 mmol) was added to anhydrous ethanol (3 mL) at room temperature and the mixture was stirred for 15 min. 1-(1H-pyrazol-1-yl)cyclopropanecarbonitrile (0.1 g, 0.75 mmol) dissolved in ethanol (2 mL) was added and the reaction mixture was heated to 70° C. for 90 min. The resulting solution was used without further purification.

Intermediate 64: Ethyl 1-(4-fluoro-1H-pyrazol-1-yl)cyclopropanecarbimidate

Step 1: 2-(4-Fluoro-1H-pyrazol-1-yl)acetonitrile

Sodium hydride (306 mg, 12.78 mmol, 60% oil dispersion) was suspended in tetrahydrofuran and the suspension was cooled to 0° C. A solution of 4-fluoro-1H-pyrazole (1.0 g, 11.62 mmol) and 2-bromoacetonitrile (1.39 g, 11.62 mmol) in tetrahydrofuran at 0° C. was added dropwise over a period of 40 min. The reaction mixture was stirred at room temperature for 12 h, and then a saturated aqueous solution of ammonium chloride was added. The mixture was extracted with diethyl ether, and the organic layer was washed with brine, dried over sodium sulfate, filtered and concentrated under reduced pressure. The crude material was purified via column chromatography (100-200 mesh silica gel, 5-10% ethyl acetate in petroleum ether) to afford 2-(4-fluoro-1H-pyrazol-1-yl)acetonitrile (1 g).

Step 2: 1-(4-Fluoro-1H-pyrazol-1-yl)cyclopropanecarbonitrile

Sodium hydride (1.26 g, 52.75 mmol, 60% oil dispersion) was washed with petroleum ether under a nitrogen atmosphere. The supernatant was removed after the solids settled. Then a solution of 2-(4-fluoro-1H-pyrazol-1-yl)acetonitrile (1.1 g, 8.79 mmol) and 1,2-dibromoethane (2.28 mL, 26.37 mmol) in dimethylsulfoxide (90 mL) was added at 0° C. over a period of 40 min. The reaction mixture was stirred at room temperature for 6 h. A saturated aqueous solution of ammonium chloride was added and the mixture was extracted with diethyl ether. The organic layer was washed with brine, dried over sodium sulfate, filtered and concentrated under reduced pressure. The crude material was purified via column chromatography (100-200 mesh silica gel, 5-12% ethyl acetate in petroleum ether) to afford 1-(4-fluoro-1H-pyrazol-1-yl)cyclopropanecarbonitrile (300 mg).

Step 3: Ethyl 1-(4-fluoro-1H-pyrazol-1-yl)cyclopropanecarbimidate

Sodium metal (47 mg, 1.98 mmol) was added to anhydrous ethanol (4 mL) at room temperature. The mixture was stirred for 15 min. A solution of 1-(4-fluoro-1H-pyrazol-1-yl)cyclopropanecarbonitrile (0.1 g, 0.66 mmol) in ethanol (2 mL) was added and the reaction mixture was heated to 70° C. for 90 min. The resulting solution was used without further purification.

Intermediate 65: Ethyl 1-(2H-1,2,3-triazol-2-yl)cyclopropanecarbimidate

The title compound was prepared by a method analogous to the one used for Intermediate 64, but using 1,2,3-triazole as the starting material.

Intermediate 66: 1-(1H-Imidazol-1-yl)cyclopropanecarbaldehyde

Step 1: Ethyl 1-(1H-imidazol-1-yl)cyclopropanecarboxylate

Ethyl 1-aminocyclopropanecarboxylate hydrochloride (850 mg, 6.58 mmol), phosphoric acid (85%, 0.2 mL), glyoxal (40%, 0.76 mL) and formaldehyde (37%, 0.5 mL) in water (4 mL) were stirred for 15 min at room temperature. The reaction mixture was then heated to 90° C. followed by the addition of ammonium chloride (354 mg) in water (3 mL). The resulting mixture was stirred at 90° C. for 1 h. The mixture was cooled to room temperature and was neutralized using aqueous potassium hydroxide (3N) at 10° C. The solvent was removed under reduced pressure and co-distilled with toluene. The crude material was purified via column chromatography (100-200 mesh silica gel, 0-5% methanol in dichloromethane) to afford ethyl 1-(1H-imidazol-1-yl)cyclopropanecarboxylate (350 mg).

Step 2: (1-(1H-Imidazol-1-yl)cyclopropyl)methanol

Diisobutylaluminum hydride (1M in tetrahydrofuran, 8 mL, 8 mmol) was added dropwise to a solution of ethyl 1-(1H-imidazol-1-yl)cyclopropanecarboxylate (0.3 g, 1.6 mmol) in anhydrous dichloromethane (20 mL) at −78° C. The reaction mixture was warmed to room temperature and stirred at that temperature for 5 h. A saturated aqueous solution of ammonium chloride was added and the mixture was stirred for 30 min. The resulting solids were filtered through a pad of Celite and the filtrate was dried over sodium sulfate. The organics were concentrated under reduced pressure and the crude material was purified via column chromatography (100-200 mesh silica gel, 0-6% methanol in dichlormethane) to afford (1-(1H-imidazol-1-yl)cyclopropyl)methanol 0.15 g). MS (ES+APCI) (M+H) 139.1.

Step 3: 1-(1H-Imidazol-1-yl)cyclopropanecarbaldehyde

To a solution of (1-(1H-imidazol-1-yl)cyclopropyl)methanol (42.39 mg, 0.307 mmol) in anhydrous ethyl acetate (10 mL) was added 2-iodoxybenzoic acid (IBX) (129 mg, 0.461 mmol). The reaction mixture was heated at reflux for 2 h. The mixture was filtered and the filtrate was concentrated to afford the title compound which was used for the next step without further purification.

Intermediate 67: Ethyl 1-(1-methyl-1H-1,2,4-triazol-5-yl)cyclopropanecarbimidate

Step 1: 5-(Chloromethyl)-1-methyl-1H-1,2,4-triazole hydrochloride

Thionyl chloride (20 mL) was added to (1-methyl-1H-1,2,4-triazol-5-yl)methanol (2.0 g) at 0° C. The reaction mixture was stirred for 2 h at 80° C. The mixture was cooled to room temperature and then was concentrated under reduced pressure. Ethyl acetate was added to the resulting precipitate and the mixture was filtered under a nitrogen atmosphere to afford 5-(chloromethyl)-1-methyl-1H-1,2,4-triazole hydrochloride (1.5 g). The material was used for the next step without further purification. MS (EI+) (M+) 131.0

Step 2: 2-(1-Methyl-1H-1,2,4-triazol-5-yl)acetonitrile

A solution of 5-(chloromethyl)-1-methyl-1H-1,2,4-triazole hydrochloride (1.5 g, 11.45 mmol) in dimethylsulfoxide (30 mL) was added to a stirred suspension of sodium cyanide (3.366 g, 68.70 mmol) in dimethylsulfoxide (20 mL), and the reaction mixture was stirred at room temperature for 16 h. The mixture was partitioned between ethyl acetate and water. The organic layer was dried over sodium sulfate and concentrated. The resulting crude product was purified via column chromatography (100-200 mesh silica gel, 10-12% ethyl acetate in petroleum ether) to afford 2-(1-methyl-1H-1,2,4-triazol-5-yl)acetonitrile (1.2 g). MS (ES+APCI) (M+H) 123.2.

Step 3: 1-(1-Methyl-1H-1,2,4-triazol-5-yl)cyclopropanecarbonitrile

Sodium hydride (60% dispersion in mineral oil, 1.06 g, 44.2 mmol) was washed twice with petroleum ether under nitrogen. Then dimethylsulfoxide (10 mL) was added at room temperature. A solution of 2-(1-methyl-1H-1,2,4-triazol-5-yl)acetonitrile (0.9 g, 7.36 mmol) and 1,2-dibromoethane (4.147 g, 22.1 mmol) in dimethylsulfoxide (20 mL) was added dropwise to the sodium hydride suspension over a period of 20 min. The reaction mixture was stirred at room temperature for 3 h. The mixture was partitioned between ethyl acetate and water. The organic layer was dried over sodium sulfate and concentrated under reduced pressure. The crude material was purified via column chromatography (100-200 mesh silica gel, 5-15% ethyl acetate in petroleum ether) to afford 1-(1-methyl-1H-1,2,4-triazol-5-yl)cyclopropanecarbonitrile (0.7 g) as a colorless oil.

Step 4: Ethyl 1-(1-methyl-1H-1,2,4-triazol-5-yl)cyclopropanecarbimidate

Sodium metal (37 mg, 1.61 mmol) was added to anhydrous ethanol (5 mL) at room temperature. The mixture was stirred for 30 min. A solution of 1-(1-methyl-1H-1,2,4-triazol-5-yl)cyclopropanecarbonitrile (0.3 g, 2.0 mmol) in ethanol (5 mL) was added and the reaction mixture was heated to 60° C. for 1 h. The resulting mixture was used without further purification. MS (ES+APCI) (M+H) 195.1.

Intermediate 68: (R)-2-(4-Chloro-1H-pyrazol-1-yl)propanoic acid

Step 1: (S)-Methyl 2-(trifluoromethylsulfonyloxy)propanoate 2,6-Lutidine (1.2 mL, 10 mmol) and methyl (S)-lactate (1.041 g, 10.0 mmol) were dissolved in a mixture of heptanes:dichloromethane (4:1, 10 mL) under nitrogen. The solution was cooled to −10° C. using an ice-brine bath. Trifluoromethanesulfonic anhydride (2.0 mL, 12 mmol) was added dropwise over 10 min while stirring the cooled solution. After the addition was completed, the reaction mixture was stirred at −10° C. for 30 min, then quenched with aqueous hydrochloric acid (0.5 M, 15 mL) and stirred at −10° C. for another 30 min. The resulting mixture was transferred to a separatory funnel and the phases were separated. Silica gel (2 g) was added to the funnel containing the organic layer and the mixture was shaken, and then filtered through a 2 g silica gel plug (eluting with 40 mL of a 3% ethyl acetate in heptanes solution). The filtrate was concentrated at room temperature to afford (S)-methyl 2-(trifluoromethylsulfonyloxy)propanoate as a clear oil (1.538 g). $^1$H NMR (500 MHz, CDCl$_3$) δ 1.72 (d, 3H), 3.87 (s, 3H), 5.24 (q, 1H).

Step 2: (R)-Methyl 2-(4-chloro-1H-pyrazol-1-yl)propanoate

4-Chloro-1H-pyrazole (668 mg, 6.51 mmol) was dissolved in ethyl acetate and (S)-methyl 2-(trifluoromethylsulfonyloxy)propanoate (1.538 g, 6.51 mmol) was added followed by potassium carbonate (2.70 g, 19.5 mmol) while stirring at room temperature. The reaction mixture was stirred for 18 h. The mixture was diluted with methyl tert-butyl ether (15 mL), filtered through Celite, and washed with a mixture of ethyl acetate:methyl tert-butyl ether (1:1, 15 mL×4). The filtrate was reduced in volume by approximately 30-40 mL then was washed with aqueous hydrochloric acid (0.1 M, 25 mL), water and brine (15 mL). The organic phase was dried over magnesium sulfate, filtered and concentrated to afford (R)-methyl 2-(4-chloro-1H-pyrazol-1-yl)propanoate as an oil (1.02 g). $^1$H NMR (500 MHz, CDCl$_3$) δ 1.77 (d, 3H), 3.76 (s, 3H), 5.05 (q, 1H), 7.46 (s, 1H), 7.54 (s, 1H); MS (EI+) (M+) 188; Chiral HPLC retention time: 3.11 min (Method: Chiralpak AD-H 0.46×25 cm, Mobile Phase: 95/5 CO$_2$/methanol; Flow: 2.5 mL/min); 73.3% ee.

Step 3: (R)-2-(4-Chloro-1H-pyrazol-1-yl)propanoic acid (R)-Methyl 2-(4-chloro-1H-pyrazol-1-yl)propanoate (1.00 g, 5.30 mmol) was suspended in a solution of aqueous hydrochloric acid (6M, 8.8 mL, 53 mmol). The reaction mixture was stirred for 18 h at reflux. The mixture was cooled to 0° C. and quenched with a saturated aqueous solution of sodium phosphate (NaH$_2$PO$_4$). The pH was adjusted to 1-2 using aqueous sodium hydroxide and hydrochloric acid. The mixture was extracted with ethyl acetate (20 mL×3). The combined organics were washed with brine, dried over magnesium sulfate, filtered and concentrated. The residue was dried under vacuum, dissolved in a hot solution of heptanes:ethyl acetate (3:1, 9 mL) and allowed to cool to room temperature. A seed crystal was added while cooling. The mixture was stirred for 18 h. The solids were collected by filtration and washed with a solution of heptanes:ethyl acetate (3:1, 2 mL×2) and heptanes (2 mL×2). The resulting solids were air dried to afford (R)-2-(4-chloro-1H-pyrazol-1-yl)propanoic acid (310 mg, 33%). $^1$H NMR (500 MHz, CDCl$_3$) δ 1.8 (d, 3H), 5.13 (q, 1H), 7.51 (s, 1H), 7.55 (s, 1H), 11.8 (s, 1H); MS (EI+) (M+) 174; Chiral HPLC retention time: 3.81 min (Method: Chiralpak AD-H 0.46×25 cm, Mobile Phase: 90/10 CO$_2$/methanol; Flow: 2.5 mL/min); >99.5% ee.

Intermediate 69: 1-(Pyridazin-3-yl)cyclopropanecarboxylic acid

Step 1: Ethyl 2-(pyridazin-3-yl)acetate

Lithium diisopropylamide (2M in tetrahydrofuran, 6.83 g, 63.7 mmol) was added dropwise to a stirred solution of 3-methylpyridazine (5.0 g, 53.12 mmol) in anhydrous tetrahydrofuran (80 mL) at −78° C. under a nitrogen atmosphere over a period of 20 min. The mixture was allowed to warm to room temperature. The mixture was stirred for 1 h at room temperature and cooled again to −78° C. Diethyl carbonate (12.57 g, 106.2 mmol) in anhydrous tetrahydrofuran (20 mL) was added at −78° C. over a period of 20 min. The reaction mixture was allowed to warm to room temperature, stirred for 16 h and partitioned between ethyl acetate and a saturated aqueous solution of ammonium chloride. The organics were dried over sodium sulfate and concentrated under reduced pressure. The resulting crude material was purified via column chromatography (100-200 mesh silica gel, 50-80% ethyl acetate in petroleum ether) to afford ethyl 2-(pyridazin-3-yl)acetate (600 mg). MS (ES+) (M+H) 167.1569.

Step 2: Ethyl 1-(pyridazin-3-yl)cyclopropanecarboxylate

Sodium hydride (60% suspension in mineral oil, 830 mg, 21.66 mmol) was washed with petroleum ether under a nitrogen atmosphere to remove the mineral oil. Dimethylsulfoxide (10 mL) was added and the resulting suspension was stirred for 5 min before adding ethyl 2-(pyridazin-3-yl)acetate (600 mg, 3.61 mmol) and 1,2-dibromoethane (2.03 g, 10.83 mmol) dissolved in dimethylsulfoxide (10 mL) at 10° C. The reaction mixture was allowed to warm to room temperature and stirred for 2 h. The mixture was partitioned between a saturated aqueous solution of ammonium chloride and ethyl acetate. The organics were dried over sodium sulfate and concentrated under reduced pressure. The resulting crude material was purified via column chromatography (100-200 silica gel mesh, 50-60% ethyl acetate in petroleum ether) to afford ethyl 1-(pyridazin-3-yl)cyclopropanecarboxylate (300 mg). MS (ES+APCI) (M+H) 193.0.

Step 3: 1-(Pyridazin-3-yl)cyclopropanecarboxylic acid

Lithium hydroxide (196.4 mg, 4.68 mmol) was added to a solution of ethyl 1-(pyridazin-3-yl)cyclopropanecarboxylate (300 mg, 156 mmol) in tetrahydrofuran and water (1:1, 10 mL) at room temperature. The reaction mixture was stirred for 2 h and concentrated. The resulting residue was dissolved in water and the pH was adjusted to 2 using 1N aqueous hydrochloric acid. The mixture was extracted with ethyl acetate. The organics were dried over sodium sulfate and concentrated to afford the title compound (160 mg) which was used as is without further purification. MS (ES+APCI) (M−H) 163.0; LCMS retention time: 2.713 minutes (Method X1)

Intermediate 70: 1-(4-Chloro-1H-pyrazol-1-yl)cyclopropanecarboxylic acid

Step 1: tert-Butyl 1-(4-chloro-1H-pyrazol-1-yl)cyclopropanecarboxylate

Into a flask was added potassium trimethylsilanolate (20.85 g, 146.31 mmol), 4-chloro-1H-pyrazole (15 g, 146.31 mmol) and 2-methyltetrahydrofuran (400 mL). The mixture was stirred for 5 min followed by the addition of tert-butyl 2,4-dibromobutyrate (27.84 mL, 146.31 mmol) over a period of 20 to 30 seconds. The reaction mixture was stirred for 60 min. Potassium trimethylsilanolate (20.85 g, 146.31 mmol) in 2-methyltetrahydrofuran (80 mL) was added over a period of 5 min. The reaction mixture was stirred for 1 h before adding tert-butyl 2,4-dibromobutyrate (1 mL, 5.3 mmol). After 30 min, an additional portion of tert-butyl 2,4-dibromobutyrate (2 mL, 10.5 mmol) was added. The mixture was stirred for 40 min before adding tert-butyl 2,4-dibromobutyrate (1 mL, 5.3 mmol) and potassium trimethylsilanolate (2 g, 14 mmol). The reaction mixture was stirred for 18 h. Hydrochloric acid (146.31 mL, 146.31 mmol) was added and the mixture was stirred for 5 min. The layers were separated, and the organics were washed with water (200 mL) and concentrated under reduced pressure. Toluene (100 mL) was added and the mixture was concentrated to dryness to afford tert-butyl 1-(4-chloro-1H-pyrazol-1-yl)cyclopropanecarboxylate (45 g). $^1$H NMR (400 MHz, CDCl$_3$): δ 1.40 (s, 9H), 1.57 (q, 2H), 1.75 (q, 2H), 7.44 (s, 1H), 7.51 (s, 1H); MS (EI+) (M+) 242; GCMS retention time: 2.37 minutes (Method O).

Step 2: 1-(4-Chloro-1H-pyrazol-1-yl)cyclopropanecarboxylic acid

To a solution of tert-butyl 1-(4-chloro-1H-pyrazol-1-yl) cyclopropanecarboxylate (45 g) in toluene (60 mL) was added trifluoroacetic acid (33.19 mL, 438.92 mmol). The reaction mixture was heated to 45° C. for 3 h, then cooled to room temperature and stirred for 18 h. A further portion of trifluoroacetic acid (2 mL) was added. The reaction mixture was heated to 45° C. and stirred for 1 h. The mixture was reduced in volume under vacuum in a jacketed vessel with the temperature set at 50° C. Toluene (200 mL) was added and the mixture was concentrated to low volume, and then this was repeated with a further 200-mL portion of toluene. Toluene (200 mL) was added, and the mixture was stirred at room temperature for 18 h. The organics were washed sequentially with a 2N aqueous solution of potassium hydroxide (150 mL), and 1N aqueous solution of potassium hydroxide (150 mL). The aqueous layers were combined and acidified to pH~1 with concentrated hydrochloric acid, then extracted with ethyl acetate (200 mL×2). The combined extracts were concentrated to low volume and the residue was diluted with ethyl acetate (100 mL) and concentrated to dryness to afford an orange solid (32 g). Toluene (136 mL) was added to the solid and the mixture was heated to 60° C. and stirred for 15 min until all the solids dissolved, then cooled to 40° C., held at that temperature for 1 h, and then cooled to 36° C. and held at that temperature for 1 h. The mixture was warmed to 50° C. and n-heptane (136 mL) was added dropwise over a period of 30 min. The mixture was kept at 50° C. for 10 min until the solution became turbid. The temperature was increased to 55° C., held for 1.5 h, cooled to room temperature over a period of 2 h and granulated over a period of 18 h. The mixture was filtered and the solids were washed with a mixture of toluene: heptanes (1:1, 55 mL) and dried in a vacuum oven at 40° C. for 4 h to afford the title compound as a white solid (11.40 g, 41.76%). $^1$H NMR (400 MHz, DMSO-d$_6$) δ 1.41-1.71 (m, 4H), 7.54 (s, 1H), 8.12 (s, 1H), 13.09 (s, 1H); MS (EI+) (M+) 186; GCMS retention time: 2.56 minutes (Method O).

Alternative preparation for 1-(4-chloro-1H-pyrazol-1-yl)cyclopropanecarboxylic acid Step 1: tert-Butyl 1-(4-chloro-1H-pyrazol-1-yl)cyclopropanecarboxylate 4-Chloro-1H-pyrazole (2.87 kg, 28.0 mol) and tert-butyl 2,4-dibromobutyrate (9.89 kg, 32.8 mol) were dissolved in 2-methyltetrahydrofuran (26.0 L) and the resulting solution was cooled to 5° C. A suspension of potassium trimethylsilanolate (9.58 kg, 67.2 mol) in tetrahydrofuran (23.5 L) was added over 30 min while maintaining the temperature below 15° C. The resulting slurry was stirred at 22° C. for 12 h. The presence of tert-butyl 1-(4-chloro-1H-pyrazol-1-yl)cyclopropanecarboxylate was confirmed by HPLC analysis [HPLC retention time: 8.76 min (Column: Halo C18, 4.6×150 mm, 2.7 µm; Mobile Phase A: acetonitrile, Mobile Phase B: 0.05% methanesulfonic acid in water; Linear Gradient: 5:95 A:B to 95:5 A:B over 9 min, then held for 1 min; Flow: 1.0 mL/min; UV detection at 210, 226, and 254 nM)]. Aqueous hydrochloric acid (2M, 22.5 L, 45.0 mol) was added while maintaining the temperature at 22° C. The aqueous layer was removed and the organic layer was washed with 13% aqueous sodium chloride solution (9.6 L). The wash layer was removed and the resulting solution of tert-butyl 1-(4-chloro-1H-pyrazol-1-yl)cyclopropanecarboxylate was distilled under reduced pressure at 40° C. until a volume of approximately 8 L was achieved. Residual tetrahydrofuran solvents were exchanged for ethyl acetate (one 9.6-L portion, followed by continuous addition of a 19.0-L portion to maintain a constant volume) by distillation under reduced pressure at 40° C. The volume was reduced to approximately 8 L to afford a solution of tert-butyl 1-(4-chloro-1H-pyrazol-1-yl)cyclopropanecarboxylate and ethyl acetate, which was used in the next step without further purification.

Step 2:
1-(4-Chloro-1H-pyrazol-1-yl)cyclopropanecarboxylic acid

A solution of tert-butyl 1-(4-chloro-1H-pyrazol-1-yl)cyclopropanecarboxylate (from the previous step) in ethyl acetate (13 L, followed by a 2-L rinse) was added to a solution of anhydrous hydrogen chloride (prepared by adding acetyl chloride (9.0 L, 126 mol) to a solution of methanol (6.2 L, 154 mol) and ethyl acetate (19.0 L)) over a period of 10 min while maintaining a temperature of 20° C. Over a period of 12 h at that temperature, a precipitate formed. The presence of 1-(4-chloro-1H-pyrazol-1-yl)cyclopropanecarboxylic acid was confirmed by HPLC analysis of the mixture [HPLC retention time: 5.49 min (Column: Halo C18, 4.6×150 mm, 2.7 μm; Mobile Phase A: acetonitrile, Mobile Phase B: 0.05% methanesulfonic acid in water; Linear Gradient: 5:95 A:B to 95:5 A:B over 9 min, then held for 1 min; Flow: 1.0 mL/min; UV detection at 210, 226, and 254 nM)]. The mixture was cooled to 10° C. and was held at that temperature for 2 h. The solids were collected by filtration, rinsing the reaction vessel with ethyl acetate (9.6 L). The solids were dried under a nitrogen flow, and then were dried in a vacuum oven at 40° C. to remove residual solvent and hydrogen chloride, to afford 1-(4-chloro-1H-pyrazol-1-yl)cyclopropanecarboxylic acid (3.3 kg, 63% over 2 steps).

Intermediate 71:
2-(2-Hydroxypropan-2-yl)isonicotinaldehyde

Step 1: 2-Acetylisonicotinonitrile

To a solution of isonicotinonitrile (52 g, 0.5 mol) in dichloromethane (1300 mL) and water (1100 mL) were added ammonium persulfate (($NH_4)_2S_2O_8$) (170 g, 0.75 mol), silver nitrate (6.8 g, 0.04 mol) and aqueous sulfuric acid (40 mL, 98% sulfuric acid in 400 mL). A solution of 3-oxo-butyric acid (110 g, 1.25 mol) in dichloromethane (100 mL) was added dropwise while keeping the mixture refluxing. The reaction mixture was refluxed for 2 h. The resulting mixture was basified to pH~8-9 using sodium carbonate powder. The mixture was filtered and the filtrate was extracted with dichloromethane (500 mL×3). The combined organics were dried over sodium sulfate, and concentrated under reduced pressure. The residue was recrystallized from ethanol to afford 2-acetylisonicotinonitrile (52.0 g, 71.9%).

Step 2: 2-(2-Hydroxypropan-2-yl)isonicotinonitrile

To a solution of 2-acetylisonicotinonitrile (67.1 g, 0.457 mol) in tetrahydrofuran (2400 mL) was added dropwise a solution of methylmagnesium bromide (3.0 M, 167.6 mL, 0.503 mol) in toluene/tetrahydrofuran mixture (3:1) at −40° C. over a period of 2.5 h. The reaction mixture was stirred at −40° C. for another 2 h. A saturated aqueous solution of ammonium chloride (50 mL) was added. The resulting mixture was warmed to room temperature and another 400 mL of a saturated aqueous solution of ammonium chloride was added. The layers were separated and the aqueous layer was extracted with dichloromethane (400 mL×2). The combined organics were dried over sodium carbonate and sodium sulfate and concentrated. The residue was purified via flash chromatography (ethyl acetate/petroleum ether 1:20, 0.3% triethylamine) to afford 2-(2-hydroxypropan-2-yl)isonicotinonitrile (33.0 g, 44.3%).

Step 3: 2-(2-Hydroxypropan-2-yl)isonicotinaldehyde

To a solution of 2-(2-hydroxypropan-2-yl)isonicotinonitrile (41.4 g, 0.255 mol) in toluene (500 mL) was added dropwise a solution of diisobutylaluminum hydride (1 mol/L in hexane, 765 mL, 0.765 mol) at −70° C. over a period of 1.5 h. The reaction mixture was stirred at −70° C. for 30 min. Methanol (30 mL) was added followed by a 20% aqueous solution of sodium tartrate (700 mL) while stirring. The layers were separated and the aqueous layer was extracted with dichloromethane (400 mL×2). The combined organics were washed with a 20% aqueous solution of sodium tartrate (700 mL). The organic phase was stirred with a 10% aqueous solution of sulfuric acid (800 mL) for 15 min. The organics were dried over sodium carbonate and sodium sulfate and concentrated under reduced pressure. A saturated aqueous solution of sodium bisulfate (400 mL) was added to the residue and the mixture was extracted with ethyl acetate (100 mL×3). The aqueous layer was neutralized with aqueous sodium carbonate and extracted with ethyl acetate (200 mL×3). The combined organics were dried over sodium sulfate and concentrated under reduced pressure to afford the title compound (23 g, 54%).

Intermediate 72: 2-(4-(Trifluoromethyl)-1H-1,2,3-triazol-1-yl)acetic acid

The title compound can be prepared by hydrolysis of the commercially available ethyl 2-(4-(trifluoromethyl)-1H-1,2,3-triazol-1-yl)acetate using procedures well known in the literature.

EXAMPLES

Example 1

(R)-Pyrrolidin-1-yl(1-(2-(3-(trifluoromethoxy)phenyl)-3H-imidazo[4,5-b]pyridin-5-yl)piperidin-3-yl)methanone

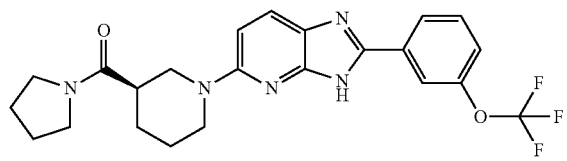 [SMILES: O=C([C@@H]1CCCN(c2ccc3nc(-c4cccc(OC(F)(F)F)c4)[nH]c3n2)C1)N1CCCC1]

Step 1: (R)-tert-Butyl 3-(pyrrolidine-1-carbonyl)piperidine-1-carboxylate

To a solution of pyrrolidine (2.134 g, 30 mmol) in N,N-dimethylformamide (240 mL) was added (R)-1-(tert-butoxycarbonyl)piperidine-3-carboxylic acid (6.878 g, 30 mmol). Then hydroxybenzotriazole (1.028 g, 6 mmol), 1-ethyl-3-[3-(dimethylamino)propyl]carbodiimide hydrochloride (5.751 g, 30 mmol), and triethylamine (7.59 g, 75 mmol) were added sequentially. The mixture was stirred at 30° C. for 16 h. The solvent was removed under reduced pressure and an aqueous solution of sodium bicarbonate (200 mL, 0.1M) was added. The mixture was extracted with ethyl acetate (200 mL×3) and the combined organics were dried over anhydrous sodium sulfate, filtered and concentrated under reduced pressure to afford (R)-tert-butyl 3-(pyrrolidine-1-carbonyl)piperidine-1-carboxylate, which was used in the next step without further purification.

Step 2: (R)-Piperidin-3-yl(pyrrolidin-1-yl)methanone

To a solution of (R)-tert-butyl 3-(pyrrolidine-1-carbonyl)piperidine-1-carboxylate in methanol (120 mL) was slowly added a solution of hydrogen chloride in 1,4-dioxane (30 mL, 4M). The mixture was stirred at 30° C. for 2 h. The solvent was removed under reduced pressure to afford (R)-piperidin-3-yl(pyrrolidin-1-yl)methanone, which was used in the next step without further purification.

Step 3: (R)-(1-(6-Amino-5-nitropyridin-2-yl)piperidine-3-yl)(pyrrolidin-1-yl)methanone To a mixture of (R)-piperidin-3-yl(pyrrolidin-1-yl)methanone in N,N-dimethylformamide (120 mL) was added diisopropylethylamine (15 mL) followed by 6-chloro-3-nitropyridin-2-amine (3.47 g, 20 mmol). The mixture was stirred at 50° C. for 16 h. The solvent was removed under reduced pressure. The residue was purified via flash column chromatography over silica gel (ethyl acetate:petroleum ether, 1:10 to 10:1) to afford (R)-(1-(6-amino-5-nitropyridin-2-yl)piperidine-3-yl)(pyrrolidin-1-yl)methanone (4.838 g, 76.3%).

Step 4: (R)-Pyrrolidin-1-yl(1-(2-(3-(trifluoromethoxy)phenyl)-3H-imidazo[4,5-b]pyridin-5-yl)piperidin-3-yl)methanone A solution of (R)-(1-(6-amino-5-nitropyridin-2-yl)piperidine-3-yl)(pyrrolidin-1-yl)methanone in ethanol was prepared (0.0625 M), and 1200 µL of this solution were added into an 8 mL vial containing 3-(trifluoromethoxy)benzaldehyde (150 µmol). Water (60 µL) and sodium hydrosulfite (65.25 mg, 375 µmol) were added under a flow of nitrogen. The vial was capped and stirred at 100° C. for 16 h. The solvent was removed by Speedvac and the mixture was purified via HPLC to afford the title compound. MS API-ES+ (M+H) 460; HPLC retention time 2.59 min (Method D).

The compounds listed in Table 1 below were prepared using an analogous route to the one described above for the preparation of (R)-pyrrolidin-1-yl(1-(2-(3-(trifluoromethoxy)phenyl)-1H-imidazo[4,5-b]pyridine-5-yl)piperidine-3-yl)methanone using the appropriate starting materials which are available commercially or prepared using preparations well-known to those skilled in the art.

TABLE 1

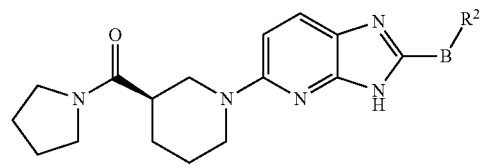

| Example | Compound Name | —B—R² | Analytical Data |
|---|---|---|---|
| 2 | (R)-(1-(2-(4-Isobutylthiazol-2-yl)-3H-imidazo[4,5-b]pyridin-5-yl)piperidin-3-yl)(pyrrolidin-1-yl)methanone | | MS API-ES+ (M + H) 439; HPLC retention time: 2.771 min (Method D) |
| 3 | (R)-(1-(2-(3-(1H-Pyrazol-1-yl)phenyl)-3H-imidazo[4,5-b]pyridin-5-yl)piperidin-3-yl)(pyrrolidin-1-yl)methanone | | MS API-ES+ (M + H) 442; HPLC retention time: 2.315 min (Method D) |
| 4 | (R)-(1-(2-(4-Isopropylthiazol-2-yl)-3H-imidazo[4,5-b]pyridin-5-yl)piperidin-3-yl)(pyrrolidin-1-yl)methanone | | MS API-ES+ (M + H) 425; HPLC retention time: 2.615 min (Method D) |
| 5 | (R)-Pyrrolidin-1-yl(1-(2-m-tolyl-3H-imidazo[4,5-b]pyridin-5-yl)piperidin-3-yl)methanone | | MS API-ES+ (M + H) 390; HPLC retention time: 2.322 min (Method D) |

TABLE 1-continued

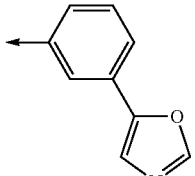

| Example | Compound Name | —B—R² | Analytical Data |
|---|---|---|---|
| 6 | (R)-(1-(2-(3-(Oxazol-5-yl)phenyl)-3H-imidazo[4,5-b]pyridin-5-yl)piperidin-3-yl)(pyrrolidin-1-yl)methanone | 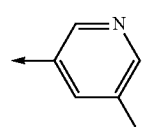 | MS API-ES+ (M + H) 443; HPLC retention time: 2.229 min (Method D) |
| 7 | (R)-(1-(2-(5-Chloropyridin-3-yl)-3H-imidazo[4,5-b]pyridin-5-yl)piperidin-3-yl)(pyrrolidin-1-yl)methanone | 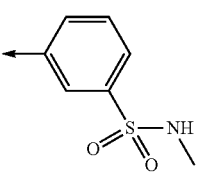 | MS API-ES+ (M + H) 411; HPLC retention time: 2.46 min (Method C) |
| 8 | (R)-N-Methyl-3-(5-(3-(pyrrolidine-1-carbonyl)piperidin-1-yl)-3H-imidazo[4,5-b]pyridin-2-yl)benzenesulfonamide | 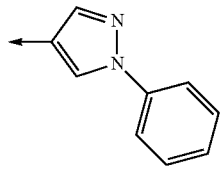 | MS API-ES+ (M + H) 469; HPLC retention time: 2.4 min (Method C) |
| 9 | (R)-(1-(2-(1-Phenyl-1H-pyrazol-4-yl)-3H-imidazo[4,5-b]pyridin-5-yl)piperidin-3-yl)(pyrrolidin-1-yl)methanone | 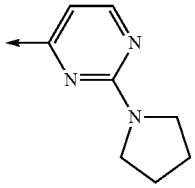 | MS API-ES+ (M + H) 442; HPLC retention time: 2.384 min (Method D) |
| 10 | (R)-Pyrrolidin-1-yl(1-(2-(2-(pyrrolidin-1-yl)pyrimidin-4-yl)-3H-imidazo[4,5-b]pyridin-5-yl)piperidin-3-yl)methanone | 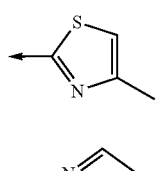 | MS API-ES+ (M + H) 447; HPLC retention time: 2.462 min (Method C) |
| 11 | (R)-(1-(2-(4-Methylthiazol-2-yl)-3H-imidazo[4,5-b]pyridin-5-yl)piperidin-3-yl)(pyrrolidin-1-yl)methanone | 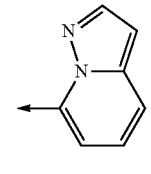 | MS API-ES+ (M + H) 397; HPLC retention time: 2.494 min (Method C) |
| 12 | (R)-(1-(2-(Pyrazolo[1,5-a]pyridin-7-yl)-3H-imidazo[4,5-b]pyridin-5-yl)piperidin-3-yl)(pyrrolidin-1-yl)methanone | 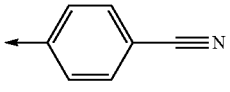 | MS API-ES+ (M + H) 416; HPLC retention time: 2.435 min (Method D) |
| 13 | (R)-4-(5-(3-(Pyrrolidine-1-carbonyl)piperidin-1-yl)-3H-imidazo[4,5-b]pyridin-2-yl)benzonitrile |  | MS API-ES+ (M + H) 401; HPLC retention time: 2.49 min (Method C) |

TABLE 1-continued

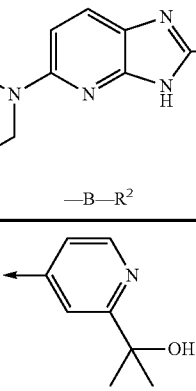

| Example | Compound Name | —B—R² | Analytical Data |
|---|---|---|---|
| 14 | (R)-(1-(2-(2-(2-Hydroxypropan-2-yl)pyridin-4-yl)-3H-imidazo[4,5-b]pyridin-5-yl)piperidin-3-yl)(pyrrolidin-1-yl)methanone | 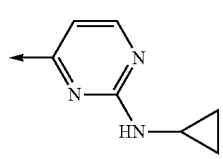 | MS API-ES+ (M + H) 435; HPLC retention time: 2.442 min (Method C) |
| 15 | (R)-(1-(2-(2-(Cyclopropylamino)pyrimidin-4-yl)-3H-imidazo[4,5-b]pyridin-5-yl)piperidin-3-yl)(pyrrolidin-1-yl)methanone | 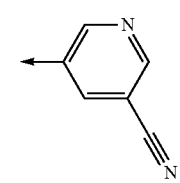 | MS API-ES+ (M + H) 433; HPLC retention time: 2.357 min (Method C) |
| 16 | (R)-5-(5-(3-(Pyrrolidine-1-carbonyl)piperidin-1-yl)-3H-imidazo[4,5-b]pyridin-2-yl)nicotinonitrile | 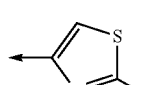 | MS API-ES+ (M + H) 402; HPLC retention time: 2.38 min (Method C) |
| 17 | (R)-(1-(2-(2-Methylthiazol-4-yl)-3H-imidazo[4,5-b]pyridin-5-yl)piperidin-3-yl)(pyrrolidin-1-yl)methanone | 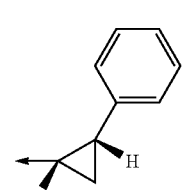 | MS API-ES+ (M + H) 397; HPLC retention time: 2.371 min (Method C) |
| 18 | ((R)-1-(2-((1S,2R)-2-Phenylcyclopropyl)-3H-imidazo[4,5-b]pyridin-5-yl)piperidin-3-yl)(pyrrolidin-1-yl)methanone | 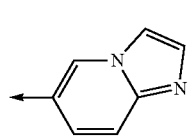 | MS API-ES+ (M + H) 416; HPLC retention time: 2.407 min (Method D) |
| 19 | (R)-(1-(2-(Imidazo[1,2-a]pyridin-6-yl)-3H-imidazo[4,5-b]pyridin-5-yl)piperidin-3-yl)(pyrrolidin-1-yl)methanone | 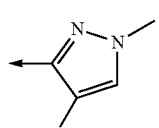 | MS API-ES+ (M + H) 416; HPLC retention time: 2.121 min (Method C) |
| 20 | (R)-(1-(2-(4-Chloro-1-methyl-1H-pyrazol-3-yl)-3H-imidazo[4,5-b]pyridin-5-yl)piperidin-3-yl)(pyrrolidin-1-yl)methanone | 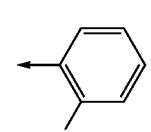 | MS API-ES+ (M + H) 414; HPLC retention time: 2.363 min (Method C) |
| 21 | (R)-(1-(2-(2-Fluorophenyl)-3H-imidazo[4,5-b]pyridin-5-yl)piperidin-3-yl)(pyrrolidin-1-yl)methanone | 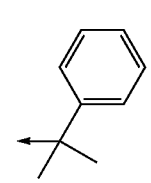 | MS API-ES+ (M + H) 394; HPLC retention time: 2.199 min (Method D) |
| 22 | (R)-(1-(2-(2-Phenylpropan-2-yl)-3H-imidazo[4,5-b]pyridin-5-yl)piperidin-3-yl)(pyrrolidin-1-yl)methanone | | MS API-ES+ (M + H) 418; HPLC retention time: 2.365 min (Method D) |

TABLE 1-continued

| Example | Compound Name | —B—R² | Analytical Data |
|---|---|---|---|
| 23 | (R)-(1-(2-(2-Hydroxy-3-isopropylphenyl)-3H-imidazo[4,5-b]pyridin-5-yl)piperidin-3-yl)(pyrrolidin-1-yl)methanone | | MS API-ES+ (M + H) 434; HPLC retention time: 2.794 min (Method D) |
| 24 | (R)-(1-(2-tert-Butyl-3H-imidazo[4,5-b]pyridin-5-yl)piperidin-3-yl)(pyrrolidin-1-yl)methanone | | MS API-ES+ (M + H) 356; HPLC retention time: 2.351 min (Method C) |
| 25 | (R)-(1-(2-(2-Morpholinopyrimidin-4-yl)-3H-imidazo[4,5-b]pyridin-5-yl)piperidin-3-yl)(pyrrolidin-1-yl)methanone | | MS API-ES+ (M + H) 463; HPLC retention time: 2.504 min (Method C) |
| 26 | (R)-(1-(2-Cyclohexyl-3H-imidazo[4,5-b]pyridin-5-yl)piperidin-3-yl)(pyrrolidin-1-yl)methanone | | MS API-ES+ (M + H) 382; HPLC retention time: 2.278 min (Method D) |
| 27 | (R)-6-(5-(3-(Pyrrolidine-1-carbonyl)piperidin-1-yl)-3H-imidazo[4,5-b]pyridin-2-yl)-2H-benzo[b][1,4]oxazin-3(4H)-one | | MS API-ES+ (M + H) 447; HPLC retention time: 2.353 min (Method C) |
| 28 | (R)-(1-(2-(Cyclohexylmethyl)-3H-imidazo[4,5-b]pyridin-5-yl)piperidin-3-yl)(pyrrolidin-1-yl)methanone | | MS API-ES+ (M + H) 396; HPLC retention time: 2.444 min (Method D) |
| 29 | (R)-(1-(2-Cyclopropyl-3H-imidazo[4,5-b]pyridin-5-yl)piperidin-3-yl)(pyrrolidin-1-yl)methanone | | MS API-ES+ (M + H) 340; HPLC retention time: 2.246 min (Method C) |
| 30 | (R)-N-(3-(5-(3-(Pyrrolidine-1-carbonyl)piperidin-1-yl)-3H-imidazo[4,5-b]pyridin-2-yl)phenyl)methanesulfonamide | | MS API-ES+ (M + H) 469; HPLC retention time: 2.388 min (Method C) |
| 31 | (R)-(1-(2-(tert-Butoxymethyl)-3H-imidazo[4,5-b]pyridin-5-yl)piperidin-3-yl)(pyrrolidin-1-yl)methanone | | MS API-ES+ (M + H) 386; HPLC retention time: 2.453 min (Method C) |
| 32 | (R)-(1-(2-(5-Ethylisoxazol-3-yl)-3H-imidazo[4,5-b]pyridin-5-yl)piperidin-3-yl)(pyrrolidin-1-yl)methanone | | MS API-ES+ (M + H) 395; HPLC retention time: 2.551 min (Method C) |

TABLE 1-continued

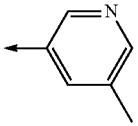

| Example | Compound Name | —B—R² | Analytical Data |
|---|---|---|---|
| 33 | (R)-(1-(2-(5-Methylpyridin-3-yl)-3H-imidazo[4,5-b]pyridin-5-yl)piperidin-3-yl)(pyrrolidin-1-yl)methanone | 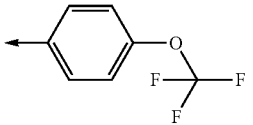 | MS API-ES+ (M + H) 391; HPLC retention time: 2.224 min (Method C) |
| 34 | (R)-Pyrrolidin-1-yl(1-(2-(4-(trifluoromethoxy)phenyl)-3H-imidazo[4,5-b]pyridin-5-yl)piperidin-3-yl)methanone | 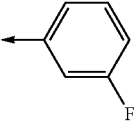 | MS API-ES+ (M + H) 460; HPLC retention time: 2.567 min (Method D) |
| 35 | (R)-(1-(2-(3-Fluorophenyl)-3H-imidazo[4,5-b]pyridin-5-yl)piperidin-3-yl)(pyrrolidin-1-yl)methanone | 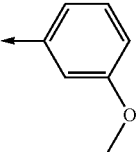 | MS API-ES+ (M + H) 394; HPLC retention time: 2.263 min (Method D) |
| 36 | (R)-(1-(2-(3-Methoxyphenyl)-3H-imidazo[4,5-b]pyridin-5-yl)piperidin-3-yl)(pyrrolidin-1-yl)methanone | 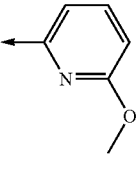 | MS API-ES+ (M + H) 406; HPLC retention time: 2.279 min (Method D) |
| 37 | (R)-(1-(2-(6-Methoxypyridin-2-yl)-3H-imidazo[4,5-b]pyridin-5-yl)piperidin-3-yl)(pyrrolidin-1-yl)methanone | 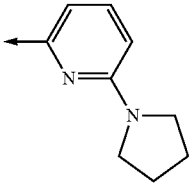 | MS API-ES+ (M + H) 407; HPLC retention time: 2.304 min (Method D) |
| 38 | (R)-Pyrrolidin-1-yl(1-(2-(6-(pyrrolidin-1-yl)pyridin-2-yl)-3H-imidazo[4,5-b]pyridin-5-yl)piperidin-3-yl)methanone | 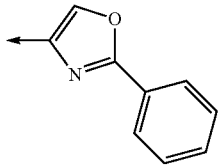 | MS API-ES+ (M + H) 446; HPLC retention time: 2.525 min (Method D) |
| 39 | (R)-(1-(2-(2-Phenyloxazol-4-yl)-3H-imidazo[4,5-b]pyridin-5-yl)piperidin-3-yl)(pyrrolidin-1-yl)methanone | 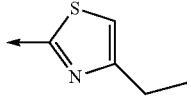 | MS API-ES+ (M + H) 443; HPLC retention time: 2.477 min (Method D) |
| 40 | (R)-(1-(2-(4-Ethylthiazol-2-yl)-3H-imidazo[4,5-b]pyridin-5-yl)piperidin-3-yl)(pyrrolidin-1-yl)methanone | 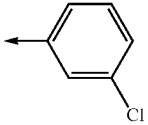 | MS API-ES+ (M + H) 411; HPLC retention time: 2.437 min (Method D) |
| 41 | (R)-(1-(2-(3-Chlorophenyl)-3H-imidazo[4,5-b]pyridin-5-yl)piperidin-3-yl)(pyrrolidin-1-yl)methanone | | MS API-ES+ (M + H) 410; HPLC retention time: 2.389 min (Method D) |

TABLE 1-continued

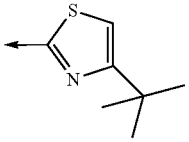

| Example | Compound Name | —B—R² | Analytical Data |
|---|---|---|---|
| 42 | (R)-(1-(2-(4-tert-Butylthiazol-2-yl)-3H-imidazo[4,5-b]pyridin-5-yl)piperidin-3-yl)(pyrrolidin-1-yl)methanone | | MS API-ES+ (M + H) 439; HPLC retention time: 2.786 min (Method D) |

Example 43

(R)-(1-(2-(3-(Difluoromethoxy)phenyl)-3H-imidazo[4,5-b]pyridin-5-yl)piperidin-3-yl)(pyrrolidin-1-yl)methanone

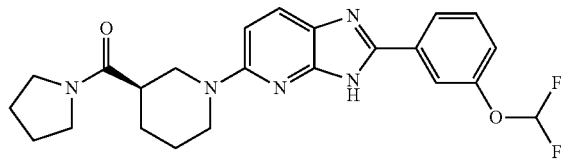 [SMILES: O=C([C@@H]1CCCN(c2ccc3nc(-c4cccc(OC(F)F)c4)[nH]c3n2)C1)N1CCCC1]

Step 1: (R)-tert-Butyl 3-(pyrrolidine-1-carbonyl)piperidine-1-carboxylate (R)-tert-Butyl 3-(pyrrolidine-1-carbonyl)piperidine-1-carboxylate was prepared by an analogous procedure to the one used for Example 1, Step 1.

Step 2: (R)-Piperidin-3-yl(pyrrolidin-1-yl)methanone

Into a flask containing (R)-tert-butyl 3-(pyrrolidine-1-carbonyl)piperidine-1-carboxylate was added dichloromethane (24 mL) followed by a solution of hydrogen chloride in 1,4-dioxane (4M, 8 mL). The reaction mixture was stirred at 30° C. for 2 h. The solvent was evaporated under reduced pressure to afford (R)-piperidin-3-yl(pyrrolidin-1-yl)methanone which was used without further purification.

Step 3: (R)-(1-(6-Amino-5-nitropyridin-2-yl)piperidine-3-yl)(pyrrolidin-1-yl)methanone A solution of 6-chloro-3-nitropyridin-2-amine (0.175M, 20 mL, 3.5 mmol) in anhydrous N,N-dimethylformamide was added to (R)-piperidin-3-yl(pyrrolidin-1-yl)methanone, followed by diisopropylethylamine (1.3 mL, 7.0 mmol). The reaction mixture was stirred at 80° C. for 16 h. The solvent was removed under reduced pressure and the residue was purified via preparative HPLC to afford (R)-(1-(6-amino-5-nitropyridin-2-yl)piperidine-3-yl)(pyrrolidin-1-yl)methanone (1.0 g, 89.6%).

Step 4: (R)-(1-(2-(3-(Difluoromethoxy)phenyl)-3H-imidazo[4,5-b]pyridin-5-yl)piperidin-3-yl)(pyrrolidin-1-yl)methanone The title compound was prepared by a method analogous to the one used for Example 1, Step 4, but the reaction mixture was stirred at 110° C. MS API-ES+ (M+H) 442; HPLC retention time: 2.431 min (Method D).

The compounds listed in Table 2 below were prepared using an analogous route to the one described above for the preparation of (R)-(1-(2-(3-(difluoromethoxy)phenyl)-3H-imidazo[4,5-b]pyridin-5-yl)piperidin-3-yl)(pyrrolidin-1-yl)methanone using the appropriate starting materials which are available commercially or prepared using preparations well-known to those skilled in the art.

TABLE 2

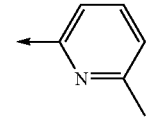

| Example | Compound Name | —B—R² | Analytical Data |
|---|---|---|---|
| 44 | (R)-(1-(2-(6-Methylpyridin-2-yl)-3H-imidazo[4,5-b]pyridin-5-yl)piperidin-3-yl)(pyrrolidin-1-yl)methanone | | MS API-ES+ (M + H) 391; HPLC retention time: 2.442 min (Method C) |

TABLE 2-continued

| Example | Compound Name | —B—R² | Analytical Data |
|---|---|---|---|
| 46 | (R)-(1-(2-(4-Chlorobenzyl)-3H-imidazo[4,5-b]pyridin-5-yl)piperidin-3-yl)(pyrrolidin-1-yl)methanone |  | MS API-ES+ (M + H) 424; HPLC retention time: 2.445 min (Method D) |
| 47 | (R)-3-(5-(3-(Pyrrolidine-1-carbonyl)piperidin-1-yl)-3H-imidazo[4,5-b]pyridin-2-yl)benzonitrile | | MS API-ES+ (M + H) 401; HPLC retention time: 2.489 min (Method C) |

Example 48

(R)-(1-(1-(2-((4-Chlorophenoxy)methyl)-3H-imidazo[4,5-b]pyridin-5-yl)piperidin-3-yl)(pyrrolidin-1-yl)methanone

Step 1: (R)-(1-(6-Amino-5-nitropyridin-2-yl)piperidin-3-yl)pyrrolidin-1-yl)methanone To a solution of (R)-piperidin-3-yl(pyrrolidin-1-yl)methanone in N,N-dimethylformamide (16.3 mL, 0.6M) was added a solution of 6-chloro-3-nitropyridin-2-amine in N,N-dimethylformamide (16.3 mL, 0.6M). Then triethylamine (3.68 mL, 26.5 mmol) was added to the mixture. The reaction mixture was stirred at 80° C. for 16 h. The solvent was removed under reduced pressure to afford (R)-(1-(6-amino-5-nitropyridin-2-yl)piperidin-3-yl)pyrrolidin-1-yl)methanone and the crude product was used without further purification.

Step 2: (R)-(1-(5,6-Diaminopyridin-2-yl)piperidin-3-yl)(pyrrolidin-1-yl)methanone To a solution of (R)-(1-(6-amino-5-nitropyridin-2-yl)piperidin-3-yl)pyrrolidin-1-yl)methanone in methanol (9.8 mmol, 0.25M) was added zinc dust (6.37 g, 98 mmol) at 0° C. followed by a saturated aqueous solution of ammonium chloride (39.2 mL). The reaction mixture was stirred at 30° C. for 16 h. The mixture was filtered and concentrated under reduced pressure. Water (100 mL) was added to the residue and the mixture was extracted with ethyl acetate (200 mL×3). The combined organics were dried over anhydrous sodium sulfate, filtered and concentrated under reduced pressure to afford (R)-(1-(5,6-diaminopyridin-2-yl)piperidin-3-yl)(pyrrolidin-1-yl)methanone. The material was used for the next step without further purification.

Step 3: (R)-(1-(1-(2-((4-Chlorophenoxy)methyl)-3H-imidazo[4,5-b]pyridin-5-yl)piperidin-3-yl)(pyrrolidin-1-yl)methanone 2-(4-Chlorophenoxy)acetic acid (75 μmol) was added into an 8-mL vial followed by a solution of (R)-(1-(5,6-diaminopyridin-2-yl)piperidin-3-yl)(pyrrolidin-1-yl)methanone in anhydrous dioxane (600 μL, 127.5 μmol, 0.21M). Triethylamine (90 μL, 648 μmol) and 1-propanephosphonic acid cyclic anhydride (120 μL, 50% in ethyl acetate, 202 μmol) were added. The vial was capped and the reaction mixture was shaken at 140° C. for 16 h. The solvent was removed by Speedvac and the residue was purified via HPLC to afford the title compound. MS API-ES+ (M+H) 440; HPLC retention time 2.473 min (Method D).

The compounds listed in Table 3 below were prepared using the route described above for the preparation of Example 48 using the appropriate starting materials which are available commercially or prepared using preparations well-known to those skilled in the art.

TABLE 3

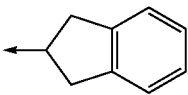

| Example | Compound Name | —B—R² | Analytical Data |
|---|---|---|---|
| 49 | (R)-(1-(2-(2,3-Dihydro-1H-inden-2-yl)-3H-imidazo[4,5-b]pyridin-5-yl)piperidin-3-yl)(pyrrolidin-1-yl)methanone | 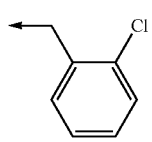 | MS API-ES+ (M + H) 416; HPLC retention time: 2.364 min (Method D) |
| 50 | (R)-(1-(2-(2-Chlorobenzyl)-3H-imidazo[4,5-b]pyridin-5-yl)piperidin-3-yl)(pyrrolidin-1-yl)methanone | 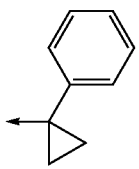 | MS API-ES+ (M + H) 424; HPLC retention time: 2.314 min (Method D) |
| 51 | (R)-(1-(2-(1-Phenylcyclopropyl)-3H-imidazo[4,5-b]pyridin-5-yl)piperidin-3-yl)(pyrrolidin-1-yl)methanone | 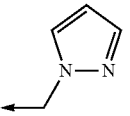 | MS API-ES+ (M + H) 416; HPLC retention time: 2.344 min (Method D) |
| 52 | (R)-(1-(2-((1H-Pyrazol-1-yl)methyl)-3H-imidazo[4,5-b]pyridin-5-yl)piperidin-3-yl)(pyrrolidin-1-yl)methanone | 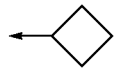 | MS API-ES+ (M + H) 380; HPLC retention time: 2.182 min (Method C) |
| 53 | (R)-(1-(2-Cyclobutyl-3H-imidazo[4,5-b]pyridin-5-yl)piperidin-3-yl)(pyrrolidin-1-yl)methanone |  | MS API-ES+ (M + H) 354; HPLC retention time: 2.301 min (Method C) |
| 54 | (R)-N-((5-(3-(Pyrrolidine-1-carbonyl)piperidin-1-yl)-3H-imidazo[4,5-b]pyridin-2-yl)methyl)benzamide | 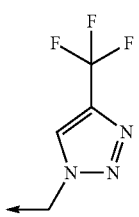 | MS API-ES+ (M + H) 433; HPLC retention time: 2.381 min (Method C) |
| 55 | (R)-Pyrrolidin-1-yl(1-(2-((4-(trifluoromethyl)-1H-1,2,3-triazol-1-yl)methyl)-3H-imidazo[4,5-b]pyridin-5-yl)piperidin-3-yl)methanone | 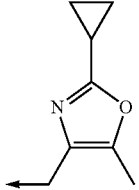 | MS API-ES+ (M + H) 449; HPLC retention time: 2.488 min (Method C) |
| 56 | (R)-(1-(2-((2-Cyclopropyl-5-methyloxazol-4-yl)methyl)-3H-imidazo[4,5-b]pyridin-5-yl)piperidin-3-yl)(pyrrolidin-1-yl)methanone | | MS API-ES+ (M + H) 435; HPLC retention time: 2.487 min (Method C) |

Example 57

(R)-6-Methyl-1-((5-(3-(pyrrolidine-1-carbonyl)piperidin-1-yl)-3H-imidazo[4,5-b]pyridin-2-yl)methyl)pyridin-2(1H)-one

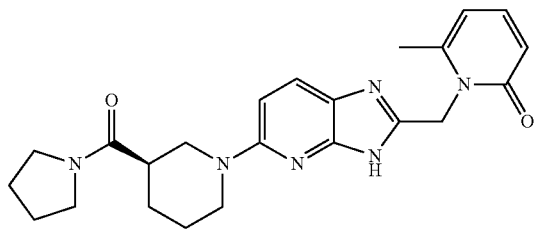 [SMILES: Cc1cccc(=O)n1Cc1nc2ccc(N3CCC[C@@H](C(=O)N4CCCC4)C3)nc2[nH]1]

Step 1: (R)—N-(2-Amino-6-(3-(pyrrolidine-1-carbonyl)piperidin-1-yl)pyridin-3-yl)-6-methyl-2-oxopyridine-1(2H)-carboxamide Into a vial were added (R)-(1-(5,6-diaminopyridin-2-yl)piperidin-3-yl)(pyrrolidin-1-yl)methanone (100 μmol), 6-methyl-2-oxopyridine-1(2H)-carboxylic acid and N,N-dimethylformamide (1.5 mL) followed by O-(7-Azabenzotriazol-1-yl)-N,N,N'N'-tetramethyluronium hexafluorophosphate (HATU) (200 μmol) and triethylamine (250 μmol). The vial was shaken for 16 h at room temperature. The mixture was concentrated via Speedvac. The residue was partitioned between dichloromethane and water. The organics were evaporated under vacuum to afford (R)—N-(2-amino-6-(3-(pyrrolidine-1-carbonyl)piperidin-1-yl)pyridin-3-yl)-6-methyl-2-oxopyridine-1(2H)-carboxamide which was used without further purification.

Step 2: (R)-6-Methyl-1-((5-(3-(pyrrolidine-1-carbonyl)piperidin-1-yl)-3H-imidazo[4,5-b]pyridin-2-yl)methyl)pyridin-2(1H)-one Into a vial were added (R)—N-(2-amino-6-(3-(pyrrolidine-1-carbonyl)piperidin-1-yl)pyridin-3-yl)-6-methyl-2-oxopyridine-1(2H)-carboxamide (1 equiv) and a solution of methanol and isobutanol (1:1, 1.5 mL). Sodium methoxide (2.0 equiv) was added and the reaction mixture was shaken at 110° C. for 2 h. Water was added and the mixture was extracted with a mixture of methanol/dichloromethane (1:1). The organics were concentrated by Speedvac and the crude material was purified via preparative HPLC to afford the title compound. MS (ES+) (M+H) 421.4; UPLC 1.09 min (Method T).

Example 58

(R)-(1-(2-(1-(1H-Pyrazol-1-yl)ethyl)-3H-imidazo[4,5-b]pyridin-5-yl)piperidin-3-yl)(pyrrolidin-1-yl)methanone

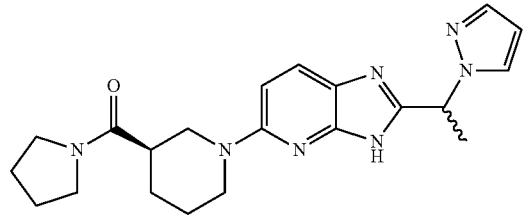 [SMILES: CC(c1nc2ccc(N3CCC[C@@H](C(=O)N4CCCC4)C3)nc2[nH]1)n1cccn1]

The title compound was prepared by a method analogous to the one used for Example 57. MS (ES+) (M+H) 394.5; UPLC retention time: 1.1 min (Method T).

Example 59

2-(2-Cyclopropylpyrimidin-4-yl)-5-(3-(pyridin-2-yl)piperidin-1-yl)-3H-imidazo[4,5-b]pyridine

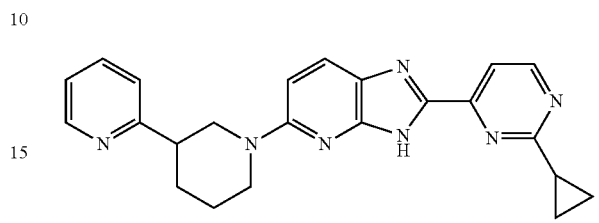

Step 1: 2-Amino-6-(3-(pyridin-2-yl)piperidin-1-yl)nicotinic acid

To a solution of 2-amino-6-chloronicotinic acid (1.6 g, 9.248 mmol) in N,N-dimethylformamide (41 mL) was added 2-(piperidin-3-yl)pyridine (1.82 g, 11.098 mmol) and triethylamine (25.455 mmol). The reaction mixture was stirred at 80° C. for 16 h. The solvent was removed under reduced pressure and the residue was purified via column chromatography to afford 2-amino-6-(3-(pyridin-2-yl)piperidin-1-yl)nicotinic acid

Step 2: 2-(2-Cyclopropylpyrimidin-4-yl)-5-(3-(pyridin-2-yl)piperidin-1-yl)-3H-imidazo[4,5-b]pyridine Into a vial containing 2-cyclopropylpyrimidine-4-carbaldehyde was added 2-amino-6-(3-(pyridin-2-yl)piperidin-1-yl)nicotinic acid (500 μL, 0.33M in ethanol) followed by ethanol (500 μL), water (50 μL), and a solution of sodium hydrosulfite (100 mg, 574 μmol) in water (50 μL). The vial was capped and shaken at 110° C. for 18 h. The mixture was filtered and the filtrate was concentrated by Speedvac. The residue was purified by HPLC to afford the title compound. MS (API-ES+) (M+H) 398.3; UPLC retention time: 1.15 min (Method U)

Example 60

(R)-1-(2-(3-(Difluoromethoxy)phenyl)-3H-imidazo[4,5-b]pyridin-5-yl)-N,N-dimethylpiperidine-3-carboxamide

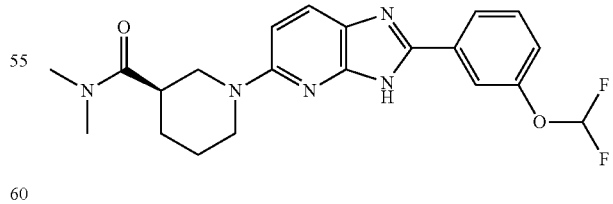

Step 1: (R)-1-(6-Amino-5-nitropyridin-2-yl)-N,N-dimethylpiperidine-3-carboxamide To a solution of 6-chloro-3-nitropyridin-2-amine (4.15 g, 24.0 mmol) in N,N-dimethylformamide (41 mL) was added (R)—N,N-dimethylpiperidine-3-carboxamide (3.74 g, 2.40 mmol) followed by triethylamine (10.7 mL, 64.800 mmol). The reaction mixture was stirred at 80° C. for 16 h. The solvent was removed under reduced pressure and the residue was purified via column chromatography to afford (R)-1-(6-amino-5-nitropyridin-2-yl)-N,N-dimethylpiperidine-3-carboxamide.

Step 2: (R)-1-(2-(3-(Difluoromethoxy)phenyl)-3H-imidazo[4,5-b]pyridin-5-yl)-N,N-dimethylpiperidine-3-carboxamide Into a 4 mL vial was added (R)-1-(6-amino-5-nitropyridin-2-yl)-N,N-dimethylpiperidine-3-carboxamide (500 µL, 0.3M) dissolved in N,N-dimethylformamide followed by 3-(difluoromethoxy)benzaldehyde (950 µL, 0.158M) dissolved in N,N-dimethylformamide. Water (50 µL) was added followed by sodium hydrosulfite (574 µmol) under a nitrogen atmosphere. The vial was capped and shaken at 110° C. for 18 h. The solvent was removed by Speedvac and the residue was purified by HPLC to afford the title compound. MS (API-ES+) (M+H) 416.2; HPLC retention time 1.392 min (Method E).

Example 61

(R)-iso-Butyl 3-(5-(3-(pyrrolidine-1-carbonyl)piperidin-1-yl)-3H-imidazo[4,5-b]pyridine-2-yl)piperidine-1-carboxylate

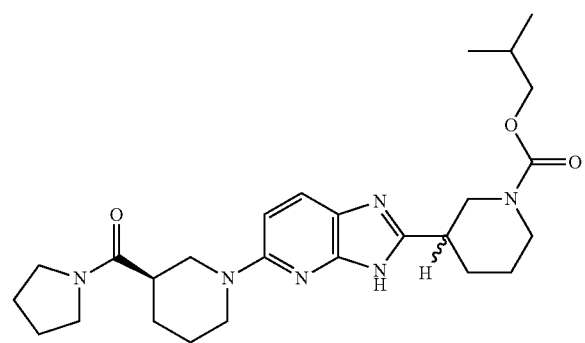 [SMILES: CC(C)COC(=O)N1CCCC(c2nc3ccc(N4CCC[C@@H](C(=O)N5CCCC5)C4)nc3[nH]2)C1]

Step 1: tert-Butyl 3-((2-amino-6-((R)-3-(pyrrolidine-1-carbonyl)piperidin-1-yl)pyridin-3-yl)carbamoyl)piperidine-1-carboxylate To a solution of (R)-(1-(5,6-diaminopyridin-2-yl)piperidin-3-yl)(pyrrolidin-1-yl)methanone (3.60 mmol) in 1,4-dioxane (20 mL) was added (R)-1-(tert-butoxycarbonyl)piperidine-3-carboxylic acid (3.60 mmol), 1-Propanephosphonic acid cyclic anhydride (10.8 mmol), and triethylamine (32.4 mmol). The reaction mixture was stirred at room temperature for 16 h. The solvent was removed under reduced pressure and a solution of methanol/dichloromethane (1:9, 50 mL) was added followed by a saturated aqueous solution of sodium bicarbonate (50 mL), and the layers were separated. The aqueous layer was extracted again with methanol/dichloromethane (1:9, 25 mL) and the combined organics were dried over anhydrous sodium sulfate, filtered and concentrated under reduced pressure to afford tert-butyl 3-((2-amino-6-((R)-3-(pyrrolidine-1-carbonyl)piperidin-1-yl)pyridin-3-yl)carbamoyl)piperidine-1-carboxylate which was used without further purification.

Step 2: (R)-tert-Butyl 3-(5-(3-(pyrrolidine-1-carbonyl)piperidin-1-yl)-3H-imidazo[4,5-b]pyridine-2-yl)piperidine-1-carboxylate To a solution of tert-butyl 3-((2-amino-6-((R)-3-(pyrrolidine-1-carbonyl)piperidin-1-yl)pyridin-3-yl)carbamoyl)piperidine-1-carboxylate in methanol/sec-butanol (1:2, 15 mL) was added a solution of 25% sodium methoxide in methanol (9.0 mL). The reaction mixture was stirred at 90° C. for 16 h. The solvent was removed under reduced pressure and a solution of methanol/dichloromethane (1:9, 50 mL) and a saturated aqueous solution of sodium bicarbonate (50 mL) were added to the residue, and the layers were separated. The aqueous layer was extracted again with methanol/dichloromethane (1:9, 25 mL). The combined organics were dried over sodium sulfate, filtered and concentrated under reduced pressure. The residue was purified via column chromatography to afford (R)-tert-butyl 3-(5-(3-(pyrrolidine-1-carbonyl)piperidin-1-yl)-3H-imidazo[4,5-b]pyridine-2-yl)piperidine-1-carboxylate.

Step 3: (R)-(1-(2-(Piperidin-3-yl)-3H-imidazo[4,5-b]pyridin-5-yl)piperidin-3-yl)pyrrolidin-1-yl)methanone A solution of hydrogen chloride in 1,4-dioxane (4M) was added to (R)-tert-butyl 3-(5-(3-(pyrrolidine-1-carbonyl)piperidin-1-yl)-3H-imidazo[4,5-b]pyridine-2-yl)piperidine-1-carboxylate to prepare a 1M solution. The reaction mixture was stirred at room temperature for 4 h. The solvent was removed under reduced pressure to afford (R)-(1-(2-(piperidin-3-yl)-3H-imidazo[4,5-b]pyridin-5-yl)piperidin-3-yl)pyrrolidin-1-yl)methanone which was used without further purification.

Step 4: (R)-iso-Butyl 3-(5-(3-(pyrrolidine-1-carbonyl)piperidin-1-yl)-3H-imidazo[4,5-b]pyridine-2-yl)piperidine-1-carboxylate To a solution of (R)-(1-(2-(piperidin-3-yl)-3H-imidazo[4,5-b]pyridin-5-yl)piperidin-3-yl)pyrrolidin-1-yl)methanone (500 µL, 150 µmol, 0.13M) in N,N-dimethylformamide was added a solution of isobutyl chloroformate in tetrahydrofuran (0.3M, 500 µL, 150 µmol) followed by diisopropylethylamine (450 µmol). The reaction mixture was stirred at room temperature for 16 h. The solvent was removed and to the residue was added a solution of methanol/dichloromethane (1:9, 50 mL) and a saturated aqueous solution of sodium bicarbonate (50 mL). The aqueous layer was removed and the organics were concentrated under reduced pressure. The residue was purified via HPLC to afford the title compound. MS (ES+) (M+H) 483; LCMS retention time 1.11 min (Method V).

The compounds listed in Table 4 below were prepared using the route described above for the preparation of Example 61 using the appropriate starting materials which are available commercially or prepared using preparations well-known to those skilled in the art.

TABLE 4

| Example | Compound Name | —B—R² | Analytical Data |
|---|---|---|---|
| 62 | (R)-(2-(1-(Cyclopentanecarbonyl)piperidin-3-yl)-3H-imidazo[4,5-b]pyridin-5-yl)piperidin-3-yl)(pyrrolidin-1-yl)methanone | | MS (ES+) (M + H) 479; UPLC retention time: 1.05 min (Method V) |
| 63 | (R)-(1-(2-(1-(Cyclopentanecarbonyl)piperidin-4-yl)-3H-imidazo[4,5-b]pyridin-5-yl)piperidin-3-yl)(pyrrolidin-1-yl)methanone | | MS (ES+) (M + H) 479; UPLC retention time: 1.02 min (Method V) |
| 64 | (R)-(1-(2-(1-(Propylsulfonyl)piperidin-3-yl)-3H-imidazo[4,5-b]pyridin-5-yl)piperidin-3-yl)(pyrrolidin-1-yl)methanone | | MS (ES+) (M + H) 489; UPLC retention time: 1.02 min (Method V) |

Example 65

((R)-1-(2-(2-Cyclopropylpyrimidin-4-yl)-3H-imidazo[4,5-b]pyridin-5-yl)piperidin-3-yl)((S)-3-fluoropyrrolidin-1-yl)methanone

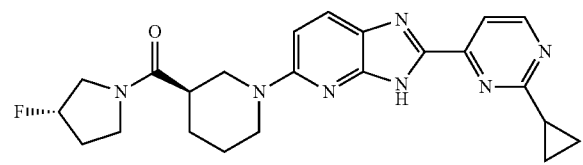 [SMILES: O=C([C@@H]1CCCN(c2ccc3nc(-c4ccnc(C5CC5)n4)[nH]c3n2)C1)N1CC[C@H](F)C1]

Step 1: (R)-Piperidine-3-carboxylic acid

To (R)-1-(tert-butoxycarbonyl)piperidine-3-carboxylic acid (7.0 mmol) was added dichloromethane (48 mL) followed by hydrochloric acid (4M, 16 mL). The reaction mixture was stirred at 30° C. for 2 h. The solvent was removed under reduced pressure to afford (R)-piperidine-3-carboxylic acid which was used without further purification.

Step 2: (R)-1-(6-Amino-5-nitropyridin-2-yl)piperidine-3-carboxylic acid

A solution of 6-chloro-3-nitropyridin-2-amine (0.175 M, 35 mL, 6.125 mmol) was added to (R)-piperidine-3-carboxylic acid, prepared during the previous step, followed by diisopropylethyl amine (2.275 mL, 12.25 mmol). The reaction mixture was stirred at 80° C. for 16 h. The solvent was removed under reduced pressure to afford (R)-1-(6-amino-5-nitropyridin-2-yl)piperidine-3-carboxylic acid which was used for the next step without further purification.

Step 3: (R)-1-(2-(2-Cyclopropylpyrimidin-4-yl)-3H-imidazo[4,5-b]pyridin-5-yl)piperidine-3-carboxylic acid (R)-1-(6-amino-5-nitropyridin-2-yl)piperidine-3-carboxylic acid, prepared during the previous step, was dissolved in a mixture of N,N-dimethylformamide (45.5 mL) and water (4.9 mL). Ammonium formate (1.925 g, 30.625 mmol) was added followed by zinc dust (1.05 g, 15.3 mmol). The reaction mixture was stirred at 45° C. for 16 h. The mixture was filtered and the filtrate was concentrated under reduced pressure. To the residue was added N,N-dimethylformamide (24.5 mL) followed by a solution of 2-cyclopropylpyrimidine-4-carbaldehyde in N,N-dimethylformamide (24.5 mL, 6.125 mmol, 0.25M) and acetic acid (3.675 mL, 61.25 mmol). The reaction mixture was stirred at 60° C. for 16 h. The solvent was removed under reduced pressure and the residue was purified via preparative HPLC to afford the title compound (0.637 g, 28.6%).

115

Step 4: ((R)-1-(2-(2-Cyclopropylpyrimidin-4-yl)-3H-imidazo[4,5-b]pyridin-5-yl)piperidin-3-yl)((S)-3-fluoropyrrolidin-1-yl)methanone (S)-3-Fluoropyrrolidine (175 µmol) was added to a vial followed by N,N-dimethylformamide (200 µL), triethylamine (35 µL, 250 µmol) and (R)-1-(2-(2-cyclopropylpyrimidin-4-yl)-3H-imidazo[4,5-b]pyridin-5-yl)piperidine-3-carboxylic acid (200 µL, 50 µmol, 0.25 M in N,N-dimethylformamide) and O-(7-azabenzotriazol-1-yl)-N,N,N',N',-tetramethyluronium hexafluorophosphate (HATU) (250 µL, 100 µmol, 0.4 M solution in N,N-dimethylformamide). The reaction mixture was shaken at 50° C. for 16 h. The solvent was evaporated by Speedvac and the residue was purified via preparative HPLC to afford the title compound. MS API-ES+ (M+H) 436; HPLC retention time 2.521 min (Method C).

The compounds listed in Table 5 below were prepared using procedures analogous to those described above for the synthesis of Example 65 using the appropriate starting materials which are available commercially or prepared using preparations well-known to those skilled in the art or prepared by a route described above.

116

Example 71

(R)-1-(2-(2-Cyclopropylpyrimidin-4-yl)-3H-imidazo[4,5-b]pyridin-5-yl)-N,N-dimethylpiperidine-3-carboxamide

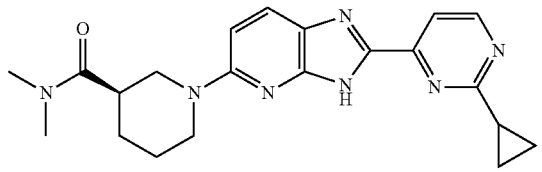 [SMILES: CN(C)C(=O)[C@@H]1CCCN(c2ccc3nc(-c4ccnc(C5CC5)n4)[nH]c3n2)C1]

Step 1: (R)-Piperidine-3-carboxylic acid

To a solution of (R)-1-(tert-butoxycarbonyl)piperidine-3-carboxylic acid (12.25 mmol) in dichloromethane (84 mL) was added a solution of hydrogen chloride in 1,4-dioxane (28 mL, 4M). The reaction mixture was stirred at 30° C. for 2 h. The solvent was removed under reduced pressure to afford (R)-piperidine-3-carboxylic acid which was used without further purification.

TABLE 5

| Example | Compound Name | R | Analytical Data |
|---|---|---|---|
| 66 | ((R)-1-(2-(2-Cyclopropylpyrimidin-4-yl)-3H-imidazo[4,5-b]pyridin-5-yl)piperidin-3-yl)((R)-2-(hydroxymethyl)pyrrolidin-1-yl)methanone | | MS API-ES+ (M + H) 448; HPLC retention time: 2.431 min (Method C) |
| 67 | ((R)-1-(2-(2-Cyclopropylpyrimidin-4-yl)-3H-imidazo[4,5-b]pyridin-5-yl)piperidin-3-yl)((R)-2-methylpyrrolidin-1-yl)methanone | | MS API-ES+ (M + H) 432; HPLC retention time: 2.694 min (Method C) |
| 68 | ((R)-1-(2-(2-Cyclopropylpyrimidin-4-yl)-3H-imidazo[4,5-b]pyridin-5-yl)piperidin-3-yl)((3R,4R)-3,4-difluoropyrrolidin-1-yl)methanone | | MS API-ES+ (M + H) 454; HPLC retention time 2.579 min (Method C) |
| 69 | ((R)-1-(2-(2-Cyclopropylpyrimidin-4-yl)-3H-imidazo[4,5-b]pyridin-5-yl)piperidin-3-yl)((R)-3-fluoropyrrolidin-1-yl)methanone | | MS API-ES+ (M + H) 436; HPLC retention time 2.531 min (Method C) |
| 70 | (R)-(1-(2-(2-Cyclopropylpyrimidin-4-yl)-3H-imidazo[4,5-b]pyridin-5-yl)piperidin-3-yl)(morpholino)methanone | | MS API-ES+ (M + H) 434; HPLC retention time 2.435 min (Method C) |

Step 2: (R)-1-(6-Amino-5-nitropyridin-2-yl)piperidine-3-carboxylic acid

A solution of 6-chloro-3-nitropyridin-2-amine in N,N-dimethylformamide (70 mL, 12.25 mmol, 0.175M) was added to (R)-piperidine-3-carboxylic acid (12.25 mmol) followed by diisopropylethylamine (4.55 mL, 24.5 mmol). The reaction mixture was stirred at 80° C. for 16 h. The solvent was removed under reduced pressure to afford (R)-1-(6-amino-5-nitropyridin-2-yl)piperidine-3-carboxylic acid which was used without further purification.

Step 3: (R)-1-(5,6-Diaminopyridin-2-yl)piperidine-3-carboxylic acid

To a solution of (R)-1-(6-amino-5-nitropyridin-2-yl)piperidine-3-carboxylic acid in N,N-dimethylformamide (91 mL) was added water (9.8 mL), ammonium formate (3.85 g, 61.25 mmol), and active zinc dust (2.1 g, 30.6 mmol) under a nitrogen atmosphere. The reaction mixture was stirred at 45° C. for 16 h. The mixture was filtered and concentrated under reduced pressure to afford (R)-1-(5,6-diaminopyridin-2-yl)piperidine-3-carboxylic acid which was used without further purification.

Step 4: (R)-1-(2-(2-Cyclopropylpyrimidin-4-yl)-3H-imidazo[4,5-b]pyridin-5-yl)piperidine-3-carboxylic acid To a solution of (R)-1-(5,6-diaminopyridin-2-yl)piperidine-3-carboxylic acid in N,N-dimethylformamide (49 mL, 12.25 mmol, 0.25M) was added a solution of 2-cyclopropylpyrimidine-4-carbaldehyde in N,N-dimethylformamide (49 mL, 12.25 mmol, 0.25M) followed by acetic acid (7.35 mL, 122.5 mmol). The reaction mixture was stirred at 60° C. for 16 h. The solvent was removed under reduced pressure and the residue was purified via HPLC to afford (R)-1-(2-(2-cyclopropylpyrimidin-4-yl)-3H-imidazo[4,5-b]pyridin-5-yl)piperidine-3-carboxylic acid.

Step 5: (R)-1-(2-(2-Cyclopropylpyrimidin-4-yl)-3H-imidazo[4,5-b]pyridin-5-yl)-N,N-dimethylpiperidine-3-carboxamide To a solution of dimethylamine (175 μmol) in N,N-dimethylformamide (200 μL) was added triethylamine (35 μL, 250 μmol) and (R)-1-(2-(2-cyclopropylpyrimidin-4-yl)-3H-imidazo[4,5-b]pyridin-5-yl)piperidine-3-carboxylic acid (200 μL, 50 μmol, 0.25M in N,N-dimethylformamide) followed by 2-(1H-7-azabenzotriazol-1-yl)-1,1,3,3-tetramethyluronium hexafluorophosphate (250 μL, 100 μmol, 0.4M in N,N-dimethylformamide). The reaction mixture was stirred at 50° C. for 16 h. The solvent was removed by Speedvac and the residue was purified via HPLC to afford the title compound. MS API-ES+ (M+H) 392; HPLC retention time 2.43 min (Method C).

Example 72

(R)-(1-(2-(1-(4-Methyl-1H-pyrazol-1-yl)cyclopropyl)-3H-imidazo[4,5-b]pyridin-5-yl)piperidin-3-yl)pyrrolidin-1-yl)methanone

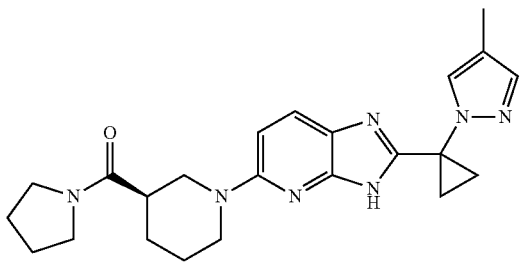 [SMILES: Cc1cnn(C2(c3nc4ccc(N5CCC[C@@H](C(=O)N6CCCC6)C5)nc4[nH]3)CC2)c1]

Into a 5 mL microwave vial were added (R)-(1-(5,6-diaminopyridin-2-yl)piperidin-3-yl)(pyrrolidin-1-yl)methanone dihydrochloride (Intermediate 1) (296 mg, 0.814 mmol) and 1-(4-methyl-1H-pyrazol-1-yl)cyclopropanecarboxylic acid (Intermediate 3) (137.5 mg, 0.827 mmol) and pyridine (2 mL). The vial was capped and triphenylphosphite (0.650 mL, 2.48 mmol) was added. The reaction mixture was stirred at 200° C. in a microwave for 10 min. To the mixture was added ethyl acetate and a saturated aqueous solution of ammonium chloride. The layers were separated and the aqueous layer was extracted with ethyl acetate (2×). The combined organics were washed sequentially with a saturated aqueous solution of sodium bicarbonate (2×) and brine (1×), then dried over sodium sulfate, filtered and concentrated under reduced pressure. The crude material was purified via HPLC to afford the title compound. MS (ESI+) (M+H) 420.2, HPLC retention time: 2.04 min (Method A).

The compounds listed in Table 6 below were prepared using procedures analogous to those described above for the synthesis of Example 72 using the appropriate starting materials which are available commercially or prepared using preparations well-known to those skilled in the art or prepared by a route described above.

TABLE 6

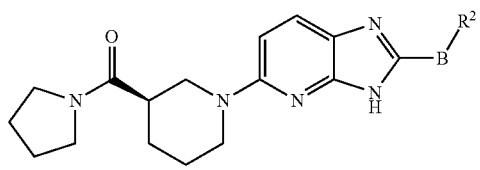

| Example | Compound Name | —B—R² | Analytical Data |
|---|---|---|---|
| 73 | (R)-(1-(2-(1-(4-Fluoro-1H-pyrazol-1-yl)cyclopropyl)-3H-imidazo[4,5-b]pyridin-5-yl)piperidin-3-yl)(pyrrolidin-1-yl)methanone | | MS (ESI+) (M + H) 424.2; HPLC retention time: 1.99 min (Method A) |

TABLE 6-continued

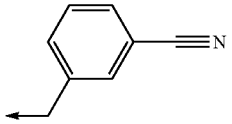

| Example | Compound Name | —B—R² | Analytical Data |
|---|---|---|---|
| 74 | (R)-3-((5-(3-(Pyrrolidine-1-carbonyl)piperidin-1-yl)-3H-imidazo[4,5-b]pyridin-2-yl)methyl)benzonitrile | 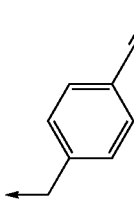 | MS (ES+) (M + H) 415.2; LCMS retention time: 1.19 min (Method M) |
| 75 | (R)-4-((5-(3-(Pyrrolidine-1-carbonyl)piperidin-1-yl)-3H-imidazo[4,5-b]pyridin-2-yl)methyl)benzonitrile | 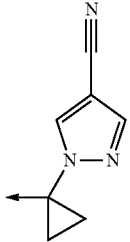 | MS (ESI+) (M + H) 415.2; LCMS retention time 1.20 min (Method M) |
| 76 | (R)-1-(1-(5-(3-(Pyrrolidine-1-carbonyl)piperidin-1-yl)-3H-imidazo[4,5-b]pyridin-2-yl)cyclopropyl)-1H-pyrazole-4-carbonitrile | 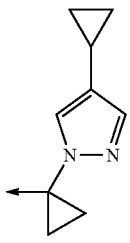 | MS (ESI+) (M + H) 431.2; HPLC retention time: 1.99 min (Method A) |
| 77 | (R)-(1-(2-(1-(4-Cyclopropyl-1H-pyrazol-1-yl)cyclopropyl)-3H-imidazo[4,5-b]pyridin-5-yl)piperidin-3-yl)(pyrrolidin-1-yl)methanone | 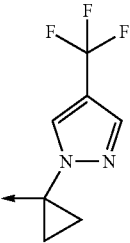 | MS (ESI+) (M + H) 446.1; HPLC retention time: 2.1377 min (Method A) |
| 78 | (R)-Pyrrolidin-1-yl(1-(2-(1-(4-(trifluoromethyl)-1H-pyrazoL-1-yl)cyclopropyl)-3H-imidazo[4,5-b]pyridin-5-yl)piperidin-3-yl)methanone |  | MS (ESI+) (M + H) 474.2; HPLC retention time: 2.34 min (Method A) |

TABLE 6-continued

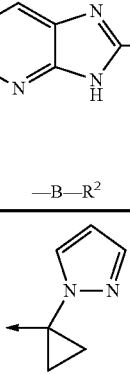

| Example | Compound Name | —B—R² | Analytical Data |
|---|---|---|---|
| 79 | (R)-(1-(2-(1-(1H-Pyrazol-1-yl)cyclopropyl)-3H-imidazo[4,5-b]pyridin-5-yl)piperidin-3-yl)(pyrrolidin-1-yl)methanone | | MS (ESI+) (M + H) 406.2; HPLC retention time: 1.8063 min (Method A) |
| 80 | (R)-(1-(2-(1-(1H-Pyrazol-1-yl)cyclobutyl)-3H-imidazo[4,5-b]pyridin-5-yl)piperidin-3-yl)(pyrrolidin-1-yl)methanone | | MS (ESI+) (M + H) 420.2; HPLC retention time: 2.04 min (Method A) |

Example 81

(R)-(1-(2-(1-(Pyridin-3-yl)cyclopropyl-1)-3H-imidazo[4,5-b]pyridin-5-yl)piperidin-3-yl)(pyrrolidin-1-yl)methanone

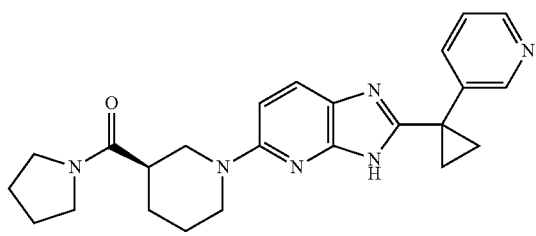 [SMILES: O=C([C@@H]1CCCN(c2ccc3nc(C4(c5cccnc5)CC4)[nH]c3n2)C1)N1CCCC1]

Step 1: (R)—N-(2-Amino-6-(3-(pyrrolidine-1-carbonyl)piperidin-1-yl)pyridin-3-yl)-1-(pyridin-3-yl)cyclopropanecarboxamide 1-(Pyridin-3-yl)cyclopropanecarboxylic acid (30.7 mg, 0.188 mmol), (R)-(1-(5,6-diaminopyridin-2-yl)piperidin-3-yl)(pyrrolidin-1-yl)methanone dihydrochloride (Intermediate 1) (75 mg, 0.19 mmol), and N-methylmorpholine (83 µL, 0.76 mmol) were combined and dissolved in N,N-dimethylformamide (1.0 mL). Benzotriazole-1-yl-oxy-tris-(dimethylamino)-phosphonium hexafluorophosphate (BOP) (122 mg, 0.207 mmol) was added and the reaction mixture was stirred at 50° C. for 18 h. The solvent was removed under reduced pressure and the residue was dissolved in dichloromethane. A saturated aqueous solution of sodium bicarbonate was added. The organics were collected and the aqueous layer was extracted with dichloromethane. The combined organics were washed with brine, dried over sodium sulfate, filtered and concentrated under reduced pressure. The residue was purified via flash chromatography (0-10% methanol in dichloromethane) to afford (R)—N-(2-amino-6-(3-(pyrrolidine-1-carbonyl)piperidin-1-yl)pyridin-3-yl)-1-(pyridin-3-yl)cyclopropanecarboxamide (69 mg, 84%). MS (AP+) (M+H) 435.2; LCMS retention time 1.51 min (Method L).

Step 2: (R)-(1-(2-(1-(Pyridin-3-yl)cyclopropyl)-3H-imidazo[4,5-b]pyridin-5-yl)piperidin-3-yl)(pyrrolidin-1-yl)methanone To a solution of (R)—N-(2-amino-6-(3-(pyrrolidine-1-carbonyl)piperidin-1-yl)pyridin-3-yl)-1-(pyridin-3-yl)cyclopropanecarboxamide (35 mg, 0.081 mmol) in isobutanol (500 µL) was added sodium methoxide (18 mg, 0.335 mmol) in methanol (250 µL). The reaction mixture was shaken 110° C. for 18 h. The solvent was evaporated under a nitrogen stream. The residue was partitioned between water (0.5 mL) and ethyl acetate (1.5 mL×3). The combined organics were dried over magnesium sulfate, filtered and concentrated under reduced pressure. The residue was purified via HPLC to afford (R)-(1-(2-(1-(pyridin-3-yl)cyclopropyl)-3H-imidazo[4,5-b]pyridin-5-yl)piperidin-3-yl)(pyrrolidin-1-yl)methanone (7.2 mg). MS (ESI+) (M+H) 417.3; HPLC retention time 1.59 min (Method A).

The compounds listed in Table 7 below were prepared using procedures analogous to those described above for the synthesis of compound of Example 81 using the appropriate starting materials which are available commercially or prepared using preparations well-known to those skilled in the art or prepared by a route described above.

TABLE 7

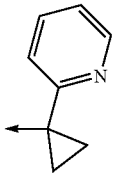

| Example | Compound Name | —B—R² | Analytical Data |
|---|---|---|---|
| 82 | (R)-(1-(2-(1-(Pyridin-2-yl)cyclopropyl)-3H-imidazo[4,5-b]pyridin-5-yl)piperidin-3-yl)(pyrrolidin-1-yl)methanone | 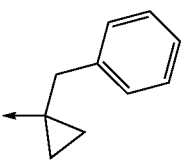 | MS (ESI+) (M + H) 417.3; HPLC retention time: 1.83 min (Method A) |
| 83 | (R)-(1-(2-(1-Benzylcyclopropyl)-3H-imidazo[4,5-b]pyridin-5-yl)piperidin-3-yl)(pyrrolidin-1-yl)methanone | 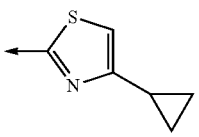 | MS (ESI+) (M + H) 430.3; HPLC retention time: 2.36 min (Method A) |
| 84 | (R)-(1-(2-(4-Cyclopropylthiazol-2-yl)-3H-imidazo[4,5-b]pyridin-5-yl)piperidin-3-yl)(pyrrolidin-1-yl)methanone | 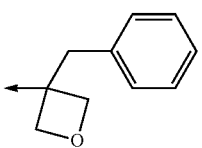 | MS (ESI+) (M + H) 423.1; HPLC retention time: 2.42 min (Method A) |
| 85 | (R)-(1-(2-(3-Benzyloxetan-3-yl)-3H-imidazo[4,5-b]pyridin-5-yl)piperidin-3-yl)(pyrrolidin-1-yl)methanone | 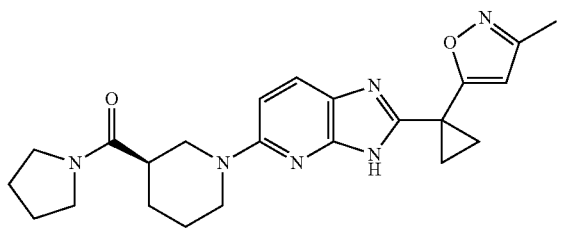 | MS (ESI+) (M + H) 446.1; HPLC retention time: 1.8063 min (Method A) |

Example 86

(R)-(1-(2-(1-(3-Methylisoxazol-5-yl)cyclopropyl)-3H-imidazo[4,5-b]pyridin-5-yl)piperidin-3-yl)(pyrrolidin-1-yl)methanone Step 1: (R)—N-(2-Amino-6-(3-(pyrrolidine-1-carbonyl)piperidin-1-yl)pyridine-3-yl)-1-(3-methylisoxazol-5-yl)cyclopropanecarboxamide 1-(3-Methylisoxazol-5-yl)cyclopropanecarboxylic acid (40 mg, 0.24 mmol), (R)-(1-(5,6-diaminopyridin-2-yl)piperidin-3-yl)(pyrrolidin-1-yl)methanone dihydrochloride (Intermediate 1) (86 mg, 0.24 mmol), and diisopropylethylamine (200 µL, 1.2 mmol) were combined and dissolved in N,N-dimethylformamide (1.25 mL). O-Benzotriazole-N,N,N',N',-tetramethyluronium hexafluorophosphate (HBTU) (109 mg, 0.287 mmol) was added and the reaction mixture was stirred at 40° C. for 18 h. The solvent was removed under reduced pressure and the residue was dissolved in dichloromethane. A saturated aqueous solution of sodium bicarbonate was added. The organics were collected and the aqueous layer was extracted with dichloromethane. The combined organics were washed with brine, dried over sodium sulfate, filtered and concentrated under reduced pressure. The residue was purified via flash chromatography (0-12% methanol in dichloromethane) to afford (R)—N-(2-amino-6-(3-(pyrrolidine-1-carbonyl)piperidin-1-yl)pyridine-3-yl)-1-(3-methylisoxazol-5-yl)cyclopropanecarboxamide (56 mg, 53%). MS (ES+) (M+H) 439.2; LCMS retention time 1.94 min (Method L).

Step 2: (R)-(1-(2-(1-(3-Methylisoxazol-5-yl)cyclopropyl)-3H-imidazo[4,5-b]pyridin-5-yl)piperidin-3-yl)(pyrrolidin-1-yl)methanone To a solution of (R)—N-(2-amino-6-(3-(pyrrolidine-1-carbonyl)piperidin-1-yl)pyridine-3-yl)-1-(3-methylisoxazol-5-yl)cyclopropanecarboxamide (94 mg, 0.21 mmol) in isobutanol (2 mL) was added sodium methoxide (25% in methanol, 98 µL, 0.43 mmol) followed by methanol (0.9 mL). The reaction mixture was stirred at 110° C. for 18 h. An additional portion of sodium methoxide (25% in methanol, 98 µL, 0.43 mmol) was added and the reaction mixture was stirred at 110° C. for 3 h. The mixture was concentrated under reduced pressure. The residue was dissolved in dichloromethane, washed with a saturated aqueous solution of sodium bicarbonate, dried over sodium sulfate, filtered and concentrated under reduced pressure. The crude material was purified via HPLC to afford (R)-(1-(2-(1-(3-methylisoxazol-5-yl)cyclopropyl)-3H-imidazo[4,5-b]pyridin-5-yl)piperidin-3-yl)(pyrrolidin-1-yl)methanone. MS (ESI+) (M+H) 421.2; HPLC retention time 2.02 min (Method A).

The compounds listed in Table 8 below were prepared using procedures analogous to those described above for the synthesis of Example 86 using the appropriate starting materials which are available commercially or prepared using preparations well-known to those skilled in the art or prepared by a route described above.

TABLE 8

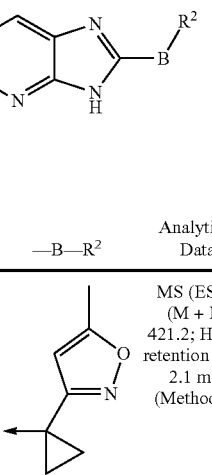

| Example | Compound Name | —B—R² | Analytical Data |
|---|---|---|---|
| 87 | (R)-(1-(2-(1-(5-Methylisoxazol-3-yl)cyclopropyl)-3H-imidazo[4,5-b]pyridin-5-yl)piperidin-3-yl)(pyrrolidin-1-yl)methanone | | MS (ESI+) (M + H) 421.2; HPLC retention time: 2.1 min (Method A) |
| 88 | (R)-(1-(2-(1-(Pyridin-3-yl)cyclobutyl)-3H-imidazo[4,5-b]pyridin-5-yl)piperidin-3-yl)(pyrrolidin-1-yl)methanone | | MS (ESI+) (M + H) 431.2; HPLC retention time: 1.99 min (Method B) |

Examples 89 and 90

(R)-(1-(2-(1-(3-Methyl-1H-pyrazol-1-yl)cyclopropyl)-3H-imidazo[4,5-b]pyridin-5-yl)piperidin-3-yl)(pyrrolidin-1-yl)methanone and (R)-(1-(2-(1-(5-methyl-1H-pyrazol-1-yl)cyclopropyl)-3H-imidazo[4,5-b]pyridin-5-yl)piperidin-3-yl)(pyrrolidin-1-yl)methanone

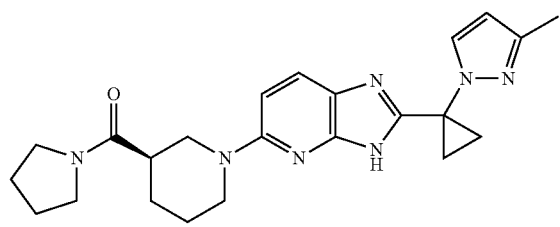

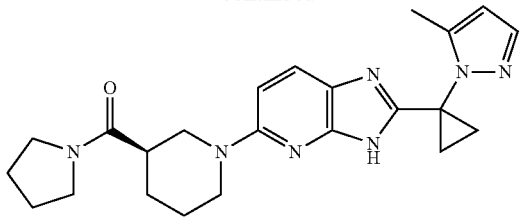

Step 1: (R)—N-(2-Amino-6-(3-(pyrrolidine-1-carbonyl)piperidin-1-yl)pyridin-3-yl)-1-(3-methyl-1H-pyrazol-1-yl)cyclopropanecarboxamide or (R)—N-(2-amino-6-(3-(pyrrolidine-1-carbonyl)piperidin-1-yl)pyridin-3-yl)-1-(5-methyl-1H-pyrazol-1-yl)cyclopropanecarboxamide Into a vial was added Intermediate 10 (60.0 mg, 0.361 mmol), (R)-(1-(5,6-diaminopyridin-2-yl)piperidin-3-yl)(pyrrolidin-1-yl)methanone dihydrochloride (Intermediate 1) (131 mg, 0.361 mmol), diisopropylethyl amine (314 µL, 1.80 mmol), O-(7-Azabenzotriazol-1-yl)-N,N,N',N',-tetramethyluronium hexafluorophosphate (HATU) (206 mg, 0.541 mmol), and N,N-dimethylformamide (3.0 mL). The reaction mixture was stirred at room temperature for 2 h. The mixture was purified via flash chromatography (0-6% methanol in dichloromethane) to afford (R)—N-(2-amino-6-(3-(pyrrolidine-1-carbonyl)piperidin-1-yl)pyridin-3-yl)-1-(3-methyl-1H-pyrazol-1-yl)cyclopropanecarboxamide or (R)—N-(2-amino-6-(3-(pyrrolidine-1-carbonyl)piperidin-1-yl)pyridin-3-yl)-1-(5-methyl-1H-pyrazol-1-yl)cyclopropanecarboxamide (62 mg).

Step 2: (R)-(1-(2-(1-(3-Methyl-1H-pyrazol-1-yl)cyclopropyl)-3H-imidazo[4,5-b]pyridin-5-yl)piperidin-3-yl)(pyrrolidin-1-yl)methanone or (R)-(1-(2-(1-(5-methyl-1H-pyrazol-1-yl)cyclopropyl)-3H-imidazo[4,5-b]pyridin-5-yl)piperidin-3-yl)(pyrrolidin-1-yl)methanone Into a vial containing (R)—N-(2-amino-6-(3-(pyrrolidine-1-carbonyl)piperidin-1-yl)pyridin-3-yl)-1-(3-methyl-1H-pyrazol-1-yl)cyclopropanecarboxamide or (R)—N-(2-amino-6-(3-(pyrrolidine-1-carbonyl)piperidin-1-yl)pyridin-3-yl)-1-(5-methyl-1H-pyrazol-1-yl)cyclopropanecarboxamide (60 mg, 0.14 mmol) and sodium methoxide (25% wt in methanol, 118 µL) was added isobutanol (0.4 mL) and methanol (0.2 mL). The reaction mixture was heated to 110° C. for 5 h. The solvent was removed under reduced pressure and the residue was purified via HPLC to afford (R)-(1-(2-(1-(3-methyl-1H-pyrazol-1-yl)cyclopropyl)-3H-imidazo[4,5-b]pyridin-5-yl)piperidin-3-yl)(pyrrolidin-1-yl)methanone or (R)-(1-(2-(1-(5-methyl-1H-pyrazol-1-yl)cyclopropyl)-3H-imidazo[4,5-b]pyridin-5-yl)piperidin-3-yl)(pyrrolidin-1-yl)methanone (Example 89, starting from Intermediate 10): MS (ESI+) (M+H) 420.3; HPLC retention time 1.85 min (Method A).

An analogous procedure was used for the synthesis of the other regioisomer, starting from 84.9 mg of Intermediate 11. Example 90: MS (ESI+) (M+H) 420.2; HPLC retention time 1.99 min (Method A).

Example 91

(R)-(1-(2-(1-(Pyrimidin-5-yl)cyclopropyl)-3H-imidazo[4,5-b]pyridin-5-yl)piperidin-3-yl)pyrrolidin-1-yl)methanone

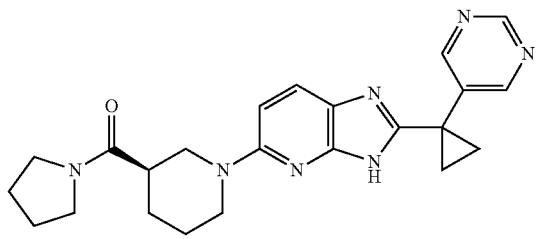 [SMILES: O=C([C@@H]1CCCN(c2ccc3nc(C4(c5cncnc5)CC4)[nH]c3n2)C1)N1CCCC1]

To a solution of (R)-(1-(5,6-diaminopyridin-2-yl)piperidin-3-yl)(pyrrolidin-1-yl)methanone dihydrochloride (64 mg, 0.18 mmol) in methanol (0.5 mL) and acetic acid (160 μL, 2.9 mmol) was added triethylamine (100 μL, 0.72 mmol). A solution of ethyl 1-(pyrimidin-5-yl)cyclopropanecarbimidate hydrochloride (40 mg, 0.18 mmol) in methanol (0.3 mL) was added. The reaction mixture was stirred at 70° C. for 18 h. The solvent was removed under reduced pressure and the residue was dissolved in ethyl acetate. The organics were washed with a saturated aqueous solution of sodium bicarbonate, and then with water, dried over sodium sulfate, filtered and concentrated under reduced pressure. The residue was purified via HPLC. MS (ESI+) (M+H) 419.9; HPLC retention time: 1.694 min (Method A).

Example 92

(R)-(1-(2-(1-(2-Methoxyphenyl)cyclopropyl)-3H-imidazo[4,5-b]pyridin-5-yl)piperidin-3-yl)(pyrrolidin-1-yl)methanone

To a solution of (R)-(1-(5,6-diaminopyridin-2-yl)piperidin-3-yl)(pyrrolidin-1-yl)methanone dihydrochloride (32 mg, 0.088 mmol) in ethanol (0.5 mL) was added triethylamine (50 μL, 1.42 mmol) and acetic acid (82 μL, 1.42 mmol). Then a solution of ethyl 1-(2-methoxyphenyl)cyclopropanecarbimidate hydrochloride (50 mg, 0.09 mmol) in ethanol (0.3 mL) was added and the reaction mixture was heated to 75° C. for 18 h. The solvent was removed under reduced pressure and the residue was partitioned between ethyl acetate and a saturated aqueous solution of sodium bicarbonate. The organic layer was washed with water, dried over sodium sulfate, filtered and concentrated under reduced pressure. The crude material was purified via HPLC to afford the title compound. MS (ESI+) (M+H) 446.1; HPLC retention time: 2.299 min (Method A).

The compounds listed in Table 9 below were prepared using procedures analogous to those described above for the synthesis of Example 92 using the appropriate starting materials which are available commercially or prepared using preparations well-known to those skilled in the art or prepared by a route described above.

TABLE 9

| Example | Compound Name | —B—R² | Analytical Data |
|---|---|---|---|
| 93 | (R)-(1-(2-(1-(Isoxazol-3-yl)cyclopropyl)-3H-imidazo[4,5-b]pyridin-5-yl)piperidin-3-yl)(pyrrolidin-1-yl)methanone | isoxazol-3-yl-cyclopropyl | MS (ESI+) (M + H) 407.3; HPLC retention time: 1.99 min (Method A) |
| 94 | (R)-(1-(2-(1-(4-Methoxyphenyl)cyclopropyl)-3H-imidazo[4,5-b]pyridin-5-yl)piperidin-3-yl)(pyrrolidin-1-yl)methanone | 4-methoxyphenyl-cyclopropyl | MS (ESI+) (M + H) 446.1; HPLC retention time: 2.2687 min (Method A) |

Example 95

(R)-(1-(2-(2-Cyclopropylpyrimidin-4-yl)-3H-imidazo[4,5-b]pyridin-5-yl)piperidin-3-yl)(pyrrolidin-1-yl)methanone

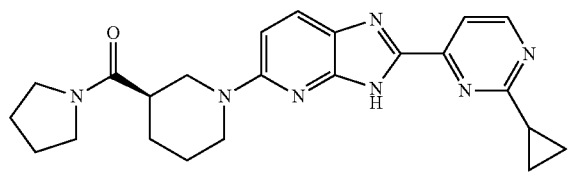

To a suspension of (R)-(1-(5,6-diaminopyridin-2-yl)piperidin-3-yl)(pyrrolidin-1-yl)methanone dihydrochloride (1.0 g, 2.76 mmol) and acetic acid (2.5 mL, 43.4 mmol) in ethanol (7 mL) was added triethylamine (1.5 mL, 10.8 mmol). A solution of ethyl 2-cyclopropylpyrimidine-4-carbimidate (530 mg, 2.77 mmol) in ethanol (3 mL) was added. The reaction mixture was heated at reflux for 30 min, then was cooled. The solvent was removed under reduced pressure and ethyl acetate (100 mL) was added to the residue followed by water (10 mL) and a saturated aqueous solution of ammonium chloride (50 mL). The layers were separated and the organics were washed with a saturated aqueous solution of sodium bicarbonate (75 mL) and brine (50 mL), dried over magnesium sulfate, filtered and concentrated under reduced pressure. To the resulting residue was added dichloromethane (4 mL) and methyl tert-butyl ether (35 mL). The mixture was stirred at 40° C. unit it was homogeneous. The solution was cooled to room temperature and stirred for 18 h. The resulting solids were filtered and rinsed with ether to afford the title compound. $^1$H NMR (400 MHz, CDCl$_3$) δ 1.10-1.17 (m, 2H) 1.18-1.23 (m, 2H), 1.57-1.70 (m, 1H) 1.82-2.05 (m, 7H) 2.27-2.34 (m, 1H) 2.63-2.72 (m, 1H) 2.97-3.07 (m, 1H) 3.14-3.22 (m, 1H) 3.43-3.54 (m, 3H) 3.58-3.67 (m, 1H) 4.37 (d, 1H) 4.53 (d, 1H) 6.76 (d, 1H) 7.95 (m, 2H) 8.67 (d, 1H) 10.46 (br, 1H). MS (ES+) (M+H) 418.5; LCMS retention time 2.72 min (Method L).

The compounds listed in Table 10 below were prepared using procedures analogous to those described above for the synthesis of compound of Example 95 using the appropriate starting materials which are available commercially or prepared using preparations well-known to those skilled in the art or prepared by a route described above.

TABLE 10

| Example | Compound Name | —B—R$^2$ | Analytical Data |
|---|---|---|---|
| 96 | (R)-Ethyl 2-methoxy-6-(5-(3-(pyrrolidine-1-carbonyl)piperidin-1-yl)-3H-imidazo[4,5-b]pyridin-2-yl)isonicotinate | | MS (ESI+) (M + H) 479.2; HPLC retention time: 2.66 min (Method A) |
| 97 | (R)-Pyrrolidin-1-yl(1-(2-(1-m-tolylcyclopropyl)-3H-imidazo[4,5-b]pyridin-5-yl)piperidin-3-yl)methanone | | $^1$H NMR (500 MHz, CDCl$_3$) δ 1.18-1.34 (m, 2H) 1.41 (d, 2H) 1.75-1.83 (m, 3H) 1.85-1.89 (m, 2H) 1.92-1.96 (m, 2H) 2.39 (s, 3H) 2.56-2.67 (m, 1H) 2.87 (t, 1H) 3.04 (t, 1H) 3.41-3.50 (m, 3H) 3.74 (q, 1H) 4.20 (d, 1H) 4.30 (d, 1H) 6.61 (d, 1H) 7.15-7.19 (m, 1H) 7.28-7.34 (m, 3H) 7.74 (d, 1H) 8.53 (br s, 1H) MS (ES+) 430.3; LCMS retention time: 2.29 min (Method L) |

TABLE 10-continued

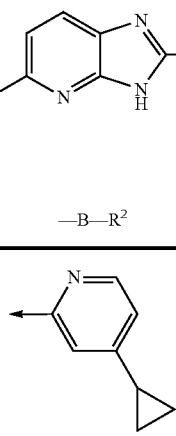

| Example | Compound Name | —B—R² | Analytical Data |
|---|---|---|---|
| 98 | (R)-(1-(2-(4-Cyclopropylpyridin-2-yl)-3H-imidazo[4,5-b]pyridin-5-yl)piperidin-3-yl)(pyrrolidin-1-yl)methanone | (4-cyclopropylpyridin-2-yl) | MS (ES + APCI) (M +H) 417.2; LCMS retention time 3.021 min (Method Z1) |
| 99 | (R)-(1-(2-(4-Cyclopropylpyrimidin-2-yl)-3H-imidazo[4,5-b]pyridin-5-yl)piperidin-3-yl)(pyrrolidin-1-yl)methanone | (4-cyclopropylpyrimidin-2-yl) | $^1$H NMR (400 MHz, CDCl$_3$) δ 1.14-1.21 (m, 2H), 1.24-1.30 (m, 3H), 1.62-1.68 (m, 1H), 1.80-1.94 (m, 3H), 1.94-2.15 (m, 4H), 2.59-2.73 (m, 1H), 3.00 (td, 1H), 3.16 (dd, 1H), 3.43-3.55 (m, 3H), 3.58-3.67 (m, 1H), 4.40 (br s, 1H), 4.51 (d, 1H), 6.73 (d, 1H), 7.10 (d, 1H), 7.93 (d, 1H), 8.61 (d, 1H), 10.15 (br s, 1H) |
| 100 | (R)-N-Methyl-5-(5-(3-(pyrrolidine-1-carbonyl)piperidin-1-yl)3H-imidazo[4,5-b]pyridin-2-yl)pyridine-3-sulfonamide | (5-(N-methylsulfamoyl)pyridin-3-yl) | 1H NMR (400 MHz, DMSO-d$_6$) δ 1.23(s, 1H), 1.53 (d, 1H), 1.65-1.74 (m, 2H), 1.75-1.83 (m, 2H), 1.85-1.94 (m, 3H), 2.60-2.72 (m, 2H), 2.94 (d, 2H), 3.26-3.30 (m, 3H), 3.43-3.58 (m, 2H), 4.35 (d, 1H), 4.42 (d, 1H), 6.91 (d, 1H), 7.78-7.90 (m. 2H), 8.81 (s, 1H), 8.92 (br s, 1H), 9.47 (br s, 1H), 13.41 (br s, 1H) MS (ES+) (M + H) 470.1; LCMS retention time: 3.845 (Method I) |
| 101 | (R)-(1-(2-(6-Cyclopropylpyrazin-2-yl)-3H-imidazo[4,5-b]pyridin-5-yl)piperidin-3-yl)(pyrrolidin-1-yl)methanone | (6-cyclopropylpyrazin-2-yl) | MS (ESI+) (M + H) 418.2; HPLC retention time: 2.3 min (Method A). |

Example 102

(R)-(1-(2-(1-(3-Methoxyphenyl)cyclopropyl)-3H-imidazo[4,5-b]pyridin-5-yl)piperidin-3-yl)(pyrrolidin-1-yl)methanone

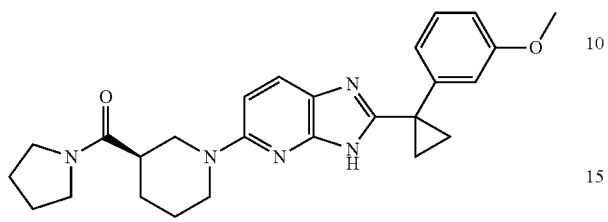

To a solution of (R)-(1-(5,6-diaminopyridin-2-yl)piperidin-3-yl)(pyrrolidin-1-yl)methanone dihydrochloride (60 mg, 0.17 mmol) in methanol (0.5 mL) and acetic acid (150 μL, 2.7 mmol) was added triethylamine (94 μL, 0.67 mmol) and a solution of ethyl 1-(3-methoxyphenyl)cyclopropanecarbimidate hydrochloride (40 mg, 0.16 mmol) in methanol (0.3 mL). The reaction mixture was heated in a microwave for 45 min at 130° C. The solvent was removed under reduced pressure and the residue was partitioned between ethyl acetate and a saturated aqueous solution of sodium bicarbonate. The organic layer was washed with water, dried over sodium sulfate, filtered and concentrated under reduced pressure. The crude material was purified via HPLC to afford the title compound. MS (ESI+) (M+H) 446.3; HPLC retention time 2.3 min (Method A).

Example 103

(R)-Pyrrolidin-1-yl(1-(2-(1-(p-tolyl)cyclopropyl)-3H-imidazo[4,5-b]pyridin-5-yl)piperidin-3-yl)methanone

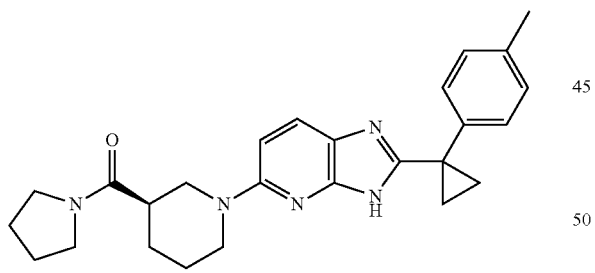

To a suspension of (R)-(1-(5,6-diaminopyridin-2-yl)piperidin-3-yl)(pyrrolidin-1-yl)methanone dihydrochloride (220 mg, 0.60 mmol) in ethanol (2 mL) was added triethylamine (250 μL, 1.8 mmol), a solution of ethyl 1-(p-tolyl)cyclopropanecarbimidate hydrochloride (140 mg, 0.58 mmol) in ethanol (1 mL), and acetic acid (0.5 mL, 8.70 mmol). The reaction mixture was heated in a microwave for 45 min at 130° C. The solvent was removed under reduced pressure. Ethyl acetate (10 mL) was added to the residue and the solution was washed with aqueous sodium hydroxide (1N, 5 mL). The aqueous layer was extracted with ethyl acetate (10 mL×3). The combined organics were washed with brine, dried over magnesium sulfate, filtered and concentrated under reduced pressure. The residue was purified via HPLC to afford the title compound. MS (ESI+) (M+H) 430.2; HPLC retention time 2.51 min (Method A).

Example 104

(R)-(1-(2-(1-(1-Methyl-1H-pyrazol-5-yl)cyclopropyl)-3H-imidazo[4,5-b]pyridin-5-yl)piperidin-3-yl)(pyrrolidin-1-yl)methanone

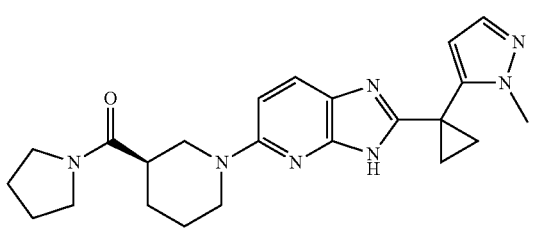 [SMILES: Cn1nccc1C1(c2nc3ccc(N4CCC[C@@H](C(=O)N5CCCC5)C4)nc3[nH]2)CC1]

To a solution of 2-(1-methyl-1H-pyrazol-5-yl)acetonitrile (14.5 mg, 0.10 mmol) in ethanol (150 μL, 2.6 mmol) was added acetyl chloride (110 μL, 1.5 mmol). The reaction mixture was stirred at room temperature for 16 h. The solvent was removed under a stream of nitrogen. Ethanol (0.5 mL) was added to the residue followed by a solution of (R)-(1-(5,6-diaminopyridin-2-yl)piperidin-3-yl)(pyrrolidin-1-yl)methanone dihydrochloride (36 mg, 0.01 mmol) and triethylamine (70 μL, 0.50 mmol) in ethanol (1 mL). Acetic acid (100 μL, 1.75 mmol) was added and the reaction mixture was heated in the microwave for 45 min at 130° C. The solvent was removed under a stream of nitrogen. Ethyl acetate (10 mL) was added to the residue. The solution was washed with aqueous sodium hydroxide (1N, 3 mL), washed with water (3 mL), washed with brine (3 mL), dried over magnesium sulfate, filtered and concentrated under reduced pressure. The crude material was purified via HPLC to afford the title compound. MS (ESI+) (M+H) 420.3; HPLC retention time 1.88 min (Method B).

Example 105

(R)-Ethyl 2-ethyl-6-(5-(3-(pyrrolidine-1-carbonyl)piperidin-1-yl)-3H-imidazo[4,5-b]pyridin-2-yl)isonicotinate

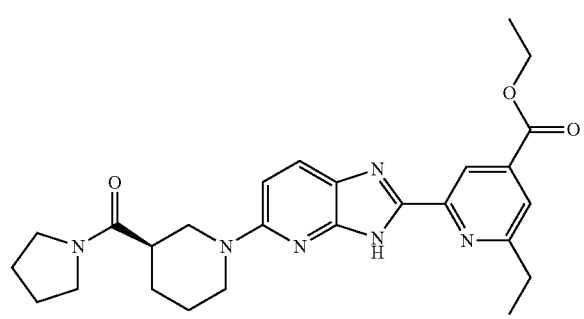 [SMILES: CCOC(=O)c1cc(CC)nc(-c2nc3ccc(N4CCC[C@@H](C(=O)N5CCCC5)C4)nc3[nH]2)c1]

To a solution (R)-(1-(5,6-diaminopyridin-2-yl)piperidin-3-yl)(pyrrolidin-1-yl)methanone dihydrochloride (116 mg, 0.595 mmol) in anhydrous ethanol (5.0 mL) was added acetic acid (0.293 mL, 5.12 mmol) followed by triethylamine (0.179 mL, 1.28 mmol). Ethyl 2-(ethoxy(imino)methyl)-6-ethylisonicotinate hydrochloride (80 mg, 0.32 mmol) was added and the reaction mixture was heated to 110° C. for 30 min. The reaction mixture was cooled to room temperature and the solvent was removed under reduced pressure. The residue was partitioned between a saturated aqueous solution of ammonium chloride (50 mL) and ethyl acetate (50 mL). The pH of the aqueous layer was adjusted to 3 using an aqueous solution of hydrochloric acid (1N). The aqueous layer was extracted with ethyl acetate (50 mL×2). The combined organic layers were washed with brine, dried over sodium sulfate, filtered and concentrated under reduced pressure. The crude material was purified via HPLC to afford the title compound. MS (ESI+) (M+H) 477.2; HPLC retention time 2.7 min (Method A).

Example 106

(R)-Pyrrolidin-1-yl(1-(2-(1-(4-(trifluoromethyl)phenyl)cyclopropyl)-3H-imidazo[4,5-b]pyridin-5-yl)piperidin-3-yl)methanone

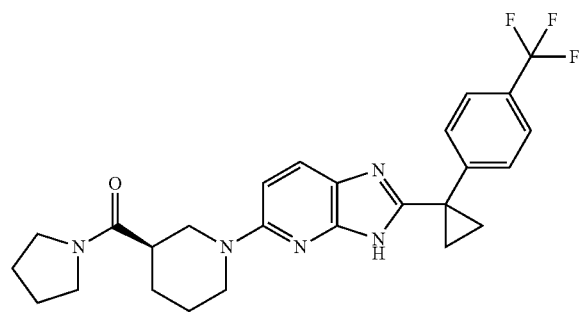 [SMILES: O=C([C@@H]1CCCN(c2ccc3nc(C4(c5ccc(C(F)(F)F)cc5)CC4)[nH]c3n2)C1)N1CCCC1]

The title compound was prepared by a method analogous to the one used for Example 92, but methanol was used as the solvent and the reaction mixture was heated to 70° C. $^1$H NMR (500 MHz, CD$_3$OD) δ 1.60-1.82 (m, 6H) 1.87-2.05 (m, 6H) 2.72-2.81 (m, 1H) 2.91-2.99 (m, 2H) 3.43 (t, 2H) 3.53 (dt, 1H) 3.68-3.75 (m, 1H) 4.26 (d, 1H) 4.53 (d, 1H) 6.78 (d, 1H) 7.52 (d, 2H) 7.65 (d, 3H).

Example 107

(R)-(1-(2-(6-Cyclopropylpyrazin-2-yl)-3H-imidazo[4,5-b]pyridin-5-yl)piperidin-3-yl)(morpholino)methanone

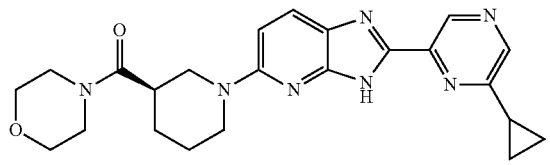 [SMILES: O=C([C@@H]1CCCN(c2ccc3nc(-c4cncc(C5CC5)n4)[nH]c3n2)C1)N1CCOCC1]

The title compound was prepared by a method analogous to the one used for Example 95, but using (R)-(1-(5,6-diaminopyridin-2-yl)piperidin-3-yl)(morpholino)methanone dihydrochloride (synthesized by hydrogenation analogous to the one used for Intermediate 1, starting from Intermediate 40) and Intermediate 30. $^1$H NMR (300 MHz, DMSO-d$_6$) δ 1.06 (dd, 2H), 1.20-1.33 (m, 3H), 1.54-1.74 (m, 3H), 1.80-1.93 (m, 1H), 2.19-2.33 (m, 2H), 2.79 (br s, 1H), 2.87-3.09 (m, 3H), 3.55 (m, 5H), 4.30-4.53 (m, 2H), 6.88 (d, 1H), 7.86 (d, 1H), 8.61 (s, 1H), 9.06 (s, 1H), 13.05 (s, 1H)

Example 108

(R)-(1-(8-(1-(4-Chloro-1H-pyrazol-1-yl)cyclopropyl)-9H-purin-2-yl)piperidin-3-yl)(pyrrolidin-1-yl)methanone

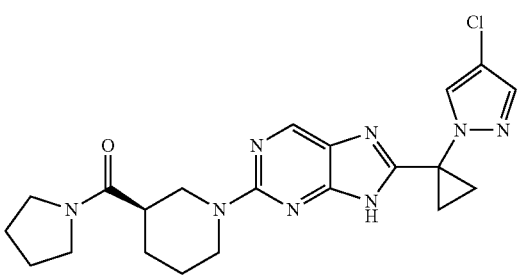 [SMILES: O=C([C@@H]1CCCN(c2ncc3nc(C4(n5cc(Cl)cn5)CC4)[nH]c3n2)C1)N1CCCC1]

To a solution of (R)-(1-(4,5-diaminopyrimidin-2-yl)piperidin-3-yl)(pyrrolidin-1-yl)methanone dihydrochloride (320 mg, 0.881 mmol) and ethyl 1-(4-chloro-1H-pyrazol-1-yl)cyclopropanecarbimidate (227 mg, 1.06 mmol) in ethanol (2 mL) was added glacial acetic acid (0.81 mL, 14 mmol) and triethylamine (0.50 mL, 3.5 mmol). The solution was heated to 110° C. for 2 h. The solvent was removed under reduced pressure and the residue was dissolved in dichloromethane. The organics were washed with a saturated aqueous solution of ammonium chloride. The aqueous layer was extracted with dichloromethane. The combined organics were dried over sodium sulfate, filtered and concentrated under reduced pressure. The crude material was purified by flash chromatography (0-10% methanol in ethyl acetate) to give the product as a red solid. The solid was further purified via flash chromatography (0-20% acetone in dichloromethane), followed by passing through a plug of basic alumina (80-100% ethyl acetate in heptanes) to give the title compound as a pink solid (75 mg, 19% yield). $^1$H NMR (500 MHz, CDCl$_3$) δ 1.46-1.55 (m, 1H), 1.75-2.00 (m, 11H), 2.51-2.57 (m, 1H), 2.85-2.90 (m, 1H), 3.04 (dd, 1H), 3.39-3.50 (m, 3H), 3.58-3.63 (m, 1H), 4.72-4.83 (m, 2H), 7.56 (s, 1H), 7.63 (s, 1H), 8.57 (br s, 1H), 9.83 (br s, 1H). MS (AP+) (M+H) 441.2; LCMS retention time 2.63 min (Method L).

Example 109-A (R)-(1-(2-(1-(4-Chloro-1H-pyrazol-1-yl)cyclopropyl)-3H-imidazo[4,5-b]pyridin-5-yl)piperidin-3-yl)(pyrrolidin-1-yl)methanone

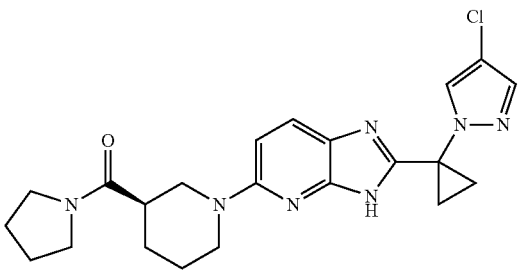 [SMILES: O=C([C@@H]1CCCN(c2ccc3nc(C4(n5cc(Cl)cn5)CC4)[nH]c3n2)C1)N1CCCC1]

To a solution of (R)-(1-(5,6-diaminopyridin-2-yl)piperidin-3-yl)(pyrrolidin-1-yl)methanone dihydrochloride (5.5 g, 15.2 mmol) and acetic acid (17.4 mL, 305 mmol) in ethanol (20 mL) was added a solution of ethyl 1-(4-chloro-1H-pyrazol-1-yl)cyclopropanecarbimidate (3.25 g, 15.2 mmol) in ethanol (30 mL) followed by triethylamine (12.7 mL, 91.2 mmol). The resulting mixture was purged with nitrogen. The reaction mixture was stirred for 18 h at 100° C. The mixture was cooled to room temperature and the solvent was removed under reduced pressure. The residue was partitioned between a saturated aqueous solution of ammonium chloride (50 mL) and dichloromethane (50 mL). The aqueous layer was extracted with dichloromethane (50 mL). The combined organics were washed with a saturated aqueous solution of sodium bicarbonate and the resulting aqueous layer was extracted with dichloromethane (50 mL). The organics were combined, washed with brine, dried over sodium sulfate, filtered and concentrated under reduced pressure. The crude material was purified via flash chromatography (0-5% methanol in dichloromethane) to afford (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone (6.33 g, 94%). $^1$H NMR (500 MHz, CDCl$_3$) δ 1.55-1.70 (m, 1H), 1.72-2.05 (m, 11H), 2.60-2.70 (m, 1H), 2.90-2.95 (m, 1H), 3.03-3.10 (m, 1H), 3.42-3.50 (m, 3H), 3.56-3.62 (m, 1H), 4.20-4.25 (m, 1H), 4.38-4.44 (m, 1H), 6.62-6.68 (m, 1H), 7.59 (s, 1H), 7.63 (s, 1H), 7.66-7.72 (m, 1H); MS (ES+) (M+H) 440; UPLC retention time 0.47 min (Method N).

Alternative preparation for (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone Step 1: (R)-1-(4-Chloro-1H-pyrazol-1-yl)-N-(3-nitro-6-(3-(pyrrolidine-1-carbonyl)piperidin-1-yl)pyridin-2-yl)cyclopropanecarboxamide

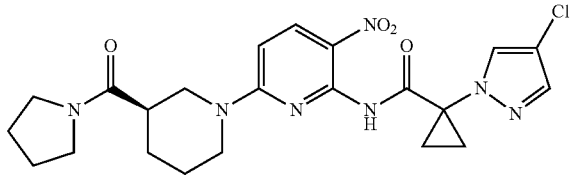 [SMILES: O=C([C@@H]1CCCN(c2ccc([N+](=O)[O-])c(NC(=O)C3(n4cc(Cl)cn4)CC3)n2)C1)N1CCCC1]

Into a 1-L Atlas jacketed reactor were added 1-(4-chloro-1H-pyrazol-1-yl)cyclopropanecarboxylic acid (49.08 g, 263.02 mmol), (R)-(1-(6-amino-5-nitropyridin-2-yl)piperidin-3-yl)(pyrrolidin-1-yl)methanone (70 g, 219.19 mmol), 4-dimethylaminopyridine (5.41 g, 43.84 mmol), toluene (600 mL) and diisopropylethylamine (95.56 mL, 547.96 mmol). The reaction mixture was heated to 45° C. and stirred for 10 min until most of the solids were dissolved. 1-Propanephosphonic acid cyclic anhydride (195.70 mL, 328.78 mmol, 50% solution in ethyl acetate) was added and the temperature was increased to 110° C. The reaction mixture was stirred for 19 h before adding more 1-propanephosphonic acid cyclic anhydride solution (25 mL). The mixture was stirred at 110° C. for 5 h. The mixture was concentrated to a low volume via distillation with jacket temperature at 80° C. A mixture of ethanol:water (1:1, 1000 mL) was added to keep the temperature around 70° C. Once the addition was complete, the mixture was cooled to 15° C. over a period of 2 h and left granulating for 18 h. The solids were filtered and rinsed with a mixture of ethanol:water (1:1, 750 mL) and dried in a vacuum oven at 40° C. with a nitrogen bleed for 18 h to afford (R)-1-(4-chloro-1H-pyrazol-1-yl)-N-(3-nitro-6-(3-(pyrrolidine-1-carbonyl)piperidin-1-yl)pyridin-2-yl)cyclopropanecarboxamide (72 g). $^1$H NMR (500 MHz, CDCl$_3$) δ 1.50-1.66 (m, 4H), 1.82-2.05 (m, 11H), 2.53-2.61 (m, 1H), 3.00-3.20 (m, 2H), 3.34-3.42 (m, 1H), 3.49 (t, 2H), 6.32 (d, 1H), 7.61 (s, 1H), 7.68 (s, 1H), 8.21 (d, 1H), 11.01 (s, 1H); MS (ES+) (M+H) 488; HPLC retention time: 7.520 min (Method: Column: Halo C18, 4.6×150 mm, 2.7 μm; Mobile Phase B: 0.1 M phosphoric acid (H$_3$PO$_4$) in water; Mobile Phase D: acetonitrile; Gradient: 80%-10% Mobile Phase B until 7.00 min; hold until 10.00 min; rapid ramp of 80% Mobile Phase B until 10.1 min; equilibrate until 12.1 min; Flow: 0.8 mL/min; Column Temperature: 30° C.; DAD1A, Sig=254 nm).

Step 2: (R)-(1-(2-(1-(4-Chloro-1H-pyrazol-1-yl)cyclopropyl)-3H-imidazo[4,5-b]pyridin-5-yl)piperidin-3-yl)(pyrrolidin-1-yl)methanone Into a flask was added (R)-1-(4-chloro-1H-pyrazol-1-yl)-N-(3-nitro-6-(3-(pyrrolidine-1-carbonyl)piperidin-1-yl)pyridin-2-yl)cyclopropanecarboxamide (107 g, 219.29 mmol) and acetic acid (750 mL, 6.74 mol). The mixture was stirred for 5 min. Zinc powder (71.70 g, 1.10 mol) was added. An exotherm to 79° C. was observed over a period of 30 sec. The reaction mixture was warmed to 100° C. and stirred for 2 h. The mixture was cooled to 50° C. and water (750 mL) was added. The mixture was stirred for 10 min and cooled to 10° C. Ethyl acetate (500 mL) was added and the mixture was stirred for 20 min and filtered through Celite rinsing with ethyl acetate (300 mL). The filtrate was cooled to 10° C. and aqueous ammonium hydroxide (936.92 mL, 6.74 mol) was added dropwise over a period of 20 min. The layers were separated and the organics were washed with a mixture of water:brine (1:1, 500 mL), and concentrated under reduced pressure. Ethyl acetate (200 mL) was added and the mixture was concentrated under reduced pressure followed by the addition of acetonitrile (500 mL). The mixture was concentrated to dryness at 45° C. to afford (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone (100 g) as an amorphous material. $^1$H NMR (500 MHz, CDCl$_3$) δ 1.55-1.70 (m, 1H), 1.72-2.05 (m, 11H), 2.60-2.70 (m, 1H), 2.90-2.95 (m, 1H), 3.03-3.10 (m, 1H), 3.42-3.50 (m, 3H), 3.56-3.62 (m, 1H), 4.20-4.25 (m, 1H), 4.38-4.44 (m, 1H), 6.62-6.68 (m, 1H), 7.59 (s, 1H), 7.63 (s, 1H), 7.66-7.72 (m, 1H); MS (ES+) (M+H) 440; HPLC retention time: 4.450 min (Method: Same as for Step 1).

Example 109-B (R)-(1-(2-(1-(4-Chloro-1H-pyrazol-1-yl)cyclopropyl)-3H-imidazo[4,5-b]pyridin-5-yl)piperidin-3-yl)(pyrrolidin-1-yl)methanone methanesulfonate

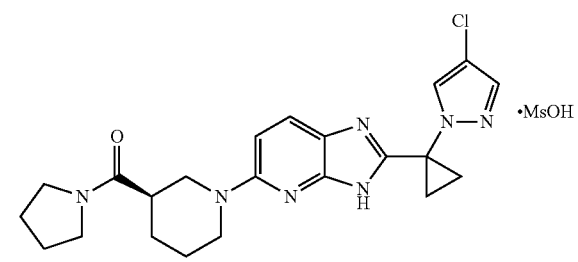 [SMILES: "·MsOH" ; O=C([C@@H]1CCCN(c2ccc3nc(C4(n5cc(Cl)cn5)CC4)[nH]c3n2)C1)N1CCCC1]

To a solution of (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone (Example 109-A, 56.49 g, 128.4 mmol) in acetonitrile (130 mL) was added methanesulfonic acid (8.33 mL, 128 mmol). The mixture was stirred for 18 h at room temperature. The mixture was filtered and the solids were rinsed with acetonitrile. The solids were collected and dried under high vacuum for 1 h to afford (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone methanesulfonate (62.5 g, 90%). $^1$H NMR (400 MHz, CDCl$_3$) δ 1.65-1.75 (m, 1H), 1.84-2.13 (m, 11H), 2.75-2.85 (m, 1H), 2.87 (s, 3H), 3.28-3.35 (m, 1H), 3.39-3.57 (m, 4H), 3.65-3.72 (m, 1H), 4.02-4.09 (m, 1H), 4.11-4.17 (m, 1H), 6.73-6.82 (m, 1H), 7.55 (s, 1H), 7.76 (s, 1H), 8.13 (d, 1H); MS (ES+) (M+H) 440; UPLC retention time 0.47 min (Method N). mp=212-214° C. Anal. Calculated for $C_{22}H_{26}ClN_7O\cdot CH_4O_3S$: C, 51.53; H, 5.64; N, 18.29; Cl, 6.61; S, 5.98. Found: C, 51.28; H, 5.65; N, 18.19; Cl, 6.56; S, 5.96.

Alternative preparation for (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone methanesulfonate To (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone (Example 109-A, 100 g), prepared by the alternative method described in Example 109-A (Step 1 and Step 2), was added acetonitrile (500 mL). The mixture was stirred for 5 min at room temperature before adding methanesulfonic acid (14.38 mL, 219.29 mmol) over a period of 15 sec. The mixture was stirred for 2 h while cooling back to 19° C. The solids were filtered and washed with acetonitrile (250 mL) and dried under nitrogen for 18 h to afford the title compound (86 g, 73% over two steps from Step 2, alternative method for Example 109-A) as a white solid. HPLC retention time: 4.451 min (Method: Same as for Step 1 in the alternative method described for Example 109-A). Chiral HPLC retention time: 3.837 min (Method: Column: OJ-H 4.6×250 mm, 5 μm; S10|(5): acetonitrile+0.1% isopropylamine, 150 bar, 4 mL/min, 40° C., 0-5.5 min: 5-45% S, 5.5-7.5 min: 45% S, 7.51-8 min: 5% S). $^1$H NMR (400 MHz, DMSO-d$_6$) δ 1.35-2.03 (m, 12H), 2.32 (s, 3H), 2.53-2.65 (m, 1H), 2.91-3.13 (m, 2H), 3.20-3.35 (m, 2H), 3.35-3.55 (m, 2H), 4.20-4.36 (m, 2H), 7.05 (d, 1H), 7.73 (s, 1H), 7.83 (d, 1H), 8.30 (s, 1H).

Alternative preparation for (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone methanesulfonate Step 1: (R)-tert-Butyl 2-amino-6-(3-(pyrrolidine-1-carbonyl)piperidin-1-yl)pyridin-3-ylcarbamate

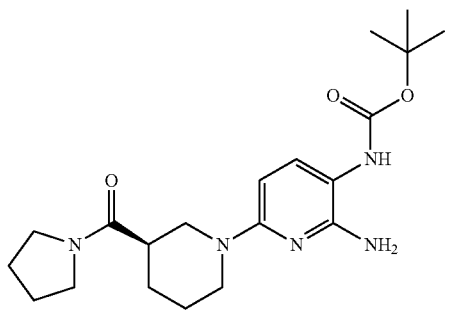 [SMILES: CC(C)(C)OC(=O)Nc1ccc(N2CCC[C@@H](C(=O)N3CCCC3)C2)nc1N]

A nitrogen-purged reaction vessel was charged sequentially with 5% palladium-on-carbon (0.208 kg, 0.10 mol), (R)-(1-(6-amino-5-nitropyridin-2-yl)piperidin-3-yl)(pyrrolidin-1-yl)methanone (1.3 kg, 4.1 mol), ethyl acetate (14 L), di-tert-butyl dicarbonate (0.906 kg, 4.15 mol), and triethylamine (0.824 kg, 8.14 mol). An additional charge of ethyl acetate (1.3 L) was added to ensure all residues were rinsed into the reaction vessel. The vessel was purged and pressurized with nitrogen, then was purged and pressurized with hydrogen to 50 psig. The reaction was heated to 40° C. and was held at that temperature for 6 h. The mixture was then cooled to 20° C. and the vessel was purged with nitrogen. The presence of (R)-tert-butyl 2-amino-6-(3-(pyrrolidine-1-carbonyl)piperidin-1-yl)pyridin-3-ylcarbamate was confirmed by HPLC analysis of the mixture [HPLC retention time: 5.25 min (Column: Halo C18, 4.6×150 mm, 2.7 μm; Mobile Phase A: acetonitrile, Mobile Phase B: 0.05% methanesulfonic acid in water; Linear Gradient: 5:95 A:B to 95:5 A:B over 9 min, then held for 1 min; Flow: 1.0 mL/min; UV detection at 210, 226, and 254 nM)]. The mixture was filtered and was rinsed with ethyl acetate (6.5 L). The filtrate was transferred to another reaction vessel, rinsing with ethyl acetate (1 L). To quench excess di-tert-butyl dicarbonate, N,N-diethylamine (59.5 g, 0.81 mol) was added while maintaining a temperature of 20° C.; the reaction mixture was held for 30 min at that temperature. Three batches of material on this scale were combined and were used in the next step without further purification.

Step 2: (R)-1-(2-(1-(4-Chloro-1H-pyrazol-1-yl)cyclopropyl)-3H-imidazo[4,5-b]pyridin-5-yl)piperidin-3-yl)(pyrrolidin-1-yl)methanone methanesulfonate

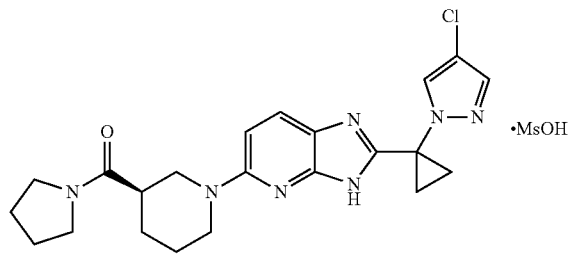 [SMILES: "·MsOH" ; O=C([C@@H]1CCCN(c2ccc3nc(C4(n5cc(Cl)cn5)CC4)[nH]c3n2)C1)N1CCCC1]

A solution of (R)-tert-butyl 2-amino-6-(3-(pyrrolidine-1-carbonyl)piperidin-1-yl)pyridin-3-ylcarbamate in ethyl acetate from the combined three batches from Step 1 (65 L total volume) was distilled under reduced pressure at 40° C. until the residual volume was approximately 8 L. An additional portion of ethyl acetate (48 L) was added, and the resulting solution was distilled under reduced pressure at 40° C. until the residual volume was approximately 8 L. Ethyl acetate (33 L), 1-(4-chloro-1H-pyrazol-1-yl)cyclopropanecarboxylic acid (2.28 kg, 12.2 mol), and N,N-diisopropylethylamine (4.74 kg, 36.7 mol) were added sequentially. To the resulting mixture at 20° C. was added a solution of 1-propanephosphonic acid cyclic anhydride in ethyl acetate (50% solution, 14.0 kg, 22.0 mol; plus a 2.0-L ethyl acetate rinse). The resulting mixture was heated to 40° C. and was held at that temperature for 8 h. The presence of (R)-tert-butyl 2-(1-(4-chloro-1H-pyrazol-1-yl)cyclopropanecarboxamido)-6-(3-(pyrrolidine-1-carbonyl)piperidin-1-yl)pyridin-3-ylcarbamate was confirmed by HPLC analysis of the mixture [HPLC retention time: 8.53 min (Column: Halo C18, 4.6×150 mm, 2.7 μm; Mobile Phase A: acetonitrile, Mobile Phase B:

0.05% methanesulfonic acid in water; Linear Gradient: 5:95 A:B to 95:5 A:B over 9 min, then held for 1 min; Flow: 1.0 mL/min; UV detection at 210, 226, and 254 nM)]. The mixture was then partitioned between ethyl acetate (38 L) and a 10% aqueous solution of citric acid (2×50 L). The organic layer was then washed sequentially with a 10% aqueous solution of potassium carbonate (31 L) and with water (24 L). The organic layer was then distilled under reduced pressure at 40° C. until the remaining volume was approximately 8 L. Acetonitrile (49 L) was added and the solution was distilled under reduced pressure at 40° C. until the remaining volume was approximately 26 L. Methanesulfonic acid (1.41 kg, 14.7 mol) was added via addition funnel, followed by an acetonitrile rinse (0.5 L). The reaction mixture was heated to 70° C. and was held at that temperature for 12 h, then was cooled to 20° C. over a period of 2 h. The resulting suspension was filtered, rinsing with acetonitrile (29 L). The solids were dried under a nitrogen flow and then in a vacuum oven (40° C.) to afford (R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone (3.1 kg, 47% over two steps). HPLC retention time: 5.85 min (Column: Halo C18, 4.6×150 mm, 2.7 μm; Mobile Phase A: acetonitrile, Mobile Phase B: 0.05% methanesulfonic acid in water; Linear Gradient: 5:95 A:B to 95:5 A:B over 12 min, then held for 2 min; Flow: 1.0 mL/min; UV detection at 210 nM). Chiral HPLC retention time: 4.30 min; Column: AS-H 4.6×150 mm, 5 μm; Mobile Phase A: supercritical carbon dioxide, Mobile Phase B: 0.1% isopropylamine in methanol; Gradient: 5% B to 45% B over 6 min, then held at 45% B for 2 min; Flow: 4.0 mL/min; Column temperature 40° C.; UV detection at 230 nM).

Example 109-C (R)-(1-(2-(1-(4-Chloro-1H-pyrazol-1-yl)cyclopropyl)-3H-imidazo[4,5-b]pyridin-5-yl)piperidin-3-yl)(pyrrolidin-1-yl)methanone hydrochloride

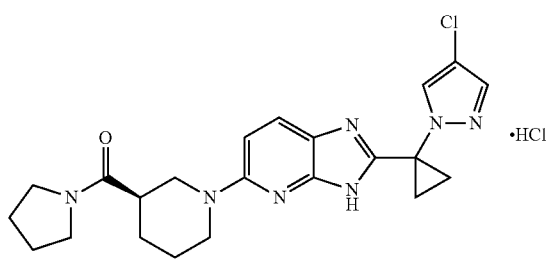 [SMILES: O=C([C@@H]1CCCN(c2ccc3nc(C4(n5cc(Cl)cn5)CC4)[nH]c3n2)C1)N1CCCC1 ; Cl]

(R)-(1-(2-(1-(4-Chloro-1H-pyrazol-1-yl)cyclopropyl)-3H-imidazo[4,5-b]pyridin-5-yl)piperidin-3-yl)(pyrrolidin-1-yl)methanone (140 mg, Example 109-A) was dissolved in 0.5 mL acetone at 22° C. A one molar equivalent of concentrated (36% in water) HCl was added, drop wise, to the rapidly stirred solution. The sample immediately turned cloudy. Sample was warmed to 40° C. and an additional acetone (0.5 mL) was added. After about 30 minutes, the sample was cooled (~1° C./min) to 22° C. White, opaque solids formed. The sample was vacuum filtered and the solids were collected/dried at room temperature (~22° C.) to afford (R)-(1-(2-(1-(4-Chloro-1H-pyrazol-1-yl)cyclopropyl)-3H-imidazo[4,5-b]pyridin-5-yl)piperidin-3-yl)(pyrrolidin-1-yl)methanone hydrochloride. $^1$H NMR (400 MHz, DMSO-d$_6$) δ 1.43-2.01 (m, 12H), 2.60 (t, 1H), 2.92-3.10 (m, 2H), 3.29 (t, 2H), 3.38-3.46 (m, 1H), 3.46-3.56 (m, 1H), 4.26 (d, 1H), 4.32 (d, 1H), 7.04 (d, 1H), 7.72 (s, 1H), 7.82 (d, 1H), 8.32 (s, 1H).

Elemental analysis and Karl Fisher confirmed the resulting crystalline form to contain 4.4% water.

Anal. Calculated for $C_{22}H_{26}ClN_7O·HCl·H_2O$: C, 53.4; H, 5.9; N, 19.8; Cl, 14.3. Found: C, 53.3; H, 6.0; N, 19.2; Cl, 14.8.

Example 110

(R)-Methyl 2-(3-(5-(3-(pyrrolidine-1-carbonyl)piperidin-1-yl)-3H-imidazo[4,5-b]pyridin-2-yl)phenyl)acetate

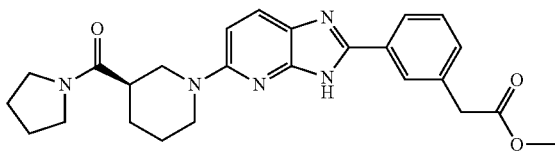 [SMILES: COC(=O)Cc1cccc(-c2nc3ccc(N4CCC[C@@H](C(=O)N5CCCC5)C4)nc3[nH]2)c1]

Into a vial was added methyl 2-(3-formylphenyl)acetate (98 mg, 0.55 mmol), (R)-(1-(6-amino-5-nitropyridin-2-yl)piperidin-3-yl)(pyrrolidin-1-yl)methanone (Intermediate 1, Step 3) (140 mg, 0.45 mmol) and ethanol (1.5 mL). Then sodium dithionate (388 mg, 2.23 mmol) and water (0.5 mL) were added to the mixture. The vial was sealed. The reaction mixture was heated to 110° C. for 18 h. The solution was cooled to room temperature. Triethylamine (0.15 mL, 1.1 mmol) was added and the solution was stirred at 100° C. for 18 h. A sample (0.8 mL) of the solution was removed and concentrated to dryness, and the resulting residue was purified via HPLC to afford the title compound. MS (ESI+) (M+H) 448.2; HPLC retention time 2.28 min (Method A).

Example 111

(R)-(1-(2-(6-(3-Hydroxyoxetan-3-yl)pyridin-2-yl)-3H-imidazo[4,5-b]pyridin-5-yl)piperidin-3-yl)(pyrrolidin-1-yl)methanone

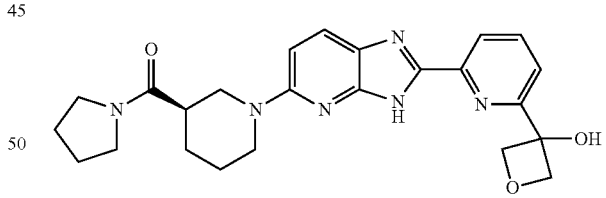

Into a flask was added 6-(3-hydroxyoxetan-3-yl)picolinaldehyde (54 mg, 0.30 mmol), (R)-(1-(6-amino-5-nitropyridin-2-yl)piperidin-3-yl)(pyrrolidin-1-yl)methanone (Intermediate 1, Step 3) (76 mg, 0.24 mmol) and ethanol (1.2 mL). Then sodium dithionate (0.20 g, 1.2 mmol), triethylamine (82 μL, 0.59 mmol) and water (1.0 mL) were added. The solution was heated to 110° C. for 18 h. The mixture was cooled to room temperature and diluted with ethyl acetate. The mixture was washed with water, washed with a saturated aqueous solution of ammonium chloride, washed with a saturated aqueous solution of sodium bicarbonate and washed with brine. The organics were dried over magnesium sulfate, filtered, and concentrated under reduced pressure. The residue was dried under high vacuum to give a green oil which was purified via HPLC to afford the title compound. MS (ESI+) (M+H) 448.9; HPLC retention time 1.89 min (Method A).

Example 112

(R)-Pyrrolidin-1-yl(1-(2-(6-(trifluoromethyl)pyridin-2-yl)-3H-imidazo[4,5-b]pyridin-5-yl)piperidin-3-yl)methanone

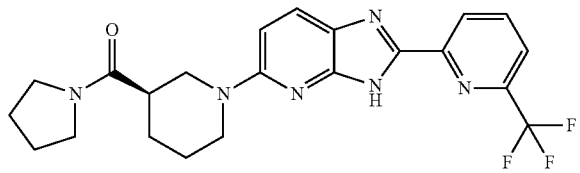

Into a tube was added 6-(trifluoromethyl)picolinaldehyde (150 mg, 0.47 mmol), (R)-(1-(6-amino-5-nitropyridin-2-yl)piperidin-3-yl)(pyrrolidin-1-yl)methanone (Intermediate 1, Step 3) (82.2 mg, 0.47 mmol), sodium dithionite (310.7 mg, 1.78 mmol), ethanol (10 mL) and water (1.5 mL). The vessel was sealed and the reaction mixture was stirred at 110° C. for 16 h. The solvent was evaporated under reduced pressure and water was added to the resulting residue. The mixture was extracted with ethyl acetate, dried over sodium sulfate and concentrated under reduced pressure. The crude material was purified via preparative TLC to afford the title compound (50 mg, 29%) as a yellow solid. MS (ES+APCI) (M+H) 445.2; LCMS retention time 2.657 min (Method G).

The compounds listed in Table 11 below were prepared using procedures analogous to those described above for the synthesis of Example 112 using the appropriate starting materials which are available commercially or prepared using preparations well-known to those skilled in the art or prepared by a route described above.

TABLE 11

| Example | Compound Name | —B—$R^2$ | Analytical Data |
|---|---|---|---|
| 113 | (R)-(1-(2-(5-Fluoropyridin-3-yl)-3H-imidazo[4,5-b]pyridin-5-yl)piperidin-3-yl)(pyrrolidin-1-yl)methanone | 5-fluoropyridin-3-yl | $^1$H NMR (400 MHz, DMSO-$d_6$) δ 1.21-1.28 (m, 3H), 1.50-1.60 (m, 1H), 1.64-1.74 (m, 2H), 1.75-1.83 (m, 2H), 1.84-1.96 (m, 2H), 2.59-2.66 (m, 1H), 2.89-3.02 (m, 2H), 3.41-3.55 (m, 2H), 4.35 (d, 1H), 4.42 (d, 1H), 6.90 (d, 1H), 7.86 (d, 1H), 8.28 (d, 1H), 8.63 (d, 1H), 9.17 (s, 1H), 13.26 (s, 1H) MS (ES + APCI) (M + H) 395.1; LCMS retention time: 2.861 min (Method C1) |
| 114 | (R)-3-(5-(3-(Pyrrolidine-1-carbonyl)piperidin-1-yl)-3H-imidazo[4,5-b]pyridin-2-yl)benzenesulfonamide | 3-sulfamoylphenyl | $^1$H NMR (400 MHz, DMSO-$d_6$) δ 1.48-1.62 (m, 1H), 1.63-1.74 (m, 2H), 1.74-1.83 (m, 2H), 1.84-1.94 (m, 3H), 2.62 (br s, 1H), 2.84-3.00 (m, 2H), 3.17 (d, 1H), 3.42-3.56 (m, 2H), 4.28-4.47 (m, 2H), 6.87 (d, 1H), 7.42-7.50 (m, 2H), 7.64-7.76 (m, 1H), 7.80-7.87 (m, 2H), 8.26 (d, 1H), 8.65 (s, 1H), 13.20 (s, 1H) MS (ES + APCI) (M − H) 453.1; LCMS retention time: 3.766 min (Method I) |

TABLE 11-continued

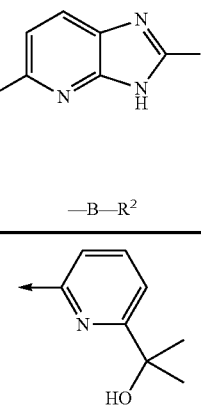

| Example | Compound Name | —B—R² | Analytical Data |
|---|---|---|---|
| 115 | (R)-(1-(2-(6-(2-Hydroxypropan-2-yl)pyridin-2-yl)-3H-imidazo[4,5-b]pyridin-5-yl)piperidin-3-yl)(pyrrolidin-1-yl)methanone | 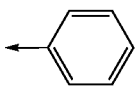 | $^1$H NMR (400 MHz, CDCl$_3$) δ 1.26-1.29 (m, 2H), 1.63 (s, 6H), 1.78-2.06 (m, 6H), 2.69 (t, 1H), 2.95-3.06 (m, 1H), 3.12-3.20 (m, 1H), 3.43-3.55 (m, 3H), 3.58-3.68 (m, 1H), 4.33 (d, 1H), 4.54 (d, 1H), 6.72 (d, 1H), 7.45 (d, 1H), 7.79-7.93 (m, 2H), 8.22 (d, 1H), 10.54 (br s, 1H) MS (ES + APCI) 435.2; LCMS retention time: 2.208 min (Method G) |
| 116 | (R)-(1-(2-Phenyl-3H-imidazo[4,5-b]pyridin-5-yl)piperidin-3-yl)(pyrrolidin-1-yl)methanone | 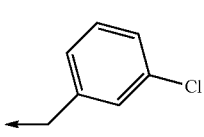 | $^1$H NMR (300 MHz, CDCl$_3$) δ 1.56-1.71 (m, 2H), 1.74-2.03 (m, 6H), 2.68 (tt, 1H), 2.93 (td, 1H), 3.12 (dd, 1H), 3.37-3.70 (m, 4H), 4.25 (d, 1H), 4.55 (d, 1H), 6.69 (d, 1H), 7.38-7.55 (m, 3H), 7.86 (d, 1H), 7.99-8.09 (m, 2H), 10.63 (br s, 1H) MS (ES + APCI) (M + H) 376.4; LCMS retention time: 2.144 min (Method G) |
| 117 | (R)-(1-(2-(3-Chlorobenzyl)-3H-imidazo[4,5-b]pyridin-5-yl)piperidin-3-yl)(pyrrolidin-1-yl)methanone | | $^1$H NMR(400 MHz, CDCl$_3$) δ 1.61-1.66 (m, 2H), 1.74-2.03 (m, 7H), 2.59-2.71 (m, 1H), 2.85-2.97 (m, 1H), 3.06 (dd, 1H), 3.40-3.52 (m, 3H), 3.56 (br s, 1H), 4.17-4.29 (m, 2H), 4.34-4.43 (m, 1H), 6.64 (d, 1H), 7.20 (m, 1H), 7.27-7.33 (m, 7H), 7.77 (br s, 1H), 8.80 (br s, 1H) MS (ES+) (M + H) 424.28; LCMS retention time: 3.12 min (Method S) |

TABLE 11-continued

| Example | Compound Name | —B—R² | Analytical Data |
|---|---|---|---|
| 118 | (R)-(1-(2-(2-Cyclopropyloxazol-4-yl)-3H-imidazo[4,5-b]pyridin-5-yl)piperidin-3-yl)(pyrrolidin-1-yl)methanone | | ¹H NMR(400 MHz, CDCl₃) δ 1.07-1.17 (m, 4H), 1.76-2.06 (m, 8H), 2.07-2.20 (m, 1H), 2.61-2.75 (m, 1H), 2.93-3.02 (m, 1H), 3.05-3.16 (m, 1H), 3.41-3.55 (m, 3H), 3.59-3.69 (m, 1H), 4.29 (d, 1H), 4.49 (d, 1H), 6.68 (d, 1H), 7.79 (d, 1H), 8.17 (s, 1H), 9.84 (br s, 1H) MS (ES + APCI) (M + H) 407.3; LCMS retention time: 2.753 min (Method Z1) |
| 119 | (R)-(1-(2-(6-(Dimethylamino)pyridin-2-yl)-3H-imidazo[4,5-b]pyridin-5-yl)piperidin-3-yl)(pyrrolidin-1-yl)methanone | | MS (ES+) (M + H) 420.42 LCMS retention time 3.15 min (Method S) |
| 120 | (R)-(1-(2-(6-(Azetidin-1-yl)pyridin-2-yl)-3H-imidazo[4,5-b]pyridin-5-yl)piperidin-3-yl)(pyrrolidin-1-yl)methanone | | ¹H NMR (400 MHz, CDCl₃) δ 1.24-1.29 (m, 2H), 1.58-1.72 (m, 1H), 1.80-2.03 (m, 5H), 2.39-2.48 (m, 2H), 2.63-2.75 (m, 1H), 2.91-3.02 (m, 1H), 3.12 (dd, 1H), 3.43-3.54 (m, 3H), 3.57-3.68 (m, 1H), 4.03-4.13 (m, 4H), 4.33 (d, 1H), 4.47 (d, 1H), 6.31 (d, 1H), 6.65-6.72 (m, 1H), 7.52-7.58 (m, 1H), 7.61 (br s, 1H), 7.84 (br s, 1H), 10.29 (br s, 1H) MS (ES+) (M + H) 432.3215; LCMS retention time: 4.78 min (Method I1) |
| 121 | (R)-(1-(2-(6-(Difluoromethoxy)pyridin-2-yl)-3H-imidazo[4,5-b]pyridin-5-yl)piperidin-3-yl)(pyrrolidin-1-yl)methanone | | 1HNMR (300 MHz, CDCl₃) δ 1.62-1.72 (m, 1H), 1.78-2.13 (m, 7H), 2.58-2.76 (m, 1H), 2.93-3.06 (m, 1H), 3.10-3.23 (m, 1H), 3.42-3.56 (m, 3H), 3.57-3.69 (m, 1H), 4.35 (d, 1H), 4.51 (d, 1H), 6.73 (d, 1H), 6.94 (d, 1H), 7.51 (t, 1H), 7.81-7.92 (m, 2H), 8.11 (d, 1H), 10.09 (br s, 1H) MS (ES + APCI) |

TABLE 11-continued

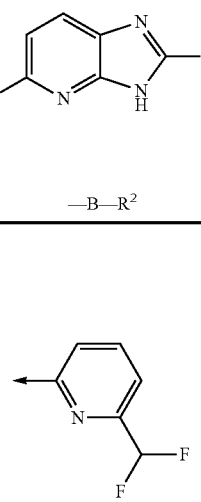

| Example | Compound Name | —B—R² | Analytical Data |
|---|---|---|---|
| | | | (M + H) 443.0; LCMS retention time: 2.559 min (Method G1) |
| 122 | (R)-(1-(2-(6-(Difluoromethyl)pyridin-2-yl)-3H-imidazo[4,5-b]pyridin-5-yl)piperidin-3-yl)(pyrrolidin-1-yl)methanone | 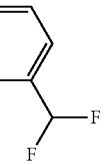 | MS (ES + APCI) (M + H) 427.1 LCMS retention time 2.425 min (Method G) |

Example 123

(R)-Methyl 6-(5-(3-(pyrrolidine-1-carbonyl)piperidin-1-yl)-1H-imidazo[4,5-b]pyridin-2-yl)picolinate

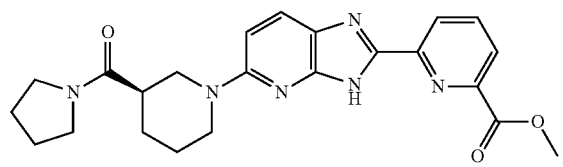 [SMILES: COC(=O)c1cccc(-c2nc3ccc(N4CCC[C@@H](C(=O)N5CCCC5)C4)nc3[nH]2)n1]

The title compound was prepared by a method analogous to the one used for Example 112, but using methanol as the solvent. ¹H NMR (300 MHz, CDCl₃) δ 1.77-2.12 (m, 8H), 2.62-2.77 (m, 1H), 2.96-3.21 (m, 2H), 3.41-3.56 (m, 3H), 3.63-3.75 (m, 1H), 4.34 (d, 1H), 4.58 (d, 1H), 6.73 (d, 1H), 7.88 (d, 1H), 7.96 (m, 1H), 8.10 (d, 1H), 8.48 (d, 1H), 10.89 (br s, 1H). MS (ES+) (M+H) 434.6744; LCMS retention time: 5.39 min (Method H).

Example 124

(R)-Ethyl 1-(3-(5-(3-(pyrrolidine-1-carbonyl)piperidin-1-yl)-3H-imidazo[4,5-b]pyridin-2-yl)phenyl)cyclopropanecarboxylate

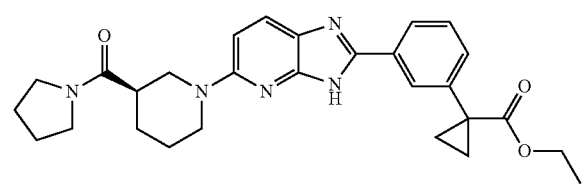 [SMILES: CCOC(=O)C1(c2cccc(-c3nc4ccc(N5CCC[C@@H](C(=O)N6CCCC6)C5)nc4[nH]3)c2)CC1]

The title compound was prepared using a method analogous to the one used for Example 112, but using ethyl 1-(3-formylphenyl)cyclopropanecarboxylate and omitting the triethylamine. MS (ESI+) (M+H) 488.1; HPLC retention time 2.6338 min (Method B).

Example 125

(R)-Methyl 3-(5-(3-(pyrrolidine-1-carbonyl)piperidin-1-yl)-3H-imidazo[4,5-b]pyridin-2-yl)benzoate

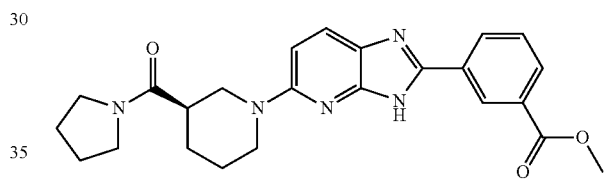

Into a vial was added methyl 3-formylbenzoate (102 mg, 0.6 mmol) and a solution of (R)-(1-(6-amino-5-nitropyridin-2-yl)piperidin-3-yl)(pyrrolidin-1-yl)methanone (140 mg, 0.4 mmol) in ethanol (1.5 mL). Sodium dithionate (388 mg, 2.2 mmol) and water (0.5 mL) were added. The vial was sealed and the solution was stirred 110° C. for 18 h. The solution was cooled to room temperature and triethylamine (0.1 mL) was added. The solution was stirred at 100° C. for 18 h. An aliquot of 0.8 mL was removed and concentrated to dryness, and the resulting residue was purified via HPLC to afford the title compound. MS (ESI+) (M+H) 434.2; HPLC retention time 2.25 min (Method A).

Example 126

(R)-2-Methoxy-6-(5-(3-(pyrrolidine-1-carbonyl)piperidin-1-yl)-3H-imidazo[4,5-b]pyridin-2-yl)isonicotinic acid

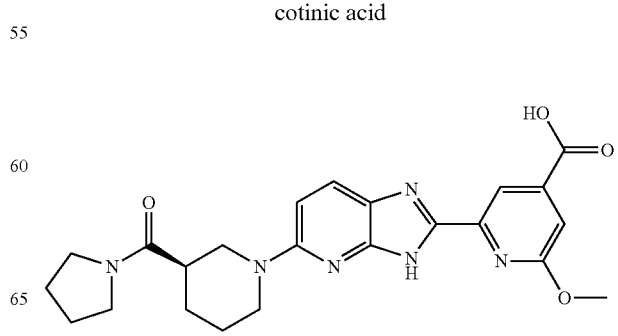

151

To a solution of (R)-ethyl 2-methoxy-6-(5-(3-(pyrrolidine-1-carbonyl)piperidin-1-yl)-3H-imidazo[4,5-b]pyridin-2-yl)isonicotinate (Example 96, 50 mg, 0.1 mmol) in tetrahydrofuran (1.0 mL) was added a solution of lithium hydroxide (14.9 mg, 0.6 mmol) in methanol (1.0 mL) and water (1.0 mL). The resulting suspension was stirred at room temperature for 2 h. The mixture was concentrated under reduced pressure. To the residue was added a saturated solution of ammonium chloride in water (10 mL). The pH of the mixture was adjusted to 3 using aqueous hydrochloric acid (1N). The mixture was extracted with ethyl acetate (20 mL×3). The organics were combined, dried over sodium sulfate, filtered, and concentrated under reduced pressure. The residue was purified via HPLC to afford the title compound. MS (ESI+) (M+H) 451.1; HPLC retention time 2.21 min (Method A).

Example 127

(R)-(1-(2-(3-(Methylsulfonyl)phenyl)-3H-imidazo[4,5-b]pyridin-5-yl)piperidin-3-yl)(pyrrolidin-1-yl)methanone

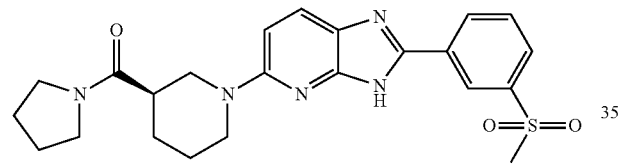

To a solution of (R)-(1-(5,6-diaminopyridin-2-yl)piperidin-3-yl)(pyrrolidin-1-yl)methanone dihydrochloride (125 mg, 0.3 mmol) in anhydrous N,N-dimethylformamide (2.5 mL) was added 3-(methylsulfonyl)benzaldehyde (76 mg, 0.4 mmol). The solution was stirred at 80° C. for 1 h. Sulfur was added (25 mg, 0.8 mmol) followed by triethylamine (140 μL, 1.0 mmol). The mixture was stirred at 85° C. for 24 h followed by stirring at room temperature for another 24 h. The mixture was concentrated under reduced pressure and the residue was partitioned between dichloromethane and water. The aqueous layer was extracted with dichloromethane and the combined extracts were dried over magnesium sulfate, filtered and concentrated under reduced pressure. The residue was purified via flash chromatography (20-100% ethyl acetate in heptanes gradient followed by 0-10% methanol in dichloromethane). The residue was repurified via flash chromatography (0-10% methanol in dichloromethane) to afford a yellow solid that was stirred in acetonitrile (3 mL) at 40° C. for 2.5 h. The solid was filtered, washed with cold acetonitrile and dried under high vacuum at 40° C. to afford the title compound. $^1$H NMR (500 MHz, CD$_3$OD) δ 1.60-1.74 (m, 1H) 1.77-1.89 (m, 2H) 1.89-2.11 (m, 4H) 2.81 (br s, 1H) 2.97-3.09 (m, 2H) 3.17-3.26 (m, 3H) 3.41-3.52 (m, 2H) 3.52-3.63 (m, 1H) 3.74 (br s, 1H) 4.37 (br s, 1H) 4.64 (d, 1H) 6.91 (br s, 1H) 7.74-7.89 (m, 2H) 8.05 (d, 1H) 8.35 (br s, 1H) 8.65 (br s, 1H).

152

Example 128

(R)-Ethyl 3-(3-(5-(3-(pyrrolidine-1-carbonyl)piperidin-1-yl)-3H-imidazo[4,5-b]pyridin-2-yl)phenyl)propanoate

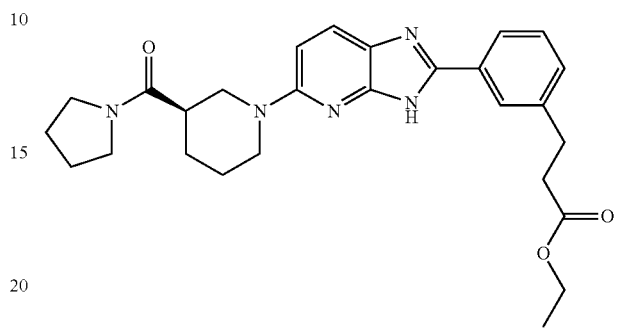

The title compound was prepared by a method analogous to the one used for Example 127, but using ethyl 3-(3-formylphenyl)propanoate as the starting material. MS (ESI+) (M+H) 476.2; HPLC retention time 2.07 min (Method A).

Example 129

(R)—N,N-Diethyl-5-(3-(pyrrolidine-1-carbonyl)piperidin-1-yl)-3H-imidazo[4,5-b]pyridine-2-carboxamide

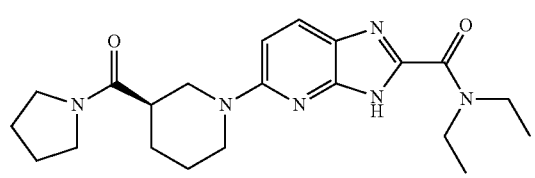 [SMILES: CCN(CC)C(=O)c1nc2ccc(N3CCC[C@@H](C(=O)N4CCCC4)C3)nc2[nH]1]

Into a vial containing (R)-(1-(5,6-diaminopyridin-2-yl)piperidin-3-yl)(pyrrolidin-1-yl)methanone dihydrochloride (125 mg, 0.3 mmol) was added formic acid (73.5 μL, 1.7 mmol) followed by 2,2,-trifluoroethanol (1.7 mL) and methyl 2,2,2-trichloroacetimidate (47.0 μL, 0.4 mmol). The vial was sealed and stirred at room temperature for 13 min. The reaction mixture was heated to 60° C. and stirred for 3 h at that temperature. An aliquot of 0.3 mL was transferred into another vial containing diethylamine (89.1 μL, 0.9 mmol). The resulting mixture was heated to 60° C. and stirred for 16 h. The reaction mixture was concentrated under reduced pressure and the resulting residue was partitioned between water and ethyl acetate. The aqueous was further extracted with ethyl acetate. The combined organics were concentrated under reduced pressure. The residue was purified via HPLC to afford the title compound. MS (ESI+) (M+H) 399.1; HPLC retention time 1.9864 min (Method A).

Example 130

(R)—N-(Pyridin-2-yl)-5-(3-(pyrrolidine-1-carbonyl)piperidin-1-yl)-3H-imidazo[4,5-b]pyridine-2-carboxamide

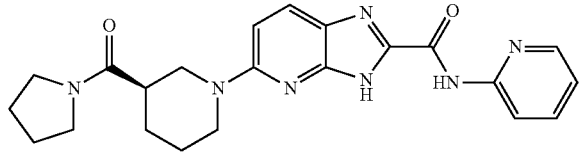 [SMILES: O=C(Nc1ccccn1)c1nc2ccc(N3CCC[C@@H](C(=O)N4CCCC4)C3)nc2[nH]1]

The title compound was prepared by a method analogous to the one used for Example 129, but using pyridin-2-amine as the amine. MS (ESI+) (M+H) 420.0; HPLC retention time 2.1276 min (Method B).

Example 131

(R)-(1-(2-(2-Cyclopropylpyrimidin-4-yl)-3H-imidazo[4,5-b]pyridin-5-yl)piperidin-3-yl)(3,3-difluoropyrrolidin-1-yl)methanone

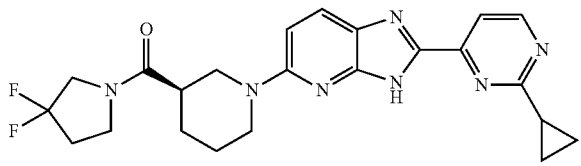 [SMILES: O=C([C@@H]1CCCN(c2ccc3nc(-c4ccnc(C5CC5)n4)[nH]c3n2)C1)N1CCC(F)(F)C1]

The title compound was prepared by a method analogous to the one used for Example 96, but using ethyl 2-cyclopropylpyrimidine-4-carbimidate. MS (ES-API+) (M+H) 454.0; HPLC retention time 3.827 min (Method Q).

Example 132

((R)-1-(2-(2-Cyclopropylpyrimidin-4-yl)-3H-imidazo[4,5-b]pyridin-5-yl)piperidin-3-yl)((S)-3-hydroxypyrrolidin-1-yl)methanone

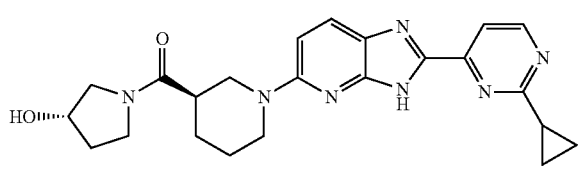 [SMILES: O=C([C@@H]1CCCN(c2ccc3nc(-c4ccnc(C5CC5)n4)[nH]c3n2)C1)N1CC[C@H](O)C1]

The title compound was prepared by a method analogous to the one used for Example 1, but using ethyl 2-cyclopropylpyrimidine-4-carbimidate. MS (ES-API+) (M+H) 434.0; HPLC retention time 3.636 min (Method Q).

Example 133

2-(2-Cyclopropylpyrimidin-4-yl)-5-(3-(6,7-dihydro-5H-pyrrolo[1,2-c]imidazol-3-yl)piperidin-1-yl)-3H-imidazo[4,5-b]pyridine

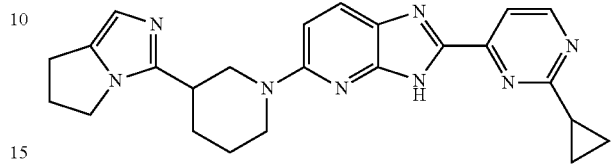

To a solution of (1-(5,6-diaminopyridin-2-yl)piperidin-3-yl)(pyrrolidin-1-yl)methanone dihydrochloride (18 mg, 0.06 mmol) and acetic acid (55 µL, 0.96 mmol) in ethanol (0.5 mL) was added triethylamine (17 µL, 0.12 mmol) followed by ethyl 2-cyclopropylpyrimidine-4-carbimidate (11.5 mg, 0.06 mmol) dissolved in ethanol (0.5 mL). The reaction mixture was heated to 70° C. for 1.25 h. The solvent was removed under reduced pressure. The residue was suspended in ethyl acetate and the undissolved solids were filtered off. The filtrate was washed with a saturated aqueous solution of ammonium chloride, washed with a saturated aqueous solution of sodium bicarbonate, and washed with brine. The organics were dried over magnesium sulfate, filtered and concentrated under reduced pressure. The crude material was purified via HPLC to afford the title compound. MS (ESI+) (M+H) 427.1; HPLC retention time 2.0183 (Method A).

Examples 134 and 135

(R)-2-(2-Cyclopropylpyrimidin-4-yl)-5-(3-(6,7-dihydro-5H-pyrrolo[1,2-c]imidazol-3-yl)piperidin-1-yl)-3H-imidazo[4,5-b]pyridine and (S)-2-(2-cyclopropylpyrimidin-4-yl)-5-(3-(6,7-dihydro-5H-pyrrolo[1,2-c]imidazol-3-yl)piperidin-1-yl)-3H-imidazo[4,5-b]pyridine

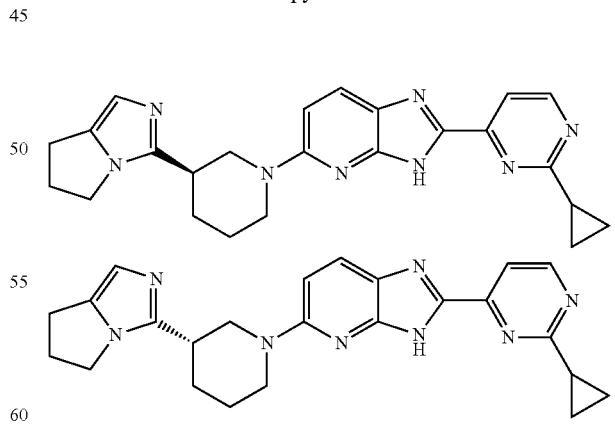

To a solution of 6-(3-(6,7-dihydro-5H-pyrrolo[1,2-c]imidazol-3-yl)piperidin-1-yl)pyridine-2,3-diamine (36 mg, 0.1 mmol) in ethanol (1.0 mL) was added triethylamine (34 µL, 0.2 mmol) followed by acetic acid (111 µL, 1.9 mmol). Then a solution of ethyl 2-cyclopropylpyrimidine-4-carbimidate (23 mg, 0.1 mmol) in ethanol (1.0 mL) was added. The reaction mixture was heated to 70° C. for 1.5 h. The solvent was removed under reduced pressure and the resulting residue was dissolved in ethyl acetate. The solids were filtered off and the filtrate was washed with a saturated aqueous solution of ammonium chloride, a saturated aqueous solution of sodium bicarbonate, and brine. Then the organics were dried over magnesium sulfate, filtered and concentrated under reduced pressure to give a solid. The solid was purified via flash chromatography (0-12% methanol in dichloromethane) to afford the title compound as a racemic mixture. The enantiomers were separated via chiral HPLC (SFC-2 instrument, Chiralcel OJ-H column 4.6 mm×25 cm, 75/25 $CO_2$/ethanol mobile phase, 0.2% isopropylamine as a modifier and a flow of 2.5 mL/min) to afford two enantiomers. Enantiomer 1 (Example 134, 3.1 mg, 6% yield): Chiral HPLC retention time 4.93 min (Method: Column: Chiralcel OJ-H 10×250; Mobile Phase 75/25 $CO_2$/Ethanol; Modifier: 0.2% isopropylamine; Flow: 10.0 mL/min); $^1$H NMR (500 MHz, $CDCl_3$) δ 1.09-1.40 (m, 8H) 1.63-1.78 (m, 1H) 1.64-1.78 (m, 2H) 1.87-2.02 (m, 1H) 2.12-2.24 (m, 1H) 2.27-2.42 (m, 1H) 2.72-2.89 (m, 1H) 3.03 (br s, 1H) 3.28-3.40 (m, 1H) 3.56-3.68 (m, 1H) 3.74 (d, 1H) 4.12-4.38 (m, 2H) 6.76-6.90 (m, 1H) 7.01-7.11 (m, 1H) 7.86-8.08 (m, 2H) 8.64-8.79 (m, 1H). Enantiomer 2 (Example 135, 4.4 mg, 9% yield): Chiral HPLC retention time 5.41 min (Method: Same as Enantiomer 1); $^1$H NMR (500 MHz, $CDCl_3$) δ 0.84-0.92 (m, 2H) 1.14 (dd, 2H) 1.70 (d, 1H) 1.92 (d, 1H) 2.16 (d, 1H) 2.27-2.39 (m, 1H) 2.79 (dt, 2H) 3.02 (d, 2H) 3.32 (br s, 2H) 3.54-3.78 (m, 2H) 3.98-4.72 (m, 4H) 6.81 (d, 1H) 7.05 (br s, 1H) 7.96 (br s, 2H) 8.68 (d, 1H).

Example 136

(R)-(1-(2-(2-Cyclopropylpyrimidin-4-yl)-6-fluoro-3H-imidazo[4,5-b]pyridin-5-yl)piperidin-3-yl)(pyrrolidin-1-yl)methanone

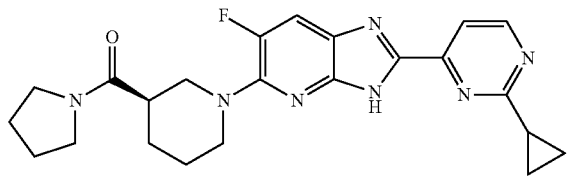 [SMILES: O=C([C@@H]1CCCN(c2nc3[nH]c(-c4ccnc(C5CC5)n4)nc3cc2F)C1)N1CCCC1]

(R)-(1-(2-(2-Cyclopropylpyrimidin-4-yl)-3H-imidazo[4,5-b]pyridin-5-yl)piperidin-3-yl)(pyrrolidin-1-yl)methanone (Example 95, 100 mg, 0.2 mmol) was dissolved in N,N-dimethylformamide. The solution was cooled to 0° C. and Selectfluor (87 mg, 0.2 mmol) was added. The reaction mixture was stirred at 0° C. for 30 min and then at room temperature for 18 h. The reaction mixture was partitioned between ethyl acetate and water. The organics were washed with brine, dried over magnesium sulfate, filtered, and concentrated under reduced pressure. The residue was purified via HPLC to afford the title compound. MS (ESI+) (M+H) 436.2; HPLC retention time 2.72 min (Method A).

Example 137

(R)-4-(1-(5-(3-(Pyrrolidine-1-carbonyl)piperidin-1-yl)-3H-imidazo[4,5-b]pyridin-2-yl)cyclopropyl)morpholin-3-one

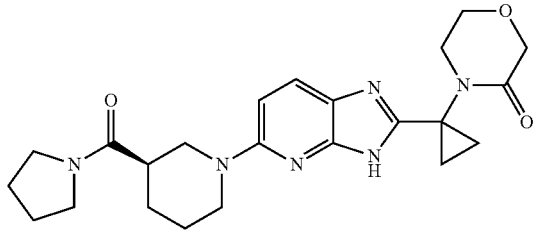 [SMILES: O=C([C@@H]1CCCN(c2ccc3nc(C4(N5CCOCC5=O)CC4)[nH]c3n2)C1)N1CCCC1]

Step 1: N-(2-Amino-6-(3-(6,7-dihydro-5H-pyrrolo[1,2-c]imidazol-3-yl)piperidin-1-yl)pyridin-3-yl)-1-(3-oxomorpholino)cyclopropanecarboxamide Into a vial were added 1-(3-oxomorpholino)cyclopropanecarboxylic acid (33 mg, 0.2 mmol), (R)-(1-(5,6-diaminopyridin-2-yl)piperidin-3-yl)(pyrrolidin-1-yl)methanone dihydrochloride (77.5 mg, 0.2 mmol), O-(7-azabenzotriazol-1-yl)-N,N,N',N',-tetramethyluronium hexafluorophosphate (135 mg, 0.4 mmol), diisopropylethyl amine (155 μL, 0.9 mmol) and N,N-dimethylformamide (3.0 mL). The reaction mixture was stirred at room temperature for 3 h. The mixture was directly loaded to a column and purified via flash chromatography (0-6% methanol in dichloromethane) to afford N-(2-amino-6-(3-(6,7-dihydro-5H-pyrrolo[1,2-c]imidazol-3-yl)piperidin-1-yl)pyridin-3-yl)-1-(3-oxomorpholino)cyclopropanecarboxamide (77.0 mg, 94.7%). MS (ES+) (M+H) 457.3; LCMS retention time 1.56 min (Method L).

Step 2: (R)-4-(1-(5-(3-(Pyrrolidine-1-carbonyl)piperidin-1-yl)-3H-imidazo[4,5-b]pyridin-2-yl)cyclopropyl)morpholin-3-one The title compound was prepared by a method analogous to the one used for Example 86, Step 2. MS (ESI+) (M+H) 439.2; HPLC retention time 1.76 min (Method A).

Example 138

(R)-(1-(2-(2-Cyclopropylpyrimidin-4-yl)-1H-imidazo[4,5-b]pyrazin-6-yl)piperidin-3-yl)(pyrrolidin-1-yl)methanone

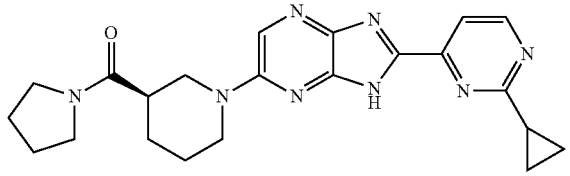 [SMILES: O=C([C@@H]1CCCN(c2cnc3nc(-c4ccnc(C5CC5)n4)[nH]c3n2)C1)N1CCCC1]

Step 1: 6-Bromo-2-(2-cyclopropylpyrimidin-4-yl)-1H-imidazo[4,5-b]pyrazine

A mixture of 5-bromopyrazine-2,3-diamine (50 mg, 0.3 mmol) and ethyl 2-cyclopropylpyrimidine-4-carbimidate (Intermediate 19, 50.7 mg, 0.3 mmol), triethylamine (73.8 µL, 0.5 mmol), acetic acid (244 µL, 4.2 mmol) and ethanol (0.8 mL) was heated to 100° C. for 30 min. The mixture was concentrated and diluted with water. Then a saturated aqueous solution of sodium bicarbonate was added and the mixture was extracted with ethyl acetate. The organics were washed with brine, dried over sodium sulfate, and concentrated under reduced pressure. The crude material was purified via flash chromatography (0-5% methanol in dichloromethane) to afford 6-bromo-2-(2-cyclopropylpyrimidin-4-yl)-1H-imidazo[4,5-b]pyrazine (21 mg, 25%).

Step 2: (R)-(1-(2-(2-Cyclopropylpyrimidin-4-yl)-1H-imidazo[4,5-b]pyrazin-6-yl)piperidin-3-yl)(pyrrolidin-1-yl)methanone A mixture of 6-bromo-2-(2-cyclopropylpyrimidin-4-yl)-1H-imidazo[4,5-b]pyrazine (86 mg, 0.3 mmol), (R)-piperidin-3-yl(pyrrolidin-1-yl)methanone (95 mg, 0.4 mmol), potassium carbonate (98.4, 0.7 mmol), cesium fluoride (124 mg, 0.8 mmol) and diglyme (1.0 mL) was heated to 150° C. for 3 days. The mixture was diluted with water and aqueous hydrochloric acid (1N). The mixture was extracted with ethyl acetate (3×). The combined organics were washed with brine, dried over sodium sulfate, and concentrated under reduced pressure. The residue was purified via HPLC to afford the title compound. MS (ESI+) (M+H) 419.3, HPLC retention time 2.44 min (Method A).

Example 139

(R)-(1-(2-(6-(1-Hydroxycyclopropyl)pyridin-2-yl)-3H-imidazo[4,5-b]pyridin-5-yl)piperidin-3-yl)(pyrrolidin-1-yl)methanone

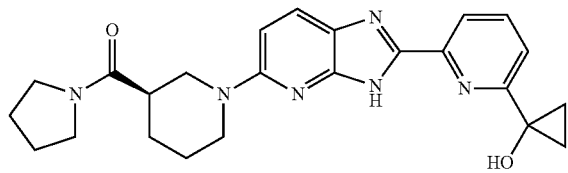 [SMILES: O=C([C@@H]1CCCN(c2ccc3nc(-c4cccc(C5(O)CC5)n4)[nH]c3n2)C1)N1CCCC1]

Step 1: (R)-(1-(2-(6-(1-((tert-Butyldimethylsilyl)oxy)cyclopropyl)pyridin-2-yl)-3H-imidazo[4,5-b]pyridin-5-yl)piperidin-3-yl)(pyrrolidin-1-yl)methanone To a solution of 6-(1-((tert-butyldimethylsilyl)oxy)cyclopropyl)picolinonitrile (45.0 mg, 0.164 mmol) in ethanol (0.3 mL) was added dropwise a solution of sodium ethoxide in ethanol (0.1 mL, 21 wt %, 0.2 mmol). The reaction mixture was stirred at room temperature for 50 min and then heated to 35° C. for 1.5 h. To the mixture was added (R)-(1-(5,6-diaminopyridin-2-yl)piperidin-3-yl)(pyrrolidin-1-yl)methanone dihydrochloride (77.2 mg, 0.2 mmol), triethylamine (47 µL, 0.3 mmol) and acetic acid (47 µL). The reaction mixture was heated to 110° C. for 50 min. The solution was transferred to a microwave vial and it was heated to 145° C. for 20 min. The solvent was removed under reduced pressure to afford (R)-(1-(2-(6-(1-((tert-butyldimethylsilyl)oxy)cyclopropyl)pyridin-2-yl)-3H-imidazo[4,5-b]pyridin-5-yl)piperidin-3-yl)(pyrrolidin-1-yl)methanone. The material was used without further purification.

Step 2: (R)-(1-(2-(6-(1-Hydroxycyclopropyl)pyridin-2-yl)-3H-imidazo[4,5-b]pyridin-5-yl)piperidin-3-yl)(pyrrolidin-1-yl)methanone Tetrabutylammonium fluoride (1M in tetrahydrofuran, 0.6 mL, 0.6 mmol) was added to a solution of (R)-(1-(2-(6-(1-((tert-butyldimethylsilyl)oxy)cyclopropyl)pyridin-2-yl)-3H-imidazo[4,5-b]pyridin-5-yl)piperidin-3-yl)(pyrrolidin-1-yl)methanone (89.7 mg, 0.2 mmol) in tetrahydrofuran (0.5 mL). The reaction mixture was stirred at room temperature for 40 min. The mixture was partitioned between water and ethyl acetate (3×). The combined organics were dried over sodium sulfate and concentrated under reduced pressure. The residue was purified via HPLC to afford the title compound. MS (ESI+) (M+H) 433.1; HPLC retention time 2.1091 min (Method B).

Example 140

(R)-(1-(2-(4-(2-Hydroxypropan-2-yl)thiazol-2-yl)-3H-imidazo[4,5-b]pyridin-5-yl)piperidin-3-yl)(pyrrolidin-1-yl)methanone

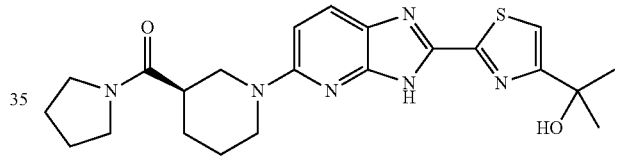

Step 1: (R)-(1-(2-(4-Bromothiazol-2-yl)-3H-imidazo[4,5-b]pyridin-5-yl)piperidin-3-yl)(pyrrolidin-1-yl)methanone (R)-(1-(2-(4-Bromothiazol-2-yl)-3H-imidazo[4,5-b]pyridin-5-yl)piperidin-3-yl)(pyrrolidin-1-yl)methanone was prepared by a method analogous to the one used for Example 139, Step 1, but using 4-bromothiazole-2-carbonitrile as the starting material (152 mg). $^1$H NMR (400 MHz, CDCl$_3$) δ 1.56-2.08 (m, 8H) 2.59-2.83 (m, 1H) 2.96-3.14 (m, 1H) 3.13-3.26 (m, 1H) 3.37-3.55 (m, 3H) 3.59-3.71 (m, 1H) 4.18-4.38 (m, 1H) 4.41-4.59 (m, 1H) 6.66-6.89 (m, 1H) 7.31 (s, 1H) 7.76-7.93 (m, 1H).

Step 2: (R)-Methyl 2-(5-(3-(pyrrolidine-1-carbonyl)piperidin-1-yl)-3H-imidazo[4,5-b]pyridin-2-yl)thiazole-4-carboxylate (R)-(1-(2-(4-Bromothiazol-2-yl)-3H-imidazo[4,5-b]pyridin-5-yl)piperidin-3-yl)(pyrrolidin-1-yl)methanone (50.8 mg, 0.1 mmol), (1,1'-bis(diphenylphosphino)ferrocene)dichloropalladium (II) (13.1 mg, 0.02 mmol) and methanol (1.0 mL) were added to a vial. The vial was evacuated and filled with carbon monoxide (3×). Triethylamine (46.0 µL, 0.3 mmol) was added and the reaction mixture was stirred at 85° C. for 1.5 h. The reaction mixture was directly loaded onto a silica gel column and purified via flash chromatography to afford (R)-methyl 2-(5-(3-(pyrrolidine-1-carbonyl)piperidin-1-yl)-3H-imidazo[4,5-b]pyridin-2-yl)thiazole-4-carboxylate (43 mg, 89%). MS (ES+) (M+H) 441.1; LCMS retention time 2.70 min (Method L).

Step 3: (R)-(1-(2-(4-(2-Hydroxypropan-2-yl)thiazol-2-yl)-3H-imidazo[4,5-b]pyridin-5-yl)piperidin-3-yl)(pyrrolidin-1-yl)methanone To a solution of (R)-methyl 2-(5-(3-(pyrrolidine-1-carbonyl)piperidin-1-yl)-3H-imidazo[4,5-b]pyridin-2-yl)thiazole-4-carboxylate (43.0 mg, 0.1 mmol) in tetrahydrofuran (0.8 mL) at 0° C. was added dropwise a solution of methylmagnesium bromide (3M in diethyl ether, 110 µL, 0.3 mmol). The reaction mixture was stirred at 0° C. for 1 h. A saturated aqueous solution of ammonium chloride was added and the mixture was extracted with ethyl acetate (4 mL×5). The combined organics were dried over sodium sulfate and concentrated under reduced pressure. The residue was purified via HPLC to afford the title compound. MS (ESI+) (M+H) 441.1; HPLC retention time 2.04 min (Method A).

Example 141

(R)-(4-(2-(1-(4-Chloro-1H-pyrazol-1-yl)cyclopropyl)-3H-imidazo[4,5-b]pyridin-5-yl)morpholin-2-yl)(pyrrolidin-1-yl)methanone

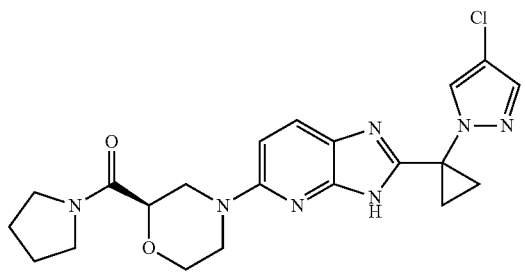

The title compound was prepared by a method analogous to the one used for Example 96. MS (ESI+) (M+H) 442.1; HPLC retention time 2.1091 min (Method A).

Example 142

(R)-(4-(2-(6-Cyclopropylpyridin-2-yl)-3H-imidazo[4,5-b]pyridin-5-yl)morpholin-2-yl)(pyrrolidin-1-yl)methanone

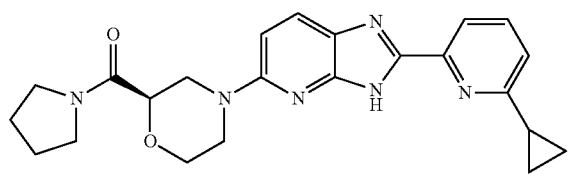

The title compound was prepared by a method analogous to the one used for Example 112, but using Intermediate 31 and 6-cyclopropylpicolinaldehyde. MS (ES+) (M+H) 418.9; LCMS retention time 2.411 (Method G).

Example 143

(R)-Pyrrolidin-1-yl(4-(2-(6-(trifluoromethyl)pyridin-2-yl)-3H-imidazo[4,5-b]pyridin-5-yl)morpholin-2-yl)methanone

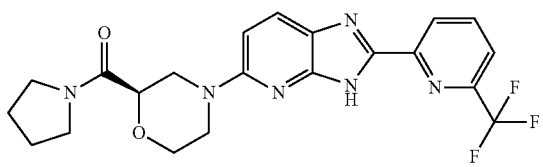 [SMILES: O=C([C@H]1CN(c2ccc3nc(-c4cccc(C(F)(F)F)n4)[nH]c3n2)CCO1)N1CCCC1]

The title compound was prepared by a method analogous to the one used for Example 112, but using 6-(trifluoromethyl)picolinaldehyde. MS (ESI+) (M+H) 447.1; HPLC retention time 2.6238 min (Method A).

Examples 144 and 145

(R)-4-(2-(3-(Difluoromethoxy)phenyl)-3H-imidazo[4,5-b]pyridin-5-yl)-2-(pyridin-2-yl)morpholine and (S)-4-(2-(3-(difluoromethoxy)phenyl)-3H-imidazo[4,5-b]pyridin-5-yl)-2-(pyridin-2-yl)morpholine

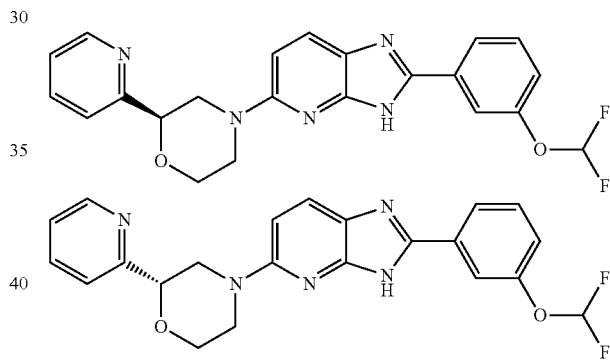

The title compounds were prepared by a method analogous to the one used for Example 112, but using 3-(difluoromethoxy)benzaldehyde to give a racemic mixture which was further purified via chiral HPLC using the following conditions: Chiralpak AS-H column 10×250; mobile phase 80/20 carbon dioxide/ethanol; flow 10.0 mL/min to afford title compounds. Enantiomer 1 (Example 144, 10% yield): Chiral HPLC retention time: 5.67 min (Method: Column: Chiralpak AS-H 10×250; Mobile Phase: 80/20 CO$_2$/Ethanol; Flow: 10.0 mL/min); $^1$H NMR (CDCl$_3$, 400 MHz): δ 2.96-3.01 (m, 1H), 3.16-3.22 (m, 1H), 3.92-3.96 (m, 1H), 4.14-4.17 (m, 1H), 4.22-4.25 (m, 1H), 4.60-4.62 (m, 1H), 4.76 (dd, 1H), 6.61 (t, 1H), 6.78 (d, 1H), 7.20-7.26 (m, 2H), 7.48-7.51 (m, 2H), 7.57 (d, 1H), 7.74-7.80 (m, 2H), 7.90-7.93 (m, 1H), 8.62-8.63 (m, 1H); Enantiomer 2 (Example 145, 10% yield): Chiral HPLC retention time: 7.17 min (Method: Same as for the other Enantiomer 1); $^1$H NMR (CDCl$_3$, 400 MHz): δ 2.95-3.03 (m, 1H), 3.15-3.26 (m, 1H), 3.91-4.01 (m, 1H), 4.14-4.21 (m, 1H), 4.22-4.28 (m, 1H), 4.58-4.64 (m, 1H), 4.78 (dd, 1H), 6.62 (t, 1H), 6.80 (m, 1H), 7.20-7.26 (m, 2H), 7.48-7.54 (m, 2H), 7.57 (d, 1H), 7.72-7.80 (m, 2H), 7.90-7.95 (m, 1H), 8.60-8.64 (m, 1H).

Example 146

(R)-(4-(2-(6-Cyclopropylpyrazin-2-yl)-3H-imidazo[4,5-b]pyridin-5-yl)morpholin-2-yl)(pyrrolidin-1-yl)methanone

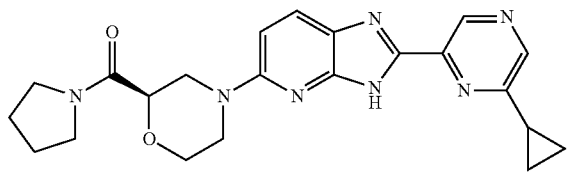

The title compound was prepared by a method analogous to Example 105 using ethyl 6-cyclopropylpyrazine-2-carbimidate (Intermediate 30) and (R)-(4-(5,6-diaminopyridin-2-yl)morpholin-2-yl)(pyrrolidin-1-yl)methanone (Intermediate 29). MS (ESI+) (M+H) 420.2; HPLC retention time 2.432 min (Method A).

Example 147

(R)-(1-(2-(2-Cyclobutylpyrimidin-4-yl)-3H-imidazo[4,5-b]pyridin-5-yl)piperidin-3-yl)(pyrrolidin-1-yl)methanone

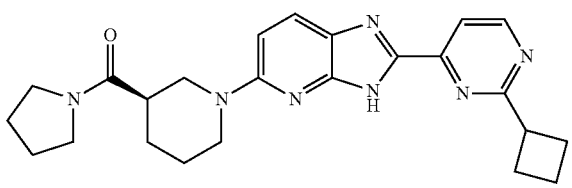 [SMILES: O=C([C@@H]1CCCN(c2ccc3nc(-c4ccnc(C5CCC5)n4)[nH]c3n2)C1)N1CCCC1]

To a solution of (R)-(1-(5,6-diaminopyridin-2-yl)piperidin-3-yl)(pyrrolidin-1-yl)methanone (135.9 mg, 0.5 mmol) in ethanol was added 2-cyclobutylpyrimidine-4-carbaldehyde (76.2 mg, 0.5 mmol), sulfur (30.1 mg, 0.9 mmol) and acetic acid (0.15 mL) at room temperature under nitrogen. The reaction mixture was stirred for 16 h at reflux. The solvent was removed under reduced pressure. Water was added to the residue and the mixture was extracted with ethyl acetate. The combined organics were dried over sodium sulfate and concentrated under reduced pressure. The crude material was purified via preparative TLC to afford the title compound as a yellow solid. MS (ES+APCI) (M+H) 432.1; LCMS retention time 2.567 min (Method G).

Example 148

(R)-Pyrrolidin-1-yl(1-(2-(2-(trifluoromethyl)pyrimidin-4-yl)-3H-imidazo[4,5-b]pyridin-5-yl)piperidin-3-yl)methanone

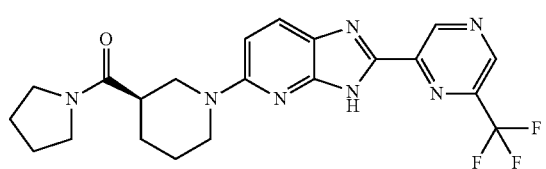 [SMILES: O=C([C@@H]1CCCN(c2ccc3nc(-c4cncc(C(F)(F)F)n4)[nH]c3n2)C1)N1CCCC1]

The title compound was prepared by a method analogous to the one used for Example 147, but using 2-(trifluoromethyl)pyrimidine-4-carbaldehyde. MS (ES+APCI) (M+H) 446.2; LCMS retention time 3.549 min (Method J).

Example 149

(R)-(1-(2-(4-Cyclopropylpyrimidin-2-yl)-3H-imidazo[4,5-b]pyridin-5-yl)piperidin-3-yl)(morpholino)methanone

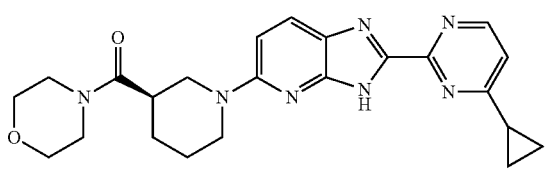 [SMILES: O=C([C@@H]1CCCN(c2ccc3nc(-c4nccc(C5CC5)n4)[nH]c3n2)C1)N1CCOCC1]

The title compound was prepared by a method analogous to the one used for Example 95, but using (R)-(1-(5,6-diaminopyridin-2-yl)piperidin-3-yl)(morpholino)methanone dihydrochloride (synthesized by hydrogenation analogous to the one used for Intermediate 1, starting from Intermediate 40) and Intermediate 42. MS (ES+APCI) (M+H) 434.2; LCMS retention time 1.996 min (Method G).

Example 150

(R)-1-(2-(6-Cyclopropylpyridin-2-yl)-3H-imidazo[4,5-b]pyridin-5-yl)-N,N-dimethylpiperidine-3-carboxamide

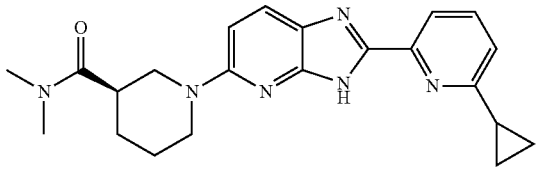 [SMILES: CN(C)C(=O)[C@@H]1CCCN(c2ccc3nc(-c4cccc(C5CC5)n4)[nH]c3n2)C1]

The title compound was prepared using a method analogous to the one used for Example 112 but using (R)-1-(6-amino-5-nitropyridin-2-yl)-N,N-dimethylpiperidine-3-carboxamide and 6-cyclopropylpicolinaldehyde as starting materials. $^1$H NMR (300 MHz, CDCl$_3$) δ 1.01-1.18 (m, 4H), 1.63-1.74 (m, 1H), 1.84 (m, 1H), 1.93 (m, 2H), 2.10 (br s, 1H), 2.85 (br s, 1H), 2.96-3.03 (m, 3H), 3.08 (m, 1H), 3.15 (s, 3H), 3.50 (s, 1H), 4.35 (d, 1H), 4.50 (d, 1H), 6.73 (d, 1H), 7.20 (d, 1H), 7.68 (d, 1H), 7.89 (d, 1H), 8.10 (br s, 1H), 10.14 (br. s, 1H); MS (ES+APCI) (M+H) 391.2; LCMS retention time 1.831 min (Method W).

Examples 151 and 152

(S)-4-(2-(3-Chlorophenyl)-3H-imidazo[4,5-b]pyridin-5-yl)-2-(pyridin-2-yl)morpholine and (R)-4-(2-(3-chlorophenyl)-3H-imidazo[4,5-b]pyridin-5-yl)-2-(pyridin-2-yl)morpholine

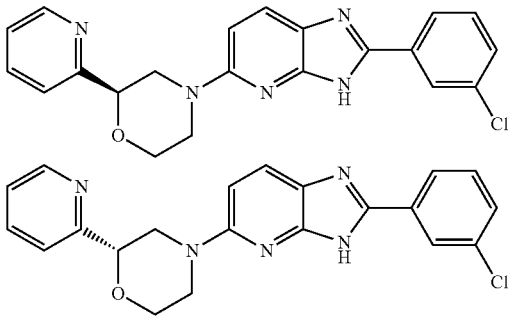

The title compounds were prepared using a method analogous to the one used for Example 112, but using 3-chlorobenzaldehyde and 3-nitro-6-(2-(pyridin-2-yl)morpholino)pyridin-2-amine as starting materials. The crude compound was purified by preparative TLC (5% acetone in dichloromethane) to provide the racemic material, which was further separated using chiral chromatography to afford title compounds. Enantiomer 1 (Example 151, 21 mg, 9% yield): MS (ES+APCI) 392.2; LCMS retention time 2.057 min (Method G1); Chiral HPLC retention time 8.767 min (Method: Column: CHIRAL PAK IC, 4.6×250 mm, 5 μm; Mobile Phase A: n-Hexane; Mobile Phase C: Ethanol; Isocratic: 75:25; Flow: 0.8 mL/min; Column Temperature: 25° C.; $^1$H NMR (300 MHz, CDCl$_3$) δ 2.98 (dd, 1H), 3.17 (m, 1H), 3.91 (m, 1H), 4.20 (m, 2H), 4.58 (m, 1H), 4.76 (dd, 1H), 6.78 (d, 1H), 7.26 (m, 1H), 7.41 (m, 2H), 7.55 (d, 1H), 7.75 (m, 1H), 7.88 (m, 2H), 8.02 (s, 1H), 8.63 (d, 1H). Enantiomer 2 (Example 152, 26 mg, 10% yield): MS (ES+APCI) (M+H) 392.2; LCMS retention time 2.06 min (Method G1). $^1$H NMR (300 MHz, CDCl$_3$) δ 2.98 (dd, 1H), 3.17 (m, 1H), 3.91 (m, 1H), 4.20 (m, 2H), 4.58 (m, 1H), 4.76 (dd, 1H), 6.78 (d, 1H), 7.26 (m, 1H), 7.41 (m, 2H), 7.55 (d, 1H), 7.75 (m, 1H), 7.88 (m, 2H), 8.02 (s, 1H), 8.63 (d, 1H); Chiral HPLC retention time 10.551 min (Same method used for enantiomer 1).

The compounds listed in Table 12 below were prepared using procedures analogous to those described above for the synthesis of Example 112 and using the appropriate starting materials which are available commercially or prepared using preparations well-known to those skilled in the art or prepared by a route described above. The temperature of the reaction mixture for Example 153 was 100° C. and for Examples 154 and 155 was 80° C.

TABLE 12

| Example | Compound Name | —B—R² | Analytical Data |
|---|---|---|---|
| 153 | (R)-(1-(2-(6-Cyclopropylpyridin-2-yl)-3H-imidazo[4,5-b]pyridin-5-yl)piperidin-3-yl)(morpholino)methanone | | LCMS retention time: 1.887 min (Method F) $^1$H NMR (300 MHz, CDCl$_3$) δ 0.99-1.16 (m, 4H), 1.62-1.74 (m, 1H), 1.77-1.89 (m, 2H), 1.90-1.99 (m, 2H), 2.05-2.17 (m, 1H), 2.72-2.86 (m, 1H), 3.01 (td, 1H), 3.15 (dd, 1H), 3.51-3.88 (m, 8H), 4.31 (d, 1H), 4.50 (d, 1H), 6.71 (d, 1H), 7.19 (d, 1H), 7.60-7.73 (m, 1H), 7.87 (d, 1H), 8.04 (d, 1H), 10.13 (br s, 1H) |
| 154 | (R)-(1-(2-(3-Chlorophenyl)-3H-imidazo[4,5-b]pyridin-5-yl)piperidin-3-yl)(morpholino)methanone | | LCMS retention time: 2.996 min (Method A2) $^1$H NMR (400 MHz, DMSO-d$_6$) δ 1.53-1.74 (m, 3H), 1.85 (d, 1H), 2.80 (d, 1H), 2.86-2.94 (m, 1H), 2.98 (dd, 1H), 3.42 (d, 1H), 3.47-3.69 (m, 8H), 4.30 (d, 1H), 4.40 (d, 1H), 6.84 (d, 1H), |

TABLE 12-continued

| Example | Compound Name | —B—R² | Analytical Data |
|---|---|---|---|
| | | | 7.45-7.57 (m, 2H), 7.81 (d, 1H), 8.07 (d, 1H), 8.13-8.18 (m, 1H), 13.03 (s, 1H) |
| 155 | (R)-(1-(2-(3-(Difluoromethoxy)phenyl)-3H-imidazo[4,5-b]pyridin-5-yl)piperidin-3-yl)(morpholino)methanone | | MS (ES + APCI) (M + H) 458.2; LCMS retention time: 2.973 min (Method B2) ¹H NMR (300 MHz, CDCl₃) δ 1.55-1.72 (m, 3H), 1.82 (m, 1H), 1.86-2.00 (m, 2H), 2.74-2.87 (m, 1H), 2.90-3.04 (m, 1H), 3.13 (dd, 1H), 3.55-3.84 (m, 6H), 4.22 (d, 1H), 4.62 (d, 1H), 6.61 (t, 1H), 6.70 (d, 1H), 7.16-7.24 (m, 1H), 7.49 (t, 1H), 7.86 (d, 2H), 10.35 (br. s, 1H). |

Example 156

(R)-1-(6-(5-(3-(Pyrrolidine-1-carbonyl)piperidin-1-yl)-1H-imidazo[4,5-b]pyridin-2-yl)pyridin-2-yl)cyclopropanecarbonitrile

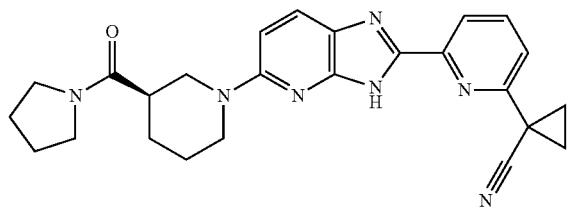 [SMILES: N#CC1(c2cccc(-c3nc4ccc(N5CCC[C@@H](C(=O)N6CCCC6)C5)nc4[nH]3)n2)CC1]

Step 1: (R)-(1-(2-(6-Bromopyridin-2-yl)-1H-imidazo[4,5-b]pyridin-5-yl)piperidin-3-yl)(pyrrolidin-1-yl)methanone (R)-(1-(2-(6-Bromopyridin-2-yl)-1H-imidazo[4,5-b]pyridin-5-yl)piperidin-3-yl)(pyrrolidin-1-yl)methanone was prepared using a method analogous to the one used for Example 112, but using (R)-(1-(6-amino-5-nitropyridin-2-yl)piperidin-3-yl)(pyrrolidin-1-yl)methanone and 6-bromopicolinaldehyde as starting materials. MS (ES+APCI) (M+H) 455.0; LCMS retention time 3.238 min (Method C1).

Step 2: (R)-1-(6-(5-(3-(Pyrrolidine-1-carbonyl)piperidin-1-yl)-1H-imidazo[4,5-b]pyridin-2-yl)pyridin-2-yl)cyclopropanecarbonitrile To a stirred solution of (R)-(1-(2-(6-bromopyridin-2-yl)-1H-imidazo[4,5-b]pyridin-5-yl)piperidin-3-yl)(pyrrolidin-1-yl)methanone (300 mg, 0.658 mmol) in toluene was added cyclopropane carbonitrile. The mixture was cooled to 0° C. then a 1M solution of sodium bis(trimethylsilyl)amide in THF was added dropwise. The reaction mixture was stirred for 16 h at room temperature. The mixture was quenched with water and then was extracted with ethyl acetate. The organic layer was dried over sodium sulfate and was concentrated under reduced pressure. The residue was purified via preparative TLC (twice) to afford (R)-1-(6-(5-(3-(pyrrolidine-1-carbonyl)piperidin-1-yl)-1H-imidazo[4,5-b]pyridin-2-yl)pyridin-2-yl)cyclopropanecarbonitrile (20 mg, 7%) MS (ES+ APCI) (M+H) 442.2; LCMS retention time 2.969 min (Method C1); ¹H NMR (400 MHz, CDCl₃) δ 1.24-1.31 (m, 4H), 1.65-1.71 (m, 2H), 1.78-2.04 (m, 6H), 2.69 (m, 1H), 3.01 (t, 1H), 3.07-3.18 (m, 1H), 3.43-3.56 (m, 3H), 3.60-3.72 (m, 1H), 4.35 (br s, 1H), 4.54 (d, 1H), 6.72 (d, 1H), 7.48 (d, 1H), 7.79-7.95 (m, 2H), 8.58 (d, 1H), 10.28 (br s, 1H).

Example 157

(R)-(1-(2-(1-Phenylethyl)-3H-imidazo[4,5-b]pyridin-5-yl)piperidin-3-yl)(pyrrolidin-1-yl)methanone

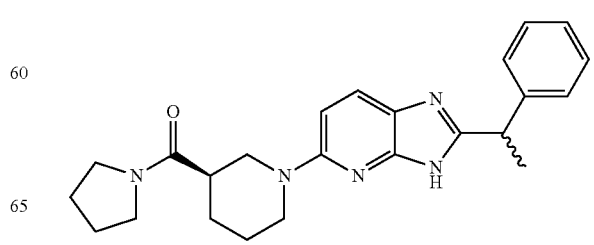

To a solution of (R)-1-(5,6-diaminopyridin-2-yl)piperidin-3-yl)(pyrrolidin-1-yl)methanone dihydrochloride (Intermediate 1) (0.5 g, 1.7 mmol) in ethanol (20 mL) was added triethylamine (1 mL) and 2-phenylpropanal (0.25 g, 1.9 mmol). The reaction mixture was heated at reflux for 12 h. The mixture was then concentrated under reduced pressure, diluted with ice cold water and extracted with ethyl acetate. The organic layers were dried, filtered and concentrated, and the resulting residue was purified by preparative TLC to afford the title compound (65 mg, 9%). MS (ES+APCI) (M+H) 404.2; LCMS retention time 2.206 min (Method Y).

Example 158

(R)-(1-(2-(6-Cyclopropylpyridin-2-yl)-3H-imidazo[4,5-b]pyridin-5-yl)piperidin-3-yl)(2,5-dihydro-1H-pyrrol-1-yl)methanone

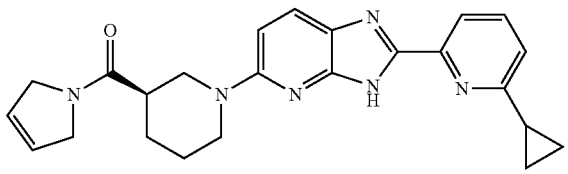 [SMILES: O=C([C@@H]1CCCN(c2ccc3nc(-c4cccc(C5CC5)n4)[nH]c3n2)C1)N1CC=CC1]

Step 1: (R)-Ethyl 1-(6-amino-5-nitropyridin-2-yl)piperidine-3-carboxylate

To a solution of (R)-ethyl piperidine-3-carboxylate (1 g, 6.33 mmol) in dimethylsulfoxide (15 mL) were added 2-amino-3-nitro-6-chloropyridine (1.098 g, 6.33 mmol) and triethylamine (1.921 g, 18.99 mmol) at room temperature. The mixture was heated to 100° C. for 18 h, then was poured into ice water and extracted with ethyl acetate. The organic layer was dried, filtered and concentrated under reduced pressure. The crude material was purified via flash chromatography (100-200 mesh silica, 30% ethyl acetate in petroleum ether) to afford (R)-ethyl 1-(6-amino-5-nitropyridin-2-yl)piperidine-3-carboxylate (650 mg, 93.5%). MS (ES+APCI) (M+H) 295.1; LCMS retention time 2.832 min (Method G).

Step 2: (R)-Ethyl 1-(5,6-diaminopyridin-2-yl)piperidine-3-carboxylate

To a solution of (R)-ethyl 1-(6-amino-5-nitropyridin-2-yl)piperidine-3-carboxylate (300 mg, 1.019 mmol) in ethanol (15 mL) was added a suspension of 10% palladium-on-carbon (200 mg) in ethanol under nitrogen atmosphere. The mixture was hydrogenated using a hydrogen balloon for 2 h at room temperature then was filtered through a pad of Celite. The filtrate was concentrated to afford (R)-ethyl 1-(5,6-diaminopyridin-2-yl)piperidine-3-carboxylate (250 mg) which was used without further purification.

Step 3: (R)-Ethyl 1-(2-(6-cyclopropylpyridin-2-yl)-3H-imidazo[4,5-b]pyridin-5-yl)piperidine-3-carboxylate To a solution of (R)-ethyl 1-(5,6-diaminopyridin-2-yl)piperidine-3-carboxylate (250 mg, 0.686 mmol) in ethanol (15 mL) was added 6-cyclopropylpicolinaldehyde (55 mg, 0.823 mmol), sulfur (43 mg, 1.372 mmol) and acetic acid (1.5 mL) at room temperature. The reaction mixture was stirred at 80° C. for 18 h. The reaction mixture was poured into ice water and extracted with ethyl acetate. The organics were concentrated under reduced pressure and the crude material was purified via preparative TLC (80% ethyl acetate in petroleum ether) to afford (R)-ethyl 1-(2-(6-cyclopropylpyridin-2-yl)-3H-imidazo[4,5-b]pyridin-5-yl)piperidine-3-carboxylate (180 mg). MS (ES+APCI) (M+H) 392.2; LCMS retention time 3.757 min (Method J).

Step 4: (R)-1-(2-(6-Cyclopropylpyridin-2-yl)-3H-imidazo[4,5-b]pyridin-5-yl)piperidine-3-carboxylic acid To a solution of (R)-ethyl 1-(2-(6-cyclopropylpyridin-2-yl)-3H-imidazo[4,5-b]pyridin-5-yl)piperidine-3-carboxylate (150 mg, 0.383 mmol) in ethanol (15 mL) was added a 2N sodium hydroxide solution (5 mL) at 0° C. The mixture was stirred at room temperature for 2 h, then was neutralized with a 2M hydrochloric acid solution and was extracted with ethyl acetate. The organic layer was dried over sodium sulfate and concentrated under reduced pressure to afford (R)-1-(2-(6-cyclopropylpyridin-2-yl)-3H-imidazo[4,5-b]pyridin-5-yl)piperidine-3-carboxylic acid (150 mg). MS (ES+APCI) (M+H) 364.2; LCMS retention time 2.974 min (Method J).

Step 5: (R)-(1-(2-(6-Cyclopropylpyridin-2-yl)-3H-imidazo[4,5-b]pyridin-5-yl)piperidin-3-yl)(2,5-dihydro-1H-pyrrol-1-yl)methanone To a stirred solution of (R)-1-(2-(6-cyclopropylpyridin-2-yl)-3H-imidazo[4,5-b]pyridin-5-yl)piperidine-3-carboxylic acid (150 mg, 0.686 mmol) in N,N-dimethylformamide (15 mL) was added 1-ethyl-3-(3-dimethylaminopropyl) carbodiimide (150 mg, 0.826 mmol), hydroxybenzotriazole (111 mg, 0.826 mmol), and 3-pyrroline (57 mg, 0.826 mmol) at room temperature. The reaction mixture was stirred for 24 h at room temperature then poured into ice water and extracted with ethyl acetate. The organic layer was concentrated under reduced pressure. The crude material was purified via preparative TLC (80% ethyl acetate in petroleum ether) to afford the title compound (30 mg, 17%). MS (ES+APCI) (M+H) 415.0; LCMS retention time 2.493 min (Method G). $^1$H NMR (300 MHz, CDCl$_3$) δ 1.09 (m, 4H), 1.70 (m, 2H), 1.90 (m, 3H), 2.09 (m, 1H), 2.69 (m, 1H), 3.02 (m, 1H), 3.16 (m, 1H), 4.28 (m, 3H), 4.51 (m, 2H), 5.84 (m, 1H), 5.93 (m, 1H), 6.71 (d, 1H), 7.20 (d, 1H), 7.66 (m, 1H), 7.87 (d, 1H), 8.04 (m, 1H), 10.18 (br s, 1H).

Example 159

(R)-(1-(8-(2-Cyclopropylpyrimidin-4-yl)-9H-purin-2-yl)piperidin-3-yl)(pyrrolidin-1-yl)methanone

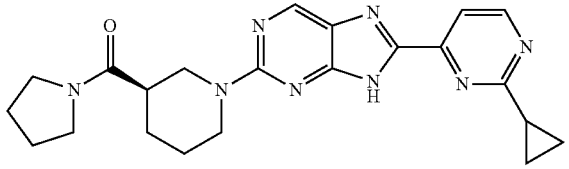

Step 1: (R)-(1-(4,5-Diaminopyrimidin-2-yl)piperidin-3-yl)(pyrrolidin-1-yl)methanone To a stirred solution of (R)-(1-(4-amino-5-nitropyrimidin-2-yl)piperidin-3-yl)(pyrrolidin-1-yl)methanone (300 mg, 0.937 mmol) in ethanol (15 mL) was added a wet suspension of palladium on carbon 10% (300 mg) in ethanol under a nitrogen atmosphere. The reaction mixture was hydrogenated using a balloon filled with hydrogen gas at room temperature for 2 h. The suspension was filtered through celite and the filtrate was used for the next step without further purification.

Step 2: (R)-(1-(8-(2-Cyclopropylpyrimidin-4-yl)-9H-purin-2-yl)piperidin-3-yl)(pyrrolidin-1-yl)methanone To a stirred solution of (R)-(1-(4,5-diaminopyrimidin-2-yl)piperidin-3-yl)(pyrrolidin-1-yl)methanone, obtained from the previous step, in ethanol (20 mL) was added 2-cyclopropylpyrimidine-4-carbaldehyde (91 mg, 0.62 mmol), sulfur (33 mg, 1.034 mmol), and acetic acid (0.5 mL). The reaction mixture was stirred at 80° C. for 16 h. The reaction mixture was concentrated under reduced pressure and partitioned between water and ethyl acetate. The organics were dried over sodium sulfate, and concentrated under reduced pressure. The crude was purified via preparative HPLC and triturated with a mixture of diethyl ether:petroleum ether to afford the title compound (50 mg, 24%). MS (ES+) (M+H) 419.3070; LCMS retention time 3.75 min (Method J1). $^1$H NMR (300 MHz, CDCl$_3$) δ 1.08-1.31 (m, 5H), 1.79-2.08 (m, 7H), 2.33 (td, 1H), 2.60 (m, 1H), 2.90-3.05 (m, 1H), 3.07-3.22 (m, 1H), 3.40-3.56 (m, 3H), 3.59-3.73 (m, 1H), 4.79-5.02 (m, 2H), 7.92 (d, 1H), 8.71 (d, 1H), 8.81 (s, 1H), 10.20 (br s, 1H).

Example 160

(R)-3-(1-(5-(3-(Pyrrolidine-1-carbonyl)piperidin-1-yl)-3H-imidazo[4,5-b]pyridin-2-yl)cyclopropyl)pyridine 1-oxide

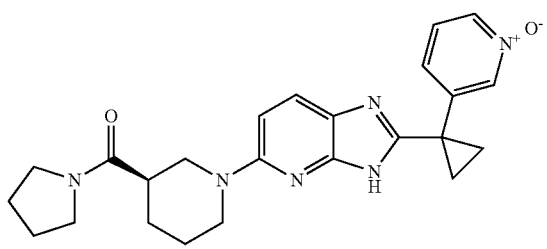

Step 1: (R)-3-(1-(2-Amino-6-(3-(pyrrolidine-1-carbonyl)piperidin-1-yl)pyridin-3-ylcarbamoyl)cyclopropyl)pyridine 1-oxide To a suspension of 3-(1-carboxycyclopropyl)pyridine 1-oxide (0.2 g, 1.1 mmol) and 2-(1H-7-azabenzotriazol-1-yl)-1,1,3,3-tetramethyl uronium hexafluorophosphate (HATU) (506 mg, 1.33 mmol) in dry dichloromethane (5 mL) was added diisopropylethylamine (0.63 mL, 3.63 mmol). The mixture was stirred at room temperature for 10 min, and then Intermediate 1 (0.48 g, 1.33 mmol) was added.

After 15 min, the mixture was quenched with water and was extracted with ethyl acetate. The organic layer was washed with brine, dried over anhydrous sodium sulfate, filtered and concentrated under reduced pressure. The resulting residue was purified via flash chromatography (100-200 mesh silica, 0-10% methanol in dichloromethane) to afford (R)-3-(1-(2-amino-6-(3-(pyrrolidine-1-carbonyl)piperidin-1-yl)pyridin-3-ylcarbamoyl)cyclopropyl)pyridine 1-oxide (250 mg). MS (ES+APCI) (M+H) 451.1; LCMS retention time 5.133 min (Method A1).

Step 2: (R)-3-(1-(5-(3-(Pyrrolidine-1-carbonyl)piperidin-1-yl)-3H-imidazo[4,5-b]pyridin-2-yl)cyclopropyl)pyridine 1-oxide To a solution of (R)-3-(1-(2-amino-6-(3-(pyrrolidine-1-carbonyl)piperidin-1-yl)pyridin-3-ylcarbamoyl)cyclopropyl)pyridine 1-oxide (0.25 g, 0.55 mmol) in isobutanol (5 mL) was added a solution of sodium methoxide (0.15 g, 2.77 mmol) in methanol (2 mL) at room temperature. The reaction mixture was heated to 110° C. for 16 h. The mixture was then cooled to room temperature, diluted with ethyl acetate, and washed with water. The organic layer was dried, filtered, and concentrated under reduced pressure. The resulting residue was purified first via flash chromatography (100-200 mesh silica gel, 0-10% methanol in dichloromethane) then via preparative HPLC to obtain the product which was further purified by chiral separation to afford (R)-3-(1-(5-(3-(pyrrolidine-1-carbonyl)piperidin-1-yl)-3H-imidazo[4,5-b]pyridin-2-yl)cyclopropyl)pyridine 1-oxide (70 mg). Chiral HPLC retention time: 13.808 min (Method: CHIRAL PAK IA, 4.6× 250 mm 5 μm column, Mobile Phase: A: 0.1% DEA in n-hexane, Mobile Phase B: ethanol; isocratic; 70:30, 1 mL/min, Temperature 25 C) min MS (ES+APCI) (M+H) 433.1; LCMS retention time 4.698 min (Method B1). $^1$H NMR (400 MHz, CD$_3$OD) δ 1.52-1.57 (m, 2H), 1.59-1.69 (m, 1H), 1.71-1.84 (m, 4H), 1.86-2.08 (m, 5H), 2.75 (t, 2H), 2.88-3.00 (m, 2H), 3.43 (t, 2H), 3.47-3.57 (m, 1H), 3.68 (br s, 1H), 4.27 (d, 1H), 4.52 (d, 1H), 6.78 (d, 1H), 7.50-7.56 (m, 1H), 7.58-7.72 (m, 2H), 8.26 (d, 1H), 8.31 (br s, 1H).

Example 161

(R)-(1-(2-(1-(Pyridin-4-yl)cyclopropyl)-3H-imidazo[4,5-b]pyridin-5-yl)piperidin-3-yl)(pyrrolidin-1-yl)methanone

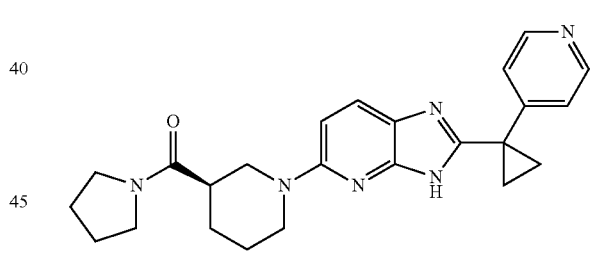

The title compound was prepared by a method analogous to the one used for Example 160, using 1-(pyridin-4-yl)cyclopropanecarboxylic acid as the starting material. MS (ES+) (M+H) 417.1; LCMS retention time 4.850 min (Method R1).

Example 162

(R)-(1-(2-(2-Cyclopropylpyrimidin-4-yl)-7-methyl-3H-imidazo[4,5-b]pyridin-5-yl)piperidin-3-yl)(pyrrolidin-1-yl)methanone

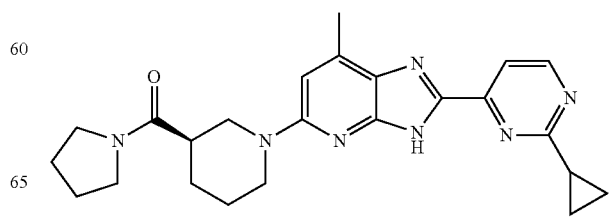

Step 1: (R)-(1-(6-Amino-4-methyl-5-nitropyridin-2-yl)piperidin-3-yl)(pyrrolidin-1-yl)methanone (R)-(1-(6-Amino-4-methyl-5-nitropyridin-3-yl)(pyrrolidin-1-yl)methanone was prepared using a method analogous to the one used for Intermediate 2, Step 1 but using 6-chloro-4-methyl-3-nitropyridin-2-amine and (R)-piperidin-3-yl(pyrrolidin-1-yl)methanone as starting materials. The reaction mixture was run at 70° C. for 1 h. MS (ES+APCI) (M+H) 333.9; LCMS retention time 4.322 min (Method Z).

Step 2: (R)-(1-(5,6-Diamino-4-methylpyridin-2-yl)piperidin-3-yl)(pyrrolidin-1-yl)methanone (R)-(1-(5,6-Diamino-4-methylpyridin-2-yl)piperidin-3-yl)(pyrrolidin-1-yl)methanone was prepared using a method analogous to the one used for Intermediate 1 step 4 but without hydrogen chloride MS (ES+) (M+H) 305.0.

Step 3: (R)-(1-(2-(2-Cyclopropylpyrimidin-4-yl)-7-methyl-3H-imidazo[4,5-b]pyridin-5-yl)piperidin-3-yl)(pyrrolidin-1-yl)methanone (R)-(1-(2-(2-Cyclopropylpyrimidin-4-yl)-7-methyl-3H-imidazo[4,5-b]pyridin-5-yl)piperidin-3-yl)(pyrrolidin-1-yl)methanone was prepared using a method analogous to the one used for Example 147 at 80° C. MS (ES+) (M+H) 456.2; LCMS retention time 2.482 min (Method G). $^1$H NMR (400 MHz, CDCl$_3$) δ 1.08-1.29 (m, 5H), 1.65-1.72 (m, 1H), 1.78-2.08 (m, 5H), 2.24-2.35 (m, 1H), 2.62 (s, 3H), 2.64-2.74 (m, 1H), 2.99 (td, 1H), 3.14 (dd, 1H), 3.43-3.55 (m, 2H), 3.63 (dt, 1H), 4.36 (d, 1H), 4.46-4.56 (m, 1H), 6.56 (s, 1H), 7.95 (d, 1H), 8.64 (d, 1H), 10.25 (br s, 1H).

Example 163

(R)-(1-(2-(3-(2H-Tetrazol-5-yl)phenyl)-3H-imidazo[4,5-b]pyridin-5-yl)piperidin-3-yl)(pyrrolidin-1-yl)methanone

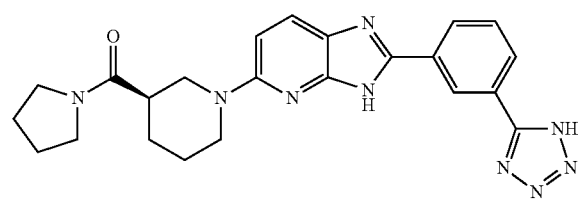 [SMILES: O=C([C@@H]1CCCN(c2ccc3nc(-c4cccc(-c5nnn[nH]5)c4)[nH]c3n2)C1)N1CCCC1]

Step 1: (R)-3-(5-(3-(Pyrrolidine-1-carbonyl)piperidin-1-yl)-3H-imidazo[4,5-b]pyridin-2-yl)benzonitrile To a solution of (R)-(1-(6-amino-5-nitropyridin-2-yl)piperidin-3-yl)(pyrrolidin-1-yl)methanone (Intermediate 1, Step 3) (50 mg, 0.15 mmol) and 3-formylbenzonitrile (34 mg, 0.31 mmol) in ethanol (2 mL) were added sodium dithionite (52 mg, 0.4 mmol), and water (0.5 mL). After 20 h at 80° C., the mixture was concentrated. The residue was partitioned between water and ethyl acetate. The organic layer was concentrated under reduced pressure and the resulting residue was purified by preparative TLC to afford (R)-3-(5-(3-(pyrrolidine-1-carbonyl)piperidin-1-yl)-3H-imidazo[4,5-b]pyridin-2-yl)benzonitrile as a yellow solid (40 mg, 81%). MS (ES+APCI) (M+H) 401.0; HPLC retention time 4.016 min (Method I).

Step 2: (R)-(1-(2-(3-(2H-Tetrazol-5-yl)phenyl)-3H-imidazo[4,5-b]pyridin-5-yl)piperidin-3-yl)(pyrrolidin-1-yl)methanone To a solution of (R)-3-(5-(3-(pyrrolidine-1-carbonyl)piperidin-1-yl)-3H-imidazo[4,5-b]pyridin-2-yl)benzonitrile (30 mg, 0.07 mmol) in N,N-dimethylformamide (2 mL) were added sodium azide (6 mg, 0.09 mmol) and iodine (3 mg). The reaction mixture was heated for 12 h at 120° C., then was cooled. The mixture was filtered, and the filtrate was concentrated. The resulting residue was triturated with diethyl ether to afford (R)-(1-(2-(3-(2H-tetrazol-5-yl)phenyl)-3H-imidazo[4,5-b]pyridin-5-yl)piperidin-3-yl)(pyrrolidin-1-yl)methanone as yellow solid (36 mg, 92%). MS (ES+APCI) (M+H) 444.1; HPLC retention time 3.551 min (Method C1). $^1$H NMR (400 MHz, DMSO-d$_6$) δ 1.50-2.00 (m, 8H), 2.60-2.68 (m, 1H), 2.83-2.97 (m, 3H), 3.25-3.31 (m, 1H), 3.42-3.50 (m, 1H), 3.52-3.60 (m, 1H), 4.32 (d, 1H), 4.42 (d, 1H), 6.83 (d, 1H), 7.47 (t, 1H), 7.81 (d, 1H), 7.94-8.02 (m, 2H), 8.79 (s, 1H), 13.02 (s, 1H).

Examples 164 and 165

(R)-1-(2-(2-Cyclopropylpyrimidin-4-yl)-3H-imidazo[4,5-b]pyridin-5-yl)-5,5-difluoro-N,N-dimethylpiperidine-3-carboxamide and (S)-1-(2-(2-cyclopropylpyrimidin-4-yl)-3H-imidazo[4,5-b]pyridin-5-yl)-5,5-difluoro-N,N-dimethylpiperidine-3-carboxamide

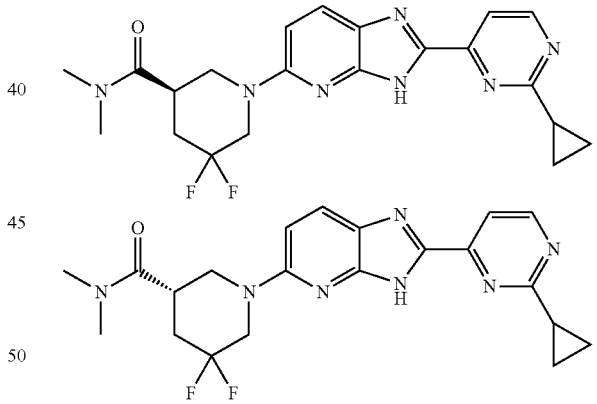

Step 1: 1-tert-Butyl 3-methyl 5-oxopiperidine-1,3-dicarboxylate

To a solution of dimethylsulfoxide (2.2 mL, 41.46 mmol) in dry dichloromethane (50 mL) at −78° C. was added dropwise at oxalyl chloride (1.57 mL, 18.2 mmol). After 10 min, a solution of 1-tert-butyl 3-methyl 5-hydroxypiperidine-1,3-dicarboxylate (4.3 g, 16.59 mmol) in dichloromethane was added dropwise. After 15 min, triethylamine (6.92 mL, 49.7 mmol) was added dropwise and the reaction mixture was then allowed to warm to room temperature. After 3 h, the mixture was diluted with dichloromethane and washed with water, dried over sodium sulfate, filtered and concentrated under reduced pressure to afford 1-tert-butyl 3-methyl 5-oxopiperidine-1,3-dicarboxylate (4.2 g) which was used in the next step without further purification.

Step 2: 1-tert-Butyl 3-methyl 5,5-difluoropiperidine-1,3-dicarboxylate

To a solution of 1-tert-butyl 3-methyl 5-oxopiperidine-1,3-dicarboxylate (4.2 g, 16.33 mmol) in dichloromethane was added bis(2-methoxyethyl)aminosulfur trifluoride (Deoxofluor, 4.74 mL, 25.71 mmol). After 3 h, ethanol (0.42 mL) was added. After 16 h, the mixture was diluted with dichloromethane, washed with water, dried over sodium sulfate, filtered, and concentrated under reduced pressure. The resulting residue was purified by silica gel chromatography to afford 1-tert-butyl 3-methyl 5,5-difluoropiperidine-1,3-dicarboxylate (3.0 g, 67% over two steps) as a pale yellow liquid.

Step 3: 1-(tert-Butoxycarbonyl)-5,5-difluoropiperidine-3-carboxylic acid

To a solution of 1-tert-butyl 3-methyl 5,5-difluoropiperidine-1,3-dicarboxylate (3.0 g, 10.74 mmol) in methanol (35 mL) was added a 1N aqueous solution of sodium hydroxide (20 mL) at below 5° C. The mixture was warmed to room temperature, and after 16 h, the mixture was concentrated under reduced pressure. The remaining aqueous layer was acidified with a 1N aqueous solution of hydrochloric acid (to pH~4) and was extracted with ethyl acetate. The organic layer was dried over sodium sulfate, filtered, and concentrated under reduced pressure to afford 1-(tert-butoxycarbonyl)-5,5-difluoropiperidine-3-carboxylic acid (2.5 g) as a pale yellow solid which was used without further purification.

Step 4: tert-Butyl 5-(dimethylcarbamoyl)-3,3-difluoropiperidine-1-carboxylate To a solution of 1-(tert-butoxycarbonyl)-5,5-difluoropiperidine-3-carboxylic acid (2.1 g, 7.92 mmol) in N,N-dimethylformamide (100 mL) were added 1,1'-carbonyldiimidazole (CDI, 2.56 g, 15.82 mmol), dimethylamine hydrochloride (1.29 g, 15.82 mmol) and triethylamine (2.4 g, 23.71 mmol). After 16 h, the mixture was diluted with ethyl acetate, then was washed sequentially with cold water (×2) and brine, The organic layer was dried over sodium sulfate, filtered, and concentrated under reduced pressure. The resulting residue was purified by silica gel chromatography to afford tert-butyl 5-(dimethylcarbamoyl)-3,3-difluoropiperidine-1-carboxylate (1.4 g, 60% over two steps) as a pale yellow solid.

Step 5: 5,5-Difluoro-N,N-dimethylpiperidine-3-carboxamide, hydrochloric acid salt To a solution of tert-butyl 5-(dimethylcarbamoyl)-3,3-difluoropiperidine-1-carboxylate (1.2 g, 4.1 mmol) in diethyl ether (25 mL) was added a solution of hydrogen chloride in ether (20 mL) at below 5° C. After 15 min, the reaction mixture was warmed to room temperature. After 4 h, the solvent was evaporated in vacuo, and the resulting residue was triturated with diethyl ether to afford 5,5-difluoro-N,N-dimethylpiperidine-3-carboxamide, hydrochloric acid salt (0.8 g, 86%) as a pale yellow solid.

Step 6: 1-(6-Amino-5-nitropyridin-2-yl)-5,5-difluoro-N,N-dimethylpiperidine-3-carboxamide To a solution of 5,5-difluoro-N,N-dimethylpiperidine-3-carboxamide (700 mg, 3.05 mmol) in dimethylsulfoxide (30 mL) were added triethylamine (619.2 mg, 6.11 mmol) and 2-amino-6-chloro-3-nitropyridine (531.1 mg, 3.059 mmol). The reaction mixture was heated to 100° C. After 16 h, the mixture was cooled to room temperature and was partitioned between ethyl acetate and water (2×). The organic layer was washed with brine, dried over sodium sulfate, filtered, and concentrated in vacuo. The resulting residue was triturated with pentane to afford 1-(6-amino-5-nitropyridin-2-yl)-5,5-difluoro-N,N-dimethylpiperidine-3-carboxamide (0.9 g) as a yellow solid. MS (ES+APCI) (M+H) 330.2; LCMS retention time: 3.066 min (Method U1).

Step 7: 1-(5,6-Diaminopyridin-2-yl)-5,5-difluoro-N,N-dimethylpiperidine-3-carboxamide To a solution of 1-(6-amino-5-nitropyridin-2-yl)-5,5-difluoro-N,N-dimethylpiperidine-3-carboxamide (400 mg, 1.21 mmol) in ethanol (50 mL) was added 10% palladium-on-carbon (300 mg). After 2 h under hydrogen, the mixture was filtered through Celite which was then washed with ethanol to afford 1-(5,6-diaminopyridin-2-yl)-5,5-difluoro-N,N-dimethylpiperidine-3-carboxamide as a filtrate that was directly used for the next step.

Step 8: (R)-1-(2-(2-Cyclopropylpyrimidin-4-yl)-3H-imidazo[4,5-b]pyridin-5-yl)-5,5-difluoro-N,N-dimethylpiperidine-3-carboxamide and (S)-1-(2-(2-cyclopropylpyrimidin-4-yl)-3H-imidazo[4,5-b]pyridin-5-yl)-5,5-difluoro-N,N-dimethylpiperidine-3-carboxamide To a solution of 1-(5,6-diaminopyridin-2-yl)-5,5-difluoro-N,N-dimethylpiperidine-3-carboxamide (363.5 mg, 1.21 mmol) in ethanol were added 2-cyclopropylpyrimidine-4-carbaldehyde (179.9 mg, 1.21 mmol), sulfur (77.7 mg, 2.42 mmol) and acetic acid (0.4 mL). After 16 h at reflux, the mixture was cooled and then was concentrated under reduced pressure. The residue was partitioned between ethyl acetate and water. The organic layer was dried over sodium sulfate, filtered, and concentrated under reduced pressure. The residue was purified by preparative TLC to afford a racemic mixture of the desired compounds. The racemic mixture was purified via chiral preparative HPLC to afford title compounds. Enantiomer 1 (Example 164, 37 mg): MS (ES+APCI) (M+H) 428.2; Chiral HPLC retention time 5.835 min (Method: Column: CHIRAL PAK IA, 4.6×250 mm, 5 µM; Mobile Phase A: n-Hexane (0.1% trifluoroacetic acid); Mobile Phase C: Ethanol; isocratic 50:50; Flow: 1.0 mL/min; Column Temperature: 25° C.). $^1$H NMR (400 MHz, CDCl$_3$) δ 1.11-1.25 (m, 4H), 2.26-2.42 (m, 3H), 3.03 (s, 3H), 3.04-3.15 (m, 1H), 3.23 (s, 3H), 3.25-3.37 (m, 2H), 4.56-4.71 (m, 2H), 6.78 (d, 1H), 7.84-7.99 (m, 2H), 8.68 (d, 1H), 10.18-10.51 (m, 2H). Enantiomer 2 (Example 165, 39 mg): MS (ES+) (M+H) 428.2; Chiral HPLC retention time 7.336 min (Method: Same as for Enantiomer 1).

Example 166

(R)-(1-(2-(Difluoro(phenyl)methyl)-3H-imidazo[4,5-b]pyridin-5-yl)piperidin-3-yl)(pyrrolidin-1-yl)methanone

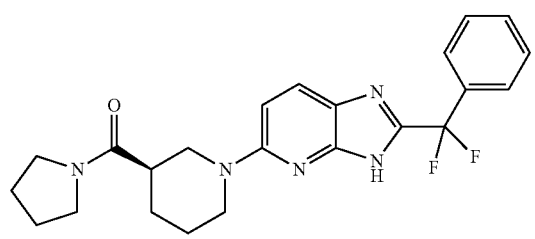 [SMILES: O=C([C@@H]1CCCN(c2ccc3nc(C(F)(F)c4ccccc4)[nH]c3n2)C1)N1CCCC1]

Step 1: (R)-(1-(2-Benzyl-3H-imidazo[4,5-b]pyridin-5-yl)piperidin-3-yl)(pyrrolidin-1-yl)methanone (R)-(1-(2-Benzyl-3H-imidazo[4,5-b]pyridin-5-yl)piperidin-3-yl)(pyrrolidin-1-yl)methanone was prepared by a method analogous to the one used for Example 163, Step 1 at a temperature of 120° C. using (R)-(1-(6-amino-5-nitropyridin-2-yl)piperidin-3-yl)(pyrrolidin-1-yl)methanone and 2-phenylacetaldehyde. MS (ES+APCI) (M+H) 390.1; LCMS retention time 3.859 min (Method I).

Step 2: (R)-(1-(2-Benzoyl-3H-imidazo[4,5-b]pyridin-5-yl)piperidin-3-yl)(pyrrolidin-1-yl)methanone Manganese (IV) oxide (2 g) was added to a solution of (R)-(1-(2-benzyl-3H-imidazo[4,5-b]pyridin-5-yl)piperidin-3-yl)(pyrrolidin-1-yl)methanone (200 mg, 0.51 mmol) in dioxane (30 mL). After heating at 120° C. for 48 h in a sealed tube, the mixture was filtered through a pad of Celite and washed with ethyl acetate. The filtrate was concentrated in vacuo and the resulting residue was purified via preparative TLC to afford (R)-(1-(2-benzoyl-3H-imidazo[4,5-b]pyridin-5-yl)piperidin-3-yl)(pyrrolidin-1-yl)methanone (80 mg). MS (ES+APCI) (M+H) 404.1; LCMS retention time 2.855 min (Method G).

Step 3: R)-(1-(2-(Difluoro(phenyl)methyl)-3H-imidazo[4,5-b]pyridin-5-yl)piperidin-3-yl)(pyrrolidin-1-yl)methanone Diethylaminosulfur trifluoride (DAST, 0.5 mL) was added to a solution of (R)-(1-(2-benzoyl-3H-imidazo[4,5-b]pyridin-5-yl)piperidin-3-yl)(pyrrolidin-1-yl)methanone (80 mg, 0.17 mmol) in chloroform (15 mL) at 0° C. After 48 h at room temperature, the mixture was diluted with dichloromethane and was washed with water. The organic layer was dried over sodium sulfate, filtered, and concentrated in vacuo. The residue was purified by preparative HPLC to afford the title compound (8 mg, 11%). MS (ES+APCI) (M+H) 426.1; LCMS retention time 3.626 min (Method C1).

Examples 167 and 168

(R)-2-(2-Cyclopropylpyrimidin-4-yl)-5-(3-(6,7-dihydro-5H-pyrrolo[2,1-c][1,2,4]triazol-3-yl)piperidin-1-yl)-3H-imidazo[4,5-b]pyridine and (S)-2-(2-cyclopropylpyrimidin-4-yl)-5-(3-(6,7-dihydro-5H-pyrrolo[2,1-c][1,2,4]triazol-3-yl)piperidin-1-yl)-3H-imidazo[4,5-b]pyridine

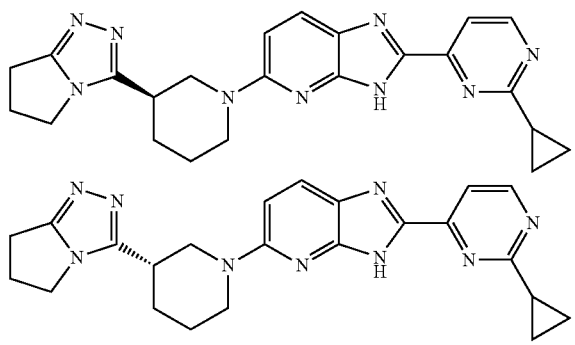

Step 1: 6-(3-(6,7-Dihydro-5H-pyrrolo[2,1-c][1,2,4]triazol-3-yl)piperidin-1-yl)pyridine-2,3-diamine, hydrochloride salt To a solution of Intermediate 45 (300 mg, 0.91 mmol) in ethanol (50 mL) was added 10% palladium-on-carbon (200 mg). After 2 h under hydrogen, the mixture was filtered over Celite and washed with ethanol. A solution of hydrogen chloride in ether was added to the filtrate and after 10 min the mixture was concentrated under reduced pressure. The residue was triturated with diethyl ether to afford 6-(3-(6,7-dihydro-5H-pyrrolo[2,1-c][1,2,4]triazol-3-yl)piperidin-1-yl)pyridine-2,3-diamine, hydrochloride salt (339 mg).

Step 2: 2-Cyclopropylpyrimidine-4-carbonitrile

To a solution of 2-cyclopropylpyrimidine-4-carbaldehyde (1.0 g, 6.68 mmol) in N,N-dimethylformamide (10 mL) were added hydroxylamine hydrochloride (500 mg, 7.02 mmol) and triethylamine (1.2 mL). The reaction mixture was heated to 50° C. and propylphosphonic anhydride (T3P) was added dropwise. After 16 h at 110° C., the mixture was cooled to room temperature, diluted with water and quenched with solid sodium bicarbonate. The mixture was extracted with ethyl acetate, then the organic layer was dried over sodium sulfate, filtered, concentrated under reduced pressure. The residue was purified via silica gel chromatography to afford 2-cyclopropylpyrimidine-4-carbonitrile (600 mg, 62%) as a pale yellow liquid. MS (ES+APCI) (M+H) 145.9; LMCS retention time 2.224 min (Method G).

Step 3: Ethyl 2-cyclopropylpyrimidine-4-carbimidate

To a solution of 2-cyclopropylpyrimidine-4-carbonitrile (600 mg, 4.13 mmol) in ethanol (10 mL) was added sodium ethoxide (561.9 mg, 8.27 mmol). After 2 h, the mixture was concentrated in vacuo. The residue was partitioned between ethyl acetate and water. The organic layer was dried over sodium sulfate, filtered and concentrated under reduced pressure to afford ethyl 2-cyclopropylpyrimidine-4-carbimidate (400 mg) as a pale yellow liquid. The material was used without further purification.

Step 4: (R)-2-(2-Cyclopropylpyrimidin-4-yl)-5-(3-(6,7-dihydro-5H-pyrrolo[2,1-c][1,2,4]triazol-3-yl)piperidin-1-yl)-3H-imidazo[4,5-b]pyridine and (S)-2-(2-cyclopropylpyrimidin-4-yl)-5-(3-(6,7-dihydro-5H-pyrrolo[2,1-c][1,2,4]triazol-3-yl)piperidin-1-yl)-3H-imidazo[4,5-b]pyridine To a solution of 6-(3-(6,7-dihydro-5H-pyrrolo[2,1-c][1,2,4]triazol-3-yl)piperidin-1-yl)pyridine-2,3-diamine, hydrochloride salt (339.1 mg) in ethanol (10 mL) was added ethyl 2-cyclopropylpyrimidine-4-carbimidate (175.1 mg, 0.91 mmol) and acetic acid (2 mL). After 16 h at reflux, the mixture was cooled and was concentrated in vacuo. The residue was partitioned between ethyl acetate and water. The organic layer was dried over sodium sulfate, filtered, and concentrated under reduced pressure. The residue was purified via preparative TLC to afford a racemic mixture that was further purified via chiral preparative HPLC to afford title compounds. Enantiomer 1 (Example 167, 17 mg): MS (ES+) (M+H) 428.0; Chiral HPLC retention time 10.085 min (Method: Column: CHIRALCEL ODH, 4.6×250 mm, 5 μm; Mobile Phase D: n-Hexane (0.1% DEA); Mobile Phase C: Ethanol, 70:30; Flow: 1.0 mL/min; Column Temperature: 25° C.). $^1$H NMR (300 MHz, CDCl$_3$) δ 1.07-1.33 (m, 4H), 1.45 (d, 2H), 1.89-

2.13 (m, 3H), 2.18-2.36 (m, 2H), 2.70-2.90 (m, 2H), 2.94-3.15 (m, 3H), 3.21-3.35 (m, 1H), 3.92-4.10 (m, 2H), 4.36 (d, 1H), 4.72 (d, 1H), 6.80 (d, 1H), 7.84-7.98 (m, 2H), 8.67 (d, 1H), 10.29 (br. s, 1H). Enantiomer 2 (Example 168, 17 mg): MS (ES+) (M+H) 428.0; Chiral HPLC retention time 13.738 min (Method: same as for Peak 1). $^1$H NMR (300 MHz, CDCl$_3$) δ 1.07-1.33 (m, 4H), 1.45 (d, 2H), 1.89-2.13 (m, 3H), 2.18-2.36 (m, 2H), 2.70-2.90 (m, 2H), 2.94-3.15 (m, 3H), 3.21-3.35 (m, 1H), 3.92-4.10 (m, 2H), 4.36 (d, 1H), 4.72 (d, 1H), 6.80 (d, 1H), 7.84-7.98 (m, 2H), 8.67 (d, 1H), 10.29 (br. s, 1H).

Example 169

2-(6-Cyclopropylpyridin-2-yl)-5-(3-(6,7-dihydro-5H-pyrrolo[2,1-c][1,2,4]triazol-3-yl)piperidin-1-yl)-3H-imidazo[4,5-b]pyridine

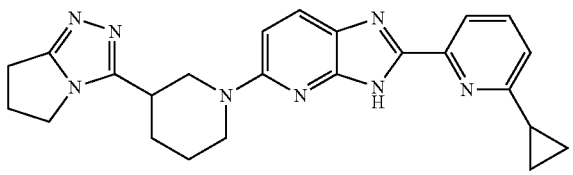 [SMILES: c1cc(-c2nc3ccc(N4CCCC(c5nnc6n5CCC6)C4)nc3[nH]2)nc(C2CC2)c1]

A mixture of 6-(3-(6,7-dihydro-5H-pyrrolo[2,1-c][1,2,4]triazol-3-yl)piperidin-1-yl)-3-nitropyridin-2-amine (Intermediate 45) (300 mg, 0.91 mmol), 2-cyclopropylpyridine-6-aldehyde (187.5 mg, 1.27 mmol), sodium dithionite (602.6 mg, 4.46 mmol), ethanol (15 mL) and water (2.4 mL) in a sealed tube was heated to 110° C. for 16 h. The mixture was concentrated under reduced pressure and the residue was partitioned between ethyl acetate and water. The organic layer was dried over sodium sulfate, filtered, and concentrated under reduced pressure. The residue was and purified via preparative TLC to afford the title compound (80 mg, 21%) as a racemic mixture. MS (ES+) (M+H) 427.3; LCMS retention time 2.687 min (Method J). $^1$H NMR (400 MHz, CDCl$_3$) δ 1.02-1.15 (m, 4H), 1.73-1.82 (m, 1H), 1.89-2.13 (m, 3H), 2.21 (d, 1H), 2.74-2.85 (m, 2H), 2.94-3.01 (m, 2H), 3.02-3.12 (m, 2H), 3.21-3.32 (m, 1H), 3.91-4.10 (m, 2H), 4.33 (d, 1H), 4.65 (d, 1H), 6.75 (d, 1H), 7.20 (d, 1H), 7.66 (t, 2H), 7.88 (d, 1H), 8.05 (d, 1H), 10.20 (br s, 1H).

Example 170 and 171

(R)-2-(6-Cyclopropylpyridin-2-yl)-5-(3-(6,7-dihydro-5H-pyrrolo[2,1-c][1,2,4]triazol-3-yl)piperidin-1-yl)-3H-imidazo[4,5-b]pyridine and/or (S)-2-(6-cyclopropylpyridin-2-yl)-5-(3-(6,7-dihydro-5H-pyrrolo[2,1-c][1,2,4]triazol-3-yl)piperidin-1-yl)-3H-imidazo[4,5-b]pyridine

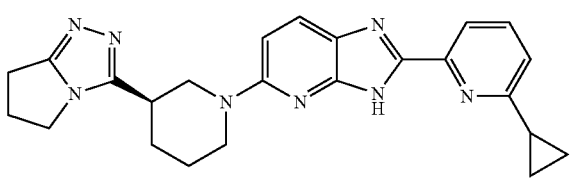

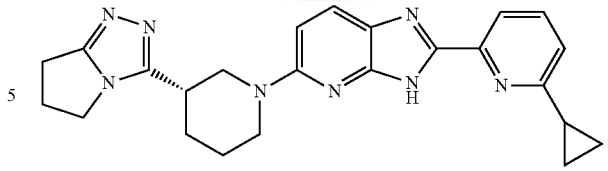

The title compounds were obtained via chiral preparative HPLC purification of Example 169. Enantiomer 1 (Example 170, 32 mg): MS (ES+) (M+H) 427.36; Chiral HPLC retention time 9.561 min (Method: Column: CHIRALCEL ODH, 4.6×250 mm, 5 μm; Mobile Phase A: n-Hexane (0.1% DEA in n-Hexane; Mobile Phase C: Ethanol, 70:30; Flow: 1.0 mL/min; Column Temperature: 25° C.) Enantiomer 2 (Example 171, 31 mg): MS (ES+) (M+H) 427.3; Chiral HPLC retention time 12.719 min (Method: Same as for Peak 1). $^1$H NMR (400 MHz, CDCl$_3$) δ 0.98-1.18 (m, 4H), 1.90-2.14 (m, 4H), 2.16-2.26 (m, 1H), 2.73-2.89 (m, 2H), 2.94-3.12 (m, 4H), 3.19-3.31 (m, 1H), 3.92-4.10 (m, 2H), 4.33 (d, 1H), 4.65 (d, 1H), 6.75 (d, 1H), 7.20 (dd, 1H), 7.67 (t, 1H), 7.89 (d, 1H), 8.05 (d, 1H), 10.22 (br s, 1H).

Example 172

(R)-6-(5-(3-(Pyrrolidine-1-carbonyl)piperidin-1-yl)-3H-imidazo[4,5-b]pyridin-2-yl)picolinamide

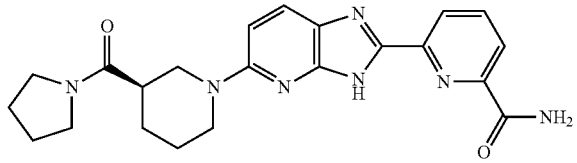 [SMILES: NC(=O)c1cccc(-c2nc3ccc(N4CCC[C@@H](C(=O)N5CCCC5)C4)nc3[nH]2)n1]

Step 1: (R)-Methyl 6-(5-(3-(pyrrolidine-1-carbonyl)piperidin-1-yl)-3H-imidazo[4,5-b]pyridin-2-yl)picolinate (R)-Methyl 6-(5-(3-(pyrrolidine-1-carbonyl)piperidin-1-yl)-3H-imidazo[4,5-b]pyridin-2-yl)picolinate (150 mg) was prepared by a method analogous to the one used for Example 112, but using (R)-(1-(6-amino-5-nitropyridin-2-yl)piperidin-3-yl)(pyrrolidin-1-yl)methanone (Intermediate 1, Step 3), methyl 6-formylpicolinate, and methanol as the solvent. MS (ES+) (M+H) 434.67; LCMS retention time 5.39 min (Method H).

Step 2: (R)-6-(5-(3-(Pyrrolidine-1-carbonyl)piperidin-1-yl)-3H-imidazo[4,5-b]pyridin-2-yl)picolinamide To (R)-methyl 6-(5-(3-(pyrrolidine-1-carbonyl)piperidin-1-yl)-3H-imidazo[4,5-b]pyridin-2-yl)picolinate (200 mg, 0.460 mmol) in toluene (5 mL) were added sequentially a freshly prepared saturated solution of ammonia in dioxane (10 mL) at −20° C., and trimethylaluminum (0.099 g, 1.348 mmol). The reaction vessel was sealed and was heated at 100° C. for 16 h. The mixture was cooled to room temperature and was partitioned between ethyl acetate, and water. The organic layer was dried over sodium sulfate and concentrated under reduced pressure. The resulting residue was triturated twice with methanol:diethyl ether (1:10) to afford the title compound (40 mg). MS (ES+) (M+H) 420.2892; LCMS retention time 3.71 min (Method I1).

Example 173

(R)—N,N-Dimethyl-6-(5-(3-(pyrrolidine-1-carbonyl)piperidin-1-yl)-3H-imidazo[4,5-b]pyridin-2-yl)picolinamide

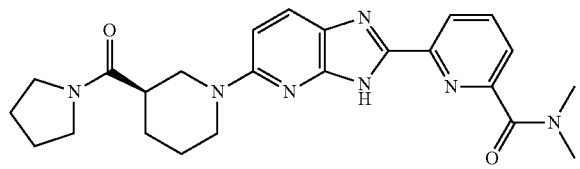

The title compound (40 mg, 20%) was prepared by a method analogous to the one used for Example 172, but for step 2 dimethylamine was used. MS (ES+) (M+H) 448.1; LCMS retention time 3.783 min (Method I). $^1$H NMR (300 MHz, CDCl$_3$) δ 1.41-1.48 (m, 1H), 1.51-1.57 (m, 1H), 1.78-2.10 (m, 7H), 2.69 (d, 1H), 3.03 (dd, 1H), 3.09 (br s, 3H), 3.20 (s, 3H), 3.39-3.58 (m, 2H), 3.59-3.73 (m, 1H), 4.29-4.39 (m, 1H), 4.52 (d, 1H), 6.73 (d, 1H), 7.59 (d, 1H), 7.82-7.97 (m, 2H), 8.33 (d, 1H), 10.24 (br s, 1H).

Example 174

(1R,4R)-2-Oxa-5-azabicyclo[2.2.1]heptan-5-yl((R)-1-(2-(2-cyclopropylpyrimidin-4-yl)-3H-imidazo[4,5-b]pyridin-5-yl)piperidin-3-yl)methanone

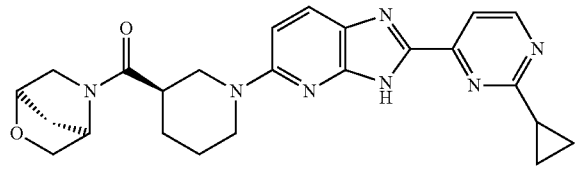

Step 1: (R)-Methyl 1-(6-amino-5-nitropyridin-2-yl)piperidine-3-carboxylate (R)-Methyl 1-(6-amino-5-nitropyridin-2-yl)piperidine-3-carboxylate was prepared by a method analogous to Example 158, Step 1, but the reaction mixture temperature was 80° C. MS (ES+APCI) (M+H) 281.1

Step 2: (R)-Methyl 1-(5,6-diaminopyridin-2-yl)piperidine-3-carboxylate (R)-Methyl 1-(5,6-diaminopyridin-2-yl)piperidine-3-carboxylate was prepared by a method analogous to Example 158, Step 2. The material was used without further purification.

Step 3: (R)-Methyl 1-(2-(2-cyclopropylpyrimidin-4-yl)-3H-imidazo[4,5-b]pyridin-5-yl)piperidine-3-carboxylate (R)-Methyl 1-(2-(2-cyclopropylpyrimidin-4-yl)-3H-imidazo[4,5-b]pyridin-5-yl)piperidine-3-carboxylate was prepared by a method analogous to Example 158, Step 3, but using 2-cyclopropylpyrimidine-4-carbaldehyde. MS (ES+APCI) (M+H) 379.0.

Step 4: (R)-1-(2-(2-Cyclopropylpyrimidin-4-yl)-3H-imidazo[4,5-b]pyridin-5-yl)piperidine-3-carboxylic acid To a solution of (R)-methyl 1-(2-(2-cyclopropylpyrimidin-4-yl)-3H-imidazo[4,5-b]pyridin-5-yl)piperidine-3-carboxylate (250 mg, 0.66 mmol) in ethanol (10 mL), was added an aqueous solution of sodium hydroxide (1N, 5 mL). The reaction mixture was stirred at room temperature for 2 h. The solvent was distilled off and the residue was partitioned between water and ethyl acetate. The aqueous layer was acidified with aqueous hydrochloric acid (10%) to pH~2. The resulting precipitate was collected by filtration and dried under vacuum to afford (R)-1-(2-(2-cyclopropylpyrimidin-4-yl)-3H-imidazo[4,5-b]pyridin-5-yl)piperidine-3-carboxylic acid (200 mg). MS (ES+APCI) (M+H) 365.2

Step 5: (1R,4R)-2-Oxa-5-azabicyclo[2.2.1]heptan-5-yl((R)-1-(2-(2-cyclopropylpyrimidin-4-yl)-3H-imidazo[4,5-b]pyridin-5-yl)piperidin-3-yl)methanone To a solution of (R)-1-(2-(2-cyclopropylpyrimidin-4-yl)-3H-imidazo[4,5-b]pyridin-5-yl)piperidine-3-carboxylic acid (70 mg, 0.192 mmol) in N,N-dimethylformamide (10 mL) were added 1-ethyl-3-(3-dimethylaminopropyl) carbodiimide (EDCl) (73.2 mg, 0.383 mmol), hydroxybenzotriazole (52 mg, 0.383 mmol), triethylamine (58.2 mg, 0.575 mmol), (1R,5S)-8-oxa-3-azabicyclo[3.2.1]octane (186 mg, 1.64 mmol) and 4-dimethylaminopyridine (3 mg) at room temperature. The reaction mixture was stirred for 18 h, poured into ice water, extracted with ethyl acetate, washed with cold water and concentrated. The crude was purified via preparative TLC (3% methanol in dichloromethane) to afford the title compound (9 mg). MS (ES+) (M+H) 446.3; LCMS retention time 1.816 min (Method F)

Example 175

(R)-(4-(2-(6-(Difluoromethyl)pyridin-2-yl)-3H-imidazo[4,5-b]pyridin-5-yl)morpholin-2-yl)(pyrrolidin-1-yl)methanone

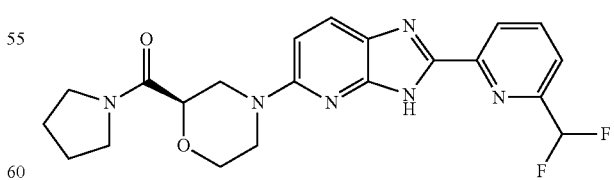

The title compound (20 mg) was prepared by a method analogous to the one used for Example 163, Step 1 but using 6-(difluoromethyl)picolinaldehyde and purifying the crude material by silica gel chromatography. MS (ES+) (M+H) 429.0; LCMS retention time 4.092 min (Method I).

Example 176

(R)-(1-(2-(2-Cyclopropylpyrimidin-4-yl)-3H-imidazo[4,5-b]pyridin-5-yl)piperidin-3-yl)(3,3-difluoroazetidin-1-yl)methanone

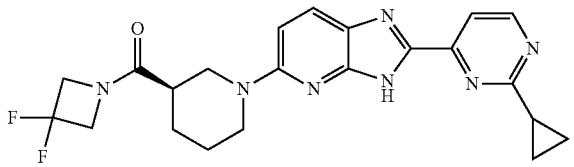 [SMILES: O=C([C@@H]1CCCN(c2ccc3nc(-c4ccnc(C5CC5)n4)[nH]c3n2)C1)N1CC(F)(F)C1]

The title compound (26 mg, 43%) was prepared by a method analogous to the one used for Example 158 but using 3,3-difluoroazetidine for step 5. MS (ES+) (M+H) 440.5090; LCMS retention time 3.649 min (Method J1). $^1$H NMR (300 MHz, CDCl$_3$) δ 1.10-1.24 (m, 4H), 1.26 (s, 1H), 1.79-1.99 (m, 3H), 2.24-2.36 (m, 1H), 2.42-2.58 (m, 1H), 2.98-3.20 (m, 2H), 4.19-4.43 (m, 3H), 4.44-4.70 (m, 3H), 6.75 (d, 1H), 7.84-7.97 (m, 2H), 8.67 (d, 1H), 10.31 (br s, 1H).

Examples 177 and 178

(2R,5S)-4-(2-(3-Chlorophenyl)-3H-imidazo[4,5-b]pyridin-5-yl)-5-methyl-2-(pyridin-2-yl)morpholine and (2S,5S)-4-(2-(3-chlorophenyl)-3H-imidazo[4,5-b]pyridin-5-yl)-5-methyl-2-(pyridin-2-yl)morpholine

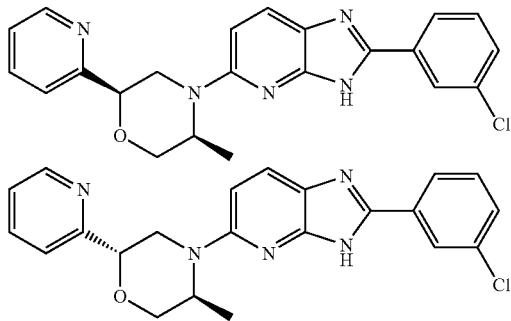

Step 1: 2-(Oxiran-2-yl)pyridine 1-oxide

To a suspension of 3-chloroperoxybenzoic acid (m-CPBA, 172 g, 1000 mmol) in dichloromethane (500 mL) was added 2-vinylpyridine (30 g, 285.7 mmol). After 30 min, the reaction mixture was heated at reflux for 36 h. The solution was then filtered and concentrated under reduced pressure. The residue was purified via neutral alumina chromatography (10% methanol in dichloromethane) to afford 2-(oxiran-2-yl)pyridine 1-oxide as a white solid (4.5 g, 10%).

Step 2: 2-(2-(Benzyl((S)-1-hydroxypropan-2-yl)amino)-1-hydroxyethyl)pyridine 1-oxide To a solution of 2-(oxiran-2-yl)pyridine 1-oxide (6.6 g, 48.48 mmol) in ethanol (150 mL) were added (S)-2-(benzylamino)propan-1-ol (16 g, 96.96 mmol) and potassium carbonate (13.3 g, 96.96 mmol), After 24 h, the mixture was concentrated under reduced pressure and the resulting residue was purified via alumina chromatography (1% methanol in dichloromethane) to afford 2-(2-(benzyl((S)-1-hydroxypropan-2-yl)amino)-1-hydroxyethyl)pyridine 1-oxide as a yellow liquid (7 g, 22%).

Step 3: 2-((5S)-4-Benzyl-5-methylmorpholin-2-yl)pyridine 1-oxide 2-(2-(Benzyl((S)-1-hydroxypropan-2-yl)amino)-1-hydroxyethyl)pyridine 1-oxide (7 g, 23.17 mmol) was dissolved in 70% sulfuric acid (70 mL) and the mixture was heated at reflux for 7 h. The mixture was cooled and then was diluted with water, neutralized with an aqueous sodium carbonate solution and extracted with ethyl acetate. The organic layer was dried over anhydrous sodium sulfate, filtered, and concentrated under reduced pressure. The residue was purified by alumina chromatography (1% methanol in dichloromethane) to afford 2-((5S)-4-benzyl-5-methylmorpholin-2-yl)pyridine 1-oxide as a yellow liquid (3 g, 45%).

Step 4: (5S)-5-Methyl-2-(pyridin-2-yl)morpholine

To a suspension of 10% palladium-on-carbon (2 g) in ethanol (30 mL) was added a solution of 2-((5S)-4-benzyl-5-methylmorpholin-2-yl)pyridine 1-oxide (3.5 g, 13.06 mmol) in ethanol (10 mL). The mixture was subjected to a hydrogen atmosphere using a balloon filled with hydrogen gas for 2 h. The mixture was filtered through Celite and the filtrate was concentrated under reduced pressure to afford (5S)-5-methyl-2-(pyridin-2-yl)morpholine (0.7 g). MS (ES+) (M+H) 179.0.

Step 5: 6-((5S)-5-Methyl-2-(pyridin-2-yl)morpholino)-3-nitropyridin-2-amine

To a solution of (5S)-5-methyl-2-(pyridin-2-yl)morpholine (0.7 g, 3.93 mmol) in dimethylsulfoxide (20 mL) was added triethylamine (0.68 g, 7.86 mmol). After 10 min, 6-chloro-3-nitropyridin-2-amine (0.68 g, 3.93 mmol) was added. After 4 h at 110° C., the mixture was cooled to room temperature, and then was partitioned between ethyl acetate and water. The organic layer was dried over sodium sulfate, filtered, and concentrated under reduced pressure. The residue was purified via silica gel chromatography (80% ethyl acetate in petroleum ether) to afford 6-((5S)-5-methyl-2-(pyridin-2-yl)morpholino)-3-nitropyridin-2-amine (0.5 g, 41%).

Step 6: (2R,5S)-4-(2-(3-Chlorophenyl)-3H-imidazo[4,5-b]pyridin-5-yl)-5-methyl-2-(pyridin-2-yl)morpholine and (2S,5S)-4-(2-(3-chlorophenyl)-3H-imidazo[4,5-b]pyridin-5-yl)-5-methyl-2-(pyridin-2-yl)morpholine To a solution of 6-((5S)-5-methyl-2-(pyridin-2-yl)morpholino)-3-nitropyridin-2-amine (200 mg, 0.634 mmol) in ethanol (10 mL) in a sealed tube were added 3-chlorobenzaldehyde (100 mg, 0.698 mmol), sodium dithionite (420 mg, 2.40 mmol) and water (0.8 mL). The reaction mixture was heated to 110° C. for 18 h. The mixture was cooled; cold water was added and the resulting mixture was stirred for 10 min. The resulting solid was isolated by filtration and was purified by preparative TLC (5% acetone in dichloromethane) to afford two diastereomers. Diastereomer 1 (Example 177, 13 mg): MS (ES+) (M+H) 406.0824; LCMS retention time 3.61 min (Method K1). Diastereomer 2 (Example 178, 21 mg): MS (ES+) (M+H) 406.1; LCMS retention time 3.69 min (Method K1).

Example 179

(R)-(1-(2-(5-(Methylsulfonyl)pyridin-3-yl)-3H-imidazo[4,5-b]pyridin-5-yl)piperidin-3-yl)(pyrrolidin-1-yl)methanone

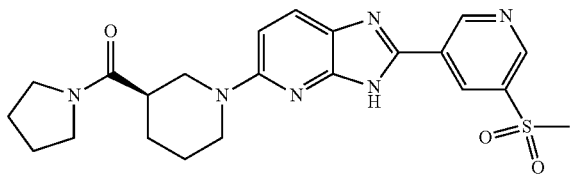 [SMILES: CS(=O)(=O)c1cncc(-c2nc3ccc(N4CCC[C@@H](C(=O)N5CCCC5)C4)nc3[nH]2)c1]

Step 1: (R)-(1-(2-(5-Bromopyridin-3-yl)-3H-imidazo[4,5-b]pyridin-5-yl)piperidin-3-yl)(pyrrolidin-1-yl)methanone To a solution of (R)-(1-(4-amino-5-nitropyrimidin-2-yl)piperidin-3-yl)(pyrrolidin-1-yl)methanone (0.5 g, 1.5 mmol) in a mixture of ethanol and water were added 5-bromonicotinaldehyde (0.35 g, 1.6 mmol) and sodium dithionate (1.1 g, 5.9 mmol). The reaction mixture was heated to 120° C. for 16 h. The reaction mixture was concentrated and partitioned between water and ethyl acetate. The organics were concentrated under reduced pressure and the resulting crude was purified via preparative TLC to afford (R)-(1-(2-(5-bromopyridin-3-yl)-3H-imidazo[4,5-b]pyridin-5-yl)piperidin-3-yl)(pyrrolidin-1-yl)methanone (400 mg, 60%).

Step 2: (R)-(1-(2-(5-(Methylsulfonyl)pyridin-3-yl)-3H-imidazo[4,5-b]pyridin-5-yl)piperidin-3-yl)(pyrrolidin-1-yl)methanone To a solution of R)-(1-(2-(5-bromopyridin-3-yl)-3H-imidazo[4,5-b]pyridin-5-yl)piperidin-3-yl)(pyrrolidin-1-yl)methanone (0.05 g, 0.1 mmol) in dimethylsulfoxide was added sodium methylsulfinate ($NaSO_2Me$) (13 mg, 0.13 mmol), copper iodide, L-proline and sodium hydroxide. The reaction mixture was heated to 90° C. for 14 h. The reaction mixture was partitioned between water and ethyl acetate. The organics were concentrated under reduced pressure and the resulting crude was purified via preparative TLC to afford the title compound (25 mg, 45%). MS (ES+APCI) (M+H) 455.0; LCMS retention time: 3.859 min (Method I).

Example 180 and 181

(3R,4R)-1-(2-(3-(Difluoromethoxy)phenyl)-3H-imidazo[4,5-b]pyridin-5-yl)-N,N,4-trimethylpiperidine-3-carboxamide and (3S,4S)-1-(2-(3-(difluoromethoxy)phenyl)-3H-imidazo[4,5-b]pyridin-5-yl)-N,N,4-trimethylpiperidine-3-carboxamide

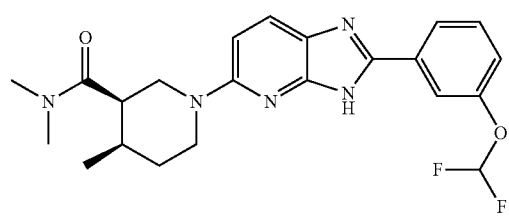

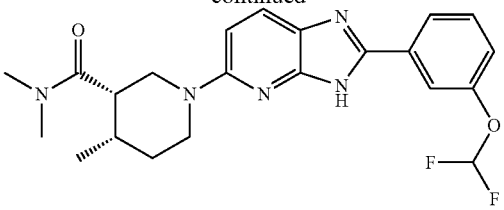

Step 1: cis-tert-Butyl 3-(dimethylcarbamoyl)-4-methylpiperidine-1-carboxylate To a solution of cis-1-(tert-butoxycarbonyl)-4-methylpiperidine-3-carboxylic acid (prepared by N-Boc protection of cis-4-methylpiperidine-3-carboxylic acid, synthesized by the method described in *Bulletin de la Societe Chimique de France* 1986, 4, 663-8.) (0.4 g, 1.64 mmol) in tetrahydrofuran were added triethylamine (0.2 mL, 1.64 mmol), dimethylamine hydrochloride (132 mg, 1.64 mmol), and 1,1'-carbonyldiimidazole (CDI, 265 mg, 1.64 mmol). After 2 h, the mixture was quenched with water and the aqueous layer was extracted with ethyl acetate (2×10 mL). The combined organic layers were dried over sodium sulfate, filtered and concentrated under reduced pressure to afford cis-tert-butyl 3-(dimethylcarbamoyl)-4-methylpiperidine-1-carboxylate (0.3 g, 68%) as a yellow solid. The material was used without further purification.

Step 2: cis-N,N-4-Trimethylpiperidine-3-carboxamide hydrochloride

To cis-tert-butyl 3-(dimethylcarbamoyl)-4-methylpiperidine-1-carboxylate (0.3 g, 1.12 mmol) was added a solution of hydrogen chloride in ether. The mixture was stirred for 30 min, and then was concentrated under reduced pressure to afford cis-N,N,4-trimethylpiperidine-3-carboxamide hydrochloride (0.16 g) as a white solid. The material was used without further purification.

Step 3: cis-1-(6-Amino-5-nitropyridin-2-yl)-N,N,4-trimethylpiperidine-3-carboxamide To a solution of N,N,4-trimethylpiperidine-3-carboxamide (0.16 g, 0.96 mmol) in dimethylsulfoxide (5 mL) were added triethylamine (0.2 mL, 0.96 mmol) and 6-chloro-3-nitropyridin-2-amine (0.168 g, 0.96 mmol). The reaction mixture was heated for 12 h at 80° C., then was cooled. The mixture was diluted with water and the aqueous layer was extracted with ethyl acetate (2×10 mL). The combined organic layers were dried over sodium sulfate, filtered, and concentrated under reduced pressure. The residue was purified via silica gel chromatography to afford cis-1-(6-amino-5-nitropyridin-2-yl)-N,N,4-trimethylpiperidine-3-carboxamide (0.2 g, 68%).

Step 4: (3R,4R)-1-(2-(3-(Difluoromethoxy)phenyl)-3H-imidazo[4,5-b]pyridin-5-yl)-N,N,4-trimethylpiperidine-3-carboxamide and (3S,4S)-1-(2-(3-(difluoromethoxy)phenyl)-3H-imidazo[4,5-b]pyridin-5-yl)-N,N,4-trimethylpiperidine-3-carboxamide The title compounds were prepared by a method analogous to the one used for Example 163, Step 1 using N,N,4-trimethylpiperidine-3-carboxamide and 6-chloro-3-nitropyridin-2-amine to afford a racemic mixture that was further purified via chiral HPLC to obtain enantiomer 1 and enantiomer 2. Enantiomer 1 (Example 180, 8.4 mg): MS (ES+APCI) (M+H) 430.2; LCMS retention time 2.965 min (Method P1). $^1$H NMR (300 MHz, DMSO-d$_6$) δ 0.86 (d, 1H), 0.95 (d, 3H), 1.50-1.62 (m, 1H), 1.73-1.86 (m, 1H), 2.27 (m, 1H), 2.68-2.75 (m, 1H), 2.82 (br s, 3H), 2.95-3.06 (m, 3H), 3.34-3.50 (m, 1H), 3.90-4.08 (m, 2H), 6.80 (d, 1H), 7.21 (d, 1H), 7.32 (t, 1H), 7.55 (d, 1H), 7.79 (d, 1H), 7.88-7.92 (m, 1H), 7.97 (d, 1H), 13.09 (s, 1H). Enantiomer 2 (Example 181, 6.6 mg): MS (ES+APCI) (M+H) 430.3; LCMS retention time 2.963 min (Method P1).

Example 182

(R)-(1-(2-(6-Cyclopropylpyridin-2-yl)-3H-imidazo[4,5-b]pyridin-5-yl)piperidin-3-yl)(pyrrolidin-1-yl)methanone

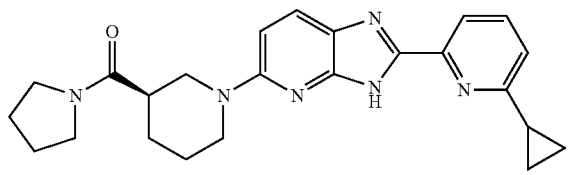 [SMILES: O=C([C@@H]1CCCN(c2ccc3nc(-c4cccc(C5CC5)n4)[nH]c3n2)C1)N1CCCC1]

To a solution of (R)-(1-(6-amino-5-nitropyridin-2-yl)piperidin-3-yl)(pyrrolidin-1-yl)methanone (250 mg, 0.711 mmol) in ethanol (15 mL) was added 6-cyclopropylpicolinaldehyde (0.137 g, 0.974 mmol), sodium dithionite (536 mg, 2.96 mmol) and water (2 mL). The reaction mixture was stirred for 16 h at 100° C. in a sealed tube. The mixture was cooled, and the solvent was removed under reduced pressure. Water was added to the residue and the mixture was extracted with ethyl acetate. The organics were dried over sodium sulfate, filtered and concentrated under reduced pressure. The crude material was purified via preparative TLC eluting with 4% methanol in dichloromethane to afford the title compound (55 mg, 17%). MS (ES+APCI) (M+H) 417.2; LCMS retention time 1.944 (Method F). $^1$H NMR (300 MHz, CDCl$_3$) δ 1.00-1.09 (m, 2H), 1.09-1.16 (m, 2H), 1.63-1.74 (m, 1H), 1.81-2.14 (m, 7H), 2.62-2.76 (m, 1H), 2.99 (dd, 1H), 3.08-3.21 (m, 1H), 3.44-3.55 (m, 3H), 3.58-3.70 (m, 1H), 4.35 (d, 1H), 4.48 (d, 1H), 6.71 (d, 1H), 7.19 (d, 1H), 7.66 (t, 1H), 7.87 (d, 1H), 8.04 (d, 1H), 10.18 (br s, 1H).

Example 183

(R)-(1-(2-(5-Cyclopropylpyridin-3-yl)-3H-imidazo[4,5-b]pyridin-5-yl)piperidin-3-yl)(pyrrolidin-1-yl)methanone

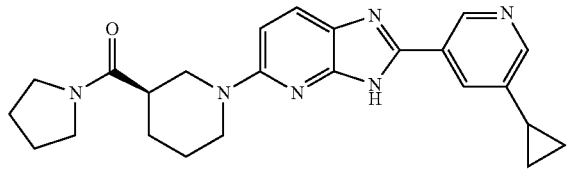

To a solution of ethyl 5-cyclopropylnicotinimidate (0.2 g, 1.04 mmol) in ethanol was added acetic acid (0.1 mL), triethylamine (0.1 mL) and a solution of (R)-(1-(5,6-diaminopyridin-2-yl)piperidin-3-yl)(pyrrolidin-1-yl)methanone dihydrochloride salt (0.4 g, 1.1 mmol) in ethanol. The reaction mixture was heated at reflux for 24 h. The solvent was removed under reduced pressure and to the resulting residue was added a saturated aqueous solution of ammonium chloride. The mixture was extracted with ethyl acetate. The organic layer was concentrated under reduced pressure. The crude material was purified via preparative TLC to afford the title compound (0.025 g). $^1$H NMR (400 MHz, DMSO-d$_6$) δ 0.85 (br s, 2H), 1.07 (d, 2H), 1.47-1.74 (m, 4H), 1.74-1.96 (m, 5H), 1.98-2.10 (m, 1H), 2.61 (br s, 2H), 2.92 (d, 2H), 3.41-3.59 (m, 2H), 4.33 (d, 1H), 4.39 (d, 1H), 6.86 (d, 1H), 7.81 (d, 1H), 8.00 (br s, 1H), 8.47 (br s, 1H), 9.05 (br s, 1H), 13.07 (br s, 1H). MS (ES+) (M+H) 417.36; LCMS retention time 3.03 min (Method S).

Example 184

(R)-(1-(2-(6-Cyclopropylpyridin-2-yl)-3H-imidazo[4,5-b]pyridin-5-yl)piperidin-3-yl)(3,3-difluoropyrrolidin-1-yl)methanone

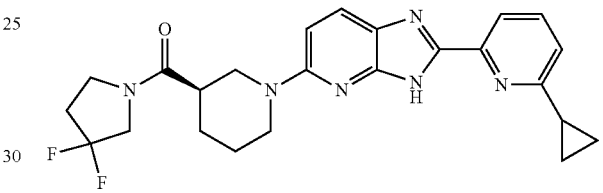

The title compound was prepared by a method analogous to the one used for Example 158, but using 3,3-difluoropyrrolidine instead of 3-pyrroline and 4-dimethylaminopyridine for the final step. $^1$H NMR (300 MHz, CDCl$_3$) δ 1.01-1.17 (m, 4H), 1.78-2.01 (m, 3H), 2.02-2.16 (m, 2H), 2.31-2.61 (m, 3H), 2.65-2.78 (m, 1H), 3.01-3.21 (m, 2H), 3.66-4.00 (m, 3H), 4.24 (d, 1H), 4.54 (t, 1H), 6.71 (dd, 1H), 7.20 (dd, 1H), 7.58-7.71 (m, 1H), 7.88 (d, 1H), 8.04 (d, 1H), 10.17 (br s, 1H). MS (ES+APCI) (M+H) 452.9; LCMS retention time 4.371 min (Method I).

Example 185

(R)-1-(2-(2-Cyclopropylpyrimidin-4-yl)-3H-imidazo[4,5-b]pyridin-5-yl)-N-ethyl-N-methylpiperidine-3-carboxamide

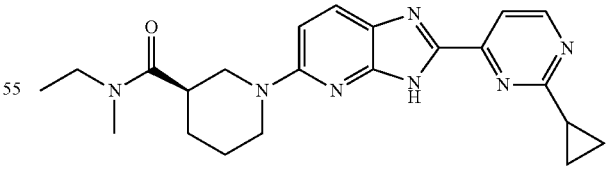

To a solution of (R)-1-(5,6-diaminopyridin-2-yl)-N-ethyl-N-methylpiperidine-3-carboxamide (200 mg, 0.722 mmol) in ethanol (10 mL) was added 2-cyclopropylpyrimidine-4-carbaldehyde (106 mg, 0.722 mmol), sulfur powder (69 mg, 2.16 mmol), and acetic acid (0.2 mL). The reaction mixture was heated to 80° C. for 18 h. The solvent was evaporated and the residue was partitioned between ethyl acetate and water. The organic layer was concentrated under reduced pressure.

The crude material was purified via preparative HPLC to afford the title compound (40 mg, 13.5%). $^1$H NMR (300 MHz, CDCl$_3$) δ 1.09-1.18 (m, 3H), 1.19-1.31 (m, 4H), 1.65-1.73 (m, 1H), 1.84 (d, 1H), 1.88-1.98 (m, 2H), 2.31 (d, 1H), 2.69-2.87 (m, 1H), 2.99 (br s, 1H), 3.03 (br s, 1H), 3.11 (br s, 1H), 3.14-3.27 (m, 1H), 3.37-3.57 (m, 2H), 4.37 (d, 1H), 4.45-4.59 (m, 1H), 6.76 (d, 1H), 7.79-7.96 (m, 1H), 8.67 (d, 1H), 10.25 (br s, 1H). MS (ES+APCI) (M+H) 406.3; LCMS retention time 3.055 min (Method U1).

Example 186

(R)-(4-(2-(6-Cyclopropylpyridin-2-yl)-3H-imidazo[4,5-b]pyridin-5-yl)morpholin-2-yl)(morpholino)methanone

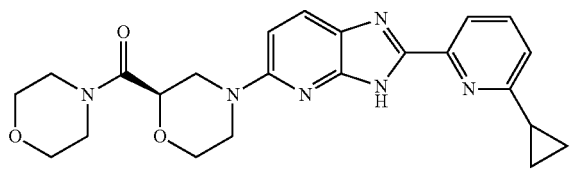 [SMILES: O=C([C@H]1CN(c2ccc3nc(-c4cccc(C5CC5)n4)[nH]c3n2)CCO1)N1CCOCC1]

The title compound was prepared by a method analogous to the one used for Example 112, but the organic extract was only washed with water instead of a saturated aqueous solution of ammonium chloride and a saturated aqueous solution of sodium bicarbonate. $^1$H NMR (300 MHz, CDCl$_3$) δ 1.02-1.17 (m, 4H), 1.99-2.16 (m, 2H), 3.14-3.31 (m, 1H), 3.38 (dd, 1H), 3.50-3.62 (m, 2H), 3.66-3.84 (m, 7H), 4.01-4.17 (m, 2H), 4.20-4.36 (m, 2H), 6.74 (d, 1H), 7.21 (d, 1H), 7.67 (t, 1H), 7.92 (d, 1H), 8.01-8.09 (m, 1H), 10.23 (br s, 1H). MS (ES+APCI) (M+H) 435.2; LCMS retention time 2.322 min (Method G).

Example 187

(R)-Pyrrolidin-1-yl(1-(8-(6-(trifluoromethyl)pyridin-2-yl)-9H-purin-2-yl)piperidin-3-yl)methanone

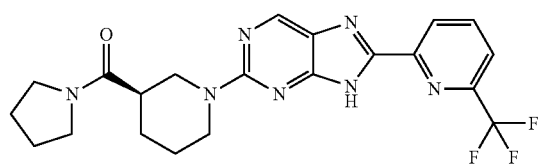 [SMILES: O=C([C@@H]1CCCN(c2ncc3nc(-c4cccc(C(F)(F)F)n4)[nH]c3n2)C1)N1CCCC1]

To a solution of ethyl 6-(trifluoromethyl)picolinimidate (291 mg, 1.3 mmol) and triethylamine (0.6 mL, 4.4 mmol) in ethanol (5 mL) was added dropwise a solution of (R)-(1-(4,5-diaminopyrimidin-2-yl)piperidin-3-yl)(pyrrolidin-1-yl)methanone dihydrochloride (400 mg, 1.1 mmol) and acetic acid (0.3 mL, 6.6 mmol) in ethanol (10 mL) at room temperature over a period of 10 min. The reaction mixture was stirred for 16 h at 120° C. The mixture was concentrated and the residue was partitioned between ethyl acetate and water. The organic layer was dried over sodium sulfate, filtered and concentrated under reduced pressure. The crude material was purified via preparative TLC to afford the title compound (110 mg, 20%). $^1$H NMR (400 MHz, DMSO-d$_6$) δ 1.18-1.32 (m, 1H), 1.48 (d, 1H), 1.71 (t, 2H), 1.76-1.83 (m, 2H), 1.89 (dt, 3H), 2.55-2.64 (m, 2H), 2.85-3.03 (m, 2H), 3.42-3.50 (m, 1H), 3.51-3.63 (m, 1H), 4.76 (d, 2H), 8.00 (d, 1H), 8.22-8.32 (m, 1H), 8.49 (d, 1H), 8.83 (br s, 1H), 13.41 (br s, 1H). MS (ES+) (M+H) 446.33; LCMS retention time 3.34 min (Method S).

Example 188

(R)-(1-(2-(2-(4-Chloro-1H-pyrazol-1-yl)propan-2-yl)-3H-imidazo[4,5-b]pyridin-5-yl)piperidin-3-yl)(pyrrolidin-1-yl)methanone

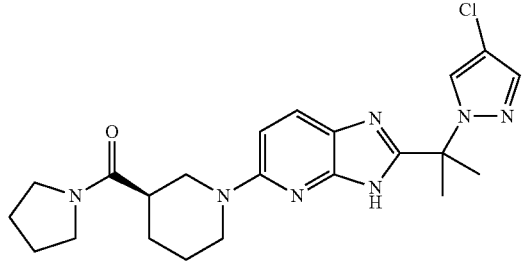

Step 1: (R)-(1-(5,6-Diaminopyridin-2-yl)piperidin-3-yl)(pyrrolidin-1-yl)methanone A solution of (R)-(1-(6-amino-5-nitropyridin-2-yl)piperidin-3-yl)(pyrrolidin-1-yl)methanone (1.5 g, 4.7 mmol) in ethanol (20 mL) was added to a suspension of 10% palladium-on-carbon (800 mg) at room temperature. The mixture was hydrogenated for 4 h, filtered through Celite and washed with ethanol. The filtrate was used for the next step without further purification.

Step 2: (R)-(1-(2-(2-(4-Chloro-1H-pyrazol-1-yl)propan-2-yl)-3H-imidazo[4,5-b]pyridin-5-yl)piperidin-3-yl)(pyrrolidin-1-yl)methanone Acetic acid (2.9 mL, 48.58 mmol) and ethyl 2-(4-chloro-1H-pyrazol-1-yl)-2-methylpropanimidate (Intermediate 54) were added to a solution of (R)-(1-(5,6-diaminopyridin-2-yl)piperidin-3-yl)(pyrrolidin-1-yl)methanone in ethanol, prepared in the previous step. The reaction mixture was heated at reflux for 18 h. The mixture was concentrated and the residue was partitioned between ethyl acetate and water. The organic layer was dried over sodium sulfate, filtered and concentrated. The crude material was purified via column chromatography (100-200 mesh silica gel, 5% methanol in ethyl acetate) to afford the title compound (530 mg, 25% yield over 2 steps). $^1$H NMR (500 MHz, CDCl$_3$) δ 1.53-1.65 (m, 1H) 1.74-2.00 (m, 7H) 2.10 (s, 6H) 2.58-2.70 (m, 1H) 2.88-2.93 (m, 1H) 3.01-3.09 (m, 1H) 3.40-3.50 (m, 3H) 3.55-3.63 (m, 1H) 4.22 (d, 1H) 4.43 (d, 1H) 6.63 (d, 1H) 7.57 (d, 2H) 7.79 (d, 1H) 10.08 (br s, 1H). MS (ES+APCI) (M+H) 442.2; LCMS retention time 2.216 min (Method N1).

Example 189

(R)-(1-(2-(1-(4-(Methylthio)-1H-pyrazol-1-yl)cyclopropyl)-3H-imidazo[4,5-b]pyridin-5-yl)piperidin-3-yl)(pyrrolidin-1-yl)methanone

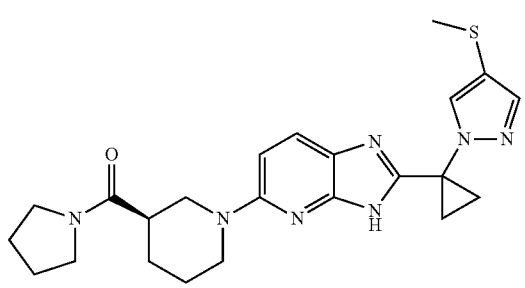 [SMILES: CSc1cnn(C2(c3nc4ccc(N5CCC[C@@H](C(=O)N6CCCC6)C5)nc4[nH]3)CC2)c1]

To a solution of (R)-(1-(5,6-diaminopyridin-2-yl)piperidin-3-yl)(pyrrolidin-1-yl)methanone dihydrochloride (189 mg, 0.653 mmol) and ethyl 1-(4-(methylthio)-1H-pyrazol-1-yl)cyclopropanecarbimidate (157 mg, 0.697 mmol) in ethanol (1.86 mL) was added acetic acid (0.372 mL) followed by triethylamine (0.545 mL, 3.91 mmol). The reaction mixture was heated to 110° C. for 2 h. The mixture was cooled to room temperature, the solvent was removed under reduced pressure and the residue was partitioned between a saturated aqueous solution of ammonium chloride (100 mL) and dichloromethane (200 mL). The aqueous layer was extracted with dichloromethane (100 mL) and the combined organics were dried over sodium sulfate, filtered and concentrated under reduced pressure. The crude material was purified via HPLC to afford the title compound. MS (ESI+) (M+H) 452.2; HPLC retention time 2.11 min (Method A).

Examples 190 and 191

[(R)-1-{2-[1-(4-Chloro-1H-pyrazol-1-yl)cyclopropyl]-3H-imidazo[4,5-b]pyridin-5-yl}(2,2,6,6-$^2$H$_4$)piperidin-3-yl](pyrrolidin-1-yl)methanone and [(S)-1-{2-[1-(4-chloro-1H-pyrazol-1-yl)cyclopropyl]-3H-imidazo[4,5-b]pyridin-5-yl}(2,2,6,6-$^2$H$_4$)piperidin-3-yl](pyrrolidin-1-yl)methanone

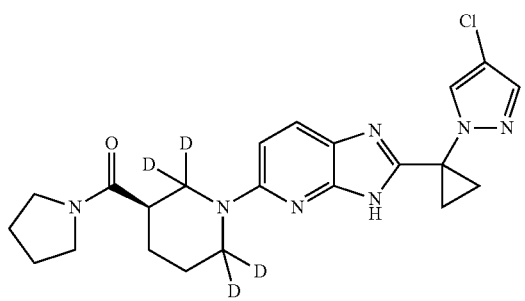

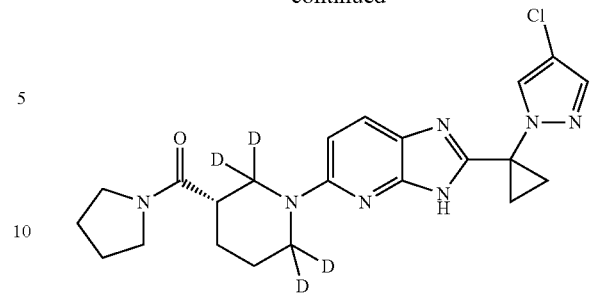

Step 1: 1-Nitrosopiperidine-3-carboxylic acid

Aqueous hydrochloric acid (2N, 20 mL) was added to piperidine-3-carboxylic acid (5.02 g, 38.87 mmol). The mixture was cooled with an ice bath and a solution of sodium nitrite (2.78 g, 40.29 mmol) in water (4 mL) was added. The reaction mixture was stirred at room temperature for 15 h. The mixture was extracted with dichloromethane (20 mL×3). The combined organics were washed with brine (2×), solids were removed by filtration and the filtrate was concentrated under reduced pressure to afford 1-nitrosopiperidine-3-carboxylic acid (4.5 g). MS (EI+) (M+) 158.

Step 2: (2,2,6,6-$^2$H$_4$)Piperidine-3-carboxylic acid

Aqueous sodium deuteroxide (1N, 35 mL) was added to 1-nitrosopiperidine-3-carboxylic acid (2.50 g, 15.32 mmol). The reaction mixture was heated at 70° C. for 48 h. The mixture was cooled to room temperature and the pH was adjusted to 3 using aqueous deuterated hydrochloric acid. The mixture was extracted with dichloromethane (30 mL×5), and the combined organics were dried over sodium sulfate/magnesium sulfate, filtered and concentrated under reduced pressure to give a solid (0.81 g) The aqueous layer was concentrated under reduced pressure and residual solvent was azeotropically distilled with methanol-d$_4$ (5 mL×2). The residue was heated at 50° C. in methanol-d$_4$ (15 mL) for 30 min and then cooled to room temperature. The insoluble solids were removed by filtration and the filtrate was evaporated and dried to give a solid (1.65 g). Both lots of isolated solids were combined, and a solution of sodium deuteroxide (0.5 M, 2.5 sodium deuteroxide in 45 mL of deuterated water (D$_2$O)) was added. The mixture was heated to 75° C. for 2 h, then was cooled to room temperature and then to 0° C. Aluminum-nickel alloy (11 g) was slowly added. The reaction mixture was stirred at room temperature for 3 days, then was heated at 35° C. for 3.5 h. The mixture was cooled to room temperature and the solids were removed by filtration. The solids were washed with deuterated water (D$_2$O) (3 mL×3). The pH of the filtrate was adjusted from 0 to 3 and the solution was concentrated under reduced pressure at 50° C. and then the resulting residue was dried under vacuum at 40° C. for 18 h. The dried residue was stirred at 40° C. in deuterated methanol-d$_4$ (12 mL). The mixture was cooled to room temperature and the solids were removed by filtration. The filtrate was concentrated under reduced pressure to afford (2,2,6,6-$^2$H$_4$)piperidine-3-carboxylic acid (1.65 g).

Step 3: Ethyl (2,2,6,6-$^2$H$_4$)piperidine-3-carboxylate

To a suspension of (2,2,6,6-$^2$H$_4$)piperidine-3-carboxylic acid (500 mg, 2.94 mmol) in ethanol at 0° C. was added thionyl chloride (0.6 mL, 8.84 mmol). The reaction mixture was stirred at room temperature for 3 h. Thionyl chloride was removed under reduced pressure to afford ethyl (2,2,6,6-$^2$H$_4$)piperidine-3-carboxylate (500 mg). The material was used without further purification.

Step 4: Ethyl 1-(6-amino-5-nitropyridin-2-yl)(2,2,6,6-$^2$H$_4$)piperidine-3-carboxylate To a solution of ethyl (2,2,6,6-$^2$H$_4$)piperidine-3-carboxylate (500 mg, 2.53 mmol) and triethylamine (1 mL, 7.59 mmol) in acetonitrile (15 mL) was added 6-chloro-3-nitropyridine (306 mg, 1.77 mmol). The reaction mixture was stirred for 3 h at 80° C. The mixture was partitioned between ethyl acetate and water. The organic layer was dried over sodium sulfate, filtered and concentrated under reduced pressure. The crude material was purified via column chromatography using 100-200 mesh silica gel (20-40% ethyl acetate in petroleum ether) to afford ethyl 1-(6-amino-5-nitropyridin-2-yl)(2,2,6,6-$^2$H$_4$)piperidine-3-carboxylate (500 mg).

Step 5: Ethyl 1-(5,6-diaminopyridin-2-yl)(2,2,6,6-$^2$H$_4$)piperidine-3-carboxylate To a suspension of 10% palladium-on-carbon (300 mg) in ethanol (20 mL) was added ethyl 1-(6-amino-5-nitropyridin-2-yl)(2,2,6,6-$^2$H$_4$)piperidine-3-carboxylate (500 mg, 1.67 mmol). The reaction mixture was submitted to an atmosphere of hydrogen for 4 h at room temperature. The mixture was filtered through Celite and was washed with ethanol to afford ethyl 1-(5,6-diaminopyridin-2-yl)(2,2,6,6-$^2$H$_4$)piperidine-3-carboxylate which was used without further purification.

Step 6: Ethyl 1-{2-[1-(4-chloro-1H-pyrazol-1-yl)cyclopropyl]-3H-imidazo[4,5-b]pyridin-5-yl}(2,2,6,6-$^2$H$_4$)piperidine-3-carboxylate To the filtrate containing ethyl 1-(5,6-diaminopyridin-2-yl)(2,2,6,6-$^2$H$_4$)piperidine-3-carboxylate from the previous step was added ethyl 1-(4-chloro-1H-pyrazol-1-yl)cyclopropanecarbimidate (Intermediate 57), acetic acid (0.5 mL) and sulfur (2 mg) at room temperature. The reaction mixture was heated at reflux for 18 h. The solvent was removed under reduced pressure and the residue was partitioned between ethyl acetate and water. The organic layer was dried over sodium sulfate, filtered and concentrated under reduced pressure. The crude material was purified via column chromatography using 100-200 mesh silica gel (30-70% ethyl acetate in petroleum ether) to afford ethyl 1-{2-[1-(4-chloro-1H-pyrazol-1-yl)cyclopropyl]-3H-imidazo[4,5-b]pyridin-5-yl}(2,2,6,6-$^2$H$_4$)piperidine-3-carboxylate (500 mg).

Step 7: 1-{2-[1-(4-Chloro-1H-pyrazol-1-yl)cyclopropyl]-3H-imidazo[4,5-b]pyridin-5-yl}(2,2,6,6-$^2$H$_4$)piperidine-3-carboxylic acid Lithium hydroxide (146 mg, 3.57 mmol) was added to a solution of ethyl 1-{2-[1-(4-chloro-1H-pyrazol-1-yl)cyclopropyl]-3H-imidazo[4,5-b]pyridin-5-yl}(2,2,6,6-$^2$H$_4$)piperidine-3-carboxylate (500 mg, 1.19 mmol) in a mixture of tetrahydrofuran:water (15 mL) at room temperature. The reaction mixture was stirred for 2 h. Tetrahydrofuran was removed under reduced pressure and the aqueous layer was diluted with aqueous hydrochloric acid (2N) until the pH was 6. The aqueous layer was extracted with ethyl acetate (2×). The combined organics were dried over sodium sulfate, filtered and concentrated under reduced pressure to afford 1-{2-[1-(4-chloro-1H-pyrazol-1-yl)cyclopropyl]-3H-imidazo[4,5-b]pyridin-5-yl}(2,2,6,6-$^2$H$_4$)piperidine-3-carboxylic acid (300 mg).

Step 8: [(R)-1-{2-[1-(4-Chloro-1H-pyrazol-1-yl)cyclopropyl]-3H-imidazo[4,5-b]pyridin-5-yl}(2,2,6,6-$^2$H$_4$)piperidin-3-yl](pyrrolidin-1-yl)methanone and [(S)-1-{2-[1-(4-chloro-1H-pyrazol-1-yl)cyclopropyl]-3H-imidazo[4,5-b]pyridin-5-yl}(2,2,6,6-$^2$H$_4$)piperidin-3-yl](pyrrolidin-1-yl)methanone Pyrrolidine (0.1 mL, 0.25 mmol) was added to a solution of 1-{2-[1-(4-chloro-1H-pyrazol-1-yl)cyclopropyl]-3H-imidazo[4,5-b]pyridin-5-yl}(2,2,6,6-$^2$H$_4$)piperidine-3-carboxylic acid (100 mg, 0.25 mmol), O-(7-azabenzotriazol-1-yl)-N,N,N',N',-tetramethyluronium hexafluorophosphate (HATU) (116 mg, 0.30 mmol) and diisopropylethylamine (0.14 mL, 0.76 mmol) in dichloromethane (10 mL) at room temperature. The reaction mixture was stirred for 2 h. The mixture was partitioned between dichloromethane and water. The organic layer was dried over sodium sulfate, filtered and concentrated under reduced pressure. The crude material was purified via preparative TLC followed by chiral separation to afford two enantiomers. Enantiomer 1 (Example 190, 37 mg, 33% yield): $^1$H NMR (500 MHz, CDCl$_3$) δ 1.57-1.61 (m, 1H), 1.75-2.04 (m, 11H), 2.62-2.64 (m, 0.5H*), 3.41-3.48 (m, 3H), 3.56-3.61 (m, 1H), 6.64 (d, 1H), 7.58 (s, 1H), 7.64 (s, 1H), 7.68 (d, 1H); Chiral HPLC retention time 13.727 min (Method: Column: CHIRAL PAK IA 4.6×250 mm, 5 µM; Mobile Phase D: 0.1% DEA in n-Hexane; Mobile Phase C: ethanol; Isocratic: 75:25; Flow Rate: 1.0 mL/min). Enantiomer 2 (Example 191, 35 mg, 31% yield): $^1$H NMR (500 MHz, CDCl$_3$) δ 1.57-1.62 (m, 1H), 1.76-2.05 (m, 11H), 2.64-2.66 (m, 0.5H*), 3.41-3.49 (m, 3H), 3.57-3.61 (m, 1H), 6.65 (d, 1H), 7.59 (s, 1H), 7.64 (s, 1H), 7.70 (d, 1H); Chiral HPLC retention time 11.905 min (Method: Same as for enantiomer 1). *For both enantiomers, $^1$H NMR integration indicates partial incorporation of deuterium at this position.

Examples 192 and 193

((R)-1-(2-((R)-1-(4-Fluoro-1H-pyrazol-1-yl)ethyl)-3H-imidazo[4,5-b]pyridin-5-yl)piperidin-3-yl)(pyrrolidin-1-yl)methanone and ((R)-1-(2-((S)-1-(4-chloro-1H-pyrazol-1-yl)ethyl)-3H-imidazo[4,5-b]pyridin-5-yl)piperidin-3-yl)(pyrrolidin-1-yl)methanone

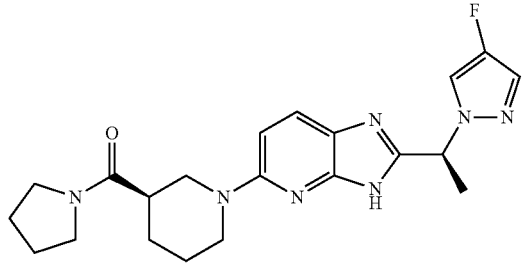

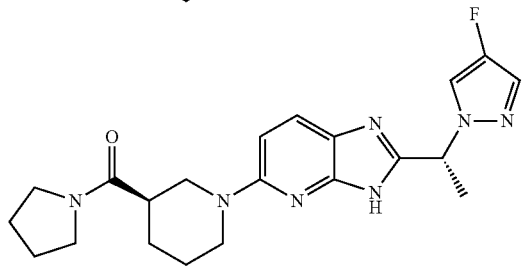

To a solution of (R)-(1-(5,6-diaminopyridin-2-yl)piperidin-3-yl)(pyrrolidin-1-yl)methanone dihydrochloride (1.02 g, 2.8 mmol) in ethanol (14.0 mL) was added acetic acid (3.21 mL, 56 mmol) followed by the addition of a solution of ethyl 2-(4-fluoro-1H-pyrazol-1-yl)propanimidate (Intermediate 59) via cannula. Triethylamine (2.34 mL) was added. The mixture was purged with nitrogen and heated to 90° C. for 18 h. The solvent was removed under reduced pressure and the residue was partitioned between a saturated aqueous solution of ammonium chloride (100 mL) and dichloromethane (100 mL). The layers were separated and the aqueous layer was again extracted with dichloromethane (200 mL). The combined organic layers were washed sequentially with a saturated aqueous solution of sodium bicarbonate (200 mL) and brine (300 mL). The organic layer was then dried over sodium sulfate, filtered and concentrated under reduced pressure. The crude material was purified via flash chromatography (0-25% methanol in dichloromethane) to afford a diastereomeric mixture of the title compounds (125 mg, 11% yield). Diastereomers were separated by preparative chiral HPLC. Diastereomer 1 (Example 192, 34 mg): Chiral HPLC retention time 7.575 min; $^1$H NMR (500 MHz, CDCl$_3$) δ 1.52-1.63 (m, 1H), 1.73-1.78 (m, 1H), 1.79-1.97 (m, 6H), 1.99 (d, 3H), 2.58-2.67 (m, 1H), 2.86-2.94 (m, 1H), 3.00-3.08 (m, 1H), 3.39-3.51 (m, 3H), 3.53-3.61 (m, 1H), 4.21 (d, 1H), 4.46 (d, 1H), 5.64 (q, 1H), 6.64 (d, 1H), 7.41 (d, 1H), 7.45 (d, 1H), 7.75 (d, 1H); MS (ES+) (M+H) 412.3. Diastereomer 2 (Example 193, 36 mg): Chiral HPLC retention time 8.903 min. (Chiral Method: Column: Phenomenex Kinetex C18 50×3.0 mm 2.6 μM; Gradient: Mobile Phase A: 0.1% formic acid in water; Mobile Phase B: 0.1% formic acid in methanol; Time (min)/% B: 0.00/0, 0.30/0, 3.00/100; 3.70/100, 3.71/0; 4.00/0; Flow: 1.0 mL/min); $^1$H NMR (500 MHz, CDCl$_3$) δ 1.52-1.64 (m, 1H), 1.74-1.81 (m, 1H), 1.81-1.98 (m, 6H), 2.00 (d, 3H), 2.59-2.69 (m, 1H), 2.87-2.95 (m, 1H), 3.01-3.10 (m, 1H), 3.40-3.51 (m, 3H), 3.55-3.62 (m, 1H), 4.23 (d, 1H), 4.45 (d, 1H), 5.65 (q, 1H), 6.65 (d, 1H), 7.43 (d, 1H), 7.47 (d, 1H), 7.75 (d, 1H); MS (ES+) (M+H) 412.3.

Example 194

(R)-(1-(2-(1-(4-Methoxy-1H-pyrazol-1-yl)cyclopropyl)-3H-imidazo[4,5-b]pyridin-5-yl)piperidin-3-yl)(pyrrolidin-1-yl)methanone

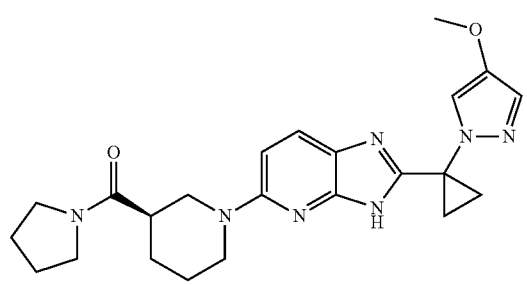

To a solution of crude ethyl 1-(4-methoxy-1H-pyrazol-1-yl)cyclopropanecarbimidate (79.5 mg, 0.380 mmol) in ethanol (1.5 mL) was added (R)-(1-(5,6-diaminopyridin-2-yl)piperidin-3-yl)(pyrrolidin-1-yl)methanone dihydrochloride (151 mg, 0.417 mmol) followed by glacial acetic acid (0.435 mL, 7.59 mmol). The mixture was degassed with nitrogen, and then triethylamine (0.318 mL, 2.28 mmol) was added. The reaction mixture was heated at 100° C. for 20 min and then at 85° C. for 18 h. The mixture was poured into a saturated aqueous solution of ammonium chloride (40 mL) and extracted with dichloromethane (50 mL×3). The combined organics were washed with a saturated aqueous solution of sodium bicarbonate. The aqueous layer was extracted with dichloromethane (40 mL×2). The combined organics were dried over sodium sulfate, filtered and concentrated under reduced pressure. The crude material was purified via HPLC to afford the title compound. MS (ESI+) (M+H) 436.2; HPLC retention time 1.85 min (Method A).

Example 195

(R)-(1-(2-(1-(2-cyclopropyloxazol-4-yl)cyclopropyl)-3H-imidazo[4,5-b]pyridin-5-yl)piperidin-3-yl)(pyrrolidin-1-yl)methanone

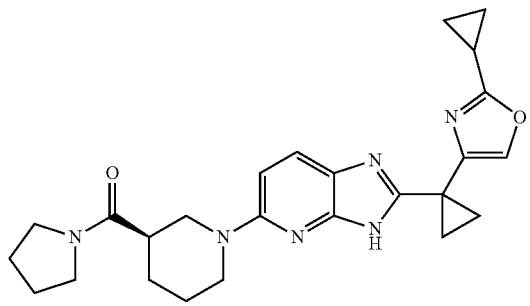 [SMILES: O=C([C@@H]1CCCN(c2ccc3nc(C4(c5coc(C6CC6)n5)CC4)[nH]c3n2)C1)N1CCCC1]

The title compound was prepared by a method analogous to the one used for Example 160, but using 1-(2-cyclopropyloxazol-4-yl)cyclopropanecarboxylic acid as the starting material to afford an enantio-enriched mixture that was further purified via chiral HPLC to afford the title compound. MS (ES+) (M+H) 447.3; LCMS retention time 2.062 min (Method N1).

Examples 196-A and 197

((R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone and ((R)-1-(2-((R)-1-(4-chloro-1H-pyrazol-1-yl)ethyl)-3H-imidazo[4,5-b]pyridin-5-yl)piperidin-3-yl)(pyrrolidin-1-yl)methanone

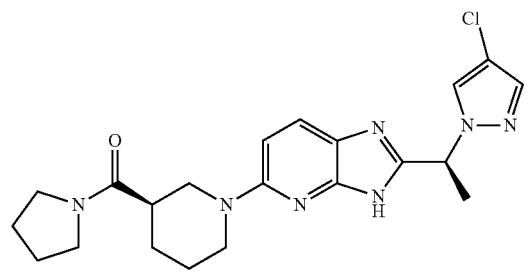

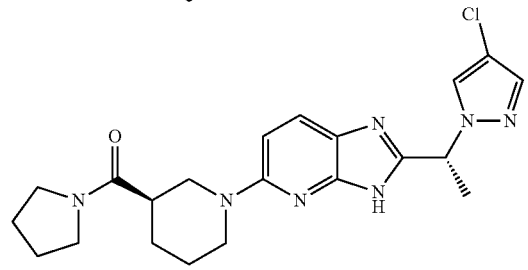

To a suspension of (R)-(1-(5,6-diaminopyridin-2-yl)piperidin-3-yl)(pyrrolidin-1-yl)methanone dihydrochloride (3.65 g, 10.1 mmol) in ethanol (15 mL) was added a solution of ethyl 2-(4-chloro-1H-pyrazol-1-yl)propanimidate crude mixture (Intermediate 60) followed by acetic acid (11.5 mL, 201 mmol) at room temperature. Triethylamine (8.4 mL, 60.4 mmol) was added dropwise and the reaction mixture was stirred at 100° C. for 1 h. The solvent was removed under reduced pressure and the residue was partitioned between ethyl acetate (250 mL) and a saturated aqueous solution of ammonium chloride (200 mL). The aqueous layer was extracted again with ethyl acetate (200 mL). The combined organics were washed sequentially with a saturated aqueous solution of sodium bicarbonate (150 mL) and brine (150 mL), and then were dried over sodium sulfate, filtered and concentrated under reduced pressure. The crude material was purified via flash chromatography (0-5% methanol in ethyl acetate) to afford a diastereomeric mixture of the title compounds. The mixture was purified via preparative chiral HPLC (Method: Column: Phenomenex Cellulose-2 250×21.2 mm 5μ; Mobile phase A: Heptane; Mobile phase B: Ethanol; Gradient: Initial—5% B, Time (min)/% B: 0.00/5, 1.50/5, 10.0/100, 11.0/100, 12.5/5; Flow rate: 28 mL/min) to afford two diastereomers. Each diastereomer was further purified via flash chromatography (0-40% of a 20% methanol in dichloromethane solution to dichloromethane) to afford title compounds as single diastereomers. Diastereomer 1: ((R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone (Example 196-A, 1.05 g, 24% yield): $^1$H NMR (500 MHz, CDCl$_3$) δ 1.54-1.66 (m, 1H), 1.75-2.00 (m, 7H), 2.04 (d, 3H), 2.59-2.70 (m, 1H), 2.89-3.00 (m, 1H), 3.08 (dd, 1H), 3.42-3.54 (m, 3H), 3.58-3.63 (m, 1H), 4.23 (br d, 1H), 4.46 (br d, 1H), 5.76 (q, 1H), 6.68 (d, 1H), 7.53 (s, 1H), 7.60 (s, 1H), 7.78 (d, 1H); MS (ES+) (M+H) 428.3; Chiral HPLC retention time 7.587 min (Method: Column: Phenomenex Kinetex C18 50×3.0 mm 2.6μ; Mobile phase A: 0.1% formic acid in water; Mobile phase B: 0.1% formic acid in methanol; Gradient: Initial—0% B, Time (min)/% B: 0.00/0, 0.30/0, 3.00/100, 3.70/100, 3.71/0, 4.00/0; Flow rate: 1.0 mL/min). Diastereomer 2: ((R)-1-(2-((R)-1-(4-chloro-1H-pyrazol-1-yl)ethyl)-3H-imidazo[4,5-b]pyridin-5-yl)piperidin-3-yl)(pyrrolidin-1-yl)methanone (Example 197, 0.84 g, 19% yield): $^1$H NMR (500 MHz, CDCl$_3$) δ 1.55-1.63 (m, 1H), 1.76-1.99 (m, 7H), 2.03 (d, 3H), 2.62-2.68 (m, 1H), 2.91-2.96 (m, 1H), 3.04-3.09 (m, 1H), 3.43-3.50 (m, 3H), 3.58-3.62 (m, 1H), 4.23 (br d, 1H), 4.47 (br d, 1H), 5.74 (q, 1H), 6.66 (d, 1H), 7.52 (s, 1H), 7.60 (s, 1H), 7.78 (d, 1H); MS (ES+) (M+H) 428.3; Chiral HPLC retention time 9.306 min (Method: same as that of Example 196-A).

Example 196-B ((R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone hydrochloride

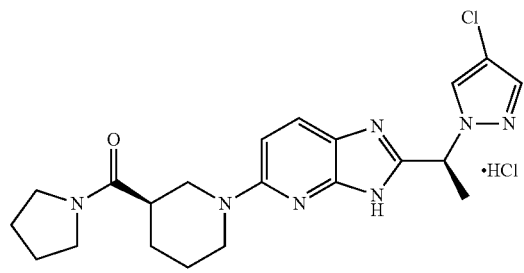

To a solution of Example 196-A (457 mg, 1.07 mmol) in THF (1.5 mL) was added freshly prepared 1N HCl in dioxane/THF (1:3, 1.07 mL). The mixture was treated with 8 mg of ((R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone hydrochloride as seed crystals, and stirred at room temperature for 4 h. Precipitated solid material was broken up with a spatula, sonicated for ca. 30 sec, and stirred for an additional 3 h at room temperature. The reaction mixture was diluted with additional THF (4.5 mL) and the white, creamy homogenous suspension was stirred for 17 h at room temperature. The suspension was filtered, and the collected solids were washed with THF (20 mL). The filter cake was dried under reduced pressure overnight at 40° C. to afford the title compound as an off-white solid (380 mg, 76%). Examination under a polarized light microscope shows fully crystalline material. $^1$H NMR (500 MHz, CD$_3$OD) δ 1.60-1.68 (m, 1H), 1.77-1.93 (m, 4H), 1.98-2.05 (m, 3H), 2.04 (d, 3H), 2.74-2.80 (m, 1H), 3.11-3.23 (m, 2H), 3.40-3.46 (m, 2H), 3.51-3.56 (m, 1H), 3.61-3.66 (m, 1H), 4.33 (br d, 1H), 4.48 (br d, 1H), 6.04 (q, 1H), 7.14 (d, 1H), 7.58 (s, 1H), 7.91 (d, 1H), 8.00 (s, 1H); MS (ES+) (M+H) 428.3; Anal. Calculated for C$_{21}$H$_{26}$ClN$_7$O.HCl: C, 52.29; H, 6.06; N, 20.32; Cl, 14.70. Found: C, 52.06; H, 6.09; N, 19.97; Cl, 14.66.

The absolute stereo configurations of Example 196-A and 197 were confirmed by the comparison of chiral HPLC retention time between Example 196-A and 197 synthesized through the method above and ((R)-1-(2-((R)-1-(4-chloro-1H-pyrazol-1-yl)ethyl)-3H-imidazo[4,5-b]pyridin-5-yl)piperidin-3-yl)(pyrrolidin-1-yl)methanone (Example 197) synthesized by the following procedure starting from (R)-2-(4-Chloro-1H-pyrazol-1-yl)propanoic acid (Intermediate 68):

Step 1: (R)-tert-Butyl 2-amino-6-(3-(pyrrolidine-1-carbonyl)piperidin-1-yl)pyridin-3-ylcarbamate

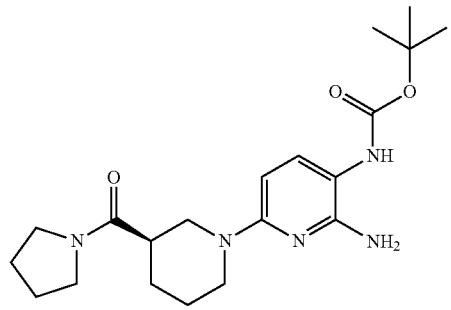 [SMILES: CC(C)(C)OC(=O)Nc1ccc(N2CCC[C@@H](C(=O)N3CCCC3)C2)nc1N]

Di-tert-butyl dicarbonate (327 mg, 1.50 mmol) and (R)-(1-(5,6-diaminopyridin-2-yl)piperidin-3-yl)(pyrrolidin-1-yl)methanone dihydrochloride salt (362, 1.00 mmol) were suspended in tetrahydrofuran (5 mL) at room temperature under nitrogen. A saturated aqueous solution of sodium bicarbonate (2.5 mL) was added and the reaction mixture was stirred at room temperature for 1.5 h. The mixture was diluted with ethyl acetate (20 mL), and then washed sequentially with water and brine. The organics were dried over sodium sulfate, filtered and concentrated under reduced pressure. The crude material was purified via flash chromatography (50-100% ethyl acetate in heptanes) to afford (R)-tert-butyl 2-amino-6-(3-(pyrrolidine-1-carbonyl)piperidin-1-yl)pyridin-3-ylcarbamate (295 mg, 76%). $^1$H NMR (500 MHz, CDCl$_3$) δ 1.49 (s, 9H), 1.52-1.58 (m, 1H), 1.70-1.72 (m, 1H), 1.78-2.00 (m, 6H), 2.56-2.63 (m, 1H). 2.84 (dt, 1H), 2.94 (dd, 1H), 3.42-3.49 (m, 3H), 3.60-3.64 (m, 1H), 4.13-4.17 (m, 1H), 4.37-

4.40 (m, 1H), 4.41 (br s, 1H), 5.88 (br s, 1H), 6.04 (d, 1H), 7.20 (d, 1H); MS (ES+) (M+H) 390.4.

Step 2: tert-Butyl 2-((R)-2-(4-chloro-1H-pyrazol-1-yl)propanamido)-6-((R)-3-(pyrrolidine-1-carbonyl)piperidin-1-yl)pyridin-3-ylcarbamate

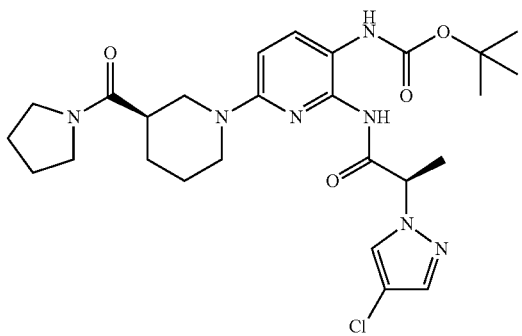 [SMILES: C[C@H](C(=O)Nc1nc(N2CCC[C@@H](C(=O)N3CCCC3)C2)ccc1NC(=O)OC(C)(C)C)n1cc(Cl)cn1]

(R)-2-(4-Chloro-1H-pyrazol-1-yl)propanoic acid (105 mg, 0.60 mmol) and (R)-tert-butyl 2-amino-6-(3-(pyrrolidine-1-carbonyl)piperidin-1-yl)pyridin-3-ylcarbamate (195 mg, 0.50 mmol) were dissolved in ethyl acetate (0.5 mL) with pyridine (0.20 mL, 2.5 mmol) at room temperature. The mixture was cooled to 0° C. 1-Propanephosphonic acid cyclic anhydride (0.375 mL, 50% solution in ethyl acetate, 1.25 mmol) was added while stirring at 0° C. The resulting mixture was stirred for 15 min, and then warmed to room temperature. After stirring for 1.5 h at room temperature, the mixture was quenched with an aqueous solution of hydrochloric acid (0.5 M, 1 mL). The mixture was partitioned between ethyl acetate (10 mL) and water (5 mL). The organic layer was washed sequentially with water (5 mL), a saturated aqueous solution of sodium bicarbonate (5 mL), and brine (5 mL). The organics were dried over magnesium sulfate, filtered, and concentrated. The residue was dried under reduced pressure to afford tert-butyl 2-((R)-2-(4-chloro-1H-pyrazol-1-yl)propanamido)-6-((R)-3-(pyrrolidine-1-carbonyl)piperidin-1-yl)pyridin-3-ylcarbamate (268 mg, 98% yield). $^1$H NMR (500 MHz, CDCl$_3$) δ 1.48 (s, 9H), 1.48-1.55 (m, 1H), 1.73-1.76 (m, 1H), 1.80-2.05 (m, 6H), 1.86 (d, 3H), 2.53-2.59 (m, 1H), 2.84-2.90 (m, 1H), 2.96-3.01 (m, 1H), 3.43-3.51 (m, 3H), 3.55-3.60 (m, 1H), 4.12 (br d, 1H), 4.33 (br d, 1H), 5.10 (br s, 1H), 6.56 (d, 1H), 7.30 (br s, 1H), 7.57 (s, 1H), 7.61 (s, 1H), 7.76 (br s, 1H), 8.58 (br s, 1H); MS (ES+) (M+H) 546.3; Chiral HPLC retention time 4.61 min (Method: Chiralpak AS-H 0.46×25 cm; Mobile Phase: CO$_2$/methanol; Flow: 2.5 mL/min); 97.1% de.

Step 3: ((R)-1-(2-((R)-1-(4-Chloro-1H-pyrazol-1-yl)ethyl)-3H-imidazo[4,5-b]pyridin-5-yl)piperidin-3-yl)(pyrrolidin-1-yl)methanone tert-Butyl 2-((R)-2-(4-chloro-1H-pyrazol-1-yl)propanamido)-6-((R)-3-(pyrrolidine-1-carbonyl)piperidin-1-yl)pyridin-3-ylcarbamate (55 mg, 0.10 mmol) was dissolved in acetic acid (0.5 mL). Methanesulfonic acid (32 μL, 0.50 mmol) was added while stirring at room temperature. The solution was stirred at room temperature for 1 h. Sodium acetate (49 mg, 0.60 mmol) was added while vortexing for 1 min. The resulting suspension was stirred for 1 h and then quenched with water (2.5 mL). The resulting mixture was extracted with ethyl acetate (5 mL×3). The combined organics were washed sequentially with a saturated aqueous solution of sodium bicarbonate (10 mL×2), water (10 mL) and brine (5 mL). The organics were dried over magnesium sulfate, filtered and concentrated. The residue was transferred to a flask containing dichloromethane and the mixture was concentrated to give a clear glass. The glass was dried under vacuum to afford the title compound (39.8 mg, 93% yield). $^1$H NMR (500 MHz, CDCl$_3$) δ 1.54-1.62 (m, 1H), 1.76-2.05 (m, 7H), 2.02 (d, 1H), 2.62-2.66 (m, 1H), 2.89-2.95 (m, 1H), 3.03-3.08 (m, 1H), 3.42-3.49 (m, 3H), 3.57-3.61 (m, 1H), 4.23 (br d, 1H), 4.46 (br d, 1H), 5.70 (q, 1H), 6.65 (d, 1H), 7.51 (s, 1H), 7.57 (s, 1H), 7.76 (br s, 1H), 10.22 (br s, 1H); MS (ES+) (M+H) 428.3; Chiral HPLC retention time 13.08 min (Method: Chiralpak AD-H 0.46×15 cm; Mobile Phase: 1.5 min 10% isopropyl alcohol/heptanes, 1.5-10 min 10% isopropyl alcohol/heptanes to 90% isopropyl alcohol/heptanes, 10-18 min 90% isopropyl alcohol/heptanes; Flow: 0.4 mL/min); 98.3% de.

Examples 198 and 199

((R)-1-(8-((S)-1-(4-Chloro-1H-pyrazol-1-yl)ethyl)-9H-purin-2-yl)piperidin-3-yl)(pyrrolidin-1-yl)methanone and ((R)-1-(8-((R)-1-(4-chloro-1H-pyrazol-1-yl)ethyl)-9H-purin-2-yl)piperidin-3-yl)(pyrrolidin-1-yl)methanone

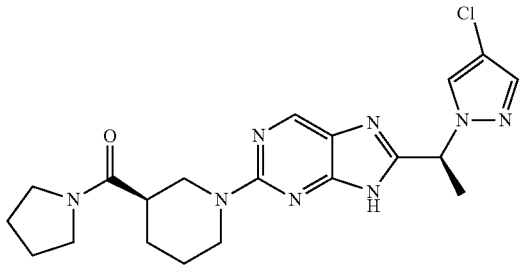

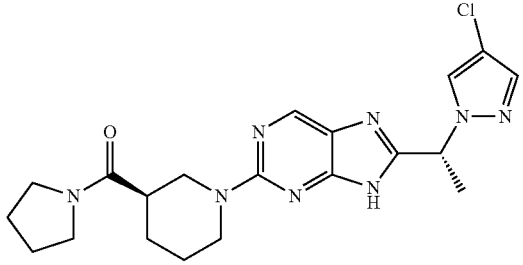

Into a flask were added (R)-(1-(5,6-diaminopyridin-2-yl)piperidin-3-yl)(pyrrolidin-1-yl)methanone dihydrochloride salt (1.24 g, 3.416 mmol), ethanol (4 mL), acetic acid (3.9 mL, 68.3 mmol), and ethyl 2-(4-chloro-1H-pyrazol-1-yl)propanimidate crude reaction mixture (758 mg, 3.76 mmol, 1.1 eq. in 8 mL of ethanol). The mixture was purged with nitrogen, and then triethylamine (2.9 mL) was added. The reaction mixture was heated at 100° C. for 16 h. The solvent was removed under reduced pressure and the residue was partitioned between a saturated aqueous solution of ammonium chloride (20 mL) and dichloromethane (20 mL). The aqueous layer was extracted with dichloromethane (20 mL). The combined organics were washed with a saturated aqueous solution of sodium bicarbonate (20 mL). The base wash was extracted again with dichloromethane (20 mL). The combined organics were washed with brine (20 mL), dried over sodium sulfate, filtered and concentrated under reduced pressure. The crude material was purified via flash chromatography (0-5% methanol in dichloromethane) to afford a diastereomeric mixture of the title compounds (0.68 g, 46% yield). The mixture was purified via preparative chiral HPLC to afford two diastereomers. Diastereomer 1 (Example 198, 189 mg, 13% yield): $^1$H NMR (500 MHz, CD$_3$OD) δ 1.50-1.59 (m, 1H), 1.75-2.03 (m, 10H), 2.63-2.70 (m, 1H), 2.90-2.96 (m, 1H), 3.01 (dd, 1H), 3.42 (t, 2H), 3.49-3.54 (m, 1H), 3.68-3.72 (m, 1H), 4.77-4.83 (m, 2H), 5.72-5.77 (m, 1H), 7.50 (s, 1H), 7.86 (s, 1H), 8.58 (s, 1H); MS (ES+) (M+H) 429.2; Chiral HPLC retention time 3.03 min (Method: Chiralcel OJ-H 10×250; Mobile Phase 80/20 CO$_2$/Methanol; Flow: 10.0 mL/min). Diastereomer 2 (Example 199, 197 mg, 14% yield): $^1$H NMR (500 MHz, CD$_3$OD) δ 1.53-1.60 (m, 1H), 1.75-2.03 (m, 10H), 2.65-2.71 (m, 1H), 2.91-2.97 (m, 1H), 3.01 (dd, 1H), 3.43 (t, 2H), 3.50-3.55 (m, 1H), 3.70-3.74 (m, 1H), 4.78-4.84 (m, 2H), 5.75 (q, 1H), 7.50 (s, 1H), 7.87 (s, 1H), 8.58 (s, 1H); MS (ES+) (M+H) 429.2; Chiral HPLC retention time 3.77 min (Method: Same as diastereomer 1).

Example 200

(R)-(1-(2-(1-(4-Chloro-1H-pyrazol-1-yl)cyclopropyl)-3H-imidazo[4,5-b]pyridin-5-yl)piperidin-3-yl)(3,3-difluoroazetidin-1-yl)methanone

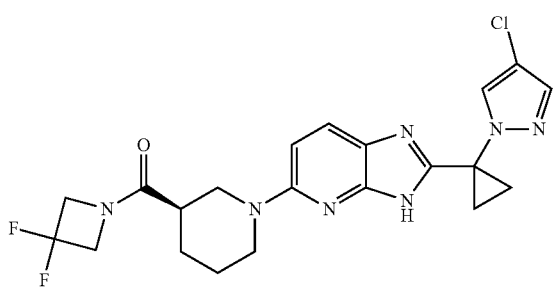 [SMILES: O=C([C@@H]1CCCN(c2ccc3nc(C4(n5cc(Cl)cn5)CC4)[nH]c3n2)C1)N1CC(F)(F)C1]

Step 1: (R)-Ethyl 1-(6-amino-5-nitropyridin-2-yl)piperidine-3-carboxylate

To a solution of (R)-ethyl piperidine-3-carboxylate hydrochloride salt (1.2 g, 6.21 mmol) in acetonitrile (20 mL) was added triethylamine (2.61 mL, 18.64 mmol). The mixture was stirred for 10 min at room temperature. 6-Chloro-3-nitropyridin-2-amine (753 mg, 4.31 mmol) was added and the reaction mixture was stirred at 80° C. for 3 h. The mixture was cooled to room temperature and water was added. The mixture was extracted with ethyl acetate. The organics were dried over sodium sulfate, filtered and concentrated under reduced pressure to afford (R)-ethyl 1-(6-amino-5-nitropyridin-2-yl)piperidine-3-carboxylate (1.1 g). MS (ES+APCI) (M+H) 295.2.

Step 2: (R)-Ethyl 1-(5,6-diaminopyridin-2-yl)piperidine-3-carboxylate

A solution of (R)-ethyl 1-(6-amino-5-nitropyridin-2-yl)piperidine-3-carboxylate (1.0 g, 6.60 mmol) in ethanol (30 mL) was added to a suspension of 10% palladium-on-carbon (500 mg) in ethanol at room temperature. The reaction mixture was hydrogenated for 4 h using a balloon filled with hydrogen gas. The mixture was filtered through a pad of Celite and the filtrate was used without further purification.

Step 3: Ethyl 1-(4-chloro-1H-pyrazol-1-yl)cyclopropanecarbimidate hydrochloride salt Dry hydrogen chloride gas was bubbled through a solution of 1-(4-chloro-1H-pyrazol-1-yl)cyclopropanecarbonitrile (1.2 g, 0.75 mmol) in ethanol (10 mL) at 0° C. for 15 min. The mixture was then stirred at room temperature for 1 h. The solvent was removed under reduced pressure to afford ethyl 1-(4-chloro-1H-pyrazol-1-yl)cyclopropanecarbimidate. The crude material was used without further purification.

Step 4: (R)-Ethyl 1-(2-(1-(4-chloro-1H-pyrazol-1-yl)cyclopropyl)-3H-imidazo[4,5-b]pyridin-5-yl)piperidine-3-carboxylate Acetic acid (2.5 mL, 41.66 mmol) was added to a solution of (R)-ethyl 1-(5,6-diaminopyridin-2-yl)piperidine-3-carboxylate, prepared in step 2, followed by ethyl 1-(4-chloro-1H-pyrazol-1-yl)cyclopropanecarbimidate hydrochloride salt, prepared in step 3). The mixture was heated at reflux for 18 h, then cooled and concentrated under reduced pressure. The residue was partitioned between ethyl acetate and water. The organics were dried over sodium sulfate, filtered and concentrated under reduced pressure. The crude material was purified via column chromatography (100-200 silica gel, 25-70% ethyl acetate in petroleum ether) to afford (R)-ethyl 1-(2-(1-(4-chloro-1H-pyrazol-1-yl)cyclopropyl)-3H-imidazo[4,5-b]pyridin-5-yl)piperidine-3-carboxylate (900 mg). MS (ES+) (M+H) 415.2; LCMS retention time 2.506 min (Method N1).

Step 5: (R)-1-(2-(1-(4-Chloro-1H-pyrazol-1-yl)cyclopropyl)-3H-imidazo[4,5-b]pyridin-5-yl)piperidine-3-carboxylic acid Lithium hydroxide (500 mg, 10.20 mmol) was added to a solution of (R)-ethyl 1-(2-(1-(4-chloro-1H-pyrazol-1-yl)cyclopropyl)-3H-imidazo[4,5-b]pyridin-5-yl)piperidine-3-carboxylate (900 mg, 2.17 mmol) in tetrahydrofuran/water (1:1, 10 mL) at room temperature. The reaction mixture was stirred for 3 h. The solvent was removed under reduced pressure and to the residue was added water. The pH of the mixture was adjusted to 6 using an aqueous solution of hydrochloric acid (1N). The mixture was extracted with ethyl acetate and the organics were dried over sodium sulfate, filtered and concentrated to afford (R)-1-(2-(1-(4-chloro-1H-pyrazol-1-yl)cyclopropyl)-3H-imidazo[4,5-b]pyridin-5-yl)piperidine-3-carboxylic acid (700 mg). MS (ES+) (M+H) 387.1; LCMS retention time 1.971 min (Method N1).

Step 6: (R)-(1-(2-(1-(4-Chloro-1H-pyrazol-1-yl)cyclopropyl)-3H-imidazo[4,5-b]pyridin-5-yl)piperidin-3-yl)(3,3-difluoroazetidin-1-yl)methanone 3,3-Difluoroazetidine (33 mg, 0.2 mmol) was added to a mixture of (R)-1-(2-(1-(4-chloro-1H-pyrazol-1-yl)cyclopropyl)-3H-imidazo[4,5-b]pyridin-5-yl)piperidine-3-carboxylic acid (100 mg, 0.25 mmol), diisopropylethylamine (0.1 mL, 0.77 mmol) and O-(7-azabenzotriazol-1-yl)-N,N,N',N',-tetramethyluronium hexafluorophosphate (HATU) (118 mg, 0.31 mmol) in anhydrous dichloromethane (5 mL) at room temperature. The reaction mixture was stirred for 2 h, then partitioned between dichloromethane and water. The organics were dried over sodium sulfate, filtered and concentrated under reduced pressure. The crude material was purified via preparative TLC to afford the title compound (40 mg, 43% yield). MS (ES+) (M+H) 462.2; LCMS retention time 2.163 minutes (Method N1). $^1$H NMR (300 MHz, CDCl$_3$) δ 1.17-1.39 (m, 1H), 1.71-2.24 (m, 7H), 2.35-2.58 (m, 1H), 2.83-3.13 (m, 2H), 4.04-4.78 (m, 6H), 6.63 (d, 1H), 7.62 (s, 2H), 7.69-7.80 (m, 1H), 9.15 (br s, 1H).

Example 201

((R)-1-(2-(1-(4-Chloro-1H-pyrazol-1-yl)cyclopropyl)-3H-imidazo[4,5-b]pyridin-5-yl)piperidin-3-yl)((R)-2-methylpyrrolidin-1-yl)methanone

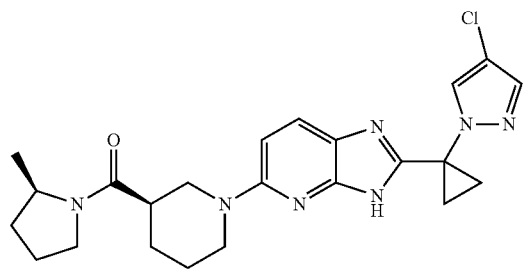 [SMILES: C[C@@H]1CCCN1C(=O)[C@@H]1CCCN(c2ccc3nc(C4(n5cc(Cl)cn5)CC4)[nH]c3n2)C1]

The title compound was prepared by a method analogous to the one used for Example 200, but using (R)-2-methylpyrrolidine for Step 5. MS (ES+) (M+H) 454.3; LCMS retention time 2.233 min (Method N1).

Example 202

((R)-1-(2-(1-(4-Chloro-1H-pyrazol-1-yl)cyclopropyl)-3H-imidazo[4,5-b]pyridin-5-yl)piperidin-3-yl)((S)-2-methylpyrrolidin-1-yl)methanone

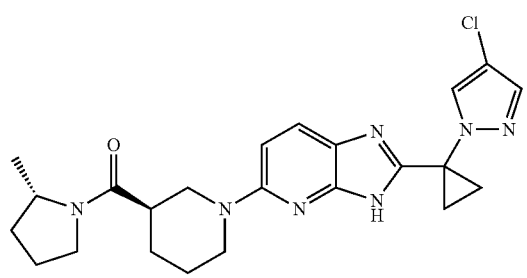 [SMILES: C[C@H]1CCCN1C(=O)[C@@H]1CCCN(c2ccc3nc(C4(n5cc(Cl)cn5)CC4)[nH]c3n2)C1]

The title compound was prepared by a method analogous to the one used for Example 200, but using (S)-2-methylpyrrolidine for Step 5. MS (ES+) (M+H) 454.2; LCMS retention time 2.228 min (Method N1).

Example 203

(R)-(1-(2-(1-(Pyrazin-2-yl)cyclopropyl)-3H-imidazo[4,5-b]pyridin-5-yl)piperidin-3-yl)(pyrrolidin-1-yl)methanone

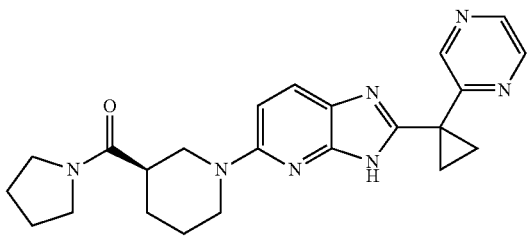 [SMILES: O=C([C@@H]1CCCN(c2ccc3nc(C4(c5cnccn5)CC4)[nH]c3n2)C1)N1CCCC1]

Step 1: (R)—N-(2-Amino-6-(3-(pyrrolidine-1-carbonyl)piperidin-1-yl)pyridin-3-yl)-1-(pyrazin-2-yl)cyclopropanecarboxamide To a solution of 1-(pyrazin-2-yl)cyclopropanecarboxylic acid (0.11 g, 0.669 mmol) in anhydrous dichloromethane (15 mL) was added O-(7-azabenzotriazol-1-yl)-N,N,N',N',-tetramethyluronium hexafluorophosphate (HATU) (0.3 g, 0.803 mmol) and diisopropylethylamine (0.35 mL, 2 mmol) at room temperature. The mixture was stirred for 10 min and then (R)-(1-(5,6-diaminopyridin-2-yl)piperidin-3-yl)(pyrrolidin-1-yl)methanone dihydrochloride (0.29 g, 0.803 mmol) was added. The reaction mixture was stirred for 30 min. The solvent was removed under reduced pressure and the residue was partitioned between ethyl acetate and water. The organic layer was dried over sodium sulfate, filtered and concentrated under reduced pressure. The crude material was purified via column chromatography (100-200 mesh silica gel, 0-5% methanol in dichloromethane) to afford (R)—N-(2-amino-6-(3-(pyrrolidine-1-carbonyl)piperidin-1-yl)pyridin-3-yl)-1-(pyrazin-2-yl)cyclopropanecarboxamide (100 mg). MS (ES+ APCI) (M+H) 436.1.

Step 2: (R)-(1-(2-(1-(Pyrazin-2-yl)cyclopropyl)-3H-imidazo[4,5-b]pyridin-5-yl)piperidin-3-yl)(pyrrolidin-1-yl)methanone To a solution of (R)—N-(2-amino-6-(3-(pyrrolidine-1-carbonyl)piperidin-1-yl)pyridin-3-yl)-1-(pyrazin-2-yl)cyclopropanecarboxamide (0.1 g, 0.22 mmol) in anhydrous methanol (0.072 mL, 1.78 mmol) was added sodium methoxide (54 mg, 1.1 mmol) and isobutanol (3.5 mL). The reaction mixture was heated at 100° C. for 18 h. The solvent was removed under reduced pressure and the crude material was purified via preparative TLC to afford the title compound (19 mg). MS (ES+APCI) (M+H) 418.1; LCMS retention time 4.792 min (Method R1).

Example 204

(R)-(1-(2-(1-(Pyrimidin-2-yl)cyclopropyl)-3H-imidazo[4,5-b]pyridin-5-yl)piperidin-3-yl)(pyrrolidin-1-yl)methanone

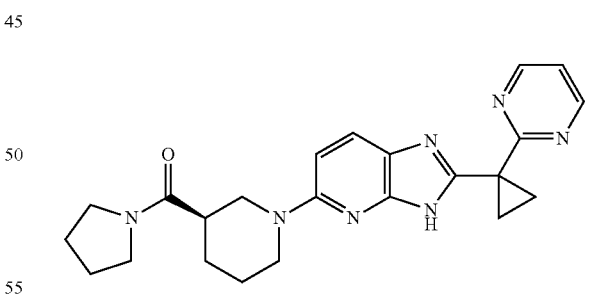

Step 1: (R)-(1-(5,6-Diaminopyridin-2-yl)piperidin-3-yl)(pyrrolidin-1-yl)methanone To a solution of (R)-(1-(6-amino-5-nitropyridin-2-yl)piperidin-3-yl)(pyrrolidin-1-yl)methanone (0.2 g, 0.62 mmol) in ethanol (10 mL) was added 10% palladium-on-carbon (200 mg). The mixture was hydrogenated at room temperature for 3 h using a balloon filled with hydrogen gas. The mixture was filtered through Celite and the filtrate was used for the next step without further purification.

Step 2: (R)-(1-(2-(1-(Pyrimidin-2-yl)cyclopropyl)-3H-imidazo[4,5-b]pyridin-5-yl)piperidin-3-yl)(pyrrolidin-1-yl)methanone 1-(Pyrimidin-2-yl)cyclopropanecarbaldehyde (0.11 g, 0.747 mmol), sulfur (40 mg, 1.24 mmol), and acetic acid (0.6 mL) were added to a solution of (R)-(1-(5,6-diaminopyridin-2-yl)piperidin-3-yl)(pyrrolidin-1-yl)methanone, prepared during the previous step, in ethanol. The reaction mixture was heated to 80° C. for 18 h. The solvent was removed under reduced pressure and the crude material was purified via preparative HPLC to afford the title compound (8 mg). MS (ES+APCI) (M+H) 418.2; LCMS retention time 3.273 min (Method S1).

Example 205

(R)-Azetidin-1-yl(1-(2-(1-(4-chloro-1H-pyrazol-1-yl)cyclopropyl)-3H-imidazo[4,5-b]pyridin-5-yl)piperidin-3-yl)methanone

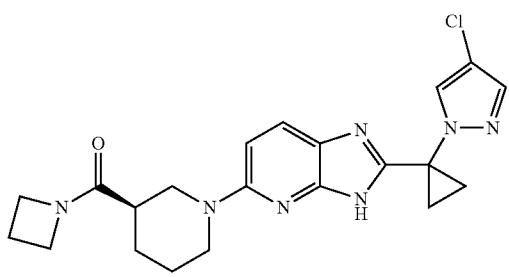 [SMILES: O=C([C@@H]1CCCN(c2ccc3nc(C4(n5cc(Cl)cn5)CC4)[nH]c3n2)C1)N1CCC1]

Step 1: (R)-Ethyl 1-(6-amino-5-nitropyridin-2-yl)piperidine-3-carboxylate

6-Chloro-3-nitropyridin-2-amine (1.25 g, 7.22 mmol) was added to a solution of (R)-ethyl piperidine-3-carboxylate (2.0 g, 10.32 mmol) and triethylamine (2.87 mL, 20.65 mmol) in acetonitrile (25 mL) at room temperature. The reaction mixture was stirred for 3 h at 80° C., then was cooled and was partitioned between ethyl acetate and water. The organics were dried over sodium sulfate, filtered and concentrated under reduced pressure. The crude material was purified via column chromatography (100-200 mesh silica gel, 0-25% ethyl acetate in petroleum ether) to afford (R)-ethyl 1-(6-amino-5-nitropyridin-2-yl)piperidine-3-carboxylate (2 g). MS (ES+APCI) (M+H) 295.0; LCMS retention time 5.246 min (Method R1).

Step 2: (R)-Ethyl 1-(5,6-diaminopyridin-2-yl)piperidine-3-carboxylate dihydrochloride A solution of (R)-ethyl 1-(6-amino-5-nitropyridin-2-yl)piperidine-3-carboxylate (400 mg, 1.36 mmol) in ethanol (10 mL) was added to a suspension of 10% palladium-on-carbon (200 mg) in ethanol at room temperature. The mixture was hydrogenated for 4 h, then was filtered through a pad of Celite and washed with ethanol. A solution of hydrogen chloride in ether was added to the filtrate to precipitate (R)-ethyl 1-(5,6-diaminopyridin-2-yl)piperidine-3-carboxylate dihydrochloride. MS (ES+) (M+H) 265.1404.

Step 3: (R)-Ethyl 1-(2-(1-(4-chloro-1H-pyrazol-1-yl)cyclopropyl)-3H-imidazo[4,5-b]pyridin-5-yl)piperidine-3-carboxylate Acetic acid (0.5 mL, 8.88 mmol), ethyl 1-(4-chloro-1H-pyrazol-1-yl)cyclopropanecarbimidate (445 mg, 1.78 mmol), a catalytic amount of sulfur, and triethylamine (0.8 mL, 5.92 mmol) were added to a suspension of (R)-ethyl 1-(5,6-diaminopyridin-2-yl)piperidine-3-carboxylate dihydrochloride (500 mg, 1.48 mmol) in ethanol (25 mL) at room temperature. The reaction mixture was heated at reflux for 18 h, then was concentrated under reduced pressure. The resulting residue was partitioned between ethyl acetate and water. The organic layer was dried over sodium sulfate, filtered and concentrated under reduced pressure. The crude material was purified via column chromatography (100-200 mesh silica gel, 25-70% ethyl acetate in petroleum ether) to afford (R)-ethyl 1-(2-(1-(4-chloro-1H-pyrazol-1-yl)cyclopropyl)-3H-imidazo[4,5-b]pyridin-5-yl)piperidine-3-carboxylate (300 mg). MS (ES+) (M+H) 415.2.

Step 4: (R)-1-(2-(1-(4-Chloro-1H-pyrazol-1-yl)cyclopropyl)-3H-imidazo[4,5-b]pyridin-5-yl)piperidine-3-carboxylic acid Lithium hydroxide (27.6 mg, 1.1 mmol) was added to a solution of (R)-ethyl 1-(2-(1-(4-chloro-1H-pyrazol-1-yl)cyclopropyl)-3H-imidazo[4,5-b]pyridin-5-yl)piperidine-3-carboxylate (300 mg, 0.77 mmol) in tetrahydrofuran/water (1:1, 6 mL) at room temperature. The reaction mixture was stirred at room temperature for 3 h. The solvent was removed under reduced pressure. The residue was dissolved in water and the pH was adjusted to 6 using aqueous hydrogen chloride (1N). The mixture was extracted with ethyl acetate. The organics were dried over sodium sulfate, filtered and concentrated under reduced pressure to afford (R)-1-(2-(1-(4-chloro-1H-pyrazol-1-yl)cyclopropyl)-3H-imidazo[4,5-b]pyridin-5-yl)piperidine-3-carboxylic acid (200 mg). MS (ES+APCI) (M+H) 387.1; LCMS retention time 3.432 min (Method S1).

Step 5: (R)-Azetidin-1-yl(1-(2-(1-(4-chloro-1H-pyrazol-1-yl)cyclopropyl)-3H-imidazo[4,5-b]pyridin-5-yl)piperidin-3-yl)methanone Azetidine (0.1 mL, 1.42 mmol) was added to a solution of (R)-1-(2-(1-(4-chloro-1H-pyrazol-1-yl)cyclopropyl)-3H-imidazo[4,5-b]pyridin-5-yl)piperidine-3-carboxylic acid (50 mg, 1.29 mmol), O-(7-azabenzotriazol-1-yl)-N,N,N',N',-tetramethyluronium hexafluorophosphate (HATU) (49 mg, 1.29 mmol) and diisopropylethylamine (0.1 mL, 3.88 mmol) in anhydrous dichloromethane (5 mL). The reaction mixture was stirred at room temperature for 2 h, then was partitioned between dichloromethane and water. The organics were dried over sodium sulfate, filtered and concentrated under reduced pressure. The crude material was purified via preparative TLC to afford the title compound (35 mg). MS (ES+APCI) (M+H) 426.1; LCMS retention time 3.440 min (Method S1).

Example 206

(R)-(1-(2-(1-(4-Chloro-1H-pyrazol-1-yl)cyclopropyl)-3H-imidazo[4,5-b]pyridin-5-yl)piperidin-3-yl)(morpholino)methanone

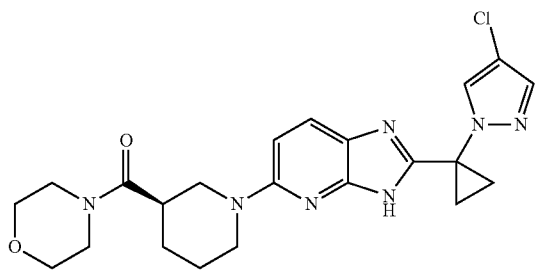 [SMILES: O=C([C@@H]1CCCN(c2ccc3nc(C4(n5cc(Cl)cn5)CC4)[nH]c3n2)C1)N1CCOCC1]

The title compound was prepared by a method analogous to the one used for Example 205, but using morpholine for Step 5. MS (ES+APCI) (M+H) 456.1; LCMS retention time: 3.502 minutes (Method S1).

Examples 207 and 208

((3R,4R)-1-(8-(1-(1H-Pyrazol-1-yl)cyclopropyl)-9H-purin-2-yl)-4-methylpiperidin-3-yl)(pyrrolidin-1-yl)methanone and ((3S,4S)-1-(8-(1-(1H-pyrazol-1-yl)cyclopropyl)-9H-purin-2-yl)-4-methylpiperidin-3-yl)(pyrrolidin-1-yl)methanone

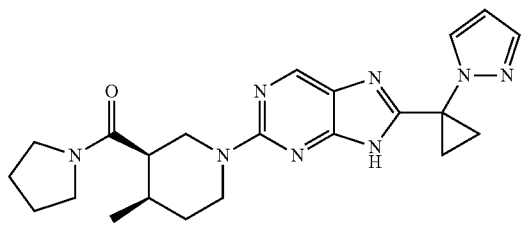

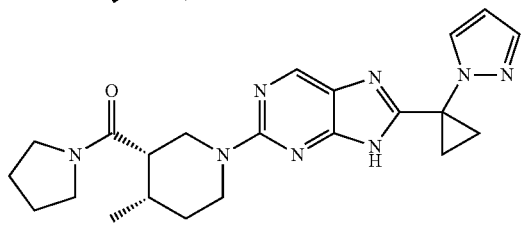

Step 1: 4-Methylpiperidine-3-carboxylic acid

4-Methylnicotinic acid (5.0 g, 36.46 mmol) in acetic acid (40 mL) was added to a wet solution of platinum oxide (500 mg) under a nitrogen atmosphere. The suspension was hydrogenated under a hydrogen atmosphere (200 PSI) at room temperature for 18 h. The mixture was filtered through a pad of Celite under nitrogen and the filtrate was concentrated under reduced pressure to afford 4-methylpiperidine-3-carboxylic acid (6.0 g). The material was used without further purification.

Step 2: Ethyl 4-methylpiperidine-3-carboxylate

Hydrogen chloride gas was bubbled into a solution of 4-methylpiperidine-3-carboxylic acid (6.0 g, 41.90 mmol) in ethanol (150 mL) and acetic acid (30 mL) at 0° C. under a nitrogen atmosphere. The reaction mixture was heated at reflux for 48 h, then was cooled and was partitioned between water and ethyl acetate. The organic layer was dried over sodium sulfate, filtered and concentrated under reduced pressure to afford ethyl 4-methylpiperidine-3-carboxylate (5.0 g). The material was used without further purification.

Step 3: cis-1-tert-Butyl 3-ethyl 4-methylpiperidine-1,3-dicarboxylate

Di-tert-butyl dicarbonate (3.26 g, 15.20 mmol) was added to a solution of ethyl 4-methylpiperidine-3-carboxylate (2.0 g, 11.68 mmol) and triethylamine (3.9 mL, 28.05 mmol) in anhydrous dichloromethane (50 mL) at 0° C. The reaction mixture was stirred at room temperature for 18 h. The mixture partitioned between dichloromethane and water. The organics were dried over sodium sulfate, filtered and concentrated under reduced pressure to afford a mixture of the cis and trans diastereomers of 1-tert-butyl 3-ethyl 4-methylpiperidine-1,3-dicarboxylate (3.0 g). The crude material was purified via column chromatography (5-10% ethyl acetate in petroleum ether) to afford cis-1-tert-butyl 3-ethyl 4-methylpiperidine-1,3-dicarboxylate (2.5 g).

Step 4: cis-1-(tert-Butoxycarbonyl)-4-methylpiperidine-3-carboxylic acid

An aqueous solution of sodium hydroxide (2N, 20 mL) was added to a solution of cis-1-tert-butyl 3-ethyl 4-methylpiperidine-1,3-dicarboxylate (2.5 g, 9.21 mmol) in methanol (20 mL) at 0° C. The reaction mixture was stirred at 0° C. for 2 h. The solvent was removed under reduced pressure and the residue was partitioned between water and ethyl acetate. The aqueous layer was acidified to pH 2 using aqueous hydrochloric acid (1N) and was extracted with ethyl acetate. The combined organics were dried over sodium sulfate, filtered and concentrated under reduced pressure to afford cis-1-(tert-butoxycarbonyl)-4-methylpiperidine-3-carboxylic acid (2.2 g).

Step 5: cis-tert-Butyl 4-methyl-3-(pyrrolidine-1-carbonyl)piperidine-1-carboxylate O-(7-Azabenzotriazol-1-yl)-N,N,N',N',-tetramethyluronium hexafluorophosphate (HATU) (4.12 g, 10.85 mmol), diisopropylethylamine (2.33 g, 18.08 mmol) and pyrrolidine (782 mg, 10.85 mmol) were added to a solution of cis-1-(tert-butoxycarbonyl)-4-methylpiperidine-3-carboxylic acid (2.2 g, 9.04 mmol) in anhydrous dichloromethane (30 mL) at room temperature. The reaction mixture was stirred at room temperature for 4 h. The mixture was quenched with water and was extracted with dichloromethane. The organics were dried over sodium sulfate, filtered and concentrated under reduced pressure to afford cis-tert-butyl 4-methyl-3-(pyrrolidine-1-carbonyl)piperidine-1-carboxylate (2.6 g).

Step 6: cis-(4-Methyl piperidin-3-yl)(pyrrolidin-1-yl)methanone

Saturated ethereal hydrogen chloride (40 mL) was added to a solution of cis-tert-butyl 4-methyl-3-(pyrrolidine-1-carbonyl)piperidine-1-carboxylate (2.6 g, 8.78 mmol) in ether (20 mL) at 0° C. The reaction mixture was stirred at room temperature for 2 h. The solvent was removed under reduced pressure to afford cis-(4-methylpiperidin-3-yl)(pyrrolidin-1-yl)methanone (1.7 g).

Step 7: cis-(1-(4-Amino-5-nitropyrimidin-2-yl)-4-methylpiperidin-3-yl)(pyrrolidin-1-yl)methanone To a solution of cis-(4-methylpiperidin-3-yl)(pyrrolidin-1-yl)methanone (1.7 g, 8.60 mmol) in acetonitrile (20 mL) was added triethylamine (3.65 mL, 26.02 mmol). The mixture was stirred for 10 min at room temperature. Then 2-chloro-5-nitropyrimidin-4-amine (1.19 g, 6.9 mmol) was added and the reaction mixture was stirred at 80° C. for 3 h. The mixture was cooled to room temperature and stirred for 1 h. Ice cold water was added and the mixture was extracted with ethyl acetate. The organics were dried over sodium sulfate, filtered and concentrated under reduced pressure. The crude material was purified via column chromatography (40-100% ethyl acetate in petroleum ether) to afford cis-(1-(4-amino-5-nitropyrimidin-2-yl)-4-methylpiperidin-3-yl)(pyrrolidin-1-yl)methanone (1.6 g). MS (ES+) (M+H) 335.3.

Step 8: cis-(1-(4,5-Diaminopyrimidin-2-yl)-4-methylpiperidin-3-yl)(pyrrolidin-1-yl)methanone A suspension of 10% palladium-on-carbon (350 mg) in ethanol was added to a solution of cis-(1-(4-amino-5-nitropyrimidin-2-yl)-4-methylpiperidin-3-yl)(pyrrolidin-1-yl)methanone (600 mg, 1.79 mmol) in ethanol (20 mL) at room temperature under nitrogen. The mixture was hydrogenated using a balloon filled with hydrogen gas at room temperature for 2 h. The suspension was filtered through a pad of Celite under a nitrogen atmosphere and the filtrate was used for the next without further purification.

Step 9: ((3R,4R)-1-(8-(1-(1H-Pyrazol-1-yl)cyclopropyl)-9H-purin-2-yl)-4-methylpiperidin-3-yl)(pyrrolidin-1-yl)methanone and ((3S,4S)-1-(8-(1-(1H-pyrazol-1-yl)cyclopropyl)-9H-purin-2-yl)-4-methylpiperidin-3-yl)(pyrrolidin-1-yl)methanone 2-(1H-Pyrazol-1-yl)acetonitrile (385 mg, 2.15 mmol), sulfur (60 mg) and acetic acid (1.7 mL, 28.73 mmol) were added to the filtrate containing (1-(4,5-diaminopyrimidin-2-yl)-4-methylpiperidin-3-yl)(pyrrolidin-1-yl)methanone, prepared in the previous step. The reaction mixture was heated at reflux for 16 h. The solvent was removed under reduced pressure and the residue was partitioned between ethyl acetate and water. The organics were dried over sodium sulfate, filtered and concentrated under reduced pressure. The crude material was purified via column chromatography (100-200 mesh silica gel, 0-4% methanol in ethyl acetate) to afford a racemic mixture of the title compounds. Enantiomers were separated by chiral HPLC. Enantiomer 1 (Example 207, 75 mg): Chiral HPLC retention time: 7.222 min (Method: Column: CHIRALPAK IA 4.6×250 mM, 5 µM; Mobile Phase D: 0.1% DEA in n-Hexane; Mobile Phase: Isopropyl alcohol (IPA); Isocratic 70:30; Flow: 1.0 mL/min). MS (ES+) (M+H) 421.3; LCMS retention time: 1.978 min (Method N1). Enantiomer 2 (Example 208, 78 mg): Chiral HPLC retention time: 8.745 min (Method: Same as enantiomer 1); MS (ES+) (M+H) 421.3; LCMS retention time: 1.966 min (Method N1).

Example 209

(R)-(1-(8-(1-(4-Fluoro-1H-pyrazol-1-yl)cyclopropyl)-9H-purin-2-yl)piperidin-3-yl)(pyrrolidin-1-yl)methanone

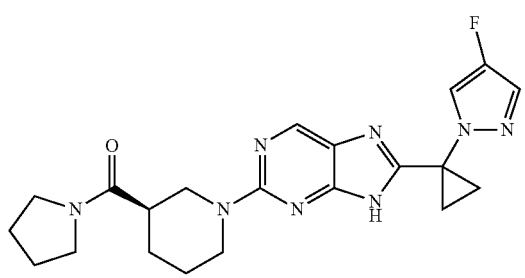 [SMILES: O=C([C@@H]1CCCN(c2ncc3nc(C4(n5cc(F)cn5)CC4)[nH]c3n2)C1)N1CCCC1]

Step 1: (R)-(1-(4,5-Diaminopyrimidin-2-yl)piperidin-3-yl)(pyrrolidin-1-yl)methanone A suspension of 10% palladium-on-carbon (100 mg) in ethanol was added to a solution of (R)-(1-(4-amino-5-nitropyrimidin-2-yl)piperidin-3-yl)(pyrrolidin-1-yl)methanone (200 mg, 0.62 mmol) in ethanol (10 mL) at room temperature under a nitrogen atmosphere. The mixture was hydrogenated using a balloon filled with hydrogen gas at room temperature for 2 h. The suspension was filtered through a pad of Celite under a nitrogen atmosphere and the filtrate was used for the next step without further purification.

Step 2: (R)-(1-(8-(1-(4-Fluoro-1H-pyrazol-1-yl)cyclopropyl)-9H-purin-2-yl)piperidin-3-yl)(pyrrolidin-1-yl)methanone Ethyl 1-(4-fluoro-1H-pyrazol-1-yl)cyclopropanecarbimidate (148 mg, 0.75 mmol) and acetic acid (0.8 mL) were added to the filtrate containing (R)-(1-(4,5-diaminopyrimidin-2-yl)piperidin-3-yl)(pyrrolidin-1-yl)methanone, prepared in the previous step. The reaction mixture was heated at reflux for 16 h. The solvent was removed under reduced pressure and the residue was partitioned between ethyl acetate and water. The organics were dried over sodium sulfate, filtered and concentrated under reduced pressure. The crude material was purified via column chromatography (100-200 mesh silica gel, 0-4% methanol in ethyl acetate) to afford the title compound. MS (ES+APCI) (M+H) 425.2; LCMS retention time: 3.545 min (Method V1).

Example 210

(R)-(1-(8-(1-(1H-Pyrazol-1-yl)cyclopropyl)-9H-purin-2-yl)piperidin-3-yl)(pyrrolidin-1-yl)methanone

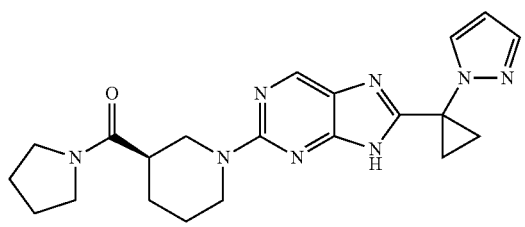

The title compound was prepared by a method analogous to the one used for Example 209, but using ethyl 1-(1H-pyrazol-1-yl)cyclopropanecarbimidate for Step 2. MS (ES+APCI) (M+H) 407.1; LCMS retention time: 3.997 minutes (Method T1).

Example 211

(R)-5-(3-(Pyrrolidine-1-carbonyl)piperidin-1-yl)-N-(6-(trifluoromethyl)pyridin-3-yl)-3H-imidazo[4,5-b]pyridine-2-carboxamide

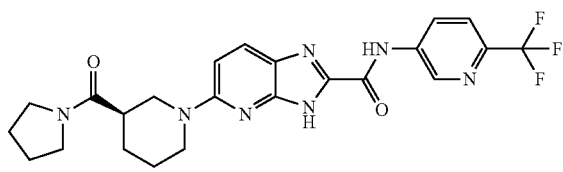 [SMILES: O=C(Nc1ccc(C(F)(F)F)nc1)c1nc2ccc(N3CCC[C@@H](C(=O)N4CCCC4)C3)nc2[nH]1]

Step 1: (R)-(1-(5,6-Diaminopyridin-2-yl)piperidin-3-yl)(pyrrolidin-1-yl)methanone dihydrochloride To a solution of (R)-(1-(6-amino-5-nitropyridin-2-yl)piperidin-3-yl)(pyrrolidin-1-yl)methanone (4.0 g) in ethanol (40 mL) was added 10% palladium-on-carbon. The mixture was stirred at room temperature for 16 h under a hydrogen atmosphere using a balloon filled with hydrogen gas. The mixture was filtered through Celite and hydrogen chloride in 1,4-dioxane (4N, 15 mL) was added to the filtrate. The solvent was removed under reduced pressure to afford (R)-(1-(5,6-diaminopyridin-2-yl)piperidin-3-yl)(pyrrolidin-1-yl)methanone dihydrochloride which was used for the next step without further purification.

Step 2: (R)-Pyrrolidin-1-yl(1-(2-(trichloromethyl)-3H-imidazo[4,5-b]pyridin-5-yl)piperidin-3-yl)methanone Formic acid (2.8 mL) and trifluoroethanol (61 mL) were added to (R)-(1-(5,6-diaminopyridin-2-yl)piperidin-3-yl)(pyrrolidin-1-yl)methanone dihydrochloride. Methyl 2,2,2-trichloroacetimidate (1.65 mL) was added and the reaction mixture was stirred at 60° C. for 3 h. The mixture was used for the next step without further workup or purification.

Step 3: (R)-5-(3-(Pyrrolidine-1-carbonyl)piperidin-1-yl)-N-(6-(trifluoromethyl)pyridin-3-yl)-3H-imidazo[4,5-b]pyridine-2-carboxamide Into a vial was added 6-(trifluoromethyl)pyridin-3-amine (2.0 eq, 300 μmol) followed by (R)-pyrrolidin-1-yl(1-(2-(trichloromethyl)-3H-imidazo[4,5-b]pyridin-5-yl)piperidin-3-yl)methanone (815 μL, 150 μmol, 0.2 M solution prepared in the previous step). The reaction mixture was shaken at 60° C. for 16 h. The solvent was removed under reduced pressure and the residue was partitioned between water and ethyl acetate (2 mL). The organics were concentrated under reduced pressure and the crude material was purified via HPLC to afford the title compound. MS (ES+) (M+H) 488.2; UPLC retention time: 1.490 minutes (Method P).

Example 212

(R)-(1-(2-(1-(4-Chloro-1H-pyrazol-1-yl)cyclopropyl)-3H-imidazo[4,5-b]pyridin-5-yl)piperidin-3-yl)(2,5-dihydro-1H-pyrrol-1-yl)methanone

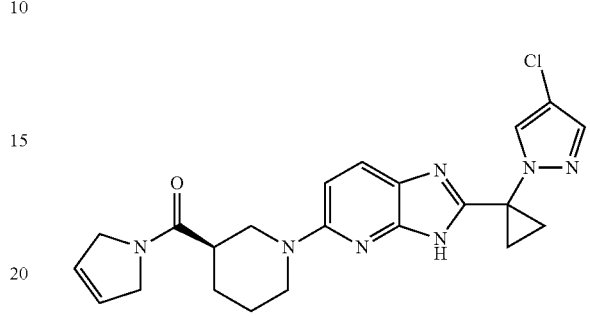

Step 1: (R)-Ethyl 1-(6-amino-5-nitropyridin-2-yl)piperidine-3-carboxylate

6-Chloro-3-nitropyridin-2-amine (0.8 g, 4.64 mmol) was added to a solution of (R)-ethyl piperidine-3-carboxylate (1.0 g, 5.16 mmol) and triethylamine (1.56 g, 15.48 mmol) in acetonitrile (20 mL) at room temperature. The reaction mixture was stirred at 80° C. for 3 h. The mixture was partitioned between ethyl acetate and water. The organics were dried over sodium sulfate and concentrated under reduced pressure. The crude material was purified via column chromatography (100-200 mesh silica gel, 10-50% ethyl acetate in petroleum ether) to afford (R)-ethyl 1-(6-amino-5-nitropyridin-2-yl)piperidine-3-carboxylate (1.0 g). MS (ES+) (M+H) 295.22.

Step 2: (R)-Ethyl 1-(5,6-diaminopyridin-2-yl)piperidine-3-carboxylate

To a solution of (R)-ethyl 1-(6-amino-5-nitropyridin-2-yl)piperidine-3-carboxylate (1.0 g, 3.39 mmol) in ethanol (30 mL) was added a suspension of 10% palladium-on-carbon (500 mg) in ethanol at room temperature. The mixture was hydrogenated using a balloon filled with hydrogen gas for 4 h. The mixture was filtered through a pad of Celite and the filtrate was used for the next step without further purification.

Step 3: (R)-Ethyl 1-(2-(1-(4-chloro-1H-pyrazol-1-yl)cyclopropyl)-3H-imidazo[4,5-b]pyridin-5-yl)piperidine-3-carboxylate Acetic acid (4.3 g, 67.2 mmol) was added to a solution of (R)-ethyl 1-(5,6-diaminopyridin-2-yl)piperidine-3-carboxylate (890 mg, 3.36 mmol), ethyl 1-(4-chloro-1H-pyrazol-1-yl)cyclopropanecarbimidate (445 mg, 1.78 mmol) and triethylamine (0.8 mL, 5.92 mmol) in ethanol (25 mL) at room temperature under a nitrogen atmosphere. The mixture was heated at reflux for 16 h, then was concentrated under reduced pressure. The resulting residue was partitioned between ethyl acetate and water. The organics were dried over sodium sulfate and concentrated under reduced pressure. The crude material was purified via column chromatography (100-200 mesh silica gel, 20-60% ethyl acetate in petroleum ether) to afford (R)-ethyl 1-(2-(1-(4-chloro-1H-pyrazol-1-yl)cyclopropyl)-3H-imidazo[4,5-b]pyridin-5-yl)piperidine-3-carboxylate (600 mg). MS (ES+) (M+H) 415.2859.

Step 4: (R)-1-(2-(1-(4-Chloro-1H-pyrazol-1-yl)cyclopropyl)-3H-imidazo[4,5-b]pyridin-5-yl)piperidine-3-carboxylic acid Lithium hydroxide (182.4 mg, 4.32 mmol) was added to a solution of (R)-ethyl 1-(2-(1-(4-chloro-1H-pyrazol-1-yl)cyclopropyl)-3H-imidazo[4,5-b]pyridin-5-yl)piperidine-3-carboxylate (600 mg, 1.44 mmol) in tetrahydrofuran:water (1:1, 20 mL) at room temperature. The reaction mixture was stirred for 3 h. The solvent was removed under reduced pressure and the resulting residue was dissolved in water. The pH of the solution was adjusted to 2 using aqueous hydrochloric acid (1N), and the product was extracted with ethyl acetate. The organics were dried over sodium sulfate and concentrated under reduced pressure to afford (R)-1-(2-(1-(4-chloro-1H-pyrazol-1-yl)cyclopropyl)-3H-imidazo[4,5-b]pyridin-5-yl)piperidine-3-carboxylic acid (500 mg). The material was used for the next step without further purification. MS (ES+) (M+H) 387.3246.

Step 5: (R)-(1-(2-(1-(4-Chloro-1H-pyrazol-1-yl)cyclopropyl)-3H-imidazo[4,5-b]pyridin-5-yl)piperidin-3-yl)(2,5-dihydro-1H-pyrrol-1-yl)methanone 3-Pyrroline (98.5 mg, 1.41 mmol) was added to a solution of (R)-1-(2-(1-(4-chloro-1H-pyrazol-1-yl)cyclopropyl)-3H-imidazo[4,5-b]pyridin-5-yl)piperidine-3-carboxylic acid (500 mg, 1.29 mmol), O-(7-azabenzotriazol-1-yl)-N,N,N',N',-tetramethyluronium hexafluorophosphate (HATU) (541 mg, 1.41 mmol) and diisopropylethylamine (334.7 mg, 2.58 mmol) in anhydrous dichloromethane (20 mL). The reaction mixture was stirred at room temperature for 2 h. The mixture was partitioned between dichloromethane and water. The organic layer was dried over sodium sulfate and concentrated under reduced pressure. The crude material was triturated with pentane to afford the title compound (510 mg). MS (ES+) (M+H) 438.0; LCMS retention time 4.935 min (Method R1).

Example 213

(R)-(4-(8-(1-(4-Chloro-1H-pyrazol-1-yl)cyclopropyl)-9H-purin-2-yl)morpholin-2-yl)(pyrrolidin-1-yl)methanone

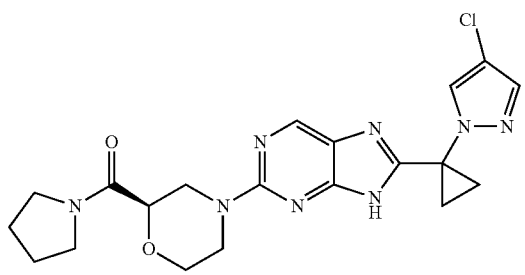

Step 1: (R)-tert-Butyl 2-(pyrrolidine-1-carbonyl)morpholine-4-carboxylate

O-(7-Azabenzotriazol-1-yl)-N,N,N',N',-tetramethyluronium hexafluorophosphate (HATU) (1.47 g, 4.3 mmol) was added to a solution of (R)-4-(tert-butoxycarbonyl)morpholine-2-carboxylic acid (1 g, 4.3 mmol) and diisopropylethylamine (1.11 g, 8.6 mmol) in anhydrous dichloromethane (20 mL) at room temperature. Pyrrolidine (0.45 mL, 5.62 mmol) was added and the reaction mixture was stirred at room temperature for 2 h. The mixture was partitioned between water and dichloromethane. The organics were dried over sodium sulfate and concentrated under reduced pressure and the resulting residue was purified via column chromatography (100-200 mesh silica gel, 0-0.5% methanol in dichloromethane) to afford (R)-tert-butyl 2-(pyrrolidine-1-carbonyl)morpholine-4-carboxylate (0.62 g).

Step 2: (R)-Morpholin-2-yl(pyrrolidin-1-yl)methanone hydrochloride

A solution of hydrogen chloride in 1,4-dioxane (20 mL) was added to a solution of (R)-tert-butyl 2-(pyrrolidine-1-carbonyl)morpholine-4-carboxylate (0.62 g, 2.1 mmol) in \ 1,4-dioxane (5 mL). The reaction mixture was stirred at room temperature for 3 h. The solvent was removed under reduced pressure and the resulting crude material was triturated with diethyl ether to afford (R)-morpholin-2-yl(pyrrolidin-1-yl)methanone hydrochloride (0.4 g).

Step 3: (R)-(4-(4-Amino-5-nitropyrimidin-2-yl)morpholin-2-yl)(pyrrolidin-1-yl)methanone 2-Chloro-5-nitropyrimidin-4-amine (106 mg, 0.612 mmol) was added to a solution of (R)-morpholin-2-yl(pyrrolidin-1-yl)methanone hydrochloride (0.15 g, 0.68 mmol) and triethylamine (0.28 mL, 2.04 mmol) in acetonitrile (10 mL) at room temperature. The reaction mixture was heated at 80° C. for 1 h, then was cooled to room temperature and stirred for 12 h. The solvent was removed under reduced pressure and the resulting crude material was triturated with diethyl ether to afford (R)-(4-(4-amino-5-nitropyrimidin-2-yl)morpholin-2-yl)(pyrrolidin-1-yl)methanone (0.11 g). MS (ES+APCI) (M+H) 323.1; LCMS retention time: 3.518 min (Method S1).

Step 4: (R)-(4-(4,5-Diaminopyrimidin-2-yl)morpholin-2-yl)(pyrrolidin-1-yl)methanone To a solution of (R)-(4-(4-amino-5-nitropyrimidin-2-yl)morpholin-2-yl)(pyrrolidin-1-yl)methanone (0.15 g, 0.46 mmol) in ethanol (15 mL) was added 10% palladium-on-carbon (300 mg). The mixture was hydrogenated using a balloon filled with hydrogen gas at room temperature for 3 h. The mixture was filtered through a pad of Celite and the filtrate was used for the next step without further purification.

Step 5: (R)-(4-(8-(1-(4-Chloro-1H-pyrazol-1-yl)cyclopropyl)-9H-purin-2-yl)morpholin-2-yl)(pyrrolidin-1-yl)methanone Ethyl 1-(4-chloro-1H-pyrazol-1-yl)cyclopropanecarbimidate (0.13 g, 0.46 mmol), sulfur (15 mg), acetic acid (0.53 mL, 9.3 mmol) and triethylamine (0.39 mL, 2.79 mmol) were added to the filtrate containing (R)-(4-(4,5-diaminopyrimidin-2-yl)morpholin-2-yl)(pyrrolidin-1-yl)methanone, prepared in the previous step, at room temperature. The reaction mixture was heated to 100° C. for 24 h. The solvent was removed under reduced pressure and the resulting crude material was purified via preparative TLC to afford the title compound (13 mg). MS (ES+APCI) (M+H) 443.0; LCMS retention time 4.485 min (Method T1).

Example 214

(R)-(1-(2-(1-(2H-1,2,3-Triazol-2-yl)cyclopropyl)-3H-imidazo[4,5-b]pyridin-5-yl)piperidin-3-yl)(pyrrolidin-1-yl)methanone

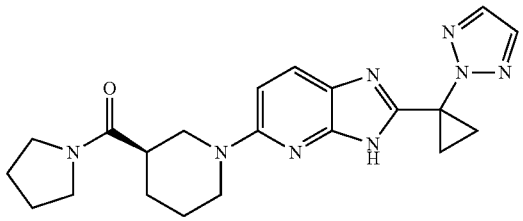 [SMILES: O=C([C@@H]1CCCN(c2ccc3nc(C4(n5nccn5)CC4)[nH]c3n2)C1)N1CCCC1]

To a solution of (R)-(1-(5,6-diaminopyridin-2-yl)piperidin-3-yl)(pyrrolidin-1-yl)methanone (0.4 g, 1.36 mmol) in ethanol was added ethyl 1-(2H-1,2,3-triazol-2-yl)cyclopropanecarbimidate (600 mg, crude), triethylamine (5 mL) and acetic acid (6 mL). The reaction mixture was heated to reflux for 12 h. The solvent was evaporated and the residue was dissolved in ethyl acetate. The solution was dried over sodium sulfate and concentrated. The crude material was purified via preparative TLC to afford the title compound (16 mg). MS (ES+) (M+H) 407.3; LCMS retention time 1.793 min (Method N1).

Example 215

(R)-(1-(2-(1-(1H-Imidazol-1-yl)cyclopropyl)-3H-imidazo[4,5-b]pyridin-5-yl)piperidin-3-yl)(pyrrolidin-1-yl)methanone

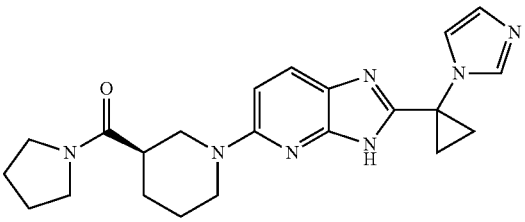 [SMILES: O=C([C@@H]1CCCN(c2ccc3nc(C4(n5ccnc5)CC4)[nH]c3n2)C1)N1CCCC1]

Step 1: (R)-(1-(5,6-Diaminopyridin-2-yl)piperidin-3-yl)(pyrrolidin-1-yl)methanone To a solution of (R)-(1-(6-amino-5-nitropyridin-2-yl)piperidin-3-yl)(pyrrolidin-1-yl)methanone (0.11 g, 0.34 mmol) in ethanol (15 mL) was added 10% palladium-on-carbon (210 mg). The resulting suspension was hydrogenated using a balloon filled with hydrogen gas for 3 h at room temperature. The mixture was filtered through a pad of Celite and the filtrate was used for the next step without further purification.

Step 2: (R)-(1-(2-(1-(1H-Imidazol-1-yl)cyclopropyl)-3H-imidazo[4,5-b]pyridin-5-yl)piperidin-3-yl)(pyrrolidin-1-yl)methanone 1-(1H-Imidazol-1-yl)cyclopropanecarbaldehyde (60 mg, 0.44 mmol), sulfur (10 mg), and acetic acid (0.5 mL) were added to the filtrate containing (R)-(1-(5,6-diaminopyridin-2-yl)piperidin-3-yl)(pyrrolidin-1-yl)methanone, prepared in the previous step, The reaction mixture was heated at 80° C. for 24 h. The solvent was removed under reduced pressure and the resulting crude material was purified via preparative TLC (10% methanol in dichloromethane) to afford the title compound. MS (ES+APCI) 406.1; LCMS retention time 4.739 min (Method R1).

Examples 216 and 217

((3R,6S)-1-(2-(1-(4-Chloro-1H-pyrazol-1-yl)cyclopropyl)-3H-imidazo[4,5-b]pyridin-5-yl)-6-methylpiperidin-3-yl)(pyrrolidin-1-yl)methanone and ((3S,6R)-1-(2-(1-(4-chloro-1H-pyrazol-1-yl)cyclopropyl)-3H-imidazo[4,5-b]pyridin-5-yl)-6-methylpiperidin-3-yl)(pyrrolidin-1-yl)methanone

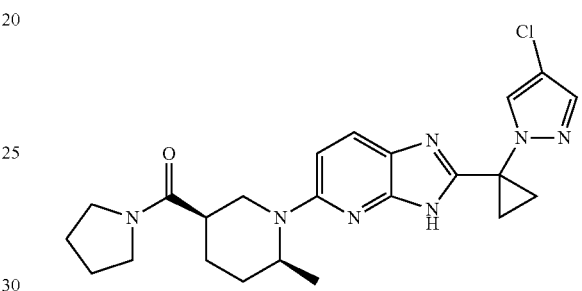

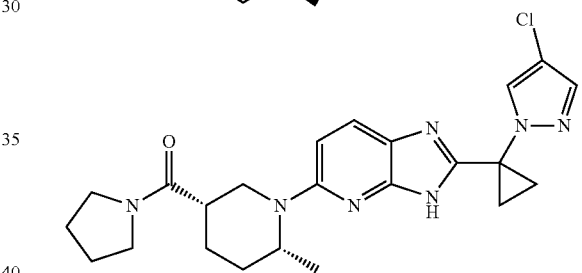

Step 1: cis-tert-Butyl 2-methyl-5-(pyrrolidine-1-carbonyl)piperidine-1-carboxylate O-(7-Azabenzotriazol-1-yl)-N,N,N',N',-tetramethyluronium hexafluorophosphate (HATU) (7.50 g, 19.72 mmol), diisopropylethylamine (7.08 mL, 39.45 mmol) and pyrrolidine (1.40 g, 19.72 mmol) were added to a solution of cis-1-(tert-butoxycarbonyl)-6-methylpiperidine-3-carboxylic acid (synthesized by N-Boc protection of cis-6-methylpiperidine-3-carboxylic acid, analogously prepared by the method described in J. Med. Chem. 2011, 54, 1871-1895.) (4.0 g, 16.44 mmol) in anhydrous dichloromethane (40 mL) at room temperature. The reaction mixture was stirred at room temperature for 4 h. Water was added and the mixture was extracted with dichloromethane. The organics were dried over sodium sulfate and concentrated under reduced pressure to afford cis-tert-butyl 2-methyl-5-(pyrrolidine-1-carbonyl)piperidine-1-carboxylate (4.0 g). The material was used without further purification.

Step 2: cis-(6-Methylpiperidin-3-yl)(pyrrolidin-1-yl)methanone hydrochloride A saturated solution of hydrogen chloride in ether (50 mL) was added to a solution of cis-tert-butyl 2-methyl-5-(pyrrolidine-1-carbonyl)piperidine-1-carboxylate (4.0 g, 13.49 mmol) in ether (10 mL) at 0° C. The reaction mixture was stirred at room temperature for 2 h. The excess ethereal hydrogen chloride was evaporated and the residue was concentrated from diethyl ether to afford cis-(6-methylpiperidin-3-yl)(pyrrolidin-1-yl)methanone hydrochloride (3.0 g). The material was used without further purification.

Step 3: cis-(1-(6-Amino-5-nitropyridin-2-yl)-6-methylpiperidin-3-yl)(pyrrolidin-1-yl)methanone To a solution of cis-(6-methylpiperidin-3-yl)(pyrrolidin-1-yl)methanone hydrochloride (0.5 g, 2.15 mmol) in acetonitrile (10 mL) was added triethylamine (0.89 mL, 6.46 mmol). The mixture was stirred at room temperature for 10 min. Then 6-chloro-3-nitropyridin-2-amine (260 mg, 1.50 mmol) was added and the reaction mixture was stirred at 80° C. for 3 h and then at room temperature for 12 h. Water was added and the mixture was extracted with ethyl acetate. The organics were dried over sodium sulfate and concentrated under reduced pressure to afford cis-(1-(6-amino-5-nitropyridin-2-yl)-6-methylpiperidin-3-yl)(pyrrolidin-1-yl)methanone (0.5 g). MS (ES+APCI) (M+H) 334.2; LCMS retention time 4.028 min (Method S1).

Step 4: cis-(1-(5,6-Diaminopyridin-2-yl)-6-methylpiperidin-3-yl)(pyrrolidin-1-yl)methanone A solution of cis-(1-(6-amino-5-nitropyridin-2-yl)-6-methylpiperidin-3-yl)(pyrrolidin-1-yl)methanone (500 mg, 1.50 mmol) in ethanol (20 mL) was added to a suspension of 10% palladium-on-carbon (250 mg) in ethanol under a nitrogen atmosphere. The suspension was hydrogenated using a balloon filled with hydrogen gas for 2 h at room temperature. The mixture was filtered through Celite and the filtrate was used for the next step without further purification.

Step 5: ((3R,6S)-1-(2-(1-(4-Chloro-1H-pyrazol-1-yl)cyclopropyl)-3H-imidazo[4,5-b]pyridin-5-yl)-6-methylpiperidin-3-yl)(pyrrolidin-1-yl)methanone and ((3S,6R)-1-(2-(1-(4-chloro-1H-pyrazol-1-yl)cyclopropyl)-3H-imidazo[4,5-b]pyridin-5-yl)-6-methylpiperidin-3-yl)(pyrrolidin-1-yl)methanone Ethyl 1-(4-chloro-1H-pyrazol-1-yl)cyclopropanecarbimidate (485 mg, 1.80 mmol) and acetic acid (1.5 mL) were added to the filtrate containing cis-(1-(5,6-diaminopyridin-2-yl)-6-methylpiperidin-3-yl)(pyrrolidin-1-yl)methanone, prepared in the previous step. The reaction mixture was stirred at 80° C. for 16 h. The solvent was removed under reduced pressure and the resulting residue was partitioned between water and ethyl acetate. The organic layer was dried over sodium sulfate and concentrated under reduced pressure. The crude material was purified via column chromatography (0-4% methanol in ethyl acetate) to afford a racemic mixture of the title compounds (180 mg). The racemic mixture was further purified via chiral HPLC to afford two enantiomers. Enantiomer 1 (Example 216, 65 mg): Chiral HPLC retention time 12.120 min (Method: CHIRAL PAK IA 4.6×250 mM, 5 µM; Mobile Phase D: 0.1% DEA in n-Hexane; Mobile Phase C: Ethanol; Isocratic: 80:20; Flow: 1.0 ml/min); MS (ES+ APCI) (M+H) 454.1; LCMS retention time: 3.636 min (Method S1). Enantiomer 2 (Example 217, 60 mg): Chiral HPLC retention time 15.424 min (Method: same as for enantiomer 1); MS (ES+APCI) (M+H) 454.2; LCMS retention time: 3.640 min (Method S1).

Examples 218 and 219

((3R,6S)-1-(8-(1-(4-Chloro-1H-pyrazol-1-yl)cyclopropyl)-9H-purin-2-yl)-6-methylpiperidin-3-yl)(pyrrolidin-1-yl)methanone and ((3S,6R)-1-(8-(1-(4-chloro-1H-pyrazol-1-yl)cyclopropyl)-9H-purin-2-yl)-6-methylpiperidin-3-yl)(pyrrolidin-1-yl)methanone

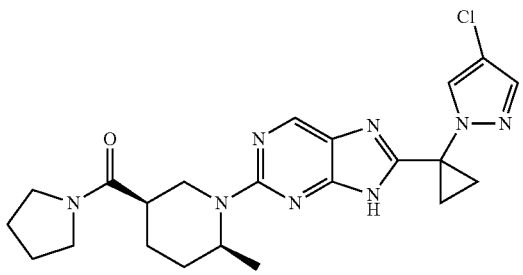

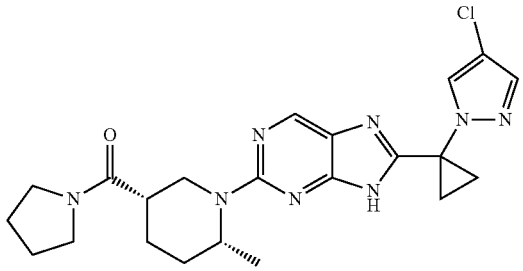

The title compounds were prepared by a method analogous to the one used for Examples 216 and 217, but using 2-chloro-5-nitropyrimidin-4-amine for Step 3. Enantiomer 1 (Example 218, 28 mg): Chiral HPLC retention time 9.672 min (Method: CHIRAL PAK IA 4.6×250 mm, 5 µm; Mobile Phase D: 0.1% DEA in n-Hexane; Mobile Phase C: Ethanol; Isocratic: 80:20; Flow: 1.0 mL/min); MS (ES+) (M+H) 455.3; LCMS retention time: 2.318 min (Method N1). Enantiomer 2 (Example 219, 18 mg): Chiral HPLC retention time 11.149 min (Method: Same as for enantiomer 1); MS (ES+) (M+H) 455.3; LCMS retention time: 2.315 min (Method N1).

Example 220

(R)-Azetidin-1-yl(1-(2-(2-cyclopropylpyrimidin-4-yl)-3H-imidazo[4,5-b]pyridin-5-yl)piperidin-3-yl)methanone

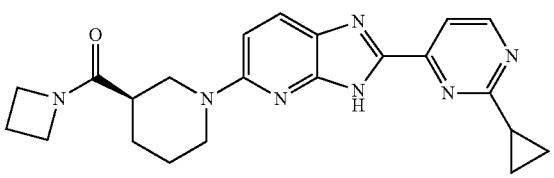 [SMILES: O=C([C@@H]1CCCN(c2ccc3nc(-c4ccnc(C5CC5)n4)[nH]c3n2)C1)N1CCC1]

217

The title compound was prepared by a method analogous to the one used for Example 71. MS API-ES+ (M+H) 404; HPLC retention time 2.447 min (Method C).

Example 221

(R)—N-(Cyclopropylmethyl)-1-(2-(2-cyclopropylpyrimidin-4-yl)-3H-imidazo[4,5-b]pyridin-5-yl)-N-methylpiperidine-3-carboxamide

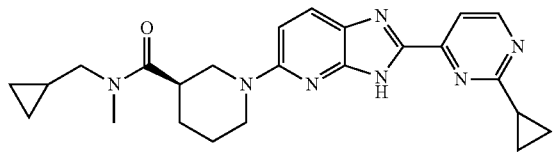 [SMILES: CN(CC1CC1)C(=O)[C@@H]1CCCN(c2ccc3nc(-c4ccnc(C5CC5)n4)[nH]c3n2)C1]

The title compound was prepared by a method analogous to the one used for Example 71. MS API-ES+ (M+H) 432; HPLC retention time 2.749 min (Method C).

Example 222

(R)-(1-(2-(1-(Pyridazin-3-yl)cyclopropyl)-3H-imidazo[4,5-b]pyridin-5-yl)piperidin-3-yl)(pyrrolidin-1-yl)methanone

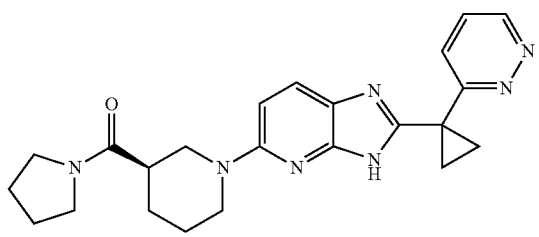 [SMILES: O=C([C@@H]1CCCN(c2ccc3nc(C4(c5cccnn5)CC4)[nH]c3n2)C1)N1CCCC1]

Step 1: (R)—N-(2-Amino-6-(3-(pyrrolidine-1-carbonyl)piperidin-1-yl)pyridin-3-yl)-1-(pyridazin-3-yl)cyclopropanecarboxamide To a mixture of 1-(pyridazin-3-yl)cyclopropanecarboxylic acid (160 mg, 0.97 mmol), O-(7-Azabenzotriazol-1-yl)-N,N,N',N',-tetramethyluronium hexafluorophosphate (HATU) (445 mg, 1.17 mmol) and diisopropylethyl amine (330 mg, 2.4 mmol) in anhydrous dichloromethane (10 mL) was added (R)-(1-(5,6-diaminopyridin-2-yl)piperidin-3-yl)(pyrrolidin-1-yl)methanone dihydrochloride (350 mg, 0.98 mmol) dissolved in anhydrous dichloromethane (10 mL) with diisopropylethyl amine (330 mg, 2.4 mmol). The reaction mixture was stirred at room temperature for 2 h, diluted with dichloromethane and washed with water. The organics were dried over sodium sulfate and concentrated under reduced pressure. The resulting crude was purified via column chromatography (100-200 silica gel mesh, 60-80% ethyl acetate in petroleum ether) to afford (R)—N-(2-amino-6-(3-(pyrrolidine-1-carbonyl)piperidin-1-yl)pyridin-3-yl)-1-(pyridazin-3-yl)cyclopropanecarboxamide (100 mg, 23%). MS (ES+APCI) (M+H) 436.2; LCMS retention time: 3.390 min (Method W1).

218

Step 2: (R)-(1-(2-(1-(Pyridazin-3-yl)cyclopropyl)-3H-imidazo[4,5-b]pyridin-5-yl)piperidin-3-yl)(pyrrolidin-1-yl)methanone Sodium methoxide (74.4 mg, 1.37 mmol) was added to a solution of (R)—N-(2-amino-6-(3-(pyrrolidine-1-carbonyl)piperidin-1-yl)pyridin-3-yl)-1-(pyridazin-3-yl)cyclopropanecarboxamide (100 mg, 0.22 mmol) in isobutanol (2 mL) and methanol (2 mL). The reaction mixture was heated to 110° C. for 16 h. The reaction mixture was concentrated under reduced pressure and the resulting crude was purified via preparative TLC to afford the title compound (35 mg). MS (ES+APCI) (M+H) 418.2; LCMS retention time: 3.439 min (Method W1).

Example 223

(R)-(1-(2-(1-(1-Methyl-1H-1,2,4-triazol-5-yl)cyclopropyl)-3H-imidazo[4,5-b]pyridin-5-yl)piperidin-3-yl)(pyrrolidin-1-yl)methanone

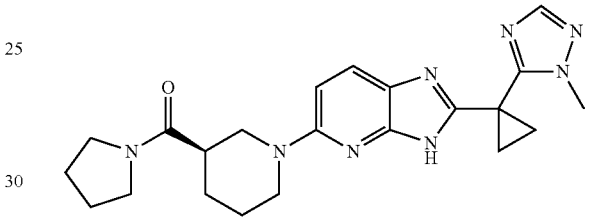

Step 1: (R)-(1-(5,6-Diaminopyridin-2-yl)piperidin-3-yl)(pyrrolidin-1-yl)methanone To a solution of (R)-(1-(6-amino-5-nitropyridin-2-yl)piperidin-3-yl)(pyrrolidin-1-yl)methanone (0.500 g, 1.56 mmol) in ethanol (25 mL) was added palladium on carbon 10% (500 mg) suspended in ethanol. The reaction mixture was hydrogenated using a balloon filled with hydrogen gas for 3 h at room temperature. The reaction mixture was filtered through Celite and the filtrate was used for the next step without further purification.

Step 2: (R)-(1-(2-(1-(1-Methyl-1H-1,2,4-triazol-5-yl)cyclopropyl)-3H-imidazo[4,5-b]pyridin-5-yl)piperidin-3-yl)(pyrrolidin-1-yl)methanone (R)-(1-(5,6-Diaminopyridin-2-yl)piperidin-3-yl)(pyrrolidin-1-yl)methanone, prepared during the previous step, was added to a suspension of ethyl 1-(1-methyl-1H-1,2,4-triazol-5-yl)cyclopropanecarbimidate (0.39 g, 2.0 mmol), sulfur (20 mg, 0.31 mmol) and acetic acid (0.96 mL, 15.5 mmol) in ethanol (10 mL) at room temperature. The reaction mixture was heated to 80° C. for 16 h. The mixture was concentrated under reduced pressure and the resulting crude was dissolved in ethyl acetate, washed with water and brine, dried over sodium sulfate and concentrated under reduced pressure. The resulting crude was purified via preparative TLC to afford the title compound (120 mg, 18%). MS (ES+APCI) (M+H) 421.2; LCMS retention time: 3.311 min (Method Y1).

Pharmacological Data

The following protocols may of course be varied by those skilled in the art.

Generation of Human DGAT2 (hDGAT2) Construct

A construct for hDGAT2 was generated with an N-terminal FLAG tag (an octapeptide with the amino acid sequence of AspTyrLysAspAspAspAspLys). For the FLAG-tagged hDGAT2 construct, the cDNA for hDGAT2 was custom-synthesized at Genscript and cloned into the pFastBac1 vector (Invitrogen) by using BamHI/XhoI restriction enzymes to generate an N-terminally FLAG-tagged pFastBac1-FLAG-hDGAT2 construct (amino acids 1-388). The construct was confirmed by sequencing in both directions.

DGAT2 Expression and Preparation of the DGAT2 Membrane Fraction

Recombinant baculovirus for the FLAG-tagged hDGAT2 was generated in SF9 insect cells using Bac-to-Bac baculovirus expression system (Invitrogen) according to the manufacturer's protocol. For the expression of hDGAT2, SF9 cells (20 L) grown in Sf900II media were infected with hDGAT2 baculovirus at a multiplicity of infection of 1 in a Wave Bioreactor System 20/50P wave bag (GE Healthcare). After 40 hours of infection, the cells were then harvested by centrifugation at 5,000×g. The cell pellets were washed by resuspending in phosphate buffered saline (PBS) and collected by centrifugation at 5,000×g. The cell paste was flash frozen in liquid $N_2$ and stored at $-80°$ C. until needed. All operations below were at 4° C. unless otherwise noted. The cells were resuspended in lysis buffer (50 mM Tris-HCl, pH 8.0, 250 mM sucrose) including 1 mM ethylenediaminetetraacetic acid (EDTA) and the complete protease inhibitor cocktail (Roche Diagnostics) at a ratio of 3 ml buffer per 1 g cell paste. The cells were lysed by dounce homogenizer. The cell debris was removed by centrifugation at 1,000×g for 20 min, and the supernatant was centrifuged at 100,000×g for 1 hour. The resulting pellet was rinsed three times by filling ultracentrifuge tubes to the top with ice cold PBS before decanting. The washed pellet was resuspended with gentle stirring for 1 hour in lysis buffer containing 8 mM 3-[(3-cholamidopropyl)dimethylammonio]-1-propanesulfonate (CHAPS) at a ratio of 1 mL buffer per 1 g of original cell paste and centrifuged again at 100,000×g for 1 hour. The resulting supernatant (hDGAT2 membrane fraction) was aliquotted, flash frozen in liquid $N_2$, and stored at $-80°$ C. until use.

In Vitro DGAT2 Assay and Determination of $IC_{50}$ Values for DGAT2 Inhibitors For determination of $IC_{50}$ values, the reactions were carried out in 384-well white Polyplates (Perkin Elmer) in a total volume of 20 µL. To 1 µL of compounds dissolved in 100% DMSO and spotted at the bottom of each well, 5 µL of 0.04% bovine serum albumin (BSA) (fatty acid free, Sigma Aldrich) was added and the mixture was incubated at room temperature for 20 minutes. To this mixture, 10 µL of hDGAT2 membrane fraction (0.01 mg/mL) diluted in 100 mM Hepes-NaOH, pH 7.4, 20 mM $MgCl_2$ containing 200 nM methyl arachidonyl fluorophosphonate (Cayman Chemical; dried from ethyl acetate stock solution under argon gas and dissolved in DMSO as 5 mM stock) was added. After this mixture was preincubated at room temperature for 2 hours, DGAT2 reactions were initiated by the addition of 4 µL of substrates containing 30 µM [1-$^{14}$C]decanoyl-CoA (custom-synthesized by Perkin Elmer, 50 mCi/mmol) and 125 µM 1,2-didecanoyl-sn-glycerol (Avanti Polar Lipids) dissolved in 12.5% acetone. The reaction mixtures were incubated at room temperature for 40 min and the reactions were stopped by addition of 5 µL of 1% $H_3PO_4$. After the addition of 45 µL MicroScint-E (Perkin-Elmer), plates were sealed with Top Seal-A covers (Perkin-Elmer) and phase partitioning of substrates and products was achieved using a HT-91100 microplate orbital shaker (Big Bear Automation, Santa Clara, Calif.). Plates were centrifuged at 2,000×g for 1 min in an Allegra 6R Centrifuge (Beckman Coulter) and then were sealed again with fresh covers before reading in a 1450 Microbeta Wallac Trilux Scintillation Counter (Perkin Elmer). DGAT2 activity was measured by quantifying the generated product [$^{14}$C]tridecanoylglycerol in the upper organic phase.

Background activity obtained using 50 µM of (1R,2R)-2-({3'-Fluoro-4'-[(6-fluoro-1,3-benzothiazol-2-yl)amino]-1,1'-biphenyl-4-yl}carbonyl)cyclopentanecarboxylic acid (US 20040224997, Example 26) for complete inhibition of DGAT2 was subtracted from all reactions. Inhibitors were tested at eleven different concentrations to generate $IC_{50}$ values for each compound. The eleven inhibitor concentrations employed typically included 50, 15.8, 5, 1.58, 0.50, 0.16, 0.05, 0.016, 0.005, 0.0016, and 0.0005 µM. The data were plotted as percentage of inhibition versus inhibitor concentration and fit to the equation, $y=100/[1+(x/IC_{50})^z]$, where $IC_{50}$ is the inhibitor concentration at 50% inhibition and z is the Hill slope (the slope of the curve at its inflection point). Table 13 below provides the $IC_{50}$ values of the Examples for inhibition of DGAT2 in accordance with the above-described assay. Results are reported as geometric mean $IC_{50}$ values. Values in the parentheses are geometric mean $IC_{50}$ values obtained by above-described assay using (R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone (Example 196-A) instead of 50 µM of (1R,2R)-2-({3'-Fluoro-4'-[(6-fluoro-1,3-benzothiazol-2-yl)amino]-1,1'-biphenyl-4-yl}carbonyl)cyclopentanecarboxylic acid for complete inhibition of DGAT2.

TABLE 13

$IC_{50}$ values of Examples for inhibition of DGAT2

| Example# | DGAT2 $IC_{50}$ (nM) |
|---|---|
| 1 | 1.7 |
| 2 | 2.71 |
| 3 | 4.82 |
| 4 | 6.64 |
| 5 | 8.24 |
| 6 | 11.5 |
| 7 | 16.3 |
| 8 | 21.1 |
| 9 | 22.1 |
| 10 | 29.2 |
| 11 | 35 |
| 12 | 54.7 |
| 13 | 63.6 |
| 14 | 72.8 |
| 15 | 89.6 |
| 16 | 102 |
| 17 | 118 |
| 18 | 196 |
| 19 | 208 |
| 20 | 221 |
| 21 | 346 |
| 22 | 357 |
| 23 | 432 |
| 24 | 731 |
| 25 | 297 |
| 26 | 1050 |
| 27 | 1390 |
| 28 | 1500 |
| 29 | 4370 |

TABLE 13-continued

IC$_{50}$ values of Examples for inhibition of DGAT2

| Example# | DGAT2 IC$_{50}$ (nM) |
|---|---|
| 30 | 1400 |
| 31 | 286 |
| 32 | 239 |
| 33 | 97 |
| 34 | 24.8 |
| 35 | 21.2 |
| 36 | 20.7 |
| 37 | 12.6 |
| 38 | 7.81 |
| 39 | 6.85 |
| 40 | 6.47 |
| 41 | 4.56 |
| 42 | 3.18 |
| 43 | 7.41 |
| 44 | 36.5 |
| 45 | 1770 |
| 46 | 188 |
| 47 | 34.5 |
| 48 | 10.7 |
| 49 | 197 |
| 50 | 460 |
| 51 | 69.7 |
| 52 | 1570 |
| 53 | 2530 |
| 54 | 2750 |
| 55 | 1120 |
| 56 | 166 |
| 57 | 702 |
| 58 | 363 |
| 59 | 858 |
| 60 | 892 |
| 61 | 86.4 |
| 62 | 241 |
| 63 | 122 |
| 64 | 113 |
| 65 | 59.3 |
| 66 | 1050 |
| 67 | 58.2 |
| 68 | 54.7 |
| 69 | 35.4 |
| 70 | 162 |
| 71 | 1470 |
| 72 | 104 |
| 73 | 96.9 (85) |
| 74 | 974 |
| 75 | 764 |
| 76 | 227 |
| 77 | 107 |
| 78 | 83.8 |
| 79 | 230 (238) |
| 80 | 1400 |
| 81 | 204 |
| 82 | 165 |
| 83 | 128 |
| 84 | 9.55 |
| 85 | 1160 |
| 86 | 288 |
| 87 | 102 |
| 88 | 190 |
| 89 | 546 |
| 90 | 315 |
| 91 | 312 |
| 92 | 242 |
| 93 | 202 |
| 94 | 107 |
| 95 | 18.2 |
| 96 | 37.3 |
| 97 | 96.9 |
| 98 | 94.4 |
| 99 | 72.5 |
| 100 | 47.8 |
| 101 | 60.5 |
| 102 | 99.6 |
| 103 | 73.7 |
| 104 | 190 |
| 105 | 28.9 |
| 106 | 5.68 |
| 107 | 153 |
| 108 | 28.7 (26.2) |
| 109-A | 13.8 |
| 109-B | 20.2 (15) |
| 110 | 41.5 |
| 111 | 697 |
| 112 | 9.23 |
| 113 | 137 |
| 114 | 90.3 |
| 115 | 67.9 |
| 116 | 66.2 |
| 117 | 409 |
| 118 | 301 |
| 119 | 22.2 |
| 120 | 21.5 |
| 121 | 14.3 |
| 122 | 10.9 |
| 123 | 276 |
| 124 | 5.27 |
| 125 | 54 |
| 126 | 3470 |
| 127 | 235 |
| 128 | 7.16 |
| 129 | 4540 |
| 130 | 1900 |
| 131 | 34.4 |
| 132 | 695 |
| 133 | 252 |
| 134 | 210 |
| 135 | 4240 |
| 136 | 6.32 |
| 137 | 1280 |
| 138 | 71.6 |
| 139 | 62.3 |
| 140 | 207 |
| 141 | 354 (301) |
| 142 | 24.8 |
| 143 | 511 |
| 145 | 411 |
| 146 | 401 |
| 147 | 9.21 |
| 148 | 187 |
| 149 | 766 |
| 150 | 47.3 |
| 152 | 285 |
| 153 | 48.1 |
| 154 | 40.5 |
| 155 | 35.6 |
| 156 | 275 |
| 157 | 211 |
| 158 | 3.58 |
| 159 | 28.2 |
| 160 | 789 |
| 161 | 218 |
| 162 | 434 |
| 163 | 3400 |
| 164 | 2800 |
| 165 | 16500 |
| 166 | 2280 |
| 168 | 1390 |
| 169 | 292 |
| 171 | 161 |
| 172 | 83 |
| 173 | 1250 |
| 174 | 1170 |
| 175 | 91.3 |
| 176 | 73.4 |
| 177 | 953 |
| 179 | 512 |
| 180 | 434 |
| 181 | 17400 |
| 182 | 6.03 |
| 183 | 37.5 |

TABLE 13-continued

IC$_{50}$ values of Examples for inhibition of DGAT2

| Example# | DGAT2 IC$_{50}$ (nM) |
|---|---|
| 184 | 15.2 |
| 185 | 231 |
| 186 | 162 |
| 187 | 10.5 |
| 188 | 31.4 |
| 189 | 34.1 |
| 190 | 35.9 |
| 191 | 6600 |
| 192 | 88.6 |
| 193 | 128 |
| 194 | 101 |
| 195 | 142 |
| 196-A | 14.5 (20.6) |
| 196-B | 38.5 |
| 197 | 33.7 |
| 198 | 43 |
| 199 | 18.9 (32.9) |
| 200 | 74.2 |
| 201 | 91 |
| 202 | 321 |
| 203 | 176 |
| 204 | 656 |
| 205 | 188 |
| 206 | 246 |
| 207 | 702 |
| 208 | 37400 |
| 209 | 101 |
| 210 | 342 |
| 211 | 845 |
| 212 | 18.9 |
| 213 | 161 |
| 214 | 396 |
| 215 | 483 |
| 216 | 9200 |
| 217 | 131 |
| 218 | 2310 |
| 219 | 82.8 |
| 220 | 270 |
| 221 | 290 |
| 222 | 531 |
| 223 | 1370 |

Determination of IC$_{50}$ Values for DGAT2 Inhibitors in Human Hepatocytes

For evaluation of the effects of DGAT2 inhibitors in a cell-based setting, cryopreserved human hepatocytes (Lot QOC, Celsis, Chicago, Ill.) were thawed and plated onto type I collagen-coated plates according to the manufacturer's instructions. After 24 hours overnight recovery period, the cells were overlayed with media containing 250 µg/ml Matrigel (BD Biosciences, San Jose, Calif.). The following day, media was aspirated and replaced with serum-free Williams Media E (Life Technologies, Grand Island, N.Y.) containing 400 µM sodium dodecanoate (Sigma-Aldrich, St. Louis, Mo.). Forty minutes later, DGAT2 inhibitors (prepared as 100× stocks in 25% DMSO, 75% Williams' Media E) were added to the desired final concentration. All wells contained a selective DGAT1 inhibitor (Example 3, WO2009016462) at a concentration (3 µM) that completely suppressed endogenous DGAT1 activity. After a 20 minute preincubation, 0.2 µCi [1,3-$^{14}$C]-glycerol (American Radio Chemicals, St. Louis, Mo.) was added to each well and mixed by gentle pipetting prior to a 3 hour incubation. At this point, media was aspirated and the cells were lysed in isopropyl alcohol:tetrahydrofuran (9:1) prior to centrifugation at 3000 rpm for 5 minutes. Radiolabeled lipids were resolved using a 2-solvent system by thin layer chromatography using standard technique (solvent 1 contained ethyl acetate: isopropyl alcohol: chloroform:methanol:0.25% potassium chloride in water (100:100:100:40.2:36.1, v/v/v/v) and solvent 2 contained hexane: diethyl ether: acetic acid (70:27:3, v/v/v)). After separation, radiolabeled lipids were visualized using a Molecular Dynamics' PhosphorImager system. The half maximal inhibitory concentrations (IC$_{50}$ values) were determined using Graph Pad Prism (GraphPad Software, Inc., La Jolla, Calif.).

Table 14 below provides IC$_{50}$ values for the Examples in accordance with the above-described assay. Results were reported as average IC$_{50}$ values, low and high IC$_{50}$ range (95% confidence interval).

TABLE 14

IC$_{50}$ values of selected DGAT2 inhibitors in primary human heptocyte.

| Example # | IC$_{50}$ (nM) |
|---|---|
| 58 | 86.8 |
| 73 | 7.9 |
| 76 | 25.1 |
| 78 | 9.4 |
| 81 | 47.7 |
| 82 | 15.8 |
| 95 | 15.9 |
| 108 | 2.8 |
| 109-A | 2.1 |
| 109-B | 5.5 |
| 141 | 10.7 |
| 175 | 71.7 |
| 196-A | 4.6 |
| 197 | 5.5 |
| 198 | 7.8 |
| 199 | 2.5 |
| 209 | 8.9 |

Acute Effects of DGAT2 Inhibitors on Plasma TAG Levels

Blockade of hepatic DGAT2 activity has been shown to inhibit the secretion of VLDL TAG (18). To evaluate the acute effects of DGAT2 inhibitors on hepatic TAG production, male Sprague Dawley rats (~200 g, Harlan Laboratories Inc.) were fed a low fat, high-sucrose diet (TD03045, Harlan Laboratories Inc.) for 2 days prior to dosing with DGAT2 inhibitors. At this time, animals were fasted for 4 hours and compounds administered as a solution in 0.5% methylcellulose. Two hours after treatment with DGAT2 inhibitors, blood was drawn from the lateral tail vein and plasma TAG levels determined using a Roche Hitachi Chemistry analyzer according to the manufacturer's instructions. Data were analyzed using Graph Pad Prism (Graph Pad Software, Inc., La Jolla, Calif.) and are shown as a box-an-whiskers plot with the whiskers defining the first and $99^{th}$ percentile. Statistical analysis was performed using one-way ANOVA followed by Dunnett's multiple comparison test. *$p<0.05$, $p<0.001$, *$p<0.0001$.

FIG. 4 provides acute effects of DGAT2 inhibitors on plasma TAG levels in Sprague Dawley rats for the Examples 95, 108 and 109-A in accordance with the above-described method.

Powder X-Ray Diffraction

Powder diffraction analysis was conducted using a Bruker D8 diffractometer equipped with a Cu radiation source, fixed slits (divergence=1.0 mm, anti-scatter=0.6 mm, and receiving=0.6 mm) and a scintillation counter detector. Data was collected in the Theta-Theta goniometer at the Cu wavelength K$\alpha_1$=1.54056 Å from 3.0 to 40.0 degrees 2-Theta using a step size of 0.040 degrees and a step time of 2.0 second. X-ray tube voltage and amperage were set at 40 kV and 40 mA respectively. Samples were prepared by placement in a Nickel Disk (Gasser & Sons, Inc. Commack, N.Y.) and rotated during data collection. Data were collected and analyzed using Bruker DIFFRAC Plus software (Version 2.6). A X-ray powder diffraction pattern and total Peak list for Crystalline Form 1 of Example 109-B are shown in Table 15. A X-ray powder diffraction pattern and total Peak list for Crystalline Form 1 of Example 109-C are shown in Table 16. In addition, a X-ray powder diffraction pattern and Total Peak list for Crystalline Form 1 of Example 196-B are shown in Table 17. Peaks with relative intensity of ≥7% were generally chosen. The peaks which were not resolved or were consistent with noise were also discarded. The powder X-ray diffraction values are generally accurate to within ±0.2 2-Theta degrees, due to slight variations of instrument and test conditions.

TABLE 15

X-ray powder diffraction pattern: Total Peak list for Crystalline Form 1 of Example 109-B.

| Angle 2-Theta ° | Intensity % |
|---|---|
| 5.8 | 94 |
| 7.9 | 18 |
| 9.5 | 7 |
| 10.4 | 7 |
| 10.7 | 16 |
| 12.2 | 10 |
| 12.8 | 32 |
| 14.3 | 10 |
| 15.8 | 20 |
| 17.0 | 17 |
| 17.4 | 15 |
| 18.2 | 30 |
| 18.6 | 21 |
| 19.8 | 100 |
| 20.5 | 39 |
| 21.4 | 15 |
| 21.8 | 25 |
| 22.6 | 82 |
| 23.3 | 33 |
| 23.9 | 27 |
| 24.5 | 12 |
| 25.5 | 19 |
| 25.7 | 26 |
| 26.6 | 18 |

TABLE 16

X-ray powder diffraction pattern: Total Peak list for Crystalline Form 1 of Example 109-C.

| Angle 2-Theta ° | Intensity % |
|---|---|
| 7.8 | 86 |
| 8.8 | 15 |
| 9.7 | 13 |
| 10.0 | 19 |
| 10.6 | 47 |
| 11.9 | 63 |
| 13.3 | 28 |
| 15.2 | 100 |
| 15.6 | 44 |
| 16.7 | 56 |
| 17.6 | 27 |
| 18.0 | 43 |
| 18.2 | 33 |
| 18.6 | 15 |
| 19.5 | 66 |
| 20.0 | 18 |
| 20.2 | 40 |
| 20.7 | 29 |
| 20.9 | 40 |
| 21.1 | 29 |
| 21.5 | 52 |
| 22.1 | 40 |
| 22.6 | 54 |
| 22.7 | 35 |
| 23.4 | 67 |
| 23.9 | 17 |
| 24.7 | 53 |
| 25.0 | 21 |
| 25.2 | 48 |
| 25.6 | 16 |
| 26.1 | 33 |
| 26.6 | 42 |
| 26.8 | 31 |
| 27.2 | 23 |
| 28.0 | 15 |
| 28.7 | 20 |
| 29.1 | 17 |
| 29.6 | 19 |
| 30.1 | 28 |
| 30.8 | 30 |
| 31.4 | 13 |
| 31.9 | 23 |
| 32.4 | 20 |
| 32.7 | 15 |
| 33.3 | 19 |
| 33.9 | 25 |
| 34.6 | 13 |
| 35.3 | 16 |
| 35.7 | 16 |

TABLE 17

X-ray powder diffraction pattern: Total Peak list for Crystalline Form 1 of Example 196-B.

| Angle 2-Theta ° | Intensity % |
|---|---|
| 7.9 | 100 |
| 9.0 | 12 |
| 9.8 | 16 |
| 10.7 | 42 |
| 11.8 | 40 |
| 13.4 | 22 |
| 15.3 | 60 |
| 15.6 | 62 |
| 16.7 | 26 |
| 17.1 | 30 |
| 17.8 | 34 |
| 18.0 | 27 |
| 18.3 | 31 |
| 19.6 | 66 |
| 20.3 | 25 |
| 20.6 | 56 |
| 21.0 | 35 |
| 21.7 | 30 |
| 22.0 | 57 |
| 22.2 | 47 |
| 22.5 | 56 |
| 23.2 | 41 |
| 23.6 | 79 |
| 24.7 | 29 |
| 25.3 | 41 |

TABLE 17-continued

X-ray powder diffraction pattern: Total Peak list for Crystalline Form 1 of Example 196-B.

| Angle 2-Theta ° | Intensity % % |
|---|---|
| 25.6 | 54 |
| 26.3 | 27 |
| 27.2 | 44 |
| 27.8 | 25 |
| 28.6 | 26 |
| 29.5 | 22 |
| 30.3 | 19 |
| 30.9 | 30 |
| 31.7 | 32 |
| 32.3 | 21 |
| 34.1 | 25 |
| 34.5 | 22 |

Solid State NMR:

A sample of the compound of Example 109-B was tightly packed into a 4 mm $ZrO_2$ rotor. Spectra were collected at room temperature and pressure on Varian 4 mm CPMAS probe positioned into a Varian Unity Inova 400 MHz ($^1$H frequency) NMR spectrometer. The packed rotor was oriented at the magic angle and spun at 12.0 kHz. The $^{13}$C solid state spectrum was collected using a proton decoupled cross-polarization magic angle spinning experiment (CPMAS). The cross-polarization contact time was set to 5.0 ms. A proton decoupling field of approximately 95 kHz was applied. 2048 scans were collected with recycle delay of 5 seconds. The carbon spectrum was referenced using an external standard of crystalline glycine, setting its upfield resonance to 176.5 ppm. The chemical shift data is dependent on the testing conditions (i.e. spinning speed and sample holder), reference material, and data processing parameters, among other factors. Typically, the solid state NMR (ss-NMR) results are accurate to within about ±0.2 ppm.

TABLE 18 ss-NMR diffraction pattern: Total Peak list for Crystalline Form 1 of Example 109-B.

| $^{13}$C Chemical Shifts [ppm][a] |
|---|
| 20.7 |
| 23.0 |
| 23.6 |
| 25.4 |
| 25.8 |
| 26.2 |
| 27.1 |
| 28.4 |
| 28.9 |
| 39.4 |
| 40.5 |
| 40.8 |
| 41.2 |
| 41.5 |
| 41.9 |
| 45.7 |
| 46.6 |
| 47.6 |
| 103.7 |
| 107.0 |
| 111.4 |
| 115.3 |
| 119.0 |
| 125.0 |
| 127.0 |
| 130.7 |
| 132.1 |

TABLE 18-continued ss-NMR diffraction pattern: Total Peak list for Crystalline Form 1 of Example 109-B.

| $^{13}$C Chemical Shifts [ppm][a] |
|---|
| 138.8 |
| 142.8 |
| 143.6 |
| 145.1 |
| 148.1 |
| 152.2 |
| 156.0 |
| 158.5 |
| 170.3 |
| 173.2 |

[a]Referenced to external sample of solid phase glycine at 176.5 ppm.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A compound of Formula (I)

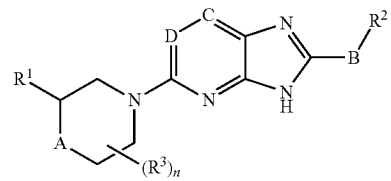

wherein:
A is $CR^6R^7$, O or S;
B is a bond, oxetanyl,

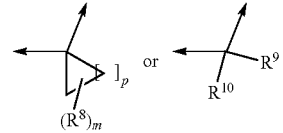

wherein m is 0, 1 or 2;
p is 1, 2, 3 or 4;
C and D are each individually selected from N, CH, CF and $C(CH_3)$, wherein if C is N then D is CH, CF or $C(CH_3)$ and if D is N then C is CH, CF or $C(CH_3)$;
$R^1$ is —C(O)-heterocyclyl, —C(O)—$NR^4R^5$, or a heteroaryl, wherein said heterocyclyl or heteroaryl is optionally substituted with 1 or 2 substituents selected independently from $(C_1$-$C_4)$alkyl, $(C_3$-$C_6)$cycloalkyl, $(C_1$-$C_4)$alkoxy, $(C_3$-$C_6)$cycloalkoxy, halo, hydroxy$(C_1$-$C_4)$alkyl, mono-N- or di-N,N—$(C_1$-$C_4)$alkylamino, mono-N- or di-N,N—($C_3$-$C_6$)cycloalkylamino, heterocyclyl, hydroxyl and cyano;

$R^2$ is ($C_1$-$C_4$)alkyl, ($C_1$-$C_4$)alkoxy, ($C_3$-$C_6$)cycloalkyl, ($C_3$-$C_6$)cycloalkoxy, aryl, aryloxy, heteroaryloxy, heteroaryl, heterocyclyl, aralkyl, heteroaralkyl, —C(O)-heterocyclyl, —C(O)—$NR^4R^5$, or —$NR^4$—C(O)—$R^5$, wherein alkyl, alkoxy, cycloalkyl, cycloalkoxy, aralkyl, heteroaralkyl, aryl, aryloxy, heteroaryloxy, heteroaryl, heterocyclyl are each optionally substituted with one, two or three substituents selected independently from ($C_1$-$C_4$)alkyl, ($C_1$-$C_4$)alkoxy, ($C_3$-$C_6$)cycloalkyl, ($C_3$-$C_6$)cycloalkoxy, —C(O)—($C_1$-$C_4$)alkyl, —C(O)—($C_3$-$C_6$)cycloalkyl, halo, —C(O)—($C_1$-$C_4$)alkoxy, —C(O)—($C_3$-$C_6$)cycloalkoxy, mono-N- or di-N,N—($C_1$-$C_4$)alkylamino, mono-N- or di-N,N—($C_3$-$C_6$)cycloalkylamino, ($C_1$-$C_4$)alkylcarbonylamino, ($C_3$-$C_6$)cycloalkylcarbonylamino, ($C_1$-$C_4$)alkylcarbonyl-N—($C_1$-$C_4$)alkylamino, ($C_1$-$C_4$)alkylcarbonyl-N—($C_3$-$C_6$)cycloalkylamino, ($C_3$-$C_6$)cycloalkylcarbonyl-N—($C_1$-$C_4$)alkylamino, ($C_3$-$C_6$)cycloalkylcarbonyl-N—($C_3$-$C_6$)cycloalkylamino, aminocarbonyl, mono-N- or di-N,N—($C_1$-$C_4$)alkylaminocarbonyl, mono-N- or di-N,N—($C_3$-$C_6$)cycloaminocarbonyl, mono-N- or di-N,N—($C_1$-$C_4$)alkylcarbonyl, mono-N- or di-N,N—($C_3$-$C_6$)cycloalkylcarbonyl, mono-N- or di-N,N—($C_1$-$C_4$)alkoxycarbonyl, mono-N- or di-N,N—($C_3$-$C_6$)cycloalkoxycarbonyl, ($C_1$-$C_4$)alkylthio, ($C_3$-$C_6$)cycloalkylthio, aminosulfonyl, ($C_1$-$C_4$)alkylsulfinyl, ($C_1$-$C_4$)alkylsulfonyl, ($C_3$-$C_6$)cycloalkylsulfinyl, ($C_3$-$C_6$)cycloalkylsulfonyl, mono-N- or di-N,N—($C_1$-$C_4$)alkylaminosulfonyl, mono-N- or di-N,N—($C_3$-$C_6$)cycloalkylaminosulfonyl, ($C_1$-$C_4$)alkylsulfonylamino, ($C_3$-$C_6$)cycloalkylsulfonylamino, ($C_1$-$C_4$)alkylsulfonyl-N—($C_1$-$C_4$)alkylamino, ($C_1$-$C_4$)alkylsulfonyl-N—($C_3$-$C_6$)cycloalkylamino, ($C_3$-$C_6$)cycloalkylsulfonyl-N—($C_1$-$C_4$)alkylamino, ($C_3$-$C_6$)cycloalkylsulfonyl-N—($C_3$-$C_6$)cycloalkylamino, aryl, heteroaryl, heterocyclyl, oxo, carboxyl, amino, hydroxyl and cyano, wherein said alkyl, cycloalkyl, aryl, heteroaryl, heterocyclyl, alkoxy and cycloalkoxy are optionally substituted independently with one to nine fluoro, or 1, 2 or 3 substituents selected from halo, —C(O)—OH, —C(O)—($C_1$-$C_4$)alkoxy, aminocarbonyl, mono-N- or di-N,N—($C_1$-$C_4$)alkylcarbonyl, mono-N- or di-N,N—($C_3$-$C_6$)cycloalkylcarbonyl, cyano, amino and hydroxyl;

$R^3$ is ($C_1$-$C_4$)alkyl, ($C_3$-$C_6$)cycloalkyl, hydroxyl or fluoro, wherein said alkyl is optionally substituted with one to nine fluoros and said ($C_3$-$C_6$)cycloalkyl is optionally substituted with one to six fluoros;

$R^4$ and $R^5$ are each independently selected from hydrogen, ($C_1$-$C_4$)alkyl, ($C_3$-$C_6$)cycloalkyl, aryl, heteroaryl, aryloxy, heteroaryloxy, aralkyl, heteroaralkyl, heterocyclyl, ($C_1$-$C_4$)alkoxy, and ($C_3$-$C_6$)cycloalkoxy, wherein $R^4$ and $R^5$ are each optionally substituted with ($C_1$-$C_4$)alkyl, ($C_1$-$C_4$)alkoxy, ($C_3$-$C_6$)cycloalkyl, ($C_3$-$C_6$)cycloalkoxy, halo or cyano, wherein each of said alkyl, cycloalkyl, alkoxy or cycloalkoxy is optionally substituted with one to nine fluoros;

$R^6$ and $R^7$ are each independently hydrogen, ($C_1$-$C_4$)alkyl, fluoro, ($C_1$-$C_4$)alkoxy, hydroxyl or cyano, wherein said alkyl is optionally substituted with one to nine fluoros;

$R^8$ is selected from fluoro, methyl or trifluoromethyl;

$R^9$ and $R^{10}$ are each independently selected from hydrogen, fluoro, ($C_1$-$C_4$)alkyl, ($C_3$-$C_6$)cycloalkyl, aryl or heteroaryl, wherein said alkyl is optionally substituted with one to nine fluoros, and said cycloalkyl is optionally substituted with one to six fluoros, and said aryl and heteroaryl are optionally substituted with 1, 2 or 3 substituents independently selected from fluoro, chloro, methyl, ethyl, isopropyl, cyclopropyl, methylthio, methoxy, cyano, trifluoromethyl, difluoromethyl, trifluoromethoxy, difluoromethoxy, oxo and trifluoromethylthio; and n is 0, 1 or 2;

or a tautomer thereof or a pharmaceutically acceptable salt of said compound or tautomer.

2. The compound of claim 1 wherein $R^1$ is —C(O)-heterocyclyl, —C(O)—$NR^4R^5$, pyridyl, 6,7-dihydro-5H-pyrrolo[2,1-c][1,2,4]triazolyl, 6,7-dihydro-5H-pyrrolo[1,2-c]imidazolyl, wherein $R^1$ is optionally substituted with 1 or 2 substituents independently selected from fluoro, methyl, hydroxyl or —$CH_2OH$;

D is CH, N, or CF;

B is a bond, oxetanyl or

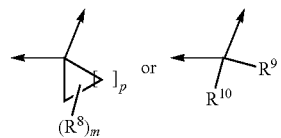

wherein p is 1 or 2;

$R^3$ is fluoro or methyl;

$R^6$ and $R^7$ are each independently hydrogen, fluoro or methyl;

$R^8$ is selected from fluoro or methyl; and $R^9$ and $R^{10}$ are each individually selected from hydrogen, fluoro, or methyl;

or a tautomer thereof or a pharmaceutically acceptable salt of said compound or tautomer.

3. The compound of claim 2 wherein $R^1$ is —C(O)-heterocyclyl or —C(O)—$NR^4R^5$ wherein said heterocyclyl is optionally substituted with 1 or 2 substituents independently selected from fluoro and methyl;

B is a bond,

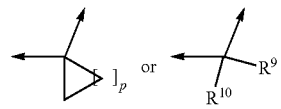

wherein p is 1 or 2;

$R^2$ is selected from phenyl, furyl, thienyl, oxazolyl, thiazolyl, imidazolyl, pyrazolyl, 1,2,3-triazolyl, 1,2,4-triazolyl, tetrazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 2H-benzo[b][1,4]oxazin-3(4H)-onyl, 2,3-dihydro-1H-indenyl, 1,2,3,4-tetrahydronaphthalenyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl, 4,5,6,7-tetrahydro-2H-indazolyl, phenyloxy, pyridinyloxy, benzyl, pyridinyl-(CH$_2$)—, pyrazolyl-(CH$_2$)—, cyclopropyl, and cyclobutyl; wherein said R$^2$ is optionally substituted with 1, 2 or 3 substituents independently selected from (C$_1$-C$_4$)alkyl, (C$_1$-C$_4$)alkoxy, (C$_3$-C$_6$)cycloalkoxy, cyclopropyl, halo, hydroxyl, amino, dimethylamino, methylamino, cyclopropylamino, aminocarbonyl, methylaminocarbonyl, (C$_1$-C$_4$)alkylthio, (C$_3$-C$_6$)cycloalkylthio, aminosulfonyl, methylaminosulfonyl, phenyl, and heteroaryl wherein heteroaryl is selected from furyl, thienyl, oxazolyl, thiazolyl, imidazolyl, pyrazolyl, triazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-only, pyrazin-2(1H)-onyl, oxetanyl, azetidinyl, and pyrrolidinyl, wherein said alkyl, cyclopropyl, azetidinyl, pyrrolidinyl, alkoxy and cycloalkoxy are optionally substituted with oxo, cyano, or up to three fluoro or hydroxyl, and said phenyl or heteroaryl is optionally substituted independently with up to three groups selected from halo, methyl, trifluoromethyl, difluoromethyl, methoxy, trifluoromethoxy, difluoromethoxy, cyano, cyclopropryl, methylthio, oxo and trifluoromethylthio; and R$^9$ and R$^{10}$ are each individually selected from hydrogen and methyl;

or a tautomer thereof or a pharmaceutically acceptable salt of said compound or tautomer.

4. The compound of claim 3 wherein R$^1$ is —C(O)-heterocyclyl or —C(O)—NR$^4$R$^5$ wherein said heterocyclyl is selected from pyrrolidinyl, 2,5-dihydro-1H-pyrrolyl, azetidinyl, piperidinyl and morpholinyl and said heterocyclyl is optionally substituted with 1 or 2 substituents independently selected from fluoro and methyl;

C is CH, N or CF;

A is CH$_2$ or O;

R$^2$ is phenyl, furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-onyl, pyrazin-2(1H)-onyl, phenyloxy, pyridinyloxy, benzyl, pyridinyl-(CH$_2$)— or pyrazolyl-(CH$_2$)—, wherein R$^2$ is optionally substituted with 1, 2 or 3 substituents independently selected from fluoro, chloro, methyl, ethyl, isopropyl, cyclopropyl, hydroxyl, amino, methylthio, methoxy, cyano, trifluoromethyl, difluoromethyl, trifluoromethoxy, difluoromethoxy, oxo and trifluoromethylthio;

R$^4$ is hydrogen or methyl;

R$^5$ is hydrogen or methyl;

or a tautomer thereof or a pharmaceutically acceptable salt of said compound or tautomer.

5. The compound of claim 4 wherein R$^1$ is —C(O)-heterocyclyl, wherein said heterocyclyl is selected from pyrrolidinyl, 2,5-dihydro-1H-pyrrolyl, 3,3-difluoroazetidinyl, 3,3-difluoropyrrolidinyl and morpholinyl;

B is

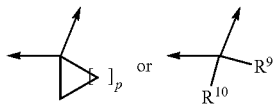

wherein p is 1 or 2; and

R$^2$ is phenyl, furyl, thienyl, oxazolyl, thiazolyl, imidazolyl, pyrazolyl, triazolyl, isoxazolyl, isothiazolyl, oxadiazolyl, thiadiazolyl, pyridinyl, pyridiazinyl, pyrimidinyl, pyrazinyl, phenyloxy, pyridinyloxy, benzyl, pyridinyl-(CH$_2$)—, or pyrazolyl-(CH$_2$)—; wherein R$^2$ is optionally substituted with 1, 2 or 3 substituents selected from independently fluoro, chloro, methyl, ethyl, isopropyl, cyclopropyl, methylthio, methoxy, cyano, trifluoromethyl, difluoromethyl, trifluoromethoxy, difluoromethoxy, oxo and trifluoromethylthio;

or a tautomer thereof or a pharmaceutically acceptable salt of said compound or tautomer.

6. The compound of claim 5 wherein

R$^2$ is N-linked pyrazolyl optionally substituted with 1, 2 or 3 substituents independently selected from fluoro, chloro, methyl, ethyl, isopropyl, cyclopropyl, hydroxyl, amino, methylthio, methoxy, cyano, trifluoromethyl, difluoromethyl, trifluoromethoxy, difluoromethoxy and trifluoromethylthio or a tautomer thereof or a pharmaceutically acceptable salt of said compound or tautomer.

7. The compound of claim 6 wherein R$^1$ is

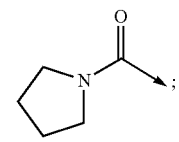

C is CH or CF;

A is CH$_2$;

n is 0; and

R$^2$ is N-linked pyrazolyl substituted at the 4 position with fluoro or chloro;

or a tautomer thereof or a pharmaceutically acceptable salt of said compound or tautomer.

8. A compound selected from the group consisting of:

(1-(2-(1-(4-fluoro-1H-pyrazol-1-yl)cyclopropyl)-3H-imidazo[4,5-b]pyridin-5-yl)piperidin-3-yl)(pyrrolidin-1-yl)methanone;

(1-(8-(1-(4-chloro-1H-pyrazol-1-yl)cyclopropyl)-9H-purin-2-yl)piperidin-3-yl)(pyrrolidin-1-yl)methanone;

(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone;

(1-(2-(2-(4-chloro-1H-pyrazol-1-yl)propan-2-yl)-3H-imidazo[4,5-b]pyridin-5-yl)piperidin-3-yl)(pyrrolidin-1-yl)methanone;

(1-{2-[1-(4-chloro-1H-pyrazol-1-yl)cyclopropyl]-3H-imidazo[4,5-b]pyridin-5-yl}(2,2,6,6-²H$_4$)piperidin-3-yl](pyrrolidin-1-yl)methanone;

(1-(2-((R)-1-(4-fluoro-1H-pyrazol-1-yl)ethyl)-3H-imidazo[4,5-b]pyridin-5-yl)piperidin-3-yl)(pyrrolidin-1-yl)methanone;

(1-(2-((S)-1-(4-fluoro-1H-pyrazol-1-yl)ethyl)-3H-imidazo[4,5-b]pyridin-5-yl)piperidin-3-yl)(pyrrolidin-1-yl)methanone;

(1-(2-((S)-1-(4-chloro-1H-pyrazol-1-yl)ethyl)-3H-imidazo[4,5-b]pyridin-5-yl)piperidin-3-yl)(pyrrolidin-1-yl)methanone;

(1-(2-((R)-1-(4-chloro-1H-pyrazol-1-yl)ethyl)-3H-imidazo[4,5-b]pyridin-5-yl)piperidin-3-yl)(pyrrolidin-1-yl)methanone;

(1-(8-((S)-1-(4-chloro-1H-pyrazol-1-yl)ethyl)-9H-purin-2-yl)piperidin-3-yl)(pyrrolidin-1-yl)methanone;

(1-(8-((R)-1-(4-chloro-1H-pyrazol-1-yl)ethyl)-9H-purin-2-yl)piperidin-3-yl)(pyrrolidin-1-yl)methanone; and (1-(8-(1-(4-fluoro-1H-pyrazol-1-yl)cyclopropyl)-9H-purin-2-yl)piperidin-3-yl)(pyrrolidin-1-yl)methanone;

or a tautomer thereof or a pharmaceutically acceptable salt of said compound or tautomer.

9. A compound selected from the group consisting of:
((R)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone,
((R)-1-(2-((R)-1-(4-Chloro-1H-pyrazol-1-yl)ethyl)-3H-imidazo[4,5-b]pyridin-5-yl)piperidin-3-yl)(pyrrolidin-1-yl)methanone,
((S)-1-(2-((S)-1-(4-Chloro-1H-pyrazol-1-yl)ethyl)-3H-imidazo[4,5-b]pyridin-5-yl)piperidin-3-yl)(pyrrolidin-1-yl)methanone, and
((S)-1-(2-((R)-1-(4-Chloro-1H-pyrazol-1-yl)ethyl)-3H-imidazo[4,5-b]pyridin-5-yl)piperidin-3-yl)(pyrrolidin-1-yl)methanone,
or a mixture of thereof;
or a tautomer thereof or a pharmaceutically acceptable salt of said compound or tautomer.

10. A compound selected from the group consisting of:
(R)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone, and
(S)-(1-(2-(1-(4-chloro-1H-pyrazol-1-yl)cyclopropyl)-3H-imidazo[4,5-b]pyridin-5-yl)piperidin-3-yl)(pyrrolidin-1-yl)methanone,
or a mixture of thereof;
or tautomer thereof or a pharmaceutically acceptable salt of said compound or tautomer.

11. The compound having the structure

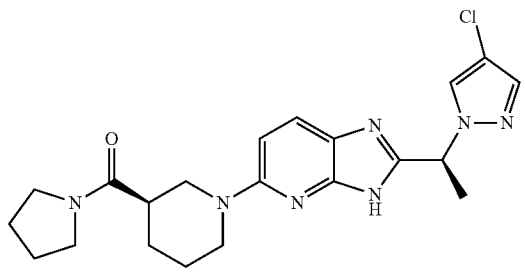 [SMILES: C[C@@H](c1nc2ccc(N3CCC[C@@H](C(=O)N4CCCC4)C3)nc2[nH]1)n1cc(Cl)cn1]

or a tautomer thereof or a pharmaceutically acceptable salt of said compound or tautomer.

12. The compound having the structure

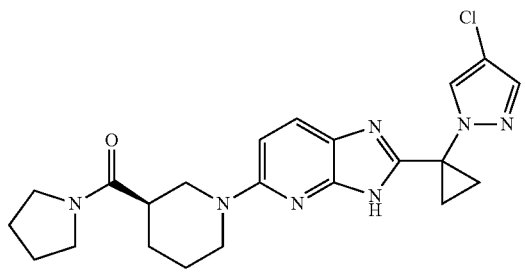 [SMILES: O=C([C@@H]1CCCN(c2ccc3nc(C4(n5cc(Cl)cn5)CC4)[nH]c3n2)C1)N1CCCC1]

or a tautomer thereof or a pharmaceutically acceptable salt of said compound or tautomer.

13. A pharmaceutical composition comprising a compound according to claim 1 or a tautomer thereof or a pharmaceutically acceptable salt of said compound or tautomer, present in a therapeutically effective amount, in admixture with at least one pharmaceutically acceptable excipient.

14. The composition of claim 13 further comprising at least one additional pharmaceutical agent selected from the group consisting of an anti-obesity agent, an anti-diabetic agent, and a cholesterol/lipid modulating agent.

15. The composition of claim 14 wherein said anti-obesity agent is selected from the group consisting of dirlotapide, mitratapide, implitapide, R56918, CCKa agonists, 5HT2c agonists, MCR4 agonist, lipase inhibitor, $PYY_{3-36}$, opioid antagonists, the combination of naltrexone with buproprion, oleoyl-estrone, obinepitide, pramlintide, tesofensine, leptin, liraglutide, bromocriptine, orlistat, exenatide, AOD-9604 and sibutramine.

16. The composition of claim 14 wherein said anti-diabetic agent is selected from the group consisting of an acetyl-CoA carboxylase-inhibitor, a diacylglycerol O-acyltransferase 1 inhibitor, AZD7687, LCQ908, monoacylglycerol O-acyltransferase inhibitors, a phosphodiesterase-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist a biguanide, liraglutide, albiglutide, exenatide, lixisenatide, dulaglutide, semaglutide, NN-9924, TTP-054, a protein tyrosine phosphatase-1B inhibitor, SIRT-1 activator, a dipeptidyl peptidase IV inhibitor, an insulin secreatagogue, a fatty acid oxidation inhibitor, an A2 antagonist, a c-jun amino-terminal kinase inhibitor, glucokinase activators, insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPR40 agonists, GPR120 modulators, high affinity nicotinic acid receptor activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 or CCR5, inhibitors of PKC isoforms, inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin, inhibitors or modulators of PDHK2 or PDHK4, inhibitors of MAP4K4, modulators of IL1 family, and modulators of RXRalpha.

17. The composition of claim 14 wherein said cholesterol/lipid modulating agent is selected from the group consisting of HMG-CoA reductase inhibitors; squalene synthetase inhibitors; fibrates; bile acid sequestrants; ACAT inhibitors; MTP inhibitors; lipooxygenase inhibitors; cholesterol absorption inhibitors; PCSK9 modulators and cholesteryl ester transfer protein inhibitors.

* * * * *